(12) United States Patent
Dal Piaz et al.

(10) Patent No.: US 7,491,722 B2
(45) Date of Patent: Feb. 17, 2009

(54) PYRIDAZIN-3(2H)-ONE DERIVATIVES

(75) Inventors: Vittorio Dal Piaz, Impruneta (IT); Nuria Aguilar Izquierdo, Barcelona (ES); Maria Antonia Buil Albero, Barcelona (ES); Marta Carrascal Riera, Barcelona (ES); Jordi Gracia Ferrer, Barcelona (ES); Maria Paola Giovannoni, Scandicci (IT); Claudia Vergelli, Grassina (IT)

(73) Assignee: Laboratorios Almirall S.A., Barcelona (ES)

( * ) Notice: Subject to any disclaimer, the term of this patent is extended or adjusted under 35 U.S.C. 154(b) by 226 days.

(21) Appl. No.: 10/539,821

(22) PCT Filed: Dec. 22, 2003

(86) PCT No.: PCT/EP03/14722

§ 371 (c)(1),
(2), (4) Date: Dec. 14, 2005

(87) PCT Pub. No.: WO2004/058729

PCT Pub. Date: Jul. 15, 2004

(65) Prior Publication Data

US 2006/0173008 A1   Aug. 3, 2006

(30) Foreign Application Priority Data

Dec. 26, 2002   (ES) .................... 200203003

(51) Int. Cl.
| | |
|---|---|
| A61K 31/501 | (2006.01) |
| A61K 31/50 | (2006.01) |
| C07D 401/04 | (2006.01) |
| C07D 403/04 | (2006.01) |
| C07D 405/04 | (2006.01) |
| C07D 409/04 | (2006.01) |
| C07D 401/14 | (2006.01) |
| C07D 403/14 | (2006.01) |
| C07D 405/14 | (2006.01) |
| C07D 409/14 | (2006.01) |
| C07D 237/14 | (2006.01) |
| A61P 17/06 | (2006.01) |
| C07D 487/04 | (2006.01) |
| C07D 401/12 | (2006.01) |
| C07D 403/12 | (2006.01) |
| C07D 405/12 | (2006.01) |
| C07D 409/12 | (2006.01) |
| C07D 473/34 | (2006.01) |
| A61P 11/06 | (2006.01) |

(52) U.S. Cl. ............... 514/252.01; 514/252.02; 514/252.03; 514/252.04; 514/252.05; 514/252.06; 544/238; 544/239; 544/236

(58) Field of Classification Search ............. 544/238, 544/224, 239; 514/247, 252.01, 252.02, 514/252.03, 252.04, 252.05, 252.06
See application file for complete search history.

(56) References Cited

U.S. PATENT DOCUMENTS

| | | | |
|---|---|---|---|
| 5,679,696 A | 10/1997 | Fenton et al. | |
| 5,859,008 A | 1/1999 | Jonas et al. | |
| 6,025,376 A | 2/2000 | Laurent et al. | |
| 2006/0052379 A1 | 3/2006 | Dal Piaz et al. | |

FOREIGN PATENT DOCUMENTS

| | | |
|---|---|---|
| DE | 2 225 218 | 12/1973 |
| GB | 1351569 | 5/1974 |
| WO | WO 93/07146 | 4/1993 |
| WO | WO 97/15561 | 5/1997 |
| WO | WO 99/06404 | 2/1999 |
| WO | WO 01/46184 A1 | 6/2001 |
| WO | WO 03/097613 | 11/2003 |
| WO | WO 03/097613 A1 | 11/2003 |
| WO | WO 2005/049581 | 6/2005 |
| WO | WO 2005/123692 A1 | 12/2005 |
| WO | WO 2005/123693 A1 | 12/2005 |

OTHER PUBLICATIONS

Spina, Drugs, 2003, 63, 23, pp. 2575-2594.*
MacKenzie, Alergology International (2004) 53: 101-110.*
Dyke, Exp. Opin. Invest. Drugs, 8(9):1301-1325, 1999.*
Stawiski, J. Invest Derm., 73(4), 261-263, 1979.*
Hanifin, J. Invest. Derm. 107(1), 51-56, 1996.*
Griffiths, Brit. J. Derm., 2002, 147, 299-307.*
Baumer, et al., Inflammation & Allergy—Drug Targets, vol. 6, No. 1, Mar. 2007, pp. 17-26 (10).*
Implications for Rheumatoid Arthritis http://www.medscape.com/viewarticle/464104_4, downloaded Jul. 8, 2007.*
European Respiratory Society, Feb. 13, 2007, http://www.newtocopd.com/currentaffairsnews/list751_item17680.aspx, downloaded Jan. 16, 2008.*
Implications for Rheumatoid Arthritis http://www.medscape.com/viewarticle/464104, downloaded Jan. 17, 2008.*

(Continued)

*Primary Examiner*—Mark L. Berch
*Assistant Examiner*—Cecilia M Jaisle
(74) *Attorney, Agent, or Firm*—Finnegan, Henderson, Farabow, Garrett & Dunner, L.L.P.

(57) ABSTRACT

Pyridazin-3(2H)-one derivatives of formula (I) are found to inhibit PDE-4. $R^1$, $R^2$ and $R^4$ are organic radicals, $R^3$ is a cyclic group, and $R^5$ is an ester or an aryl or heteroaryl group.

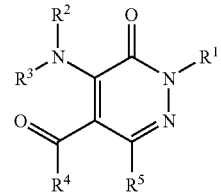

(I)

26 Claims, No Drawings

OTHER PUBLICATIONS

Targan, et al., Inflammatory Bowel Disease: From Bench to Bedside, 2nd Edition, pp. 553-571, 2003.*

Prehn, et al., J. Clin. Immunol., vol. 21, No. 5, 2001, pp. 357-364.*

Margaretha Van der Mey et al., "Novel Selective PDE4 Inhibitors, 1. Synthesis, Structure-Activity Relations, and Molecular Modeling of 4-(3,4-Dimethoxyphenyl)-2$H$-phthalazin-1-ones and Analogues", J. Med., Chem., 2001, 44, 2511-2522.

Luca Costantino et al., "Isoxazolo-[3, 4-$d$]-pyridazin-7-(6$H$)-one as a Potential Substrate for New Aldose Reductase Inhibitors", J. Med. Chem., 1999, 42, 1894-1900.

Entry No. 3603 for Emorfazone in Merck Index (1994).

Sato, M. et al., "Studies on Mechanisms of Action of Emorfazone," Arznem. Forsch./Drug Res., 32(l)(4):379-382 (1983).

English-language abstract for WO 97/15561 (May 1, 1997).

English-language machine translation of DE 2 225 218 from esp@cenet database (Dec. 20, 1973).

U.S. Appl. No. 10/578,594, filed May 8, 2006.

Daniela Barlocco, et al., Phenylpiperazinylalkylamino Substituted Pyridazinones as Potent $\alpha_1$ Adrenoceptor Antagonists, J. Med., Chem., 44:2403-2410 (2001).

Giovanna Ciciani, et al., "Synthesis and Evaluation of In Vitro Antitumor Activity of Some Substituted 5-Pyridazinyl-Styrylketones," II Farmaco, 46 (7,8)873-885 (1991).

Luca Costantino, et al., "Isoxazolo-[3,4-d]-pyridazin-7-(6H)-one as a Potential Substrate for New Aldose Reductase Inhibitors," J. Med. Chem., 42:1894-1900 (1999).

Vittorio Dal Piaz, et al., "5-Acyl-6-aryl-4-nitro-3(2H)pyridazinones and Related 4-Amino Compounds: Synthesis and Pharmacological Evaluation," Journal of Pharmaceutical Sciences, 80(4):341-348 (1991).

Vittorio Dal Piaz, et al., "4,5-Functionalized 6-phenyl-3(2H)-pyridazinones: synthesis and evaluation of antinociceptive activity," Eur. J. Med. Chem., 31:65-70 (1996).

International Search Report for WO 2004/058729 dated Mar. 10, 2004.

Spanish Search Report for P 200203003 dated May 17, 2004.

* cited by examiner

PYRIDAZIN-3(2H)-ONE DERIVATIVES

This application is a national stage application under 35 U.S.C. § 371 of international application number PCT/EP2003/014722, filed on Dec. 22, 2003, which claims the benefit of priority from Spanish application number P200203003, filed on Dec. 26, 2002.

The present invention relates to new therapeutically useful pyridazin-3(2H)-one derivatives, to processes for their preparation and to pharmaceutical compositions containing them. These compounds are potent and selective inhibitors of phosphodiesterase 4 (PDE4) and are thus useful in the treatment, prevention or suppression of pathological conditions, diseases and disorders known to be susceptible of being improved by inhibition of PDE4.

Phosphodiesterases (PDEs) comprise a superfamily of enzymes responsible for the hydrolysis and inactivation of the second messengers cyclic adenosine monophosphate (cAMP) and cyclic guanosine monophosphate (cGMP). Eleven different PDE families have been identified to date (PDE1 to PDE11) which differ in substrate preference, catalytic activity, sensitivity to endogenous activators and inhibitors, and encoding genes.

The PDE4 isoenzyme family exhibits a high affinity for cyclic AMP but has weak affinity for cyclic GMP. Increased cyclic AMP levels caused by PDE4 inhibition are associated with the suppression of cell activation in a wide range of inflammatory and immune cells, including lymphocytes, macrophages, basophils, neutrophils, and eosinophils. Moreover, PDE4 inhibition decreases the release of the cytokine Tumor Necrosis Factor α (TNFα). The biology of PDE4 is described in several recent reviews, for example M. D. Houslay, *Prog. Nucleic Acid Res. Mol. Biol.* 2001, 69, 249-315; J. E. Souness et al. *Immunopharmacol.* 2000 47, 127-162; or M. Conti and S. L. Jin, *Prog. Nucleic Acid Res. Mol. Biol.* 1999, 63, 1-38.

In view of these physiological effects, PDE4 inhibitors of varied chemical structures have been recently disclosed for the treatment or prevention of chronic and acute inflammatory diseases and of other pathological conditions, diseases and disorders known to be susceptible to amelioration by inhibition of PDE4. See, for example, U.S. Pat. Nos. 5,449,686, 5,710,170, WO 98/45268, WO 99/06404, WO 01/57025, WO 01/57036, WO 01/46184, WO 97/05105, WO 96/40636, U.S. Pat. Nos. 5,786,354, 5,773,467, 5,753,666, 5,728,712, 5,693,659, 5,679,696, 5,596,013, 5,541,219, 5,508,300, 5,502,072 or H. J. Dyke and J. G. Montana, *Exp. Opin. Invest. Drugs* 1999, 8, 1301-1325.

A few compounds having the capacity to selectively inhibit phosphodiesterase 4 are in active development. Examples of these compounds are cipamfylline (European Patent number 0 389 282 B1), arofyline (European patent number 0 435 811 B1), cilomilast, roflumilast (European Patent number 0 706 513 B1), mesopram (European Patent number 0 859 766 B1) and pumafentrine (PCT Patent application number 98/21208 A1).

We have now found that a novel series of pyridazin-3(2H)-one derivatives are potent and selective inhibitors of PDE4 and are therefore useful in the treatment or prevention of these pathological conditions, diseases and disorders, in particular asthma, chronic obstructive pulmonary disease, rheumatoid arthritis, atopic dermatitis, psoriasis or irritable bowel disease.

The compounds of the present invention can also be used in combination with other drugs known to be effective in the treatment of these diseases. For example, they can be used in combination with steroids or immunosuppressive agents, such as cyclosporin A, rapamycin or T-cell receptor blockers. In this case the administration of the compounds allows a reduction of the dosage of the other drugs, thus preventing the appearance of the undesired side effects associated with both steroids and immunosuppressants.

Like other PDE4 inhibitors (see references above) the compounds of the invention can also be used for blocking the ulcerogenic effects induced by a variety of etiological agents, such as antiinflammatory drugs (steroidal or non-steroidal antiinflammatory agents), stress, ammonia, ethanol and concentrated acids. They can be used alone or in combination with antacids and/or antisecretory drugs in the preventive and/or curative treatment of gastrointestinal pathologies like drug-induced ulcers, peptic ulcers, *H. Pylori*-related ulcers, esophagitis and gastro-esophageal reflux disease.

They can also be used in the treatment of pathological situations where damage to the cells or tissues is produced through conditions like anoxia or the production of an excess of free, radicals. Examples of such beneficial effects are the protection of cardiac tissue after coronary artery occlusion or the prolongation of cell and tissue viability when the compounds of the invention are added to preserving solutions intended for storage of transplant organs or fluids such as blood or sperm. They are also of benefit on tissue repair and wound healing.

Accordingly, the present invention provides novel compounds of formula (I):

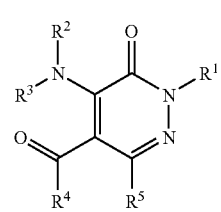

wherein
$R^1$ and $R^2$ represent independently from each other:
a hydrogen atom;
a group selected from acyl, hydroxycarbonyl, alkoxycarbonyl, carbamoyl, monoalkylcarbamoyl or di-alkylcarbamoyl;
an alkyl, alkenyl or alkynyl group, which is optionally substituted by one or more, for example 1, 2, 3 or 4, substituents selected from halogen atoms and hydroxy, alkoxy, aryloxy, alkylthio, oxo, amino, mono- or di-alkylamino, acylamino, carbamoyl, mono- or di-alkylcarbamoyl groups;
an aryl or heteroaryl group which is optionally substituted by one or more, for example 1, 2, 3 or 4, substituents selected from halogen atoms and hydroxy, hydroxyalkyl, hydroxycarbonyl, alkoxy, alkylenedioxy, alkoxyacyl, aryloxy, acyl, acyloxy, alkylthio, amino, nitro, cyano, mono- or di-alkylamino, acylamino, carbamoyl, mono- or di-alkylcarbamoyl, difluoromethyl, trifluoromethyl, difluoromethoxy or trifluoromethoxy groups;
a saturated or unsaturated heterocyclic group which is optionally substituted by one or more, for example 1, 2, 3 or 4, substituents selected from halogen atoms and hydroxy, hydroxyalkyl, hydroxycarbonyl, alkoxy, alkylenedioxy, alkoxyacyl, aryloxy, acyl, acyloxy, alkylthio, oxo, amino, nitro, cyano, mono- or di-alkylamino, acylamino, carbamoyl, mono- or di-alkylcarbamoyl, difluoromethyl, trifluoromethyl, difluoromethoxy or trifluoromethoxy groups;
a group of formula

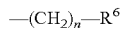

wherein n is an integer from 0 to 4 and $R^6$ represents:
a cycloalkyl or cycloalkenyl group;
an aryl group, which is optionally substituted by one or more, for example 1, 2, 3 or 4, substituents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
or a 3- to 7-membered ring comprising from 1 to 4 heteroatoms selected from nitrogen, oxygen and sulphur, which ring is optionally substituted by one or more, for example 1, 2, 3 or 4, substituents selected from halogen atoms and alkyl, hydroxy, alkoxy, alkylenedioxy, amino, mono- or di-alkylamino, nitro, cyano or trifluoromethyl groups;

$R^3$ represents a monocyclic or polycyclic aryl or heteroaryl group, which is optionally substituted by one or more, for example 1, 2, 3 or 4, substituents selected from
halogen atoms;
alkyl and alkylene groups, which are optionally substituted by one or more, for example 1, 2, 3 or 4, substituents selected from halogen atoms; and phenyl, hydroxy, hydroxyalkyl, alkoxy, aryloxy, alkylthio, oxo, amino, mono- or di-alkylamino, acylamino, hydroxycarbonyl, alkoxycarbonyl, carbamoyl, mono- or di-alkylcarbamoyl groups
phenyl, hydroxy, hydroxyalkyl, alkoxy, cycloalkoxy, nitro, aryloxy, alkylthio, alkylsulphinyl, alkylsulphonyl, alkylsulphamoyl, acyl, amino, mono- or di-alkylamino, acylamino, hydroxycarbonyl, alkoxycarbonyl, carbamoyl, mono- or di-alkylcarbamoyl, ureido, N'-alkylureido, N',N'-dialkylureido, alkylsulphamido, aminosuphonyl, mono- or di-alkylaminosulphonyl, cyano, difluoromethoxy, or trifluoromethoxy groups;

$R^5$ represents a group —$COOR^7$ or a monocyclic or polycyclic aryl or heteroaryl group, which is optionally substituted by one or more, for example 1, 2, 3 or 4, substituents selected from:
halogen atoms;
alkyl and alkenyl groups, which are optionally substituted by one or more, for example 1, 2, 3 or 4, substituents selected from halogen atoms and phenyl, hydroxy, hydroxyalkyl, alkoxy, aryloxy, alkylthio, oxo, amino, mono- or di-alkylamino, acylamino, hydroxycarbonyl, alkoxycarbonyl, carbamoyl, mono- or di-alkylcarbamoyl groups; y
phenyl, hydroxy, alkylenedioxy, alkoxy, cycloalkyloxy, alkylthio, alkylsulphinyl; alkylsulphonyl, alkylsulfamoyl, amino, mono- or di-alkylamino, acylamino, nitro, acyl, hydroxycarbonyl, alkoxycarbonyl, carbamoyl, mono- or di-alkylcarbamoyl, ureido, N'-alkylureido, N',N'-dialkylureido, alkylsulphamido, aminosuphonyl, mono- or di-alkylaminosulphonyl, cyano, difluoromethoxy or trifluoromethoxy groups;

wherein $R^7$ represents an alkyl group which is optionally substituted by one or more, for example 1, 2, 3 or 4, substituents selected from halogen atoms and hydroxy, alkoxy, aryloxy, alkylthio, oxo, amino, mono- or di-alkylamino, acylamino, hydroxycarbonyl, alkoxycarbonyl, carbamoyl and mono- or di-alkylcarbamoyl groups or a group of formula

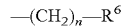

wherein n and $R^6$ are as defined above, and
$R^4$ represents:
a hydrogen atom;
a hydroxy, alkoxy, amino, mono- or di-alkylamino group;
an alkyl, alkenyl or alkynyl group which is optionally substituted by one or more, for example 1, 2, 3 or 4, substituents selected from halogen atoms and hydroxy, alkoxy, aryloxy, alkylthio, oxo, amino, mono- or di-alkylamino, acylamino, hydroxycarbonyl, alkoxycarbonyl, carbamoyl and mono- or di-alkylcarbamoyl groups;
or a group of formula

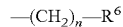

wherein n and $R^6$ are as defined above.
as well as the N-oxides obtainable from the heteroaryl radicals present in the structure when these heteroradicals comprise N atoms and pharmaceutically acceptable salts thereof,
with the proviso that when $R^5$ is neither an optionally substituted heteroaryl group nor a group $COOR^7$, then $R^3$ is an optionally substituted heteroaryl group.

Certain pyridazin-3(2H)-one derivatives of similar structure, which do not fall within the scope of the present invention, have been disclosed in *J. Pharm. Sci.* 1991, 80, 341-348 and *J. Med. Chem.* 1999, 42, 1894-1900.

Further objectives of the present invention are to provide processes for preparing said compounds; pharmaceutical compositions comprising an effective amount of said compounds; the use of the compounds in the manufacture of a medicament for the treatment of diseases susceptible of being improved by inhibition of PDE4; and methods of treatment of diseases susceptible to amelioration by inhibition of PDE4, which methods comprise the administration of the compounds of the invention to a subject in need of treatment.

As used herein the term alkyl embraces optionally substituted, linear or branched radicals having 1 to 20 carbon atoms or, preferably 1 to 12 carbon atoms. More preferably alkyl radicals are "lower alkyl" radicals having 1 to 8, preferably 1 to 6 and more preferably 1 to 4 carbon atoms.

Examples include methyl, ethyl, n-propyl, i-propyl, n-butyl, sec-butyl, t-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

As used herein, the term alkenyl embraces optionally substituted, linear or branched, mono or polyunsaturated radicals having 1 to 20 carbon atoms or, preferably, 1 to 12 carbon atoms. More preferably alkenyl radicals are "lower alkenyl" radicals having 2 to 8, preferably 2 to 6 and more preferably 2 to 4 carbon atoms. In particular it is preferred that the alkenyl radicals are mono or diunsaturated.

Examples include vinyl, allyl, 1-propenyl, isopropenyl, 1-butenyl, 2-butenyl, 3-butenyl, 1-pentenyl, 2-pentenyl, 3-pentenyl and 4-pentenyl radicals.

As used herein, the term alkynyl embraces optionally substituted, linear or branched, mono or polyunsaturated radicals having 1 to 20 carbon atoms or, preferably, 1 to 12 carbon atoms. More preferably, alkynyl radicals are "lower alkynyl" radicals having 2 to 8, preferably 2 to 6 and more preferably 2 to 4 carbon atoms. In particular, it is preferred that the alkynyl radicals are mono or diunsaturated.

Examples include 1-propynyl, 2-propynyl, 1-butynyl, 2-butynyl and 3-butynyl radicals.

When it is mentioned that alkyl, alkenyl or alkynyl radicals may be optionally substituted it is meant to include linear or branched alkyl, alkenyl or alkynyl radicals as defined above, which may be unsubstituted or substituted in any position by one or more substituents, for example by 1, 2 or 3 substituents. When two or more substituents are present, each substituent may be the same or different.

A said optionally substituted alkenyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, substituents on an alkenyl group are themselves unsubstituted.

A said optionally substituted alkynyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, substituents on an alkynyl group are themselves unsubstituted.

A said optionally substituted alkyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, substituents on an alkyl group are themselves unsubstituted. Preferred optionally substituted alkyl groups are unsubstituted or substituted with 1, 2 or 3 fluorine atoms.

As used herein, the term alkylene embraces divalent alkyl moieties typically having from 1 to 6, for example from 1 to 4, carbon atoms. Examples of $C_1$-$C_4$ alkylene radicals include methylene, ethylene, propylene, butylene, pentylene and hexylene, radicals.

A said optionally substituted alkylene group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

When an alkylene radical is present as a substituent on another radical it shall be deemed to be a single substituent, rather than a radical formed by two substituents.

As used herein, the term alkoxy (or alkyloxy) embraces optionally substituted, linear or branched oxy-containing radicals each having alkyl portions of 1 to 10 carbon atoms. More preferred alkoxy radicals are "lower alkoxy" radicals having 1 to 8, preferably 1 to 6 and more preferably 1 to 4 carbon atoms.

An alkoxy group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkoxy group are themselves unsubstituted.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy and 2-hydroxypropoxy.

As used herein, the term alkylthio embraces radicals containing an optionally substituted, linear or branched alkyl radicals of 1 to 10 carbon atoms attached to a divalent sulfur atom. More preferred alkylthio radicals are "lower alkylthio" radicals having 1 to 8, preferably 1 to 6 and more preferably 1 to 4 carbon atoms.

An alkylthio group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkythio group are themselves unsubstituted.

Preferred optionally substituted alkylthio radicals include methylthio, ethylthio, n-propylthio, i-propylthio, n-butylthio, sec-butylthio, t-butylthio, trifluoromethylthio, difluoromethylthio, hydroxymethylthio, 2-hydroxyethylthio and 2-hydroxypropylthio.

As used herein, the term monoalkylamino embraces radicals containing an optionally substituted, linear or branched alkyl radicals of 1 to 10 carbon atoms attached to a divalent —NH— radical. More preferred monoalkylamino radicals are "lower monoalkylamino" radicals having 1 to 8, preferably 1 to 6 and more preferably 1 to 4 carbon atoms.

A monoalkylamino group typically contains an alkyl group which is unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substitutents on a monoalkylamino group are themselves unsubstituted.

Preferred optionally substituted monoalkylamino radicals include methylamino, ethylamino, n-propylamino, i-propylamino, n-butylamino, sec-butylamino, t-butylamino, trifluoromethylamino, difluoromethylamino, hydroxymethylamino, 2-hydroxyethylamino and 2-hydroxypropylamino.

As used herein, the term dialkylamino embraces radicals containing a trivalent nitrogen atoms with two optionally substituted, linear or branched alkyl radicals of 1 to 10 carbon atoms attached thereto. More preferred dialkylamino radicals are "lower dialkylamino" radicals having 1 to 8, preferably 1 to 6 and more preferably 1 to 4 carbon atoms in each alkyl radical.

A dialkylamino group typically contains two alkyl groups, each of which is unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a dialkylamino group are themselves unsubstituted.

Preferred optionally substituted dialkylamino radicals include dimethylamino, diethylamino, methyl(ethyl)amino, di(n-propyl)amino, n-propyl(methyl)amino, n-propyl(ethyl) amino, di(i-propyl)amino, i-propyl(methyl)amino, i-propyl (ethyl)amino, di(n-butyl)amino, n-butyl(methyl)amino, n-butyl(ethyl)amino, n-butyl(i-propyl)amino, di(sec-butyl) amino, sec-butyl(methyl)amino, sec-butyl(ethyl)amino, sec-butyl(n-propyl)amino, sec-butyl(i-propyl)amino, di(t-butyl) amino, t-butyl(methyl)amino, t-butyl(ethyl)amino, t-butyl(n-propyl)amino, t-butyl(i-propyl)amino, trifluoromethyl (methyl)amino, trifluoromethyl(ethyl)amino, trifluoromethyl(n-propyl)amino, trifluoromethyl(i-propyl) amino, trifluoromethyl(n-butyl)amino, trifluoromethyl(sec-butyl)amino, difluoromethyl(methyl)amino, difluoromethyl (ethyl)amino, difluoromethyl(n-propyl)amino, difluoromethyl(i-propyl)amino, difluoromethyl(n-butyl)) amino, difluoromethyl(sec-butyl)amino, difluoromethyl(t-butyl)amino, difluoromethyl(trifluoromethyl)amino, hydroxymethyl(methyl)amino, ethyl(hydroxymethyl)amino, hydroxymethyl(n-propyl)amino, hydroxymethyl(i-propyl) amino, n-butyl(hydroxymethyl)amino, sec-butyl(hydroxymethyl)amino, t-butyl(hydroxymethyl)amino, difluoromethyl(hydroxymethyl)amino, hydroxymethyl(trifluoromethyl)amino, hydroxyethyl(methyl)amino, ethyl(hydroxyethyl)amino, hydroxyethyl(n-propyl)amino, hydroxyethyl(i-propyl)amino, n-butyl(hydroxyethyl)amino, sec-butyl(hydroxyethyl)amino, t-butyl(hydroxyethyl)amino, difluoromethyl(hydroxyethyl)amino, hydroxyethyl(trifluoromethyl)amino, hydroxypropyl(methyl)amino, ethyl(hydroxypropyl)amino, hydroxypropyl(n-propyl)amino, hydroxypropyl(i-propyl)amino, n-butyl(hydroxypropyl)amino, sec-butyl(hydroxypropyl)amino, t-butyl(hydroxypropyl)amino, difluoromethyl(hydroxypropyl)amino, hydroxypropyl(trifluoromethyl)amino.

As used herein, the term hydroxyalkyl embraces linear or branched alkyl radicals having 1 to 10 carbon atoms, preferably 1 to 6 carbon atoms, any one of which may be substituted with one or more hydroxyl radicals.

Examples of such radicals include hydroxymethyl, hydroxyethyl, hydroxypropyl, hydroxybutyl and hydroxyhexyl.

As used herein, the term alkoxycarbonyl embraces optionally substituted, linear or branched radicals each having alkyl portions of 1 to 10 carbon atoms and attached to an oxycarbonyl radical. More preferred alkoxycarbonyl radicals are "lower alkoxycarbonyl" radicals, in which the alkyl moiety has 1 to 8, preferably 1 to 6 and more preferably 1 to 4 carbon atoms.

An alkoxycarbonyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkoxycarbonyl group are themselves unsubstituted.

Preferred optionally substituted alkoxycarbonyl radicals include methoxycarbonyl, ethoxycarbonyl, n-propoxycarbonyl, i-propoxycarbonyl, n-butoxycarbonyl, sec-butoxycarbonyl, t-butoxycarbonyl, trifluoromethoxycarbonyl, difluoromethoxycarbonyl, hydroxymethoxycarbonyl, 2-hydroxyethoxycarbonyl and 2-hydroxypropoxycarbonyl.

As used herein, the term monoalkylcarbamoyl embraces radicals containing an optionally substituted, linear or branched alkyl radicals of 1 to 10 carbon atoms and attached to the nitrogen of a —NHCO— radical. More preferred monoalkylcarbamoyl radicals are "lower monoalkylcarbamoyl" radicals in which the alkyl moiety has 1 to 8, preferably 1 to 6 and more preferably 1 to 4 carbon atoms.

A monoalkylcarbamoyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a monoalkylcarbamoyl group are themselves unsubstituted.

Preferred optionally substituted monoalkylcarbamoyl radicals include methylcarbamoyl, ethylcarbamoyl, n-propylcarbamoyl, i-propylcarbamoyl, n-butylcarbamoyl, sec-butylcarbamoyl, t-butylcarbamoyl, trifluoromethylcarbamoyl, difluoromethylcarbamoyl, hydroxymethylcarbamoyl, 2-hydroxyethylcarbamoyl and 2-hydroxypropylcarbamoyl.

As used herein, the term dialkylcarbamoyl embraces radicals containing a radical NCO— where the nitrogen is attached to two optionally substituted, linear or branched alkyl radicals of 1 to 10 carbon atoms. More preferred dialkylcarbamoyl radicals are "lower dialkylcarbamoyl" radicals having 1 to 8, preferably 1 to 6 and more preferably 1 to 4 carbon atoms in each alkyl radical.

A dialkylcarbamoyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a dialkylcarbamoyl group are themselves unsubstituted.

Preferred optionally substituted dialkylcarbamoyl radicals include dimethylcarbamoyl, diethylcarbamoyl, methyl(ethyl)carbamoyl, di(n-propyl)carbamoyl, n-propyl(methyl)carbamoyl, n-propyl(ethyl)carbamoyl, di(i-propyl)carbamoyl, i-propyl(methyl)carbamoyl, i-propyl(ethyl)carbamoyl, di(n-butyl)carbamoyl, n-butyl(methyl)carbamoyl, n-butyl(ethyl)carbamoyl, n-butyl(i-propyl)carbamoyl, di(sec-butyl)carbamoyl, sec-butyl(methyl)carbamoyl, sec-butyl(ethyl)carbamoyl, sec-butyl(n-propyl)carbamoyl, sec-butyl(i-propyl)carbamoyl, di(t-butyl)carbamoyl, t-butyl(methyl)carbamoyl, t-butyl(ethyl)carbamoyl, t-butyl(n-propyl)carbamoyl, t-butyl(i-propyl)carbamoyl, trifluoromethyl(methyl)carbamoyl, trifluoromethyl(ethyl)carbamoyl, trifluoromethyl(n-propyl)carbamoyl, trifluoromethyl(i-propyl)carbamoyl, trifluoromethyl(n-butyl)carbamoyl, trifluoromethyl(sec-butyl)carbamoyl, difluoromethyl(methyl)carbamoyl, difluoromethyl(ethyl)carbamoyl, difluoromethyl(n-propyl)carbamoyl, difluoromethyl(i-propyl)carbamoyl, difluoromethyl(n-butyl))carbamoyl, difluoromethyl(sec-butyl)carbamoyl, difluoromethyl(t-butyl)carbamoyl, difluoromethyl(trifluoromethyl)carbamoyl, hydroxymethyl(methyl)carbamoyl, ethyl(hydroxymethyl)carbamoyl, hydroxymethyl(n-propyl)carbamoyl, hydroxymethyl(i-propyl)carbamoyl, n-butyl(hydroxymethyl)carbamoyl, sec-butyl(hydroxymethyl)carbamoyl, t-butyl(hydroxymethyl)carbamoyl, difluoromethyl(hydroxymethyl)carbamoyl, hydroxymethyl(trifluoromethyl)carbamoyl, hydroxyethyl(methyl)carbamoyl, ethyl(hydroxyethyl)carbamoyl, hydroxyethyl(n-propyl)carbamoyl, hydroxyethyl(i-propyl)carbamoyl, n-butyl(hydroxyethyl)carbamoyl, sec-butyl(hydroxyethyl)carbamoyl, t-butyl(hydroxyethyl)carbamoyl, difluoromethyl(hydroxyethyl)carbamoyl, hydroxyethyl(trifluoromethyl)carbamoyl, hydroxypropyl(methyl)carbamoyl, ethyl(hydroxypropyl)carbamoyl, hydroxypropyl(n-propyl)carbamoyl, hydroxypropyl(i-propyl)carbamoyl, n-butyl(hydroxypropyl)carbamoyl, sec-butyl(hydroxypropyl)carbamoyl, t-butyl(hydroxypropyl)carbamoyl, difluoromethyl(hydroxypropyl)carbamoyl, hydroxypropyl(trifluoromethyl)carbamoyl.

As used herein, the term alkylsulfinyl embraces radicals containing an optionally substituted, linear or branched alkyl radicals of 1 to 10 carbon atoms attached to a divalent —SO— radical. More preferred alkylsulfinyl radicals are "lower alklsulfinyl" radicals having 1 to 8, preferably 1 to 6 and more preferably 1 to 4 carbon atoms.

An alkylsulfinyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a alkylsulfinyl group are themselves unsubstituted.

Preferred optionally substituted alkylsulphinyl radicals include methylsulphinyl, ethylsulphinyl, n-propylsulphinyl, i-propylsulphinyl, n-butylsulphinyl; sec-butylsulphinyl, t-butylsulphinyl, trifluoromethylsulphinyl, difluoromethylsulphinyl, hydroxymethylsulphinyl, 2-hydroxyethylsulphinyl and 2-hydroxypropylsulphinyl.

As used herein, the term alkylsulfonyl embraces radicals containing an optionally substituted, linear or branched alkyl radicals of 1 to 10 carbon atoms attached to a divalent —SO$_2$— radical. More preferred alkylsulfonyl radicals are "lower alkylsulfonyl" radicals having 1 to 8, preferably 1 to 6 and more preferably 1 to 4 carbon atoms.

An alkylsulfonyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a monoalkylaminosulfonyl group are themselves unsubstituted.

As used herein, the term monoalkylaminosulfonyl embraces radicals containing an optionally substituted, linear or branched alkyl radicals of 1 to 10 carbon atoms and attached to the nitrogen of a —NHSO$_2$— radical. More preferred monoalkylaminosulfonyl radicals are "lower monoalkylaminosulfonyl" radicals having 1 to 8, preferably 1 to 6 and more preferably 1 to 4 carbon atoms.

A monoalkylaminosulfonyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a monoalkylaminosulfonyl group are themselves unsubstituted.

Preferred optionally substituted monoalkylaminosulphonyl radicals include methylaminosulphonyl, ethylaminosulphonyl, n-propylaminosulphonyl, i-propylaminosulphonyl; n-butylaminosulphonyl, sec-butylaminosulphonyl, t-butylaminosulphonyl, trifluoromethylaminosulphonyl, difluoromethylaminosulphonyl, hydroxymethylaminosulphonyl, 2-hydroxyethylaminosulphonyl and 2-hydroxypropylaminosulphonyl.

As used herein, the term dialkylaminosulfonyl embraces radicals containing a radical NSO$_2$— where the nitrogen is attached to two optionally substituted, linear or branched alkyl radicals of 1 to 10 carbon atoms. More preferred dialkylaminosulfonyl radicals are "lower dialkylaminosulfonyl" radicals having 1 to 8, preferably 1 to 6 and more preferably to 4 carbon atoms in each alkyl radical.

A dialkylaminosulfonyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a dialkylaminosulphonyl group are themselves unsubstituted.

Preferred optionally substituted dialkylaminosulphonyl radicals include dimethylaminosulphonyl, diethylaminosulphonyl, methyl(ethyl)aminosulphonyl, di(n-propyl)aminosulphonyl, n-propyl(methyl)aminosulphonyl, n-propyl(ethyl)aminosulphonyl, di(i-propyl)aminosulphonyl, i-propyl(methyl)aminosulphonyl, i-propyl(ethyl)aminosulphonyl, di(n-butyl)aminosulphonyl, n-butyl(methyl)aminosulphonyl; n-butyl(ethyl)aminosulphonyl, n-butyl(i-propyl)aminosulphonyl, di(sec-butyl)aminosulphonyl, sec-butyl(methyl)aminosulphonyl, sec-butyl(ethyl)aminosulphonyl, sec-butyl(n-propyl)aminosulphonyl, sec-butyl(i-propyl)aminosulphonyl, di(t-butyl)aminosulphonyl, t-butyl(methyl)aminosulphonyl, t-butyl(ethyl)aminosulphonyl, t-butyl(n-propyl)aminosulphonyl, t-butyl(i-propyl)aminosulphonyl, trifluoromethyl(methyl)aminosulphonyl, trifluoromethyl(ethyl)aminosulphonyl, trifluoromethyl(n-propyl)aminosulphonyl, trifluoromethyl(i-propyl)aminosulphonyl, trifluoromethyl(n-butyl)aminosulphonyl, trifluoromethyl(sec-butyl)aminosulphonyl, difluoromethyl(methyl)aminosulphonyl, difluoromethyl(ethyl)aminosulphonyl, difluoromethyl(n-propyl)aminosulphonyl, difluoromethyl(i-propyl)aminosulphonyl difluoromethyl(n-butyl))aminosulphonyl, difluoromethyl(sec-butyl)aminosulphonyl, difluoromethyl(t-butyl)aminosulphonyl, difluoromethyl(trifluoromethyl)aminosulphonyl, hydroxymethyl(methyl)aminosulphonyl, ethyl(hydroxymethyl)aminosulphonyl, hydroxymethyl(n-propyl)aminosulphonyl, hydroxymethyl(i-propyl)aminosulphonyl, n-butyl(hydroxymethyl)aminosulphonyl, sec-butyl(hydroxymethyl)aminosulphonyl, t-butyl(hydroxymethyl)aminosulphonyl, difluoromethyl(hydroxymethyl)aminosulphonyl, hydroxymethyl(trifluoromethyl)aminosulphonyl, hydroxyethyl(methyl)aminosulphonyl, ethyl(hydroxyethyl)aminosulphonyl, hydroxyethyl(n-propyl)aminosulphonyl, hydroxyethyl(i-propyl)aminosulphonyl, n-butyl(hydroxyethyl)aminosulphonyl, sec-butyl(hydroxyethyl)aminosulphonyl; t-butyl(hydroxyethyl)aminosulphonyl, difluoromethyl(hydroxyethyl)aminosulphonyl, hydroxyethyl(trifluoromethyl)aminosulphonyl, hydroxypropyl(methyl)aminosulphonyl, ethyl(hydroxypropyl)aminosulphonyl, hydroxypropyl(n-propyl)aminosulphonyl, hydroxypropyl(i-propyl)aminosulphonyl, n-butyl(hydroxypropyl)aminosulphonyl, sec-butyl(hydroxypropyl)aminosulphonyl, t-butyl(hydroxypropyl)aminosulphonyl, difluoromethyl(hydroxypropyl)aminosulphonyl and hydroxypropyl(trifluoromethyl)aminosulphonyl.

As used herein, the term alkylsulfamoyl embraces radicals containing an optionally substituted, linear or branched alkyl radical of 1 to 10 carbon atoms and attached to the nitrogen of a —NSO$_2$— radical. More preferred alkylsulfamoyl radicals are "lower alkylsulfamoyl" radicals having 1 to 8, preferably 1 to 6 and more preferably 1 to 4 carbon atoms.

An alkylsulphamoyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkylsulphamoyl group are themselves unsubstituted.

Preferred optionally substituted alkylsulfamoyl radicals include methylsulphamoyl, ethylsulphamoyl, n-propylsulphamoyl, i-propylsulphamoyl, n-butylsulphamoyl, sec-butylsulphamoyl, t-butylsulphamoyl, trifluoromethylsulphamoyl, difluoromethylsulphamoyl, hydroxymethylsulphamoyl, 2-hydroxyethylsulphamoyl and 2-hydroxypropylsulphamoyl.

As used herein, the term alkylsulphamido embraces radicals containing an optionally substituted, linear or branched alkyl radicals of 1 to 10 carbon atoms and attached to one of the nitrogen atoms of a —NHSO$_2$NH— radical. More preferred alkylsulphamido radicals are "lower alkylsulphamido" radicals having 1 to 8, preferably 1 to 6 and more preferably 1 to 4 carbon atoms.

An alkylsulphamido group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkylsulphamido group are themselves unsubstituted.

Preferred optionally substituted alkylsulphamido radicals include methylsulphamido, ethylsulphamido, n-propylsulphamido, i-propylsulphamido, n-butylsulphamido, sec-butylsulphamido, t-butylsulphamido, trifluoromethylsulphamido, difluoromethylsulphamido, hydroxymethylsulphamido, 2-hydroxyethylsulphamido and 2-hydroxysulphamido.

As used herein, the term N'-alkylureido embraces radicals containing an optionally substituted, linear or branched alkyl radical of 1 to 10 carbon atoms attached to the terminal nitrogen of a —NHCONH— radical. More preferred N'-alkylureido radicals are "lower N'-alkylureido" radicals in which the alkyl moiety has 1 to 8, preferably 1 to 6 and more preferably 1 to 4 carbon atoms.

An N'-alkylureido group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an N'-alkylureido group are themselves unsubstituted.

Preferred optionally substituted N'-alkylureido radicals include N'-methylureido, N'-ethylureido, N'-n-propylureido, N'-i-propylureido, N'-n-butylureido, N'-sec-butylureido, N'-t-butylureido, N'-trifluoromethylureido, N'-difluoromethylureido, N'-hydroxymethylureido, N'-2-hydroxyethylureido and N'-2-hydroxypropylureido.

As used herein, the term N',N'-dialkylureido embraces radicals containing a radical —NHCON where the terminal nitrogen is attached to two optionally substituted, linear or branched alkyl radicals of 1 to 10 carbon atoms. More preferred N',N'-dialkylureido radicals are "lower N',N'-dialkylureido" radicals-having 1 to 8, preferably 1 to 6 and more preferably 1 to 4 carbon atoms in each alkyl radical.

A N',N'-dialkylureido group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an N',N'-dialkylureido group are themselves unsubstituted.

Preferred optionally substituted N',N'-dialkylureido radicals include N',N'-dimethylureido, N',N'-diethylureido, N'-methyl, N'-ethylureido, N',N'-di(n-propyl)ureido, N'-n-propyl, N'-methylureido, N'-n-propyl, N'-ethylureido, N',N'-di(i-propyl)ureido, N'-i-propyl, N'-methylureido, N'-1-propyl, N'-ethylureido, N',N'-di(n-butyl)ureido, N'-n-butyl, N'-methylureido, N'-n-butyl, N'-ethylureido, N'-n-butyl, N'-(i-propyl)ureido, N',N'-di(sec-butyl)ureido, N'-sec-butyl, N'-methylureido, N'-sec-butyl, N'-ethylureido, N'-sec-butyl, N'-(n-propyl)ureido, N'-sec-butyl, N'(i-propyl)ureido, N',N'di(t-butyl)ureido, N'-t-butyl, N'-methylureido, N'-t-butyl, N'-ethylureido, N'-t-butyl, N'-(n-propyl)ureido, N'-t-butyl, N'-(i-propyl)ureido, N'-trifluoromethyl, N'-methylureido, N'-trifluoromethyl, N'-ethylureido, N'-trifluoromethyl, N'-(n-propyl)ureido, N'-trifluoromethyl, N'-(i-propyl)ureido, N'-trifluoromethyl, N'-(n-butyl)ureido, N'-trifluoromethyl, N'-(sec-butyl)ureido, N'-difluoromethyl, N'-methylureido, N'-difluoromethyl, N'-ethylureido, N'-difluoromethyl, N'(n-propyl)ureido, N'-difluoromethyl, N'-(i-propyl)ureido, N'-difluoromethyl, N'-(n-butyl)ureido, N'-difluoromethyl, N'-(sec-butyl)ureido, N-difluoromethyl, N'-(t-butyl)ureido, N'-difluoromethyl, N'-trifluoromethylureido, N'-hydroxymethyl, N'-methylureido, N'-ethyl, N'-hydroxymethylureido, N'-hydroxymethyl, N'-(n-propyl)ureido, N'-hydroxymethyl, N'-(i-propyl)ureido, N'-n-butyl, N'-hydroxymethylureido, N'-sec-butyl, N'-hydroxymethylureido, N'-t-butyl, N'-hydroxymethylureido, N'-difluoromethyl, N'-hydroxymethylureido, N'-hydroxymethyl, N'-trifluoromethylureido, N'-hydroxyethyl, N'-methylureido, N'-ethyl, N'-hydroxyethylureido, N'-hydroxyethyl, N'-(n-propyl)ureido, N'-hydroxyethyl, N'-(i-propyl)ureido, N'-(n-butyl), N'-hydroxyethylureido, N'(sec-butyl), N'-hydroxyethylureido, N'-(t-butyl), N'-hydroxyethylureido, N'-difluoromethyl, N'-hydroxyethylureido, N'-hydroxyethyl, N'-trifluoromethylureido, N'-hydroxypropyl, N'-methylureido, N'-ethyl, N'-hydroxypropylureido, N'-hydroxypropyl, N'-(n-propyl)ureido, N'-hydroxypropyl, N'-(i-propyl)ureido, N'-(n-butyl), N'-hydroxypropylureido, N'(sec-butyl), N'-hydroxypropylureido, N'(t-butyl), N'-hydroxypropylureido, N'-difluoromethyl, N'-hydroxypropylureido y N'-hydroxypropyl, N'-trifluoromethylureido.

As used herein, the term acyl embraces optionally substituted, linear or branched radicals having 2 to 20 carbon atoms or, preferably 2 to 12 carbon atoms attached to a carbonyl radical. More preferably acyl radicals are "lower acyl" radicals of formula—COR, wherein R is a hydrocarbon group, preferably an alkyl group, having 2 to 8, preferably 2 to 6 and more preferably 2 to 4 carbon atoms.

An acyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an acyl group are themselves unsubstituted.

Preferred optionally substituted acyl radicals include acetyl, propionyl, butiryl, isobutiryl, isovaleryl, pivaloyil, valeryl, lauryl, myristyl, stearyl and palmityl, As used herein, the term aryl radical embraces typically a $C_5$-$C_{14}$ monocyclic or polycyclic aryl radical such as phenyl, naphthyl, anthranyl and phenanthryl. Phenyl is preferred.

A said optionally substituted aryl radical is typically unsubstituted or substituted with 1, 2 or 3 substituents which may be the same or different. The substituents are preferably selected from halogen atoms, preferably fluorine atoms, hydroxy groups, alkoxycarbonyl groups in which the alkyl moiety has from 1 to 4 carbon atoms, hydroxycarbonyl groups, carbamoyl groups, nitro groups, cyano groups, $C_1$-$C_4$ alkyl groups, $C_1$-$C_4$ alkoxy groups and $C_1$-$C_4$ hydroxyalkyl groups. When an aryl radical carries 2 or more substituents, the substituents may be the same or different. Unless otherwise specified, the substituents on an aryl group are typically themselves unsubstituted.

As used herein, the term heteroaryl radical embraces typically a 5- to 14-membered ring system, preferably a 5- to 10-membered ring system, comprising at least one heteroaromatic ring and containing at least one heteroatom selected from O, S and N. A heteroaryl radical may be a single ring or two or more fused rings wherein at least one ring contains a heteroatom.

A said optionally substituted heteroaryl radical is typically unsubstituted or substituted with 1, 2 or 3 substituents which may be the same or different. The substituents are preferably selected from halogen atoms, preferably fluorine, chlorine or bromine atoms, alkoxycarbonyl groups in which the alkyl moiety has from 1 to 4 carbon atoms, nitro groups, hydroxy groups, $C_1$-$C_4$ alkyl groups and $C_1$-$C_4$ alkoxy groups. When an heteroaryl radical carries 2 or more substituents, the substituents may be the same or different. Unless otherwise specified, the substituents on a heteroaryl radical are typically themselves unsubstituted.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidnyl and the various pyrrolopyridyl radicals.

The mention of optionally substituted heteroaryl radicals or rests within the present invention is intended to cover the N-oxides obtainable from these radicals when they comprise N-atoms.

Oxadiazolyl, oxazolyl, pyridyl, pyrrolyl, imidazolyl, thiazolyl, thiadiazolyl, thienyl, furanyl, quinolinyl, isoquinolinyl, indolyl, benzoxazolyl, naphthyridinyl, benzofuranyl, pyrazinyl, pyrimidinyl and the various pyrrolopyridyl radicals are preferred.

As used herein, the term cycloalkyl embraces saturated carbocyclic radicals and, unless otherwise specified, a cycloalkyl radical typically has from 3 to 7 carbon atoms.

A cycloalkyl radical is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. When a cycloalkyl radical carries 2 or more substituents, the substituents may be the same or different. Typically the substituents on a cycloalkyl group are themselves unsubstituted.

Examples include cyclopropyl, cyclobutyl, cyclopentyl, cyclohexyl and cycloheptyl. It is preferably cyclopropyl, cyclopentyl and cyclohexyl.

As used herein, the term cycloalkenyl embraces partially unsaturated carbocyclic radicals and, unless otherwise specified, a cycloalkenyl radical typically has from 3 to 7 carbon atoms.

A cycloalkenyl radical is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. When a cycloalkenyl radical carries 2 or more substituents, the substituents may be the same or different. Typically, the substituents on a cycloalkenyl group are themselves unsubstituted.

Examples include cyclobutenyl, cyclopentenyl, cyclohexenyl and cycloheptenyl. Cyclopentenyl and cyclohexenyl are preferred.

As used herein, the term heterocyclyl radical embraces typically a non-aromatic, saturated or unsaturated $C_3$-$C_{10}$ carbocyclic ring, such as a 5, 6 or 7 membered radical, in which one or more, for example 1, 2, 3 or 4 of the carbon atoms preferably 1 or 2 of the carbon atoms are replaced by a heteroatom selected from N, O and S. Saturated heterocyclyl radicals are preferred. A heterocyclic radical may be a single ring or two or more fused rings wherein at least one ring contains a heteroatom. When a heterocyclyl radical carries 2 or more substituents, the substituents may be the same or different.

A said optionally substituted heterocyclyl radical is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a heterocyclyl radical are themselves unsubstituted.

Examples of heterocyclic, radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, cromanyl, isocromanyl, imidazolidinyl, imidazolyl, oxiranyl, azaridinyl, 4,5-dihydro-oxazolyl and 3-aza-tetrahydrofuranyl.

Where a heterocyclyl radical carries 2 or more substituents, the substituents may be the same or different.

As used herein, some of the atoms, radicals, moieties, chains and cycles present in the general structures of the invention are "optionally substituted". This means that these atoms, radicals, moieties, chains and cycles can be either unsubstituted or substituted in any position by one or more, for example 1, 2, 3 or 4, substituents, whereby the hydrogen atoms bound to the unsubstituted atoms, radicals, moieties, chains and cycles are replaced by chemically acceptable atoms, radicals, moieties, chains and cycles. When two or more substituents are present, each substituent may be the same or different. The substituents are typically themselves unsubstituted.

Typically when a cyclic radical is bridged by an alkylene or alkylenedioxy radical, the bridging alkylene radical is attached to the ring at non-adjacent atoms.

As used herein, the term halogen atom embraces chlorine, fluorine, bromine and iodine atoms. A halogen atom is typically a fluorine, chlorine or bromine atom, most preferably chlorine or fluorine. The term halo when used as a prefix has the same meaning.

As used herein, an acylamino group is typically a said acyl group attached to an amino group.

As used herein an alkylenedioxy group is typically —O—R—O—, wherein R is a said alkylene group.

As used herein, an alkoxyacyl group is typically a said alkoxy group attached to a said acyl group.

As used herein, an acyloxy group is typically a said acyl group attached to an oxygen atom.

As used herein, a cycloalkoxy group is typically a said cycloalkyl group attached to an oxygen atom.

Compounds containing one or more chiral centre may be used in enantiomerically or diastereoisomerically pure form, or in the form of a mixture of isomers.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

According to one embodiment of the present invention in the compounds of formula (I) $R^2$ represents a hydrogen atom or an aryl group, for example a phenyl group, which is optionally substituted by one or more, for example 1, 2, 3 or 4, substituents selected from halogen atoms and nitro, $C_1$-$C_4$ alkoxy, $C_1$-$C_4$ hydroxyalkyl and —$CO_2$—($C_1$-$C_4$ alkyl) groups. More preferably, $R^2$ is a hydrogen-atom or a phenyl group which is unsubstitued or substituted with 1 or 2 unsubstituted substituents selected from fluorine, chlorine, nitro, $C_1$-$C_4$ hydroxyalkyl and —$CO_2$—($C_1$-$C_2$ alkyl) substituents. Most preferably $R^2$ is hydrogen.

In another embodiment of the present invention in the compounds of formula (I) $R^1$ represents a group selected from:

a ($C_{1-4}$) alkyl group which is optionally substituted by one or more, for example 1, 2, 3 or 4 hydroxy groups;

a group of formula

—$(CH_2)_n$—$R^6$ wherein n is an integer from 1 to 3 and $R^6$ represents a ($C_{3-6}$) cycloalkyl group.

More preferably, $R^1$ is an unsubstituted $C_1$-$C_4$ alkyl, an unsubstituted $C_1$-$C_4$ hydroxyalkyl or an unsubstituted cyclopropyl-($C_1$-$C_4$ alkyl)-group.

In still another embodiment of the present invention the compounds of formula (I) $R^3$ represents a group selected from monocyclic or polycyclic aryl or heteroaryl groups, which are optionally substituted by one or more, for example 1, 2, 3 or 4, substituents selected from:
halogen atoms;
($C_1$-$C_4$) alkyl groups, which are optionally substituted by one or more, for example 1, 2, 3 or 4 hydroxy groups;
and ($C_1$-$C_4$) alkoxy, nitro, hydroxy, hydroxycarbonyl, carbamoyl, ($C_1$-$C_4$ alkoxy)-carbonyl and cyano groups In another embodiment of the present invention in the compounds of formula (I), $R^3$ represents a monocyclic or polycyclic aryl or heteroaryl group, which is optionally substituted by one or more, for example 1, 2, 3 or 4, substituents selected from:
halogen atoms;
alkyl and alkylene groups, which are optionally substituted by one or more, for example 1, 2, 3 or 4, substituents selected from halogen atoms; and
phenyl, hydroxy, hydroxycarbonyl, hydroxyalkyl, alkoxycarbonyl, alkoxy, cycloalkoxy, nitro, aryloxy, alkylthio, alkylsulphinyl, alkylsulphonyl, alkylsulphamoyl, acyl, amino, mono- or di-alkylamino, acylamino hydroxycarbonyl, alkoxycarbonyl, carbamoyl, mono- or di-alkylcarbamoyl, ureido, N'-alkylureido, N',N'-dialkylureido, alkylsulphamido, aminosulphonyl, mono- or di-alkylaminosulphonyl, cyano, difluoromethoxy or trifluoromethoxy groups;

More preferably, $R^3$ represents a phenyl group, a naphthyl group or a 5- to 14-membered monocylic or polycyclic heteroaryl group containing 1, 2 or 3 heteroatoms selected from N, O and S, the phenyl, naphthyl and heteroaryl groups being unsubstituted or substituted with 1 or 2 unsubstituted substituents selected from:
halogen atoms, for example fluorine and chlorine atoms;
$C_1$-$C_4$ alkyl and $C_1$-$C_4$ hydroxyalkyl groups; and
$C_1$-$C_4$ alkoxy, nitro, hydroxy, hydroxycarbonyl, carbamoyl, ($C_1$-$C_4$ alkoxy)-carbonyl and cyano groups.

Still more preferably $R^3$ represents a phenyl group, a naphtyl group or a substituted or unsubstituted heteroaryl group selected from substituted or unsubstituted oxadiazolyl, oxazolyl, pyridyl, pyrrolyl, imidazolyl, thiazolyl, thiadiaz-olyl, thienyl, furanyl, quinolinyl, isoquinolinyl, indolyl, benzoxazolyl, naphthyridinyl, benzofuranyl, pyrazinyl, pyrimidinyl and the various pyrrolopyridyl radicals.

In another embodiment of the present invention in the compounds of formula (I) $R^4$ represents
an unsubstituted mono-($C_1$-$C_4$ alkyl)amino or di-($C_1$-$C_4$ alkyl)amino group;
a $C_1$-$C_4$ alkyl group which is unsubstituted or substituted by one or more, for example 1 or 2, substituents selected from hydroxy, $C_1$-$C_4$ alkoxy, amino, mono-($C_1$-$C_4$ alkyl)amino and di-($C_1$-$C_4$ alkyl)amino groups;
an unsubstituted phenyl-($C_1$-$C_4$ alkyl)-group; or
a group of formula —($CH_2$)$_n$—$R^6$ wherein n is 2 and $R^6$ represents a radical selected from phenyl, pyridyl and thienyl optionally substituted by one or more substituents selected from halogen atoms and alkyl, hydroxy, alkoxy, alkylenedioxy, amino, mono- or di-alkylamino, nitro, ciano and trifluoromethyl groups.

More preferably, $R^4$ represents an alkyl group having from 1 to 6 carbon atoms and which is unsubstituted or substituted by one or more, for example 1, 2, 3 or 4, substituents selected from halogen atoms and hydroxy groups.

In yet another embodiment of the present invention in the compounds of formula (I) $R^5$ represents a group COOR$^7$ or a monocyclic or polycyclic aryl or heteroaryl group, which is optionally substituted by one or more substituents selected from halogen atoms, $C_1$-$C_4$ alkyl groups, $C_1$-$C_4$ alkoxycarbonyl groups, a hydroxycarbonyl group and $C_1$-$C_4$ alkoxy groups, wherein $R^7$ is as defined above.

In another preferred embodiment of the present invention in the compounds of formula (I) $R^5$ represents a group —COOR$^7$ or a monocyclic or polycyclic aryl or heteroaryl group, which is optionally substituted by one or more, for example 1, 2, 3 or 4, substituents selected from halogen atoms and $C_1$-$C_4$ alkoxy groups, wherein $R^7$ has the meaning defined above.

More preferably, $R^5$ represents —$CO_2R^7$, wherein $R^7$ represents an unsubstituted $C_1$-$C_4$ alkyl group, or $R_5$ represents a phenyl group or a 5- to 10-membered monocyclic or polycyclic heteroaryl group containing 1 or 2 heteroatoms selected from N, O and S, the phenyl and heteroaryl groups being unsubstituted or substituted by 1 or 2 substituents selected from $C_1$-$C_4$ alkoxy groups and halogen atoms, for example chlorine and fluorine atoms.

Still more preferably $R^5$ represents a phenyl group, or a substituted or unsubstituted heteroaryl group selected from substituted or unsubstituted oxadiazolyl, oxazolyl, pyridyl, pyrrolyl, imidazolyl, thiazolyl, thiadiazolyl, thienyl, furanyl, quinolinyl, isoquinolinyl, indolyl, benzoxazolyl, naphthyridinyl, benzofuranyl, pyrazinyl, pyrimidinyl and the various pyrrolopyridyl radicals.

Finally in another embodiment of the present invention, when $R^5$ represents a polycyclic heteroaryl group it is typically a group of formula (XXIII):

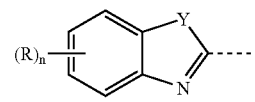

(XXIII)

wherein Y represents an O atom, a S atom or a —NH— group, n is 0, 1 or 2 and each R is the same or different and is a halogen atom or a $C_1$-$C_4$ alkoxy group.

Particular individual compounds of the invention include:
5-acetyl-2-ethyl-4-[(3-fluorophenyl)amino]-6-pyridin-3-ylpyridazin-3(2H)-one
5-acetyl-4-[(3-chlorophenyl)amino]-2-ethyl-6-pyridin-3-ylpyridazin-3(2H)-one
5-acetyl-4-[(3,5-dichlorophenyl)amino]-2-ethyl-6-pyridin-3-ylpyridazin-3(2H)-one
5-acetyl-2-ethyl-4-(1-naphthylamino)-6-pyridin-3-ylpyridazin-3(2H)-one
methyl 4-[(5-acetyl-2-ethyl-3-oxo-6-pyridin-3-yl-2,3-dihydropyridazin-4-yl)amino]benzoate
5-acetyl-2-ethyl-4-[(2-fluorophenyl)amino]-6-pyridin-3-ylpyridazin-3(2H)-one
5-acetyl-4-[(2-chlorophenyl)amino]-2-ethyl-6-pyridin-3-ylpyridazin-3(2H)-one
5-acetyl-2-ethyl-4-{[4-(hydroxymethyl)phenyl]amino}-6-pyridin-3-ylpyridazin-3(2H)-one 3-[(5-acetyl-2-ethyl-3-oxo-6-pyridin-3-yl-2,3-dihydropyridazin-4-yl)amino]benzonitrile 5-acetyl-4-[(3-chlorophenyl)amino]-2-(cyclopropylmethyl)-6-pyridin-3-ylpyridazin-3(2H)-one 5-acetyl-2-(cyclopropylmethyl)-4-[(3,5-dichlorophenyl)amino]-6-pyridin-3-ylpyridazin-3(2H)-one 5-acetyl-2-(cyclopropylmethyl)-4-[(2-fluorophenyl)amino]-6-pyridin-3-ylpyridazin-3(2H)-one 5-acetyl-4-[(2-chlorophenyl)amino]-2-(cyclopropylmethyl)-6-pyridin-3-ylpyridazin-3(2H)-one 3-{[5-acetyl-2-(cyclopropylmethyl)-3-oxo-6-pyridin-3-yl-2,3-dihydropyridazin-4-yl]amino}benzonitrile methyl 4-{[5-acetyl-2-(2-hydroxyethyl)-3-oxo-6-pyridin-3-yl-2,3-dihydropyridazin-4-yl]amino}benzoate 5-acetyl-4-[(2-fluorophenyl)amino]-2-(2-hydroxyethyl)-6-pyridin-3-ylpyridazin-3(2H)-one 5-acetyl-4-[(2-chlorophenyl)amino]-2-(2-hydroxyethyl)-6-pyridin-3-ylpyridazin-3(2H)-one 5-acetyl-4-[(3-chlorophenyl)amino]-2-(2-hydroxyethyl)-6-pyridin-3-ylpyridazin-3(2H)-one 5-acetyl-4-[(3-chlorophenyl)amino]-2-ethyl-6-pyridin-2-ylpyridazin-3(2H)-one 3-[(5-acetyl-2-ethyl-3-oxo-6-pyridin-2-yl-2,3-dihydropyridazin-4-yl)amino]benzonitrile 5-acetyl-2-ethyl-4-{[4-(hydroxymethyl)phenyl]amino}-6-pyridin-2-ylpyridazin-3(2H)-one 3-{[5-acetyl-2-(cyclopropylmethyl)-3-oxo-6-pyridin-2-yl-2,3-dihydropyridazin-4-yl]amino}benzonitrile 5-acetyl-4-[(3-chlorophenyl)amino]-2-(cyclopropylmethyl)-6-pyridin-2-ylpyridazin-3(2H)-one 5-acetyl-2-(cyclopropylmethyl)-4-{[4-(hydroxymethyl)phenyl]amino}-6-pyridin-2-ylpyridazin-3(2H)-one 5-acetyl-2-(cyclopropylmethyl)-4-[(3,5-dichlorophenyl)amino]-6-pyridin-2-ylpyridazin-3(2H)-one 3-{[5-acetyl-2-(2-hydroxyethyl)-3-oxo-6-pyridin-2-yl-2,3-dihydropyridazin-4-yl]amino}benzonitrile 5-acetyl-4-[(3-chlorophenyl)amino]-2-(2-hydroxyethyl)-6-pyridin-2-ylpyridazin-3(2H)-one 5-acetyl-4-[(3,5-dichlorophenyl)amino]-2-(2-hydroxyethyl)-6-pyridin-2-ylpyridazin-3(2H)-one 5-acetyl-2-(2-hydroxyethyl)-4-{[4-(hydroxymethyl)phenyl]amino}-6-pyridin-2-ylpyridazin-3(2H)-one 5-acetyl-2-ethyl-4-[(3-fluorophenyl)amino]-6-pyridin-4-ylpyridazin-3(2H)-one 5-acetyl-4-[(3-chlorophenyl)amino]-2-ethyl-6-pyridin-4-ylpyridazin-3(2H)-one 5-acetyl-2-ethyl-4-(1-naphthylamino)-6-pyridin-4-ylpyridazin-3(2H)-one 5-acetyl-2-ethyl-4-[(2-methylphenyl)amino]-6-pyridin-4-ylpyridazin-3(2H)-one methyl 4-[(5-acetyl-2-ethyl-3-oxo-6-pyridin-4-yl-2,3-dihydropyridazin-4-yl)amino]benzoate 5-acetyl-2-ethyl-4-[(2-methoxyphenyl)amino]-6-pyridin-4-ylpyridazin-3(2H)-one 5-acetyl-2-ethyl-4-[(3-methoxyphenyl)amino]-6-pyridin-4-ylpyridazin-3(2H)-one 5-acetyl-2-ethyl-4-[(2-fluorophenyl)amino]-6-pyridin-4-ylpyridazin-3(2H)-one 5-acetyl-4-[(2-chlorophenyl)amino]-2-ethyl-6-pyridin-4-ylpyridazin-3(2H)-one 3-[(5-acetyl-2-ethyl-3-oxo-6-pyridin-4-yl-2,3-dihydropyridazin-4-yl)amino]benzonitrile 5-acetyl-2-ethyl-4-{[4-(hydroxymethyl)phenyl]amino}-6-pyridin-4-ylpyridazin-3(2H)-one 4-[(5-acetyl-2-ethyl-3-oxo-6-pyridin-4-yl-2,3-dihydropyridazin-4-yl)amino]benzoic acid 5-acetyl-2-(cyclopropylmethyl)-4-[(2-fluorophenyl)amino]-6-pyridin-4-ylpyridazin-3(2H)-one 5-acetyl-4-[(2-chlorophenyl)amino]-2-(cyclopropylmethyl)-6-pyridin-4-ylpyridazin-3(2H)-one 3-{[5-acetyl-2-(cyclopropylmethyl)-3-oxo-6-pyridin-4-yl-2,3-dihydropyridazin-4-yl]amino}benzonitrile 5-acetyl-2-(cyclopropylmethyl)-4-{[4-(hydroxymethyl)phenyl]amino}-6-pyridin-4-ylpyridazin-3(2H)-one 5-acetyl-4-[(3-chlorophenyl)amino]-2-(cyclopropylmethyl)-6-pyridin-4-ylpyridazin-3(2H)-one 5-acetyl-4-[(2-fluorophenyl)amino]-2-(2-hydroxyethyl)-6-pyridin-4-ylpyridazin-3(2H)-one 5-acetyl-4-[(2-chlorophenyl)amino]-2-(2-hydroxyethyl)-6-pyridin-4-ylpyridazin-3(2H)-one 3-{[5-acetyl-2-(2-hydroxyethyl)-3-oxo-6-pyridin-4-yl-2,3-dihydropyridazin-4-yl]amino}benzonitrile 5-acetyl-2-(2-hydroxyethyl)-4-{[4-(hydroxymethyl)phenyl]amino}-6-pyridin-4-ylpyridazin-3(2H)-one 5-acetyl-4-[(3-chlorophenyl)amino]-2-(2-hydroxyethyl)-6-pyridin-ylpyridazin-3(2H)-one 5-acetyl-4-[(3-chlorophenyl)amino]-2-ethyl-6-thien-2-ylpyridazin-3(2H)-one 5-acetyl-4-[bis(3-fluorophenyl)amino]-2-ethyl-6-pyridin-3-ylpyridazin-3(2H)-one 5-acetyl-4-[bis-(4-methoxycarbonylphenyl)-amino]-2 ethyl-6-pyridin-3-ylpyridazin-3(2H)-one 5-acetyl-4-{bis[4-(hydroxymethyl)phenyl]amino}-2-ethyl-6-pyridin-3-ylpyridazin-3(2H)-one 5-acetyl-4-[bis(3-nitrophenyl)amino]-2-ethyl-6-pyridin-4-ylpyridazin-3(2H)-one 5-acetyl-4-[bis(3-fluorophenyl)amino]-2-ethyl-6-pyridin-4-ylpyridazin-3(2H)-one 5-acetyl-4-[bis(3-chlorophenyl)amino]-2-(cyclopropylmethyl)-6-pyridin-3-ylpyridazin-3(2H)-one 5-acetyl-4-[bis(3,5-dichlorophenyl)amino]-2-(cyclopropylmethyl)-6-pyridin-3-ylpyridazin-3(2H)-one 5-acetyl-4-[bis(4-methoxycarbonylphenyl)amino]-2-(2-hydroxyethyl)-6-pyridin-3-ylpyridazin-3(2H)-one 5-acetyl-4-[bis(3-chlorophenyl)amino]-2-(2-hydroxyethyl)-6-pyridin-2-ylpyridazin-3(2H)-one 5-acetyl-4-[bis(3-chlorophenyl)amino]-2-(cyclopropylmethyl)-6-pyridin-4-ylpyridazin-3(2H)-one 5-acetyl-2-ethyl-6-phenyl-4-(pyridin-3-ylamino)pyridazin-3(2H)-one 5-acetyl-4-[(3,5-dichloropyridin-4-yl)amino]-2-ethyl-6-phenylpyridazin-3(2H)-one 5-acetyl-2-ethyl-6-phenyl-4-(pyrazin-2-ylamino)pyridazin-3(2H)-one 5-acetyl-2-ethyl-6-phenyl-4-(pyrimidin-2-ylamino)pyridazin-3(2H)-one 5-acetyl-2-ethyl-6-phenyl-4-(quinolin-8-ylamino)pyridazin-3(2H)-one 5-acetyl-2-ethyl-4-[(5-nitropyridin-2-yl)amino]-6-phenylpyridazin-3(2H)-one 5-acetyl-2-ethyl-4-(1h-indol-4-ylamino)-6-phenylpyridazin-3(2H)-one 5-acetyl-4-(1,3-benzothiazol-6-ylamino)-2-ethyl-6-phenylpyridazin-3(2H)-one 5-acetyl-2-ethyl-6-phenyl-4-(thianthren-1-ylamino)pyridazin-3(2H)-one methyl 3-[(5-acetyl-2-ethyl-3-oxo-6-phenyl-2,3-dihydropyridazin-4-yl)amino]thiophene-2-carboxylate 5-acetyl-2-ethyl-4-[(4-methylpyridin-2-yl)amino]-6-phenylpyridazin-3(2H)-one 5-acetyl-2-ethyl-6-phenyl-4-(1h-1,2,4-triazol-5-ylamino)pyridazin-3(2H)-one 5-acetyl-2-ethyl-4-[(6-methoxypyridin-3-yl)amino]-6-phenylpyridazin-3(2H)-one
5-acetyl-2-ethyl-4-(2H-indazol-5-ylamino)-6-phenylpyridazin-3(2H)-one
methyl 4-[(5-acetyl-2-ethyl-3-oxo-6-phenyl-2,3-dihydropyridazin-4-yl)amino]thiophene-3-carboxylate
5-acetyl-2-ethyl-6-phenyl-4-(pyridin-2-ylamino)pyridazin-3(2H)-one
3-[(5-acetyl-2-ethyl-3-oxo-6-phenyl-2,3-dihydropyridazin-4-yl)amino]thiophene-2-carboxylic acid
5-acetyl-2-ethyl-4-[(3-methylcinnolin-5-yl)amino]-6-phenylpyridazin-3(2H)-one
5-acetyl-2-ethyl-4[(2-methylquinolin-8-yl)amino]-6-phenylpyridazin-3(2H)-one
5-acetyl-2-ethyl-6-phenyl-4-(quinolin-5-ylamino)pyridazin-3(2H)-one
5-acetyl-2-ethyl-4-(1h-indol-5-ylamino)-6-phenylpyridazin-3(2H)-one
5-acetyl-2-ethyl-4-(isoquinolin-5-ylamino)-6-phenylpyridazin-3(2H)-one
5-acetyl-2-ethyl-4-[(6-methoxyquinolin-8-yl)amino]-6-phenylpyridazin-3(2H)-one
5-acetyl-4-[(5-bromoquinolin-8-yl)amino]-2-ethyl-6-phenylpyridazin-3(2H)-one
5-acetyl-2-ethyl-4-[(4-methylpyrimidin-2-yl)amino]-6-phenylpyridazin-3(2H)-one
5-acetyl-6-(3-chlorophenyl)-2-ethyl-4-(pyridin-3-ylamino)pyridazin-3(2H)-one
5-acetyl-6-(3-chlorophenyl)-2-(cyclopropylmethyl)-4-(pyridin-3-ylamino)pyridazin-3(2H)-one
5-acetyl-2-ethyl-6-(3-fluorophenyl)-4-(pyridin-3-ylamino)pyridazin-3(2H)-one
5-acetyl-6-(3-fluorophenyl)-2-isopropyl-4-(pyridin-3-ylamino)pyridazin-3(2H)-one
5-acetyl-2-(cyclopropylmethyl)-6-(3-fluorophenyl)-4-(pyridin-3-ylamino)pyridazin-3(2H)-one
5-acetyl-2-ethyl-6-(4-fluorophenyl)-4-(pyridin-3-ylamino)pyridazin-3(2H)-one
5-acetyl-6-(1h-benzimidazol-2-yl)-4-[(3-chlorophenyl)amino]-2-ethylpyridazin-3(2H)-one
5-acetyl-6-(1,3-benzoxazol-2-yl)-4-[(3-chlorophenyl)amino]-2-ethylpyridazin-3(2H)-one
5-acetyl-6-(1,3-benzoxazol-2-yl)-2-ethyl-4-[(3-fluorophenyl)amino]pyridazin-3(2H)one
5-acetyl-6-benzooxazol-2-yl-4-[bis-(3-chlorophenyl)-amino]-2-ethyl-pyridazin-3(2H)-one
5-acetyl-6-benzooxazol-2-yl-4-[bis-(3-fluorophenyl)-amino]-2-ethyl-pyridazin-3(2H)-one
3-[(5-acetyl-2-ethyl-3-oxo-6-pyridin-3-yl-2,3-dihydropyridazin-4-yl)amino]benzamide
5-acetyl-2-ethyl-4-(isoquinolin-1-ylamino)-6-phenylpyridazin-3(2H)-one
5-acetyl-4-[(2-butylquinazolin-4-yl)amino]-2-ethyl-6-phenylpyridazin-3(2H)-one
5-acetyl-4-(1,2-benzisothiazol-3-ylamino)-2-ethyl-6-phenylpyridazin-3(2H)-one
5-acetyl-2-ethyl-6-phenyl-4-ylaminopyridazin-3(2H)-one
5-acetyl-2-ethyl-4-[(2-hydroxy-7h-purin-6-yl)amino]-6-phenylpyridazin-3(2H)-one
5-acetyl-2-ethyl-6-phenyl-4-(quinazolin-4-ylamino)pyridazin-3(2H)-one
5-acetyl-4-[(4-chloro-1H-indazol-3-yl)amino]-2-ethyl-6-phenylpyridazin-3(2H)-one
5-acetyl-4-[(7-chloroquinolin-4-yl)amino]-2-ethyl-6-phenylpyridazin-3(2H)-one
5-acetyl-4-[(4,6-dichloropyrimidin-2-yl)amino]-2-ethyl-6-phenylpyridazin-3(2H)-one
5-acetyl-2-ethyl-4-[(6-hydroxy-2H-pyrazolo[3,4-d]pyrimidin-4-yl)amino]-6-phenylpyridazin-3(2H)-one
5-acetyl-2-ethyl-4-[(2-methylquinolin-4-yl)amino]-6-phenylpyridazin-3(2H)-one
5-acetyl-2-ethyl-4-(1H-imidazol-2-ylamino)-6-phenylpyridazin-3(2H)-one
5-acetyl-2-ethyl-6-phenyl-4-(quinolin-4-ylamino)pyridazin-3(2H)-one
5-acetyl-4-(cinnolin-4-ylamino)-2-ethyl-6-phenylpyridazin-3(2H)-one
5-acetyl-2-ethyl-6-phenyl-4-(1H-pyrazolo[3,4-d]pyrimidin-4-ylamino)pyridazin-3(2H)-one
5-acetyl-2-ethyl-6-phenyl-4-(thieno[2,3-d]pyrimidin-4-ylamino)pyridazin-3(2H)-one
5-acetyl-2-ethyl-4-(1H-indazol-6-ylamino)-6-phenylpyridazin-3(2H)-one
5-acetyl-4-[(3-chlorophenyl)amino]-2-ethyl-6-(2-methoxypyridin-4-yl)pyridazin-3(2H)-one
5-acetyl-2-ethyl-4-{[4-(hydroxymethyl)phenyl]amino}-6-(6-methoxypyridin-3-yl)pyridazin-3(2H)-one
5-acetyl-2-ethyl-4-[(3-methoxyphenyl)amino]-6-thien-3-ylpyridazin-3(2H)one
5-acetyl-6-(1-benzofuran-5-yl)-2-ethyl-4[(3-fluorophenyl)amino]pyridazin-3(2H)-one
1-ethyl-5-[(3-methoxyphenyl)amino]-n,n-dimethyl-6-oxo-3-pyridin-3-yl-1,6-dihydropyridazine-4-carboxamide
5-[(3-chlorophenyl)amino]-1-ethyl-n-methyl-6-oxo-3-pyridin-4-yl-1,6-dihydropyridazine-4-carboxamide
2-ethyl-4-[(3-fluorophenyl)amino]-5-glycoloyl-6-pyridin-4-ylpyridazin-3(2H)-one
2-ethyl-4-[(3-fluorophenyl)amino]-5-(methoxyacetyl)-6-pyridin-3-ylpyridazin-3(2H)-one
5-[(dimethylamino)acetyl]-2-ethyl-4-[(3-methoxyphenyl)amino]-6-pyridin-3-ylpyridazin-3(2H)-one
2-ethyl-4-[(3-fluorophenyl)amino]-5-[(methylamino)acetyl]-6-pyridin-4-ylpyridazin-3(2H)-one
3-{[2-ethyl-3-oxo-5-(3-phenylpropanoyl)-6-pyridin-4-yl-2,3-dihydropyridazin-4-yl]amino}benzamide
ethyl 4-acetyl-5-[(3-chlorophenyl)amino]-1-ethyl-6-oxo-1,6-dihydropyridazine-3-carboxylate
ethyl 4-acetyl-5-amino-1-ethyl-6-oxo-1,6-dihydropyridazine-3-carboxylate
5-acetyl-6-(1,3-benzoxazol-2-yl)-2-ethyl-4-{[4-(hydroxymethyl)phenyl]amino}pyridazin-3(2H)-one
5-acetyl-2-ethyl-4-(isoquinolin-4-ylamino)-6-phenylpyridazin-3(2H)-one
5-acetyl-2-ethyl-4-(1,6-naphthyridin-8-ylamino)-6-phenylpyridazin-3(2H)-one
5-acetyl-2-ethyl-4-[(5-methoxypyridin-3-yl)amino]-6-phenylpyridazin-3(2H)-one
5-acetyl-2-ethyl-6-pyridin-4-yl-4-(pyridin-3-ylamino)pyridazin-3(2H)-one
5-acetyl-2-ethyl-4-[(4-methylpyridin-3-yl)amino]-6-pyridin-4-ylpyridazin-3(2H)-one
5-acetyl-2-ethyl-4-(isoquinolin-4-ylamino)-6-pyridin-3-ylpyridazin-3(2H)-one
5-acetyl-2-ethyl-6-pyridin-3-yl-4-[(3,4,5-trifluorophenyl)amino]pyridazin-3(2H)-one
5-acetyl-2-ethyl-4-[(4-methylpyridin-3-yl)amino]-6-pyridin-3-ylpyridazin-3(2H)-one
5-acetyl-2-ethyl-4-(isoquinolin-4-ylamino)-6-pyridin-3-ylpyridazin-3(2H)-one
5-acetyl-2-ethyl-6-pyridin-3-yl-4-[(3,4,5-trifluorophenyl)amino]pyridazin-3(2H)-one
5-acetyl-2-ethyl-4-(quinolin-5-ylamino)-6-thien-2-ylpyridazin-3(2H)-one 5-acetyl-2-ethyl-4-(pyridin-3-ylamino)-6-thien-2-ylpyridazin-3(2H)-one
4-[(5-acetyl-2-ethyl-3-oxo-6-thien-2-yl-2,3-dihydropyridazin-4-yl)amino]benzonitrile
5-acetyl-2-ethyl-6-thien-2-yl-4-[(3,4,5-trifluorophenyl)amino]pyridazin-3(2H)-one
5-Acetyl-4-(bis(4-cyanophenyl)amino)-2-ethyl-6-thien-2-ylpyridazin-3(2H)-one
5-acetyl-2-(cyclopropylmethyl)-4-(quinolin-5-ylamino)-6-thien-2-ylpyridazin-3(2H)-one
5-acetyl-2-(cyclopropylmethyl)-4-(pyridin-3-ylamino)-6-thien-2-ylpyridazin-3(2H)-one
5-acetyl-2-ethyl-4-(quinolin-5-ylamino)-6-thien-3-ylpyridazin-3(2H)-one
5-acetyl-4-[(3-chlorophenyl)amino]-2-ethyl-6-thien-3-ylpyridazin-3(2H)-one
5-acetyl-2-ethyl-4-(pyridin-3-ylamino)-6-thien-3-ylpyridazin-3(2H)-one
4-[(5-acetyl-2-ethyl-3-oxo-6-thien-3-yl-2,3-dihydropyridazin-4-yl)amino]benzonitrile
5-acetyl-2-ethyl-6-thien-3-yl-4-[(3,4,5-trifluorophenyl)amino]pyridazin-3(2H)-one
2-ethyl-6-phenyl-5-(3-phenylpropanoyl)-4-(quinolin-5-ylamino)pyridazin-3(2H)-one
2-ethyl-6-phenyl-5-(3-phenylpropanoyl)-4-(pyridin-3-ylamino)pyridazin-3(2H)-one
2-ethyl-4-(isoquinolin-4-ylamino)-6-phenyl-5-(3-phenylpropanoyl)pyridazin-3(2H)-one
2-ethyl-6-phenyl-4-(quinolin-5-ylamino)-5-(3-thien-3-ylpropanoyl)pyridazin-3(2H)-one
2-ethyl-6-phenyl-4-(pyridin-3-ylamino)-5-(3-thien-3-ylpropanoyl)pyridazin-3(2H)-one
5-acetyl-4-[(3-chlorophenyl)amino]-2-ethyl-6-(1H-imidazo[4,5-b]pyridin-2-yl)pyridazin-3(2H)-one
5-acetyl-6-(1,3-benzothiazol-2-yl)-4-[(3-chlorophenyl)amino]-2-ethylpyridazin-3(2H)-one
5-acetyl-6-(1-benzofuran-2-yl)-4-[(3-chlorophenyl)amino]-2-ethylpyridazin-3(2H)-one
5-acetyl-2-ethyl-6-pyridin-3-yl-4-(pyridin-3-ylamino)pyridazin-3(2H)-one
4-[(5-acetyl-2-ethyl-3-oxo-6-pyridin-3-yl-2,3-dihydropyridazin-4-yl)amino]benzoic acid
5-acetyl-2-ethyl-4-[(1-oxidopyridin-3-yl)amino]-6-phenylpyridazin-3(2H)one
ethyl 3-(5-acetyl-2-ethyl-3-oxo-6-pyridin-4-yl-2,3-dihydropyridazin-4-ylamino)benzoate
3-[(5-acetyl-2-ethyl-3-oxo-6-pyridin-4-yl-2,3-dihydropyridazin-4-yl)amino]benzamide
5-acetyl-2-ethyl-6-phenyl-4-(thieno[2,3-b]pyridin-3-ylamino)pyridazin-3(2H)-one
5-acetyl-2-ethyl-4-[(6-fluoropyridin-3-yl)-amino]-6-phenylpyridazin-3(2H)-one
5-acetyl-2-ethyl-4-[(2-methylpyridin-3-yl)amino]-6-phenylpyridazin-3(2H)-one
5-acetyl-4-{[2-(dimethylamino)pyridin-3-yl]amino}-2-ethyl-6-phenylpyridazin-3(2H)-one
5-[(5-acetyl-2-ethyl-3-oxo-6-phenyl-2,3-dihydropyridazin-4-yl)amino]pyridine-2-carboxylic-acid
5-acetyl-2-ethyl-4-[(2-methoxypyridin-3-yl)amino]-6-phenylpyridazin-3(2H)-one
5-acetyl-2-ethyl-4-(1H-indazol-4-ylamino)-6-phenylpyridazin-3(2H)one
5-acetyl-4-[(2-chloropyridin-3-yl)amino]-2-ethyl-6-phenylpyridazin-3(2H)-one
5-acetyl-4-[(5-chloropyridin-3-yl)amino]-2-ethyl-6-phenylpyridazin-3(2H)-one
5-[(5-acetyl-2-ethyl-3-oxo-6-phenyl-2,3-dihydropyridazin-4-yl)amino]nicotinamide
5-acetyl-2-ethyl-4-(1,7-naphthyridin-8-ylamino)-6-phenylpyridazin-3(2H)-one
2-ethyl-5-glycoloyl-4-[(2-methylpyridin-3-yl)amino]-6-phenylpyridazin-3(2H)-one
methyl 5-[(5-acetyl-2-ethyl-3-oxo-6-phenyl-2,3-dihydropyridazin-4-yl)amino]nicotinic acid
5-[(5-acetyl-2-ethyl-3-oxo-6-phenyl-2,3-dihydropyridazin-4-yl)amino]nicotinic acid
5-acetyl-2-ethyl-4-(1,5-naphthyridin-3-ylamino)-6-phenylpyridazin-3(2H)-one
5-acetyl-2-ethyl-4-[(8-hydroxy-1,7-naphthyridin-5-yl)amino]6-phenylpyridazin-3(2H)-one
5-acetyl-2-ethyl-6-phenyl-4-(thien-2-ylamino)pyridazin-3(2H)-one
5-acetyl-2-ethyl-6-phenyl-4-[(2-phenylpyridin-3-yl)amino]pyridazin-3(2H)-one
ethyl {5-[(5-acetyl-2-ethyl-3-oxo-6-phenyl-2,3-dihydropyridazin-4-yl)amino]pyridin-2-yl}acetate
5-acetyl-2-ethyl-4-[(6-methylpyridin-3-yl)amino]-6-phenylpyridazin-3(2H)-one
5-acetyl-2-ethyl-4-[(6-hydroxypyridin-2-yl)amino]-6-phenylpyridazin-3(2H)-one
5-acetyl-2-ethyl-4-[(2-fluoropyridin-3-yl)amino]-6-phenylpyridazin-3(2H)-one
5-acetyl-4-[(6-chloro-4-methylpyridin-3-yl)amino]-2-ethyl-6-phenylpyridazin-3(2H)-one
5-acetyl-2-ethyl-4-[(3-hydroxypyridin-2-yl)amino]-6-phenylpyridazin-3(2H)-one
5-acetyl-2-ethyl-4[(4-methoxypyridin-3-yl)amino]-6-phenylpyridazin-3(2H)-one
5-acetyl-2-ethyl-4-(isoquinolin-8-ylamino)-6-phenylpyridazin-3(2H)-one
5-acetyl-2-ethyl-6-phenyl-4-(quinolin-7-ylamino)pyridazin-3(2H)-one
5-acetyl-4-[(5-chloropyridin-3-yl)amino]-2-ethyl-6-(3-fluorophenyl)pyridazin-3(2H)-one
5-acetyl-2-ethyl-6-(4-fluorophenyl)-4-[(2-methoxypyridin-3-yl)amino]pyridazin-3(2H)-one
5-acetyl-2-ethyl-6-(4-fluorophenyl)-4-[(2-methylpyridin-3-yl)amino]pyridazin-3(2H)-one
5-acetyl-4-[(2-chloropyridin-3-yl)amino]-2-ethyl-6-(4-fluorophenyl)pyridazin-3(2H)-one
5-acetyl-2-ethyl-6-(4-fluorophenyl)-4-[(4-methylpyridin-3-yl)amino]pyridazin-3(2H)-one
5-acetyl-2-ethyl-6-(4-fluorophenyl)-4-[(2-fluoropyridin-3-yl)amino]pyridazin-3(2H)-one
5-acetyl-4-[(2-chloropyridin-3-yl)amino]-2-(cyclopropylmethyl)-6-(4-fluorophenyl)pyridazin-3(2H)-one
5-acetyl-2-(cyclopropylmethyl)-6-(4-fluorophenyl)-4-[(2-methoxypyridin-3-yl)amino]pyridazin-3(2H)-one
5-acetyl-2-(cyclopropylmethyl)-6-(4-fluorophenyl)-4-[(2-methylpyridin-3-yl)amino]pyridazin-3(2H)-one
5-acetyl-2-(cyclopropylmethyl)-6-(4-fluorophenyl)-4-[(2-fluoropyridin-3-yl)amino]pyridazin-3(2H)-one
5-acetyl-2-(cyclopropylmethyl)-6-(4-fluorophenyl)-4-[(4-methylpyridin-3-yl)amino]pyridazin-3(2H)-one
5-acetyl-2-(cyclopropylmethyl)-6-(4-fluorophenyl)-4-[(pyridin-3-yl)amino]pyridazin-3(2H)-one
5-acetyl-6-(3-chlorophenyl)-2-ethyl-4-[(2-methylpyridin-3-yl)amino]pyridazin-3(2H)-one
5-acetyl-6-(3-chlorophenyl)-4-[(2-chloropyridin-3-yl)amino]-2-ethylpyridazin-3(2H)-one
5-acetyl-6-(3-chlorophenyl)-2-ethyl-4-[(4-methylpyridin-3-yl)amino]pyridazin-3(2H)-one methyl 5-[(5-acetyl-2-ethyl-3-oxo-6-phenyl-2,3-dihydropyridazin-4-yl)amino]quinoline-8-carboxylate
5-acetyl-2-ethyl-4-[(4-methylpyridin-3-yl)amino]-6-phenylpyridazin-3(2H)-one
5-acetyl-2-ethyl-4-(isoquinolin-4-ylamino)-6-(4-methoxyphenyl)pyridazin-3(2H)-one
5-acetyl-2-ethyl-6-(4-methoxyphenyl)-4-(pyridin-3-ylamino)pyridazin-3(2H)-one
5-acetyl-2-ethyl-6-(4-methoxyphenyl)-4-(quinolin-5-ylamino)pyridazin-3(2H)-one
5-acetyl-2-ethyl-6-(4-methoxy-phenyl)-4-(1-oxy-quinolin-5-ylamino)-2H-pyridazin-3-one
5-acetyl-2-ethyl-4-(isoquinolin-4-ylamino)-6-(3-methoxyphenyl)pyridazin-3(2H)-one
5-acetyl-2-ethyl-6-(3-methoxyphenyl)-4(pyridin-3-ylamino)pyridazin-3(2H)-one
5-acetyl-2-ethyl-6-(3-methoxyphenyl)-4-(quinolin-5-ylamino)pyridazin-3(2H)-one
5-acetyl-2-ethyl-6-(3-methoxyphenyl)-4-[(1-oxidoquinolin-5-yl)amino]pyridazin-3(2H)-one
5-acetyl-2-ethyl-4-(isoquinolin-4-ylamino)-6-(4-methylphenyl)pyridazin-3(2H)-one
5-acetyl-2-ethyl-6-(4-methylphenyl)-4-(pyridin-3-ylamino)pyridazin-3(2H)-one
5-acetyl-2-ethyl-6-(4-methylphenyl)-4-(quinolin-5-ylamino)pyridazin-3(2H)-one
5-acetyl-2-ethyl-6-(4-methylphenyl)-4-[(1-oxidoquinolin-5-yl)amino]pyridazin-3(2H)-one
5-acetyl-2-ethyl-6-(4-methylphenyl)-4-[(4-methylpyridin-3-yl)amino]pyridazin-3(2H)-one
5-acetyl-2-ethyl-4-(isoquinolin-4-ylamino)-6-(3-methylphenyl)pyridazin-3(2H)-one
5-acetyl-2-ethyl-6-(3-methylphenyl)-4-(pyridin-3-ylamino)pyridazin-3(2H)-one
5-acetyl-2-ethyl-6-(3-methylphenyl)-4-(quinolin-5-ylamino)pyridazin-3(2H)-one
5-acetyl-2-ethyl-6-(3-methylphenyl)-4-[(4-methylpyridin-3-yl)amino]pyridazin-3(2H)-one
methyl 4-[4-acetyl-1-ethyl-5-(isoquinolin-4-ylamino)-6-oxo-1,6-dihydropyridazin-3-yl]benzoate
methyl 4-[4-acetyl-1-ethyl-6-oxo-5-(pyridin-3-ylamino)-1,6-dihydropyridazin-3-yl]benzoate
4-[4-acetyl-1-ethyl-6-oxo-5-(pyridin-3-ylamino)-1,6-dihydropyridazin-3-yl]benzoic acid
methyl 4-{4-acetyl-1-ethyl-5-[(4-methylpyridin-3-yl)amino]-6-oxo-1,6-dihydropyridazin-3-yl}benzoate
4-{4-acetyl-1-ethyl-5-[(4-methylpyridin-3-yl)amino]-6-oxo-1,6-dihydropyridazin-3-yl}benzoic acid
methyl 3-[4-acetyl-1-ethyl-6-oxo-5-(pyridin-3-ylamino)-1,6-dihydropyridazin-3-yl]benzoate
3-[4-acetyl-1-ethyl-6-oxo-5-(pyridin-3-ylamino)-1,6-dihydropyridazin-3-yl]benzoic acid
5-acetyl-4-[(3-chloro-4-fluorophenyl)amino]-2-ethyl-6-pyridin-4-ylpyridazin-3(2H)-one
5-acetyl-4-[bis(3-chloro-4-fluorophenyl)amino]-2-ethyl-6-pyridin-4-ylpyridazin-3(2H)-one
5-acetyl-4-[(3-chloro-4-fluorophenyl)amino]-2-ethyl-6-pyridin-3-ylpyridazin-3(2H)-one
5-acetyl-4-[bis(3-chloro-4-fluorophenyl)amino]-2-ethyl-6-pyridin-3-ylpyridazin-3(2H)-one
methyl [4-acetyl-6-oxo-3-phenyl-5-(quinolin-5-ylamino)pyridazin-1(6H)-yl]acetate
[4-acetyl-6-oxo-3-phenyl-5-(quinolin-5-ylamino)pyridazin-1(6H)-yl]acetic acid
5-acetyl-2-ethyl-4-[(3-methylpyridin-2-yl)amino]-6-phenylpyridazin-3(2H)one
5-acetyl-2-ethyl-6-phenyl-4-(1H-pyrazol-3-ylamino)pyridazin-3(2H)-one
5-acetyl-2-ethyl-6-phenyl-4-(9H-purin-6-ylamino)pyridazin-3(2H)one
5-acetyl-2-ethyl-4-[(3-methylisoxazol-5-yl)amino]-6-phenylpyridazin-3(2H)-one
5-acetyl-2-ethyl-4-[(8-hydroxyquinolin-5-yl)amino]-6-phenylpyridazin-3(2H)-one
5-acetyl-2-ethyl-4-(1H-indazol-7-ylamino)-6-phenylpyridazin-3(2H)-one
5-acetyl-4-[(6-bromoquinolin-8-yl)amino]-2-ethyl-6-phenylpyridazin-3(2H)-one
5-acetyl-2-ethyl-4-[(5-methylisoxazol-3-yl)amino]-6-phenylpyridazin-3(2H)-one
5-acetyl-2-ethyl-4-(isoxazol-3-ylamino)-6-phenylpyridazin-3(2H)-one
5-acetyl-2 (cyclopropylmethyl)-6-phenyl-4-(quinolin-5-ylamino)pyridazin-3(2H)-one
5-acetyl-2-(cyclopropylmethyl)-6-phenyl-4-(quinolin-8-ylamino)pyridazin-3(2H)-one
5-acetyl-2-ethyl-4-[(1-methyl-1H-pyrazol-3-yl)amino]-6-phenylpyridazin-3(2H)-one
5-acetyl-2-ethyl-4-[(1-oxidoquinolin-5-yl)amino]-6-phenylpyridazin-3(2H)-one
5-acetyl-2-ethyl-4-[(2-oxidoisoquinolin-5-yl)amino]-6-phenylpyridazin-3(2H)-one
5-acetyl-6-(3-chlorophenyl)-2-ethyl-4-(quinolin-5-ylamino)pyridazin-3(2H)-one
5-acetyl-6-(3-chlorophenyl)-2-ethyl-4-(quinolin-8-ylamino)pyridazin-3(2H)-one
5-acetyl-2-ethyl-6-pyridin-4-yl-4-(quinolin-5-ylamino)pyridazin-3(2H)-one
5-acetyl-2-ethyl-6-pyridin-3-yl-4-(quinolin-5-ylamino)pyridazin-3(2H)-one
5-acetyl-2-ethyl-4-[(8-fluoroquinolin-5-yl)amino]-6-phenylpyridazin-3(2H)-one
5-acetyl-2-(cyclopropylmethyl)-6-(4-fluorophenyl)-4-(quinolin-8-ylamino)pyridazin-3(2H)-one
5-acetyl-2-ethyl-6-(4-fluorophenyl)-4-(quinolin-5-ylamino)pyridazin-3(2H)-one
5-acetyl-2-ethyl-6-(4-fluorophenyl)-4-(quinolin-8-ylamino)pyridazin-3(2H)-one
5-acetyl-2-(cyclopropylmethyl)-6-(4-fluorophenyl)-4-(quinolin-5-ylamino)pyridazin-3(2H)-one
5-acetyl-6-(3-chlorophenyl)-2-ethyl-4-[(1-oxidoquinolin-5-yl)amino]pyridazin-3(2H)-one
5-acetyl-2-ethyl-4-[(2-methylquinolin-5-yl)amino]-6-phenylpyridazin-3(2H)-one
5-acetyl-6-(3-chlorophenyl)-2-ethyl-4-(isoquinolin-5-ylamino) pyridazin-3(2H)-one
5-acetyl-2-ethyl-6-(4-fluorophenyl)-4-[(1-oxidoquinolin-5-yl)amino]pyridazin-3(2H)-one
5-acetyl-2-ethyl-6-(3-fluorophenyl)-4-(quinolin-5-ylamino)pyridazin-3(2H)-one
5-acetyl-2-ethyl-6-(3-fluorophenyl)-4-[(1-oxidoquinolin-5-yl)amino]pyridazin-3(2H)-one
5-[(5-acetyl-2-ethyl-3-oxo-6-phenyl-2,3-dihydropyridazin-4-yl)amino]quinoline-8-carboxylic acid
and pharmaceutically acceptable salts thereof.
Of outstanding interest are:
5-Acetyl-2-ethyl-4-[(3-fluorophenyl)amino]-6-pyridin-3-ylpyridazin-3(2H)-one
5-Acetyl-2-ethyl-4-(1-naphthylamino)-6-pyridin-3-ylpyridazin-3(2H)-one
5-Acetyl-4-[(3-chlorophenyl)amino]-2-ethyl-6-pyridin-4-ylpyridazin-3(2H)-one 5-Acetyl-2-ethyl-4-(1-naphthylamino)-6-pyridin-4-ylpyridazin-3(2H)-one
5-Acetyl-2-ethyl-4-[(2-methylphenyl)amino]-6-pyridin-4-ylpyridazin-3(2H)-one
5-Acetyl-2-ethyl-4-[(3-methoxyphenyl)amino]-6-pyridin-4-ylpyridazin-3(2H)-one
4[(5-Acetyl-2-ethyl-3-oxo-6-pyridin-4-yl-2,3-dihydropyridazin-4-yl)amino]benzoic acid
5-Acetyl-4-[(3-chlorophenyl)amino]-2-(2-hydroxyethyl)-6-pyridin-4-ylpyridazin-3(2H)-one
5-Acetyl-4-[(3-chlorophenyl)amino]-2-ethyl-6-thien-2-ylpyridazin-3(2H)-one
5-Acetyl-2-ethyl-6-phenyl-4-(pyridin-3-ylamino)pyridazin-3(2H)-one
5-Acetyl-2-ethyl-6-phenyl-4-quinolin-8-ylamino)pyridazin-3(2H)-one
5-Acetyl-2-ethyl-4-(1H-indol-4-ylamino)-6-phenylpyridazin-3(2H)-one
5-Acetyl-2-ethyl-6-phenyl-4-(quinolin-5-ylamino)pyridazin-3(2H)-one
5-Acetyl-6-(3-fluorophenyl)-2-isopropyl-4-(pyridin-3-ylamino)pyridazin-3(2H)-one
5-Acetyl-2-(cyclopropylmethyl)-6-(3-fluorophenyl)-4-(pyridin-3-ylamino)pyridazin-3(2H)-one
5-Acetyl-2-ethyl-6-(4-fluorophenyl)-4-(pyridin-3-ylamino)pyridazin-3(2H)-one
5-Acetyl-2-ethyl-4-(isoquinolin-5-ylamino)-6-phenylpyridazin-3(2H)-one
5-Acetyl-6-(1,3-benzoxazol-2-yl)-2-ethyl-4-[(3-fluorophenyl)amino]pyridazin-3(2H)-one and pharmaceutically acceptable salts thereof.

The compounds of the present invention may be prepared by one of the processes described below.

Compounds (I) may be obtained as shown in Scheme 1.

using an organic hydrogen donor and a transfer agent, such as ammonium formate or hydrazine by methods known per se, e.g. V. Dal Piaz et al. *Heterocycles,* 1991, 32, 1173.

Condensation of 4-aminopyridazin-3(2H)-ones (III) with an aryl or heteroaryl bromide of formula (A) wherein $R^3$ is as hereinbefore defined, gives compounds (Ia), wherein $R^1$, $R^3$, $R^4$ and $R^5$ are as hereinbefore defined. The reaction is carried out in the presence of a copper salt such as cuprous iodide and an inorganic base such as potassium phosphate, potassium carbonate or sodium carbonate and can also be performed in the presence of an organic base, preferably a diamine base such as N,N'-dimethylethylenediamine in an inert solvent such as toluene, dioxane or dimethylformamide, at a temperature from −20° C. to the boiling point of the solvent. It can also be performed neat.

Alternatively, condensation of 4-aminopyridazin-3(2H)-one derivative (III), wherein $R^1$, $R^4$ and $R^5$ are as hereinbefore defined, with a boronic acid of formula (IVa), wherein $R^3$ is as hereinbefore defined, gives compound (Ia), wherein $R^1$, $R^3$, $R^4$ and $R^5$ are as hereinbefore defined. The reaction is carried out in the presence of a copper salt such as cupric acetate and an organic base, preferably an amine base such as triethylamine, in an inert solvent such as dioxane, methylene chloride or tetrahydrofuran, at a temperature from −20° C. to the boiling point of the solvent. Compounds (Ia) are equal to compounds (I) when $R^2$ is hydrogen.

Condensation of an 4-aminopyridazin-3(2H)-one derivative (Ia), wherein $R^1$, $R^3$, $R^4$ and $R^5$ are as hereinbefore defined, with a boronic acid (IVb), wherein $R^2$ is as herein-

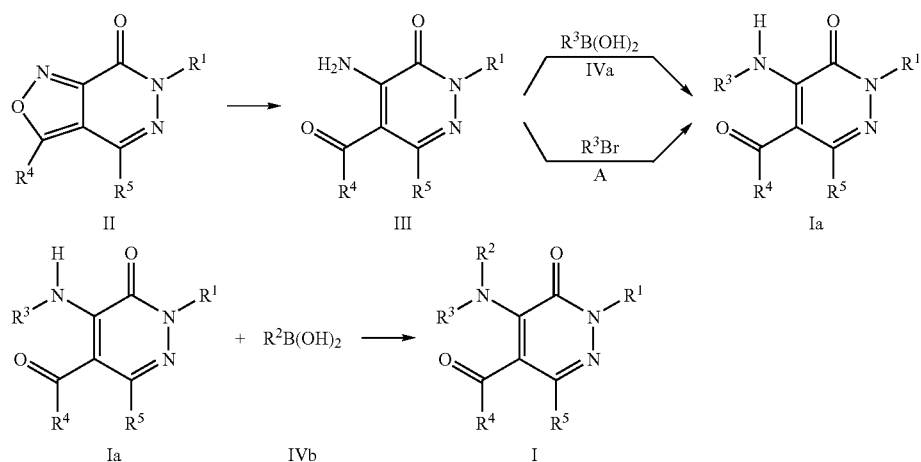

Scheme 1

An isoxazolo[3,4-d]pyridazin-7(6H)-one of formula (II), wherein $R^1$, $R^4$ and $R^5$ are as hereinbefore defined, is hydrogenated to yield an 4-aminopyridazin-3(2H)-one derivative (III), wherein $R^1$, $R^4$ and $R^5$ are as hereinbefore defined. The hydrogenation may be performed using for example hydrogen in the presence of a catalyst by methods known per se, e.g. V. Dal Piaz et al. *Heterocycles,* 1991, 32, 1173. Alternatively, the reaction may be accomplished by transfer hydrogenation before defined, gives compounds (I), wherein $R^1$, $R^2$, $R^3$, $R^4$ and $R^5$ are as hereinbefore defined. The reaction is carried out in the presence of a copper salt such as cupric acetate in the presence of an organic base, preferably an amine base such as triethylamine, in an inert solvent such as dioxane, methylene chloride or tetrahydrofuran, at a temperature from −20° C. to the boiling point of the solvent.

Alternatively, compounds (I) may be obtained as shown in Scheme 2.

Scheme 2

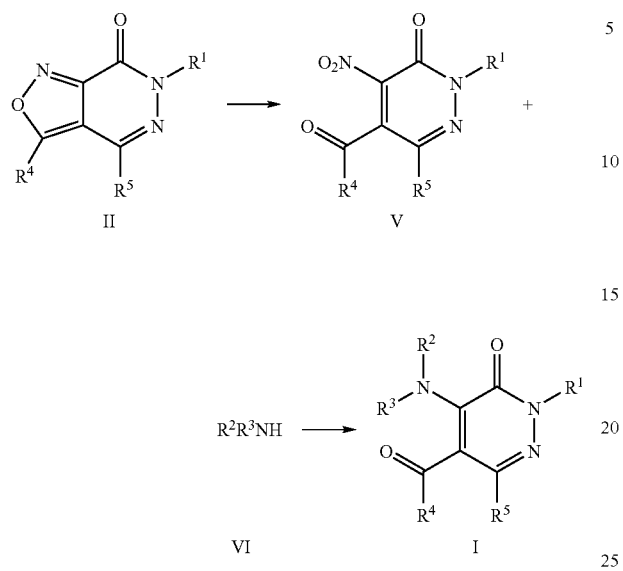

Oxidation of an isoxazolo[3,4-d]pyridazin-7(6H)-one of formula (II), wherein $R^1$, $R^4$ and $R^5$ are as hereinbefore defined, gives a 4-nitropyridazin-3(2H)-one derivative of formula (V), wherein $R^1$, $R^4$ and $R^5$ are as hereinbefore defined. The reaction may be performed using an oxidizing agent such as cerium ammonium nitrate under acidic conditions by methods known per se, e.g. V. Dal Piaz et al. *Synthesis*, 1989, 213.

Condensation of the 4-nitropyridazin-3(2H)-one derivative of formula (V), wherein $R^1$, $R^4$ and $R^5$ are as hereinbefore defined, with the corresponding amine (VI), wherein $R^2$ and $R^3$ are as hereinbefore defined, following methods known per se, e.g. G. Ciciani et al. *Farmaco* 1991, 46, 873, gives compound (I), wherein $R^1$, $R^2$, $R^3$, $R^4$ and $R^5$ are as hereinbefore defined.

According to one aspect of the present invention some specific compounds of formula (I) and in particular those of formula (XXIV) may also be obtained as shown in Scheme 3.

Scheme 3

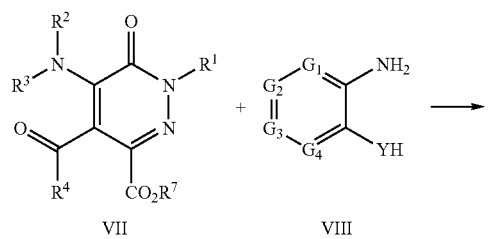

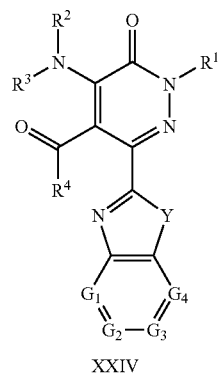

Condensation of compounds (VII), in which $R^7$ is an alkyl group, with an ortho-substituted aryl or heteroarylamine of formula (VIII), wherein each $G_1$, $G_2$, $G_3$ and $G_4$ independently represent a nitrogen or carbon atom and —YH represents an amino, a mercapto or a hydroxy substituent, in the presence of a dehydrating agent such as trimethylaluminium, gives pyridazin-3(2H)-ones of formula (I) wherein $R^1$, $R^4$ and $R^5$ are as hereinbefore defined and Y represents a sulphur atom, an oxygen atom or a —NH— group. The reaction is preferably carried out in a solvent such as toluene at a temperature between −78 degrees and room temperature.

Isoxazolo[3,4-d]pyridazin-7(6H)-ones of formula (II) may be obtained as shown in Scheme 4.

Scheme 4

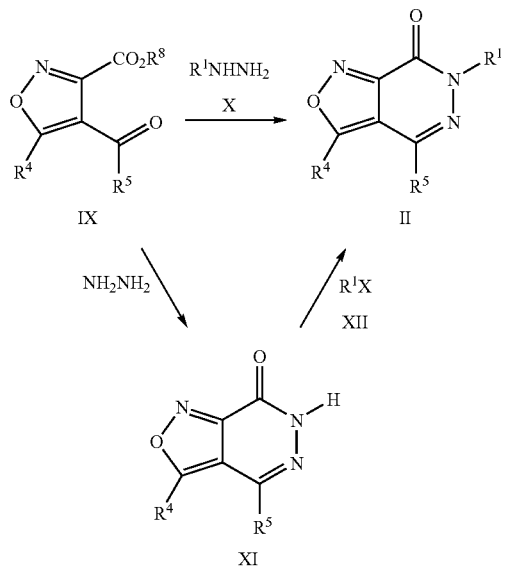

Isoxazole derivatives of formula (IX), where $R^4$ and $R^5$ are as hereinbefore defined and $R^8$ is an alkyl group, are condensed with a hydrazine of formula (X), where $R^1$ is as hereinbefore defined, by methods known per se, e.g. G. Renzi et al., *Gazz. Chim. Ital.* 1965, 95, 1478, to give isoxazolo[3,4-d]pyridazin-7(6H)-ones of formula (II) wherein $R^1$, $R^4$ and $R^5$ are as hereinbefore defined.

Alternatively, isoxazole derivatives of formula (IX), where $R^4$ and $R^5$ are as hereinbefore defined and $R^8$ is an alkyl group, are condensed with hydrazine, by methods known per se, e.g. G. Renzi et al., *Gazz. Chim. Ital.* 1965, 95, 1478, to give isoxazolo[3,4-d]pyridazin-7(6H)-ones of formula (XI) wherein $R^4$ and $R^5$ are as hereinbefore defined. Subsequent reaction with an alkylating agent of formula (XII), wherein $R^1$ is as hereinbefore defined and X is a leaving group such as a chlorine or a bromine atom or a methanesulfonate, p-toluenesulfonate or a benzenesulfonate group by methods known per se, e.g. V. Dal Piaz et al. *Drug Des. Discovery* 1996, 14, 53; or condensation with an alcohol of formula (XII) wherein $R^1$ is as hereinbefore described and X is a hydroxy group in the presence of triphenylphosphine and diethylazodicarboxylate by methods known per se, e. G. O. Mitsunobu et al. *J. Am. Chem. Soc.* 1972, 94, 679; gives isoxazolo[3,4-d]pyridazin-7(6H)-ones of formula (II) wherein $R^1$, $R^4$ and $R^5$ are as hereinbefore defined.

Isoxazolo[3,4-d]pyridazin-7(6H)-ones of formula (II) may also be obtained as shown in Scheme 5.

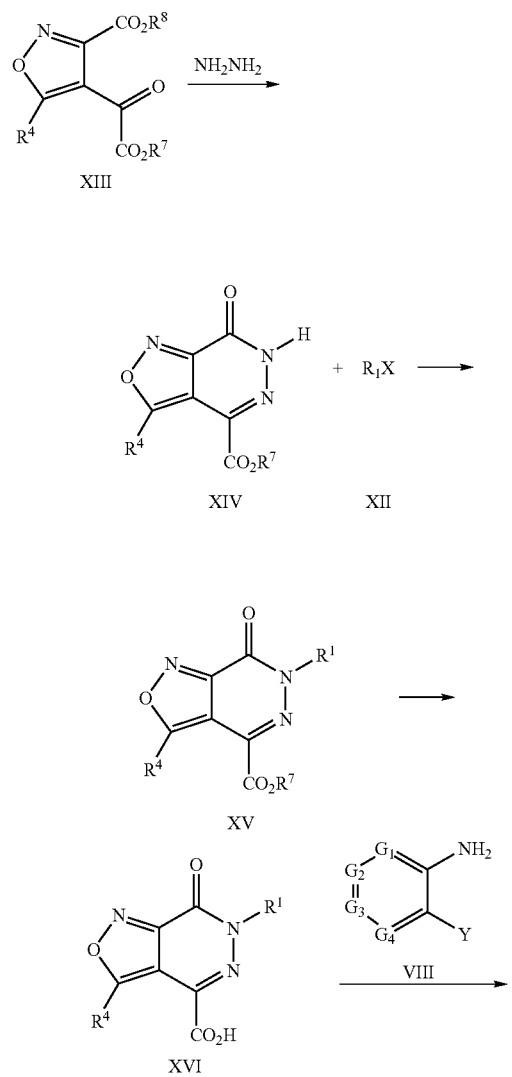

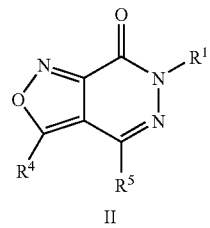

Isoxazole derivatives of formula (XIII), wherein $R^4$ is hereinbefore defined and $R^7$ and $R^8$ are an alkyl group, are condensed with hydrazine, by methods known per se, e.g. G. Renzi et. al., *Gazz Chim. Ital.* 1965, 95, 1478, to give isoxazolo[3,4-d]pyridazin-7(6H)-ones of formula (XIV) wherein $R^4$ is as hereinbefore defined and $R^7$ is an alkyl group. Subsequent reaction with an alkylating agent of formula (XII), wherein $R^1$ is as hereinbefore defined and X is a leaving group such as a chlorine or a bromine atom or a methanesulfonate, p-toluenesulfonate or a benzenesulfonate group, by methods known per se, e.g. V. Dal Piaz et al. *Drug Des. Discovery* 1996, 14, 53; or condensation with an alcohol of formula (XII) wherein $R^1$ is as hereinbefore described and X is a hydroxy group in the presence of triphenylphosphine and diethylazodicarboxylate by methods known per se, e.g. O. Mitsunobu et al. *J. Am. Chem. Soc.* 1972, 94, 679; gives isoxazolo[3,4-d]pyridazin-7(6H)-ones of formula (XV), wherein $R^1$ and $R^4$ are as hereinbefore defined and $R^7$ is an alkyl group. Compounds (XV) are treated with sodium or potassium hydroxide and further neutralization with an inorganic acid such as hydrochloric or sulfuric acid provides the corresponding carboxylic acid derivative of formula (XVI), wherein $R^1$ and $R^4$ are as hereinbefore defined. The reaction is preferably carried out in a solvent such as methanol, ethanol, tetrahydrofuran or an aqueous mixture of one of the above mentioned solvents at its boiling point. Condensation of compounds (XVI) with an ortho-substituted aryl or heteroarylamine of formula (VIII), wherein each $G_1$, $G_2$, $G_3$ and $G_4$ independently represent a nitrogen or carbon atom and Y represents an amino, a mercapto or a hydroxy substituent, in the presence of a dehydrating agent such as polyphosphoric acid or trimethylsilylpolyphosphate gives isoxazolo[3,4-d]pyridazin-7(6H)-ones of formula (II) wherein $R^1$, $R^4$ and $R^5$ are as hereinbefore defined. The reaction is preferably carried out in a highly boiling point solvent such as 1,2-dichlorobenzene at its boiling point.

Pyridazin-3(2H)-ones of formula (VII) may be obtained as shown in Scheme 6

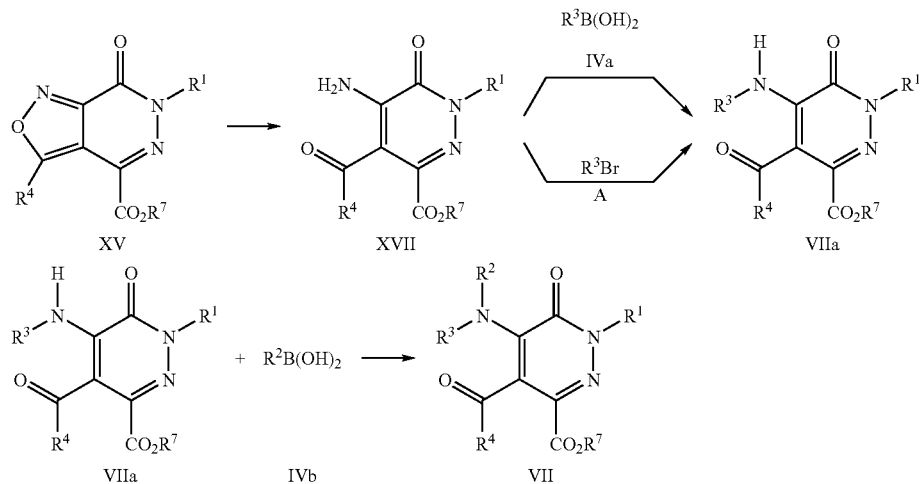

An isoxazolo[3,4-d]pyridazin-7(6H)-one of formula (XV), wherein $R^1$ and $R^4$ are as hereinbefore defined and $R^7$ is an alkyl group, is hydrogenated to yield an 4-aminopyridazin-3(2H)-one derivative (XVII), wherein $R^1$ and $R^4$ are as hereinbefore defined and $R^7$ is an alkyl group. The hydrogenation may be performed using for example hydrogen in the presence of a catalyst by methods known per se, e.g. V. Dal Piaz et al. *Heterocycles*, 1991, 32, 1173. Alternatively, the reaction may be accomplished by transfer hydrogenation using an organic hydrogen donor and a transfer agent, such as ammonium formate or hydrazine by methods known per se, e. g. V. Dal Piaz et al. *Heterocycles*, 1991, 32, 1173. Condensation of an 4-aminopyridazin-3(2H)-one derivative (XVII), wherein $R^1$, $R^3$ and $R^4$ are as hereinbefore defined and $R^7$ is an alkyl group with an aryl or heteroaryl bromide of formula (A) wherein $R^3$ is as hereinbefore defined, gives compounds (VIIa), wherein $R^1$, $R^3$, $R^4$ and $R^5$ are as hereinbefore defined. The reaction is carried out in the presence of a copper salt such as cuprous iodide and an inorganic base such as potassium phosphate, potassium carbonate or sodium carbonate and can also be performed in the presence of an organic base, preferably a diamine base such as N,N'-dimethylethylenediamine in an inert solvent such as toluene, dioxane or dimethylformamide, at a temperature from −20° C. to the boiling point of the solvent or without solvent. Alternatively, condensation of an 4-aminopyridazin-3(2H)-one derivative (XVII), wherein $R^1$, $R^3$ and $R^4$ are as hereinbefore defined and $R^7$ is an alkyl group, with a boronic acid (IVa), wherein, $R^3$ is as hereinbefore defined, gives compounds (VIIa), wherein $R^1$, $R^3$ and $R^4$ are as hereinbefore defined and $R^7$ is an alkyl group. The reaction is carried out in the presence of a copper salt such as cupric acetate in the presence of an organic base, preferably an amine base such as triethylamine, in an inert solvent such as dioxane, methylene chloride or tetrahydrofuran, at a temperature from −20° C. to the boiling point of the solvent. Compounds (VIIa) are equal to compounds (VII) when $R^2$ is hydrogen. Condensation of an 4-aminopyridazin-3(2H)-one derivative (VIIa), wherein $R^1$, $R^3$ and $R^4$ are as hereinbefore defined and $R^7$ is an alkyl group, with a boronic acid (IVb), wherein $R^2$ is as hereinbefore defined, gives compounds (VII), wherein $R^1$, $R^2$, $R^3$ and $R^4$ are as hereinbefore defined and $R^7$ is an alkyl group. The reaction is carried out in the presence of a copper salt such as cupric acetate in the presence of an organic base, preferably an amine base such as triethylamine, in an inert solvent such as dioxane, methylene chloride or tetrahydrofuran, at a temperature from −20° C. to the boiling point of the solvent.

Isoxazole derivatives of formula (IX) and (XIII) may be obtained as shown in Scheme 7.

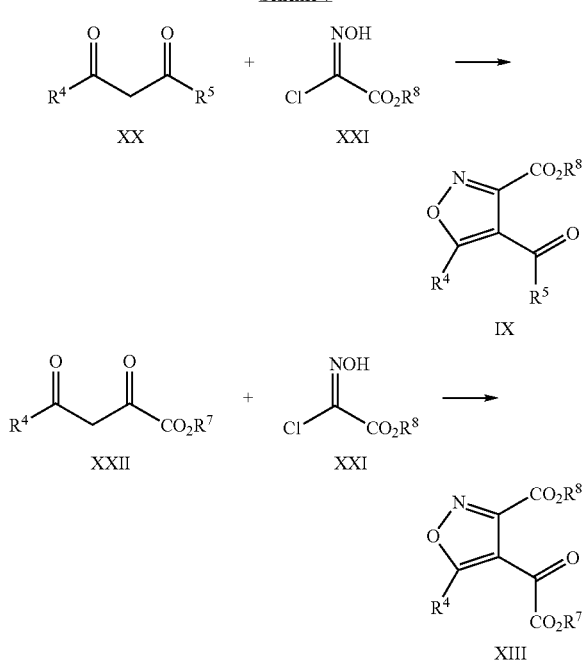

Reaction of a 1,3-dicarbonylic compound of general formula (XX), wherein $R^4$ and $R^5$ are as hereinbefore defined, and a 2-chloro-2-(hydroxyimino)acetate derivative of formula (XXI), wherein $R^8$ is as hereinbefore defined, following methods known per se, e. g. G. Renzi et al., *Gazz. Chim. Ital.*

1965, 95, 1478, gives isoxazole derivatives of formula (IX), wherein $R^4$ and $R^5$ are as hereinbefore defined and $R^8$ is an alkyl group.

Reaction of a 2,4-dioxoester derivative of general formula (XXII), wherein $R^4$ is as herein before defined and $R^7$ is an alkyl group, and a 2 chloro-2-(hydroxyimino)acetate derivative of formula (XXI), wherein $R^8$ is as hereinbefore defined, following methods known per se, e. g. G. Renzi et al., *Gazz. Chim. Ital.* 1965, 95, 1478, gives isoxazole derivatives of formula (XIII), wherein $R^4$ is as hereinbefore defined and $R^7$ and $R^8$ are an alkyl group.

Scheme 8

According to one aspect of the present invention some specific compounds of formula (I) and in particular those of formula (Ic) may also be obtained as shown in Scheme 8.

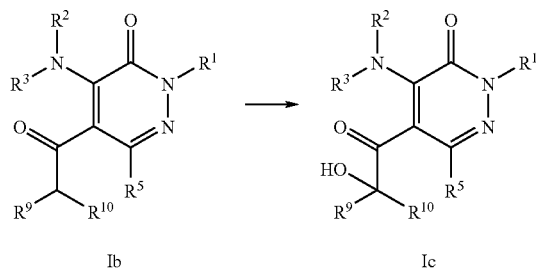

Reaction of a pyridizinone of formula (Ib) wherein $R^1$, $R^2$, $R^3$ and $R^5$ are as hereinbefore defined and $R^4$ is the rest —$CHR^9R^{10}$ wherein are $R^9$ and $R^{10}$ alkyl or aryl groups with an hypervalent iodine compound by methods known per se (Moriarty, R. M; Hu, H; Gupta S. C., Tetrahedron Lett, 1981, 22, 1283-86) gives the α-hydroxylated derivative (Ic) wherein $R^1$, $R^2$, $R^3$ and $R^5$ are as hereinbefore defined.

Scheme 9

4-Aminopyridazin-3(2H)-ones of formula (III) may also be obtained as shown in Scheme 9.

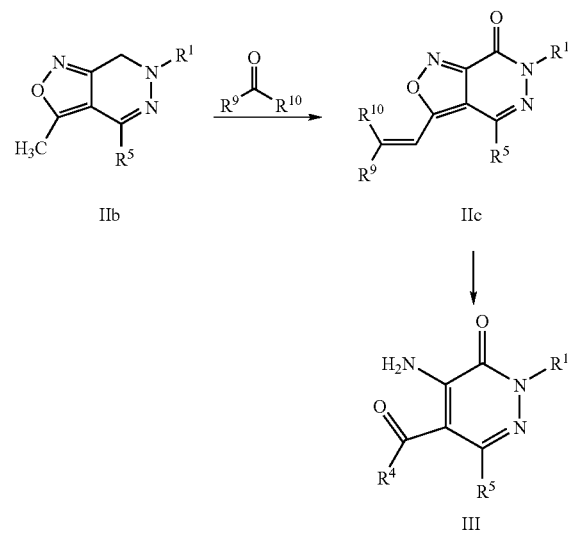

Condensation of an isoxazolo[3,4-d]pyridazin-7(6H)-one of formula (IIb) wherein $R^1$ and $R^5$ are as defined above with an aldehyde or a ketone of formula $R^9COR^{10}$, by methods known per se, eg. G. Ciciani et al. *Il Farmaco* 1991, 46, 873 leads to a substituted vinyl derivative of formula (IIc) which is then reduced using for example hydrogen in the presence of a catalyst such as palladium on charcoal in a solvent such as methanol, ethanol or ethyl acetate to yield the corresponding 4-aminopyridazin-3(2H)-one (III).

When the defined groups $R^1$ to $R^5$ are susceptible to chemical reaction under the conditions of the hereinbefore described processes or are incompatible with said processes, conventional protecting groups may be used in accordance with standard practice, for example see T. W. Greene and P. G. M. Wuts in 'Protective Groups in Organic Chemistry', 3$^{rd}$ Edition, John Wiley & Sons (1999). It may be that deprotection will form the last step in the synthesis of compounds of formula (I).

In still another aspect the present invention encompasses intermediate compounds of formula (XVII), (VIIa) and (VII) useful in the synthesis of compounds of formula (I).

The compounds of formulae (IVa), (IVb), (VI), (X), (XII), (VIII), (XX), and (XXII) are known compounds or can be prepared by analogy with known methods.

Pharmacological Activity

PDE4 Assay Procedure

Compounds to be tested were resuspended in DMSO at a stock concentration of 1 mM. The compounds were tested at different concentrations varying from 10 μM to 10 pM to calculate an IC$_{50}$. These dilutions were done in 96-well plates. In some cases, plates containing diluted compounds were frozen before being assayed. In these cases, the plates were thawed at room temperature and stirred for 15 minutes.

Ten microliters of the diluted compounds were poured into a "low binding" assay plate. Eighty microliters of reaction mixture containing 50 mM Tris pH 7.5, 8.3 mM MgCl$_2$, 1.7 mM EGTA, and 15 nM [3H]-cAMP were added to each well. The reaction was initiated by adding ten microliters of a solution containing PDE4. The plate was then incubated under stirring for 1 hour at room temperature. After incubation the reaction was stopped with 50 microlitres of SPA beads, and the reaction was allowed to incubate for another 20 minutes at room temperature before measuring radioactivity using standard instrumentation.

The reaction mixture was prepared by adding 90 ml of H$_2$O to 10 ml of 10× assay buffer (500 mM Tris pH 7.5, 8.3 mM MgCl$_2$, 17 mM EGTA), and 40 microlitres 1 μCi/μL [3H]-cAMP. SPA beads solution was prepared by adding 500 mg to 28 ml H$_2$O for a final concentration of 20 mg/ml beads and 18 mM zinc sulphate.

The results are shown in Table 1.

| Example | IC$_{50}$ PDE4 (nM) |
|---|---|
| 1 | 2.3 |
| 4 | 6.8 |
| 31 | 4.5 |
| 32 | 0.59 |
| 33 | 0.11 |
| 36 | 6.4 |
| 41 | 16 |
| 51 | 29 |
| 52 | 5.2 |
| 63 | 24 |
| 67 | 10 |
| 69 | 2 |

-continued

| Example | IC$_{50}$ PDE4 (nM) |
|---|---|
| 82 | 0.3 |
| 84 | 2.6 |
| 91 | 9.4 |
| 92 | 11 |
| 93 | 8.3 |
| 96 | 5.1 |

It can be seen from Table 1 that the compounds of formula (I) are potent inhibitors of phosphodiesterase 4 (PDE 4). Preferred pyridazin-3(2H)-one derivatives of the invention possess an IC$_{50}$ value for the inhibition of PDE4 (determined as defined above) of less than 100 nM, preferably less than 50 nM and most preferably less than 30 nM. The compounds are also capable of blocking the production of some pro-inflammatory cytokines such as, for example, TNFα.

Thus, they can be used in the treatment of allergic, inflammatory and immunological diseases, as well as those diseases or conditions where the blockade of pro-inflammatory cytokines or the selective inhibition of PDE 4 could be of benefit. These disease states include asthma, chronic obstructive pulmonary disease, allergic rhinitis, rheumatoid arthritis, osteoarthritis, osteoporosis, bone-formation disorders, glomerulonephritis, multiple sclerosis; ankylosing spondylitis, Graves ophtalmopathy, myasthenia gravis, diabetes insipidus, graft rejection, gastrointestinal disorders such as irritable bowel disease, ulcerative colitis, or Crohn disease, septic shock, adult distress respiratory syndrome, and skin diseases such as atopic dermatitis, contact dermatitis, acute dermatomyositis and psoriasis. They can also be used as improvers of cerebrovascular function as well as in the treatment of other CNS related diseases such as dementia, Alzheimer's disease, depression, and as nootropic agents.

The compounds of the present invention are also of benefit when administered in combination with other drugs such as steroids and immunosuppressive agents, such as cyclosporin A, rapamycin or T-cell receptor blockers. In this case the administration of the compounds allows a reduction Of the dosage of the other drugs, thus preventing the appearance of the undesired side effects associated with both steroids and immunosuppressants.

Like other PDE4 inhibitors (see references above) the compounds of the invention can also be used for blocking, after preventive and/or curative treatment, the erosive and ulcerogenic effects induced by a variety of etiological agents, such as antiinflammatory drugs (steroidal or non-steroidal antiinflammatory agents), stress, ammonia, ethanol and concentrated acids.

They can be used alone or in combination with antacids and/or antisecretory drugs in the preventive and/or curative treatment of gastrointestinal pathologies like drug-induced ulcers, peptic ulcers, H. Pylori-related ulcers, esophagitis and gastro-esophageal reflux disease.

They can also be used in the treatment of pathological situations where damage to the cells or tissues is produced through conditions like anoxia or the production of an excess of free radicals. Examples of such beneficial effects are the protection of cardiac tissue after coronary artery occlusion or the prolongation of cell and tissue viability when the compounds of the invention are added to preserving solutions intended for storage of transplant organs or fluids such as blood or sperm. They are also of benefit on tissue repair and wound healing.

Accordingly, the pyridazin-3(2H)-one derivatives of the invention and pharmaceutically acceptable salts thereof, and pharmaceutical compositions comprising such compound and/or salts thereof, may be used in a method of treatment of disorders of the human body which comprises administering to a patient requiring such treatment an effective amount of a pyridazin-3(2H)-one derivative of the invention or a pharmaceutically acceptable salt thereof.

The results of table I show that the compounds of formula (I) are potent inhibitors of phosphodiesterase 4 (PDE4) and are therefore useful in the treatment or prevention of pathological conditions, diseases and disorders known to be susceptible of amelioration by inhibition of PDE4, such as asthma, chronic obstructive pulmonary disease, rheumatoid arthritis, atopic dermatitis, psoriasis or irritable bowel disease.

The compounds of the present invention can also be used in combination with other drugs known to be effective in the treatment of these diseases. For example, in combination with steroids, immunosuppressive agents, T-cell receptor blockers and/or antiinflammatory drugs for simultaneous, separate or sequential use in the treatment of the human or animal body.

Accordingly, another embodiment of he invention is the use of the compounds of formula (I) in the manufacture of a medicament for treatment or prevention of pathological conditions, diseases and disorders known to be susceptible of amelioration by inhibition of PDE4, as well as a method for treating a subject afflicted with a pathological condition or disease susceptible to amelioration by inhibition of PDE4, which comprises administering to said subject an effective amount of a compound of formula (I).

The present invention also provides pharmaceutical compositions which comprise, as an active ingredient, at least a pyridazin-3(2H)-one derivative of formula (I) or a pharmaceutically acceptable salt thereof in association with at least one pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Compositions for topical administration may take the form of ointments, creams or lotions, all containing the compound of the invention; such preparations may be made by methods well-known in the art.

Effective doses are normally in the range of 10-600 mg of active ingredient per day. Daily dosage may be administered in one or more treatments, preferably from 1 to 4 treatments, per day.

The present invention will be further illustrated by the following examples. The examples are given by way of illustration only and are not to be construed as a limiting.

The syntheses of the compounds of the invention and of the intermediates for use therein are illustrated by the following Examples (including Preparation Examples (Preparations 1 to 99)) which do not limit the scope of the invention in way.

$^1$H Nuclear Magnetic Resonance Spectra were recorded on a Varian Gemini 300 spectrometer.

Low Resolution Mass Spectra (m/z) were recorded on a Micromass ZMD mass spectrometer using ESI ionization.

Melting points were recorded using a Perkin Elmer DSC-7 apparatus.

The chromatographic separations were obtained using a Waters 2695 or 2795 system equipped with a Symmetry C18 (2.1×10 mm, 3.5 mM) column using one of the following methods:

Method A). The mobile phase was formic acid (0.4 mL), ammonia (0.1 mL), methanol (500 mL) and acetonitrile (500 mL) (B) and formic acid (0.46 mL), ammonia (0.115 mL) and water (1000 mL) (A): initially from 0% to 95% of B in 10.5 min at a flow rate of 0.4 ml/min, from 10.5 to 11.0 min the flow rate was lineary increased to 0.8 ml/min and maintained in these conditions until minute 12.0. Reequilibration time between two injections was 2 min. The injection volume was 5 microliter. Diode array chromatograms were collected at 210 nM.

Method B) The mobile phase was formic acid (0.4 mL), ammonia (0.1 mL), methanol (500 mL) and acetonitrile (500 mL) (B) and formic acid (0.46 mL), ammonia (0.115 mL) and water (1000 mL) (A): initially from 0% to 95% of B in 20 min, and then 4 min. with 95% of B. The reequilibration time between two injections was 5 min. The flow rate was 0.4 mL/min. The injection volume was 5 microliter. Diode array chromatograms were collected at 210 nM.

PREPARATION EXAMPLES

Preparation 1 (Scheme 7)

Ethyl 5-methyl-4-(pyridin-3-ylcarbonyl)isoxazole-3-carboxylate

To an ice-cooled solution of sodium ethoxide (5.9 g, 110 mmol) in absolute ethanol (150 mL) 1-pyridin-3-yl-butane-1,3-dione (Ohta, S. et al., *Chem. Pharm. Bull.*, 1981, 29, 2762) (16.4 g, 100 mmol) was added portionwise and the mixture was stirred at 0° for 30 min. A solution of ethyl chloro(hydroximino)acetate (16.7 g, 110 mmol) in absolute ethanol (50 mL) was added dropwise and the final mixture was stirred at room temperature overnight. The mixture was concentrated and the residue thus obtained was suspended in ethyl acetate, washed with saturated —NH4Cl solution, water and brine, dried and concentrated to yield the title compound: (25.7 g, 98% yield) as a yellow solid.

δ(CDCl$_3$): 1.15 (t, 3H), 2.58 (s, 3H), 4.18 (q, 2H), 7.42 (m, 1H), 8.10 (m, 1H), 8.81 (m, 1H), 8.95 (m, 1H).

Preparation 2 (Scheme 7)

Ethyl 5-methyl-4-(pyridin-2-ylcarbonyl)isoxazole-3-carboxylate

Obtained as a yellow solid (99%) from 1-pyridin-2-yl-butane-1,3-dione (Chiswell et al., *Inorg. Chim. Acta* 1972, 6, 629) and ethyl chloro(hydroximino)acetate following the experimental procedure described in Preparation 1.

LRMS: m/Z 261 (M+1)$^+$.

Preparation 3 (Scheme 4)

3-Methyl-4-pyridin-3-ylisoxazolo[3,4-d]pyridazin-7(6H)-one

Hydrazine monohydrate (6.0 g, 120 mmol) was added dropwise to a solution of the title compound of Preparation 1 (26.0 g, 100 mmol) in dry-ethanol (500 mL) and the resulting mixture was stirred overnight. After cooling with an ice bath, a precipitate was formed which was collected by filtration and washed with diethyl ether to yield the title compound (17.2 g, 76% yield) as a yellow solid.

δ(DMSO-d6): 2.57 (s, 3H), 7.58 (m, 1H), 8.10 (m, 1H), 8.72 (d, 1H), 8.80 (s,1H).

Preparation 4 (Scheme 4)

3-Methyl-4-pyridin-2-ylisoxazolo[3,4-d]pyridazin-7(6H)-one

Obtained as a yellow solid (60%) from the title compound of Preparation 2 using the experimental procedure described in Preparation 3.

δ(DMSO-d6): 2.92 (s, 3H), 7.58 (m, 1H), 7.98 (m, 2H), 8.77 (m, 1H).

Preparation 5 (Scheme 4)

6-Ethyl-3-methyl-4-pyridin-3-ylisoxazolo[3,4-d]pyridazin-7(6H)-one

To a suspension of the title compound of Preparation 3 (17.2 g, 75.6 mmol) and anhydrous potassium carbonate (62 g, 453 mmol) in dry dimethylformamide (100 mL) was added ethyl bromide (57.0 g, 525 mmol) and the resulting mixture stirred at r.t. overnight. The mixture was concentrated and the residue thus obtained was suspended in dichloromethane, washed with water and brine, dried and concentrated to yield the title compound (8.44 g, 44% yield) as a yellow solid.

δ(CDCl$_3$): 1.42 (t, 3H), 2.58 (s, 3H), 4.23 (q, 2H), 7.55 (m,1H), 7.92 (m,1H), 8.80 (m, 2H).

Preparation 6 (Scheme 4)

6-Ethyl-3-methyl-4-pyridin-2-ylisoxazolo[3,4-d]pyridazin-7(6H)-one

Obtained (27%) from the title compound from Preparation 4 following the experimental procedure described in Preparation 5.

δ(CDCl₃): 1.41 (t, 3H), 2.98 (s, 3H), 4.33 (q, 2H), 7.42 (m,1H), 7.92 (m,1H), 8.05 (m, 1H), 8.68 (m, 1H).

Preparation 7 (Scheme 4)

6-Ethyl-3-methyl-4-pyridin-4-ylisoxazolo[3,4-d]pyridazin-7(6H)-one

Obtained (82%) from 3-methyl-4-pyridin-4-yl-6H-isoxazolo[3,4-d]pyridazin-7-one (V. Dal Piaz et al., *J. Pharmac. Sci.*, 1991, 80, 341-348) following the experimental procedure described in Preparation 5.

δ(CDCl₃): 1.39 (t, 3H), 2.58 (s, 3H), 4.31 (q, 2H), 7.52 (d, 2H), 8.80 (d, 2H).

Preparation 8 (Scheme 4)

6-(Cyclopropylmethyl)-3-methyl-4-pyridin-3-ylisoxazolo[3,4-d]pyridazin-7(6H)-one Obtained (44%) from the title compound from Preparation 3 and cyclopropylmethyl bromide following the experimental procedure described in Preparation 5.

δ(DMSO-d₆): 0.40 (m, 4H), 1.32 (m, 1H), 2.58 (s, 3H), 4.00 (d, 2H), 7.60 (m,1H), 8.10 (m,1H), 8.78 (m, 1H), 8.11 (m, 1H).

Preparation 9 (Scheme 4)

6-(Cyclopropylmethyl)-3-methyl-4-pyridin-2-ylisoxazolo[3,4-d]pyridazin-7(6H)-one Obtained (98%) from the title compound from Preparation 4 and cyclopropylmethyl bromide following the experimental procedure described in Preparation 5.

δ(CDCl₃): 0.55 (m, 4H), 1.42 (m, 1H), 2.98 (s, 3H), 4.03 (d, 2H), 7.40 (m, 1H), 7.82 (m,1H), 8.01 (m, 1H), 8.72 (m, 1H).

Preparation 10 (Scheme 4)

6-(Cyclopropylmethyl)-3-methyl-4-pyridin-4-ylisoxazolo[3,4-d]pyridazin-7(6H)-one Obtained (85%) from 3-methyl-4-pyridin-4-yl-6H-isoxazolo[3,4-d]pyridazin-7-one (V. Dal Piaz et al., *J. Pharmac. Sci.*, 1991, 80, 341-348) and cyclopropylmethyl bromide following the experimental procedure described in Preparation 5.

δ(DMSO-d₆): 0.54 (m, 4H), 1.35 (m, 1H), 2.58 (s, 3H), 4.01 (d, 2H), 7.65 (d, 2H), 8.78 (d, 2H).

Preparation 11 (Scheme 4)

6-(2-Hydroxyethyl)-3-methyl 4-pyridin-3-ylisoxazolo[3,4-d]pyridazin-7(6H)-one

Obtained (66%) from the title compound from Preparation 3 and 2-bromoethanol following the experimental procedure described in Preparation 5.

δ(DMSO-d₆): 2.60 (s, 3H), 4.05 (m, 2H), 4.41 (t, 3H), 7.52 (m,1H), 7.95 (m, 1H), 8.10 (m,1H), 8.60 (m, 2H).

Preparation 12 (Scheme 4)

6-(2-Hydroxyethyl)-3-methyl-4-pyridin-2-ylisoxazolo[3,4-d]pyridazin-7(6H)-one

Obtained (92%) from the title compound from Preparation 4 and 2-bromoethanol following the experimental procedure described in Preparation 5.

δ(CDCl₃): 2.41 (m, 1H), 2.97 (s, 3H), 4.13 (m, 2H), 4.43 (m, 2H), 7.42 (m, 1H), 7.85 (m,1H), 8.00 (m, 1H), 8.70 (m, 1H).

Preparation 13 (Scheme 4)

6-(2-Hydroxyethyl)-3-methyl-4-pyridin-4-ylisoxazolo[3,4-d]pyridazin-7(6H)-one

Obtained (70%) from 3-methyl-4-pyridin-4-yl-6H-isoxazolo[3,4-d]pyridazin-7-one (V. Dal Piaz et al., *J. Pharmac. Sci.*, 1991, 80, 341-348) and 2-bromoethanol following the experimental procedure described in Preparation 5.

δ(DMSO-d₆): 2.60 (s, 3H), 3.78 (q, 2H), 4.18 (t, 2H), 4.83 (t, 1H), 7.68 (d, 2H), 8.78 (d, 2H).

Preparation 14 (Scheme 1)

5-Acetyl-4-amino-2-ethyl-6-pyridin-3-ylpyridazin-3(2H)-one

A mixture of the title compound of Preparation 5 (8.44 g, 33 mmol) and 10% palladium on charcoal (1.7 g) in ethanol (400 mL) was shaken under hydrogen at room temperature and 2 bar for 6 h. The catalyst was filtered off and the solvent was removed under reduced pressure to yield the title compound (6.43 g, 76% yield).

δ(CDCl₃): 1.42 (t, 3H), 1.82 (s, 3H), 4.25 (q, 2H), 7.45 (m,1H), 7.80 (m,1H), 8.70 (m, 2H).

Preparation 15 (Scheme 1)

5-Acetyl-4-amino-2-ethyl-6-pyridin-2-pyridazin-3(2H)-one

Obtained after column chromatography purification (40%) from the title product of Preparation 6 following the procedure described in Preparation 14.

δ(CDCl₃): 1.41 (t, 3H), 1.80 (s, 3H), 4.30 (q, 2H), 7.05 (bs, 2H), 7.38(m, 1H), 7.82 (m, 2H), 8.62 (m, 1H).

Preparation 16 (Scheme 1)

5-Acetyl-4-amino-2-ethyl-6-pyridin-4-ylpyridazin-3(2H)-one

Obtained (92%) from the title product of Preparation 7 following the procedure described in Preparation 14.

δ(CDCl₃): 1.37 (t, 3H), 1.82 (s, 3H), 4.24 (q, 2H), 7.44 (d, 2H), 8.70 (d, 2H).

Preparation 17 (Scheme 1)

5-Acetyl-4-amino-2-(cyclopropylmethyl)-6-pyridin-3-ylpyridazin-3(2H)-one

A mixture of the title compound of Preparation 9 (1.0 g, 3.50 mmol), 10% palladium on charcoal (56 mg) and ammonium formate (3.97 g, 63 mmol) in methanol (30 mL) was refluxed for 2 hours. Then the catalyst was filtered off and the solvent was removed under reduced pressure. The resulting residue was partitioned between dichloromethane and water and the organic layer was washed with water twice. It was dried and solvent removed under reduced pressure to yield the title compound (471 mg, 47%).

δ(CDCl₃): 0.45 (m, 4H), 1.37 (m, 1H), 1.81 (s, 3H), 4.02 (d, 2H), 7.40 (m,1H), 7.80 (m,1H), 8.72 (m, 2H).

Preparation 18 (Scheme 1)

5-Acetyl-4-amino-2-(cyclopropylmethyl)-6-pyridin-2-ylpyridazin-3(2H)-one

Obtained (90%) from the title product of Preparation 9 following the procedure described in Preparation 17.

δ(CDCl₃): 0.45 (m, 4H), 1.38 (m, 1H), 1.80 (s, 3H), 4.03 (d, 2H), 7.01 (bs, 2H), 7.52 (m, 1H), 7.83 (m,2H), 8.62; (m, 1H).

Preparation 19 (Scheme 1)

5-Acetyl-4-amino-2-(cyclopropylmethyl)-6-pyridin-4-ylpyridazin-3(2H)-one

Obtained (96%) from the title product of Preparation 10 following the procedure described in Preparation 14.

δ(DMSO-d₆): 0.41 (m, 4H), 1.28 (m, 1H), 1.82 (s, 3H), 3.97 (d, 2H), 7.42 (d, 2H), 7.82 (bs, 2H), 8.65 (d, 2H).

Preparation 20 (Scheme 1)

5-Acetyl-4-amino-2-(2-hydroxyethyl)-6-pyridin-3-ylpyridazin-3(2H)-one

Obtained (50%) from the title product of Preparation 11 following the procedure described in Preparation 17. It was refluxed for 2 hours and then stirred at room temperature overnight.

δ(CDCl₃): 1.78 (s, 3H), 4.22 (m, 2H), 4.41 (m, 3H), 7.45 (m,1H), 7.80 (m, 1H), 8.78 (m,2H).

Preparation 21 (Scheme 1)

5-Acetyl-4-amino-2-(2-hydroxyethyl)-6-pyridin-2-ylpyridazin-3(2H)-one

Obtained (64%) from the title product of Preparation 12 following the procedure described in Preparation 17.

δ(CDCl₃): 1.78 (s, 3H), 4.13 (t, 2H), 4.40 (t, 2H), 7.10 (bs, 2H), 7.38 (m, 1H), 7.82 (m, 2H), 8.62 (m, 1H).

Preparation 22 (Scheme 1)

5-Acetyl-4-amino-2-(2-hydroxyethyl)-6-pyridin-4-ylpyridazin-3(2H)-one

Obtained (55%) from the title product of Preparation 13 following the procedure described in Preparation 14.

δ(DMSO-d₆): 1.82 (s, 3H), 3.75 (m, 2H), 4.18 (t, 2H), 4.81 (bs, 1H), 7.48 (d, 2H), 7.85 (bs, 1H), 8.63 (d, 2H).

Preparation 23 (Scheme 7)

Ethyl 5-methyl-4-thiene-2-carbonyl)isoxazole-3-carboxylate

Obtained as a solid (50%) from 1-thiophen-2-yl-butane-1,3-dione (Gash, V. W.; *Can J. Chem.,* 1967, 45, 2109-12) and ethyl chloro(hydroximino)acetate following the experimental procedure described in Preparation 1.

δ(CDCl₃): 1.15 (t, 3H), 2.55 (s, 3H), 4.20 (q, 2H), 7.20-7.70 (m, 3H).

Preparation 24 (Scheme 4)

3-Methyl-4-thien-2-ylisoxazolo[3,4-d]pyridazin-7(6H)-one

Obtained as a solid (57%) from the title compound of Preparation 23 using the experimental procedure described in Preparation 3.

δ(CDCl₃): 2.78 (s, 3H), 7.18-7.59 (m, 3H), 9.62 (s, 1H).

Preparation 25 (Scheme 4)

6-Ethyl-3-methyl-4-thien-2-ylisoxazolo[3,4-d]pyridazin-7(6H)-one

Obtained (83%) from the title compound from Preparation 24 following the experimental procedure described in Preparation 5.

δ(CDCl₃): 1.41 (t, 3H), 2.78 (s, 3H), 4.28 (q, 2H), 7.18-7.59 (m, 3H).

Preparation 26 (Scheme 1)

5-Acetyl-4-amino-2-ethyl-6-thien-2-ylpyridazin-3(2H)-one

Obtained (50%) from the title product of Preparation 25 following the procedure described in Preparation 14.

δ(CDCl₃): 1.41 (t, 3H), 1.98 (s, 3H), 4.22 (q, 2H), 7.10-7.41 (m, 3H).

Preparation 27 (Scheme 7)

Ethyl 4-(4-fluorobenzoyl)-5-methylisoxazole-3-carboxylate

Obtained (95%) from 1-(4-fluorophenyl)butane-1,3-dione (Joshi, K. C.; Pathak, V. N.; Garg, U. *J. Indian Chem. Soc.* 1983, 60, 1074-1076) and ethyl chloro(hydroximino)acetate following the experimental procedure described in Preparation 1.

δ(CDCl₃): 1.1 (t, 3H), 2.50 (s, 3H), 4.20 (q, 2H), 7.20 (m, 2H), 7.80 (m, 2H).

Preparation 28 (Scheme 4)

4-(4-Fluorophenyl)-3-methylisoxazolo[3,4-d]pyridazin-7(6H)-one

Obtained (87%) from the title compound of Preparation 27, using the experimental procedure described in Preparation 3.

δ(CDCl₃): 2.55 (s, 3H), 7.30 (m, 2H), 7.60 (m, 2H).

Preparation 29 (Scheme 4)

6-Ethyl-4-(4-fluorophenyl)-3-methylisoxazolo[3,4-d]pyridazin-7(6H)-one

To a suspension of the title compound of Preparation 28 (0.49 g, 2.0 mmol) and anhydrous potassium carbonate (0.55 g, 4.0 mmol) in dry dimethylformamide (5.3 mL) was added ethyl bromide (0.44 g, 4.03 mmol) and the resulting mixture heated at 110° C. for 40 minutes. Then ice-water was added (30 mL) and the resulting precipitate collected by filtration to afford the title compound (0.47 g, 86%) as a yellow solid.

δ(CDCl$_3$): 1.40 (t, 3H), 2.58 (s, 3H), 4.23 (q, 2H), 7.20 (m,2H), 7.58 (m,2H).

Preparation 30 (Scheme 2)

5-Acetyl-2-ethyl-6-(4-fluorophenyl)-4-nitropyridazin-3(2H)-one

To a stirred suspension of the title compound of Preparation 29 (0.5 g, 1.83 mmol) in a mixture of acetic acid (7.3 mL), water (7.3 mL) and nitric acid (2.5 mL), cerium ammonium nitrate (6.0 g, 11 mmol) was added portionwise during 40 min. Addition of ice-cold water gave a crude precipitate which was filtered and washed with cold water to yield the title product (45% yield).

δ(CDCl$_3$): 1.43 (t, 3H), 2.20 (s, 3H), 4.40 (q, 2H), 7.20 (m, 2H), 7.48 (m, 2H).

Preparation 31 (Scheme 7)

Ethyl 4-(3-fluorobenzoyl)-5-methylisoxazole-3-carboxylate

Obtained (79%) from 1-(3-fluorophenyl)butane-1,3-dione (Joshi, K. C.; Pathak, V. N.; Garg, U. *J. Indian Chem. Soc.* 1983, 60, 1074-1076) and ethyl chloro(hydroximino)acetate following the experimental procedure described in Preparation 1.

δ(CDCl$_3$): 1.10 (t, 3H), 2.60 (s, 3H), 4.15 (q, 2H), 7.30 (m, 4H).

Preparation 32 (Scheme 4)

4-(3-Fluorophenyl)-3-methylisoxazolo[3,4-d]pyridazin-7(6H)-one

Obtained (81%) from the title compound of Preparation 31 following the experimental procedure described in Preparation 3.

δ(CDCl$_3$): 2.60 (s, 3H), 7.3 (m, 4H), 9.90 (s, 1H).

Preparation 33 (Scheme 4)

6-Ethyl-4-(3-fluorophenyl)-3-methylisoxazolo[3,4-d]pyridazin-7(6H)-one

Obtained (84%) from the title compound from Preparation 32 following the experimental procedure described in Preparation 5.

δ(CDCl$_3$): 1.40 (t, 3H), 2.58 (s, 3H), 4.30 (q, 2H), 7.30 (m, 3H), 7.50 (m, 1H).

Preparation 34 (Scheme 4)

6-(Cyclopropylmethyl)-4-(3-fluorophenyl)-3-methylisoxazolo[3,4-d]pyridazin-7(6H)-one Obtained (37%) from the title compound from Preparation 32 and cyclopropylmethyl bromide following the experimental procedure described in Preparation 5. The product was purified by column chromatography.

δ(CDCl$_3$): 0.52 (m, 4H), 1.38 (m, 1H), 2.58 (s, 3H), 4.07 (d, 2H), 7.30 (m, 3H), 7.55 (m, 1H).

Preparation 35 (Scheme 4)

4-(3-Fluorophenyl)-6-isopropyl-3-methylisoxazolo[3,4-d]pyridazin-7(6H)-one

To a stirred solution of the title compound of preparation 32 (2.0 g, 8.16 mmol) in 30 mL of dry THF, triphenylphosphine (2.16 g, 8.24 mmol) and isopropanol (0.68 mL, 8.97 mmol) were added. The mixture was cooled to 0° C. and then diethylazadicarboxylate (1.3 mL, 8.24 mmol) was added dropwise. The final mixture was let to warm up to room temperature and the stirred for 24 h. Finally solvent was removed and the final product was isolated by column chromatography in a 37% yield.

δ(CDCl$_3$): 1.38 (d, 6H), 2.58 (s, 3H), 5.41 (h, 1H), 7.32 (m, 3H), 7.52 (m, 1H).

Preparation 36 (Scheme 2)

5-Acetyl-2-ethyl-6-(3-fluorophenyl)-4-nitropyridazin-3(2H)-one

Obtained (40%) from the title product of Preparation 33 following the experimental procedure described in Preparation 30.

δ(CDCl$_3$): 1.50 (t, 3H), 2.20 (s, 3H), 4.40 (q, 2H), 7.20 (m, 3H), 7.46 (m, 1H).

Preparation 37 (Scheme 2)

5-Acetyl-2-(cyclopropylmethyl)-6-(3-fluorophenyl)-4-nitropyridazin-3(2H)-one

Obtained (23%) from the title product of Preparation 34 following the experimental procedure described in Preparation 30.

δ(CDCl$_3$): 0.54 (m, 4H), 1.51 (m, 1H), 2.21 (s, 3H), 4.16 (d, 2H), 7.22 (m, 3H), 7.45 (m, 1H).

Preparation 38 (Scheme 2)

5-Acetyl-6-(3-fluorophenyl)-2-isopropyl-4-nitropyridazin-3(2H)-one

Obtained (40%) from the title product of Preparation 35 following the experimental procedure described in Preparation 30.

δ(CDCl$_3$): 1.44 (d, 6H), 2.20 (s, 3H), 5.45 (h, 1H), 7.16 (m, 3H), 7.50 (m, 1H).

Preparation 39 (Scheme 4)

4-(3-Chlorophenyl)-6-(cyclopropylmethyl)-3-methylisoxazolo[3,4-d]pyridazin-7(6H)-one Obtained (97%) from 4-(3-chlorophenyl)-3-methyl-6H-isoxazolo[3,4-d]pyridazin-7-one (Dal Piaz, V et al., *J. Med. Chem.* 1997, 40, 1417) and cyclopropylmethyl bromide following the experimental procedure described in Preparation 5. The product was purified by column chromatography.

LRMS: m/z 316 (M+1)$^+$.

Preparation 40 (Scheme 2)

5-Acetyl-6-(3-chlorophenyl)-2-(cyclopropylmethyl)-4-nitropyridazin-3(2H)-one Obtained (21%) from the title product of Preparation 39 following the experimental procedure described in Preparation 30.

LRMS: m/z 348 (M+1)$^+$.

Preparation 41 (Scheme 7)

Ethyl 4-[ethoxy(oxo)acetyl]-5-methylisoxazole-3-carboxylate

To a well stirred solution of sodium methoxide (10.5 g, 0.15 mol) in 100 mL of dry ethanol, diethyl oxalate (21 mL, 0.15 mol) was added dropwise and the mixture was warmed to 45° C. Then dry acetone (45 mL, 0.60 mol) was added and after 30 min the final mixture was refluxed for 3 hours and stirred at room temperature overnight. Finally solvent was removed and 100 mL of fresh dry ethanol were added. The mixture was cooled to, 0° C. and a solution of ethyl chloro (hydroximino)acetate (27.2 g, 0.18 mol) in 25 mL of dry ethanol was added dropwise. Then it was stirred at 0° C. for 30 min and at room temperature for 3 days. Finally solvent was removed and the crude thus obtained was partitioned between ethyl acetate and water. It was dried and solvent removed to yield the desired product (90%) as an orange oil.

$\delta$(CDCl$_3$): 1.39 (m, 6H), 2.68 (s; 3H), 4.40 (m, 4H).

Preparation 42 (Scheme 5)

Ethyl 3-methyl-7-oxo-6,7-dihydroisoxazolo[3,4-d]pyridazine 4-carboxylate

Obtained as a solid (57%) from the title compound of Preparation 41 using the experimental procedure described in Preparation 3.

$\delta$(CDCl$_3$): 1.41 (t, 3H), 3.01 (s, 3H), 4.50 (q, 2H), 6.30 (s, 1H).

Preparation 43 (Scheme 5)

Ethyl 6-ethyl-3-methyl-7-oxo-6,7-dihydroisoxazolo[3,4-d]pyridazine-4-carboxylate Obtained (90%) from the title compound of Preparation 42 following the experimental procedure described in Preparation 5.

$\delta$(CDCl$_3$): 1.42 (m, 6H), 3.00 (s, 3H), 4.25 (q, 2H), 4.48 (q, 2H)

Preparation 44 (Scheme 6)

Ethyl 4-acetyl-5-amino-1-ethyl-6-oxo-1,6-dihydro-pyridazine-3-carboxylate

Obtained (98%) from the title product of Preparation 43 following the procedure described in Preparation 14.

$\delta$(CDCl$_3$): 1.38 (m, 6H), 2.30 (s, 3H), 4.22 (q, 2H), 4.42 (q, 2H), 7.50 (bs, 2H).

Preparation 45 (Scheme 6)

Ethyl 4-acetyl-5-[(3-chlorophenyl)amino]-1-ethyl-6-oxo-1,6-dihydropyridazine-3-carboxylate A mixture of the title compound of Preparation 44 (506 mg, 2.0 mmol), 3-chlorophenylboronic acid (626 mg, 4.0 mmol), anhydrous cupric acetate (540 mg, 3.0 mmol), triethylamine (0.56 mL, 4.0 mmol) and activated molecular sieves (1.6 g, 4 Å) in dry dichloromethane (25 mL) was stirred under air exposure at room temperature for 48 h. The reaction was filtered and the solvent removed under reduced pressure. The resulting residue was recrystallized from ethyl acetate (202 mg, 64% yield).

$\delta$(CDCl$_3$): 1.38 (t, 3H), 1.42 (t, 3H), 2.01 (s, 3H), 4.42 (m, 4H), 6.97 (m, 1H), 7.16 (m, 1H), 7.35 (m, 2H), 7.05 (s, 1H).

Preparation 46 (Scheme 5)

6-Ethyl-3-methyl-7-oxo-6,7-dihydro-isoxazolo[3,4-d]pyridazine-4-carboxylic acid To a stirred solution of the title compound of preparation 43 (2.73 g, 11 mmol) in 90 mL of a 2:1 methanol/THF mixture, a solution of lithium hydroxide (1.87 g, 45 mmol) in 6 mL of water was added dropwise. The final mixture was stirred at room temperature for 5 hours and then diluted with some water and acidified with HCl 2N. It was extracted with ethyl acetate, dried and solvent removed to yield (89%) the title product.

$\delta$(DMSO-d$_3$): 1.35 (t, 3H), 2.98 (s, 3H), 4.15 (q, 2H).

Preparation 47 (Scheme 5)

4-(1,3-Benzoxazol-2-yl)-6-ethyl-3-methylisoxazolo[3,4-d]pyridazin-7(6H)-one

To a 100° C. pre-warmed suspension of PPSE (6 g) in 10 mL of 1,2-dichlorobenzene, a solution of 2-aminophenol (0.48 g, 4.4 mmol) in 10 mL of 1,2-dichlorobenzene was added and the mixture was stirred for a while. Then the title compound of preparation 46 (1.08 g, 4.84 mmol) was added in portions and the mixture was refluxed overnight. Then it was let to cool down and poured onto ice-water vigorously stirring. It was neutralized with potassium carbonate and extracted with dichloromethane. The organic layer was dried and solvent removed to yield a crude product that was purified by column chromatography. The title product was isolated (44%).

$\delta$(CDCl$_3$): 1.42 (t, 3H), 3.25 (s, 3H), 4.38 (q, 2H), 7.41 (m, 2H), 7.70 (m, 1H), 7.82 (m, 1H).

Preparation 48 (Scheme 1)

5-Acetyl-4-amino-6-(1,3-benzoxazol-2-yl)-2-ethylpyridazin-3(2H)-one

Obtained (98%) from the title product of Preparation 47 following the procedure described in Preparation 14.

Preparation 49

5-Acetyl-4-amino-2-ethyl-6-phenylpyridazin-3(2H)-one

A mixture of 6-ethyl-3-methyl-4-phenylisoxazolo[3,4-d]pyridazin-7(6H)-one (Dal Piaz, V et al, *J. Med. Chem.* 1997, 40, 1417) (2.0 g, 7.83 mmol) and 10% palladium on charcoal (400 mg) in ethanol (400 ml) was shaken under hydrogen at room temperature and 2 bar for 3 h. The catalyst was filtered off and the solvent was removed under reduced pressure to yield the title compound (1.97 g, 98% yield).

m.p. 150.8-152.7° C. δ(CDCl$_3$): 1.43 (t, 3H), 1.67 (bs, 2H), 1.78 (s, 3H), 4.26 (q, 2H), 7.45 (s, 5H).

Preparation 50

5-Acetyl-4-amino-6-thiophen-2-yl-2H-pyridazin-3-one

Obtained (78%) from the title compound of Preparation 24 following the procedure described in Preparation 17.

δ(CDCl$_3$): 2.00 (s, 3H), 7.07-7.50 (m, 3H).

Preparation 51

5-Acetyl-4-amino-2-cyclopropylmethyl-thiophen-2-yl-2H-pyridazin-3-one

Obtained (60%) from the title compound of Preparation 50 and cyclopropylmethyl bromide following the procedure described in Preparation 5.

δ(CDCl$_3$): 0.42-0.62 (m, 4H), 1.40 (m, 1H), 1.99 (s, 3H), 4.06 (d, 2H), 7.04-7.50 (m, 3H).

Preparation 52

Ethyl 5-methyl-4-(thien-3-ylcarbonyl)isoxazole-3-carboxylate

Obtained as a solid (70%) from 1-thiophen-3-yl-butane-1,3-dione (Hams, J; Levine, H; *J. Am. Chem. Soc.*, 1948, 70, 3360) and ethyl chloro(hydroximino)acetate following the experimental procedure described in Preparation 1.

δ(CDCl$_3$): 1.17 (t, 3H), 2.58 (s, 3H), 4.20 (q, 2H), 7.36-7.70 (m, 3H).

Preparation 53

3-Methyl-4-thien-3-ylisoxazolo[3,4-d]pyridazin-7(6H)-one

Obtained as a solid (38%) from the title compound of Preparation 52 using the experimental procedure described in Preparation 3.

δ(CDCl$_3$): 2.60 (s, 3H), 7.36-8.00 (m, 3H), 12.62 (s, 1H).

Preparation 54

6-Ethyl-3-methy-4-thien-3 ylisoxazolo[3,4-d]pyridazin-7(6H)-one

Obtained (71%) from the title compound from Preparation 53 following the experimental procedure described in Preparation 5.

δ(CDCl$_3$): 1.42 (t, 3H), 2.67 (s, 3H), 4.26 (q, 2H), 7.30-7.62 (m, 3H).

Preparation 55

5-Acetyl-4-amino-2-ethyl-6-thien-3-ylpyridazin-3(2H)-one

Obtained (84%) from the title product of Preparation 54 following the procedure described in Preparation 14.

δ(CDCl$_3$): 1.41 (t, 3H), 1.88 (s, 3H), 4.26 (q, 2H), 7.17-7.48 (m, 3H).

Preparation 56

6-Ethyl-4-phenyl-3-styryl-6H-isoxazolo[3,4-d]pyridazin-7-one

To a freshly prepared solution of sodium methoxide (108 mg, 1.96 mmol) in methanol (2 ml), a solution of 6-ethyl-3-methyl-4-phenyl-6H-isoxazolo[3,4-d]pyridazin-7-one (500 mg, 1.96 mmol) (Dal Piaz, V.; Giovannoni, M. P.; Castellana, C.; et al, *J. Med. Chem.* 1997, 40, 1417-1421) in of dry methanol (2 ml) was added and the mixture was stirred for a while. Then, benzaldehyde (0.40 ml, 3.92 mmol) was added dropwise and the final mixture was refluxed for 2 hours. The resulting suspension was let to cool down and the final product (514 mg, 76%-yield) was collected by filtration.

δ(CDCl$_3$): 1.40 (t, 3H), 4.31, (q, 2H), 6.80 (d, 1H), 7.35 (m, 5H), 7.68 (m, 6H).

Preparation 57

6-Ethyl-4-phenyl-3-(2-thiophen-3-yl-vinyl)-6H-isoxazolo[3,4-d]pyridazin-7-one

Obtained (75%) from 6-ethyl-3-methyl-4-phenyl-6H-isoxazolo[3,4-d]pyridazin-7-one (500 mg, 1.96 mmol) (Dal Piaz, V.; Giovannoni, M. P.; Castellana, C.; et al, *J. Med. Chem.* 1997, 40, 1417-1421) and thiophene-3-carbaldehyde following the procedure described in Preparation 56.

δ(CDCl$_3$): 1.42 (t, 3H), 4.30 (q, 2H), 6.58 (d, 1H), 6.98 (d, 1H), 7.28 (m, 1H), 7.42 (m, 1H), 7.63 (m, 6H).

Preparation 58

4-Amino-2-ethyl-6-phenyl-5-(3-phenylpropionyl)pyridazin-3(2H)-one

A mixture of the title compound of preparation 56 (514 mg, 1.50 mmol) and 10% palladium on charcoal (100 mg) in ethanol (100 ml) was shaken under hydrogen at room temperature and 2 bar overnight. The catalyst was filtered off and the solvent was removed under reduced pressure to yield the title compound (487 mg, 95% yield).

m.p. 115.1-116.1° C. δ(CDCl$_3$): 1.40 (t, 3H), 2.28 (t, 2H), 2.68 (t, 2H), 4.25 (q, 2H), 6.78 (m, 2H), 7.05 (m, 3H), 7.45 (m, 5H).

Preparation 59

4-Amino-2-ethyl-6-phenyl-5-(3-thien-3-ylpropanoyl)pyridazin-3(2H)-one

Obtained (67%) from the title compound of Preparation 57 following the procedure described in Preparation 58.

δ(CDCl$_3$): 1.41 (t, 3H), 2.30 (t, 2H), 2.70 (t, 2H), 4.25 (q, 2H), 6.08 (d, 1H), 6.54-6.62 (m, 2H), 7.08-7.58 (m, 7H).

Preparation 60

4-(Benzofuran-2-carbonyl)-5-methyl-isoxazole 3-carboxylic acid ethyl ester

Obtained as a solid (80%) from: 1-benzofuran-2-yl-butane-1,3-dione (Richard, F.; Carreyre, H.; Coustard, J. M.;

Bachman, C.; Perot, G., *Tetrahedron* 1998, 54(49), 14757-14766) and ethyl chloro(hydroximino)acetate following the experimental procedure described in Preparation 1.

δ(CDCl$_3$): 1.10 (t, 3H), 2.21 (s, 3H), 4.15 (q, 2H), 7.16-7.80 (m, 5H).

Preparation 61

4-Benzofuran-2-yl-3-methyl-6H-isoxazolo[3,4-d]pyridazin-7-one

Obtained as a solid (65%) from the title compound of Preparation 60 using the experimental procedure described in Preparation 3.

δ(CDCl$_3$): 2.99 (s, 3H), 7.29-7.49 (m, 3H), 7.70-7080 (m, 2H).

Preparation 62

4-Benzofuran-2-yl-6-ethyl-3-methyl-6H-isoxazolo[3,4-d]pyridazin-7-one

Obtained (67%) from the title compound from Preparation 61 following the experimental procedure described in Preparation 5.

δ(CDCl$_3$): 1.44 (t, 3H), 3.07 (s, 3H), 4.32 (q, 2H), 7.27-7.76 (m, 5H).

Preparation 63

5-Acetyl-4-amino-6-benzofuran-2-yl-2-ethyl-2H-pyridazin-3-one

Obtained (90%) from the title product of Preparation 62 following the procedure described in Preparation 17.

δ(CDCl$_3$): 1.44 (t, 3H), 1.99 (s, 3H), 4.27 (q, 2H), 7.16 (s, 1H), 7.27-7.72 (m, 6H).

Preparation 64

6-(Cyclopropylmethyl)-4-(4-fluorophenyl)-3-methylisoxazolo[3,4-d]pyridazin-7(6H)-one Obtained (46%) from the title compound from Preparation 28 and cyclopropylmethyl bromide following the experimental procedure described in Preparation 5. The product was purified by column chromatography.

δ(CDCl$_3$): 0.54 (m, 4H), 1.38 (m, 1H), 2.58 (s, 3H), 4.08 (d, 2H), 7.28 (d, 2H), 7.57 (dd, 2H).

Preparation 65

5-Acetyl-2-(cyclopropylmethyl)-6-(4-fluorophenyl)-4-nitropyridazin-3(2H)-one

Obtained (37%) from the title product of Preparation 64 following the experimental procedure described in Preparation 30.

δ(CDCl$_3$): 0.46 (m, 2H), 0.62 (m, 2H), 1.45 (m, 1H), 2.21 (s, 3H), 4.18 (d, 2H), 7.21 (m, 2H), 7.45 (m, 2H).

Preparation 66

4-Nitro-[2,7]naphthyridin-1-ol

To a stirred solution of 2H-[2,7]naphthyridin-1-one (300 mg, 2.05 mmol) (Baldwin, J. J.; Mensler, K.; Ponticello, G. S, *J. Org. Chem.* 1978, 43(25), 4878-80.) in 98% sulfuric acid (2 ml), 60% nitric acid (0.30 ml) was added dropwise and the mixture was warmed to 85° C. during 3 h. Addition, of ice-cold water and basification to pH 7, gave a precipitate which was filtered and washed with ethyl ether to yield the title product as a yellow solid (87%).

δ(DMSO-d6): 8.23 (d, 1H), 8.60 (d, 1H), 8.88 (s, 1H), 9.18 (d, 1H).

Preparation 67

4-Amino-[2,7]naphthyridin-1-ol

A mixture of the title compound of Preparation 66 (100 mg, 0.52 mmol) and Ni-Raney (10 mg) in methanol (15 ml) was shaken under hydrogen at room temperature and 1 atm overnight. Then catalyst was filtered off and the solvent was removed under reduced pressure to yield the title compound (100%).

LRMS: m/Z 162 (M+1)$^+$

Preparation 68

4(4-Methoxy-benzoyl)-5-methyl-isoxazole-3-carboxylic acid ethyl ester

Obtained as a yellow oil (63%) from 1-(4-methoxy-phenyl)-butane-1,3-dione (Popic, V. V. et al., *Synthesis* 1991(3), 19.5) and ethyl chloro(hydroximino)acetate following the experimental procedure described in Preparation 1. The final product was purified by column cromatography (n-Hex/EtOAc 9:1 to 1:1).

δ(CDCl$_3$): 1.18 (t, 3H), 2.58 (s, 3H), 3.90 (s, 3H), 4.20 (q, 2H), 6.95 (d, 2H), 7.80 (d, 2H).

Preparation 69

4-(4-Methoxy-phenyl)-3-methyl-6H-isoxazolo[3,4-d]pyridazin-7-one

Obtained as a white solid (91%) from the title compound of Preparation 68 using the experimental procedure described in Preparation 3.

δ(DMSO-d$_6$): 2.54 (s, 3H), 3.84 (s, 3H), 7.09 (d, 2H), 7.56 (d, 2H).

LRMS (m/z): 258 (M+1)$^+$.

Preparation 70

6-Ethyl-4-(4-methoxyphenyl)-3-methyl-6H-isoxazolo[3,4-d]pyridazin-7-one

Obtained as a yellow solid (79%) from the title compound from Preparation 69 following the experimental procedure described in Preparation 5.

δ(DMSO-d$_6$): 1.30 (t, 3H), 2.57 (s, 3H), 3.84 (s, 3H), 4.13 (q, 2H), 7.10 (d, 2H), 7.60 (d, 2H).

LRMS (m/z): 286 (M+1)$^+$.

Preparation 71

5-Acetyl-4-amino-2-ethyl-6-(4-methoxy-phenyl)-2H-pyridazin-3-one

Obtained (84%) from the title product of Preparation 70 following the procedure described in Preparation 14.

δ(DMSO-d$_6$): 1.29 (t, 3H), 1.75 (s, 3H), 3.81 (s, 3H), 4.10 (q, 2H), 7.03 (d, 2H), 7.35 (d, 2H).

Preparation 72

4-(3-Methoxy-benzoyl)-5-methyl-isoxazole-3-carboxylic acid ethyl ester

The title compound was synthesized (76%) from 1-(3-methoxy-phenyl)-butane-1,3-dione (Popic, V. V. et al., *Synthesis* 1991 (3); 195) following the procedure described in Preparation 1.
δ(DMSO-d$_6$): 1.00 (t, 3H), 2.57 (s, 3H), 3.8 (s, 3H), 4.08 (q, 2H), 7.25-7.35 (m, 3H), 7.45 (m, 1H).

Preparation 73

4-(3-Methoxy-phenyl)-3-methyl-6H-isoxazolo[3,4-d]pyridazin-7-one

Obtained as a solid (69%) from the title compound of Preparation 72 using the experimental procedure described in Preparation 3.
δ(DMSO-d$_6$): 2.57 (s, 3H), 3.82 (s, 3H), 7.10 (d, 1H), 7.15-7.20 (m, 2H), 7.45 (t, 1H), 12.75 (s, NH).

Preparation 74

6-Ethyl-4-(3-methoxy-phenyl)-3-methyl-6H-isoxazolo[3,4-d]pyridazin-7-one

Obtained as a solid (80%) from the title compound of Preparation 73 using the experimental procedure described in Preparation 5.
δ(DMSO-d$_6$): 1.35 (t, 3H), 2.57 (s, 3H), 3.82 (s, 3H), 4.15 (q, 2H), 7.10-7.25 (m, 3H), 7.45 (t, 1H).

Preparation 75

5-Acetyl-4-amino-2-ethyl-6-(3-methoxy-phenyl)-2H-pyridazin-3-one

Obtained as a solid (72%) from the title compound of Preparation 74 using the experimental procedure described in Preparation 14.
δ(DMSO-d$_6$): 1.35 (t, 3H), 1.78 (s, 3H), 3.82 (s, 3H), 4.10 (q, 2H), 6.90-7.10 (m, 3H), 7.40 (t, 1H), 7.78 (bs, 2H, NH$_2$).

Preparation 76

5-Methyl-4-(4-methyl-benzoyl)-isoxazole-3-carboxylic acid ethyl ester

The title compound was synthesized (83%) from 1-p-tolyl-butane-1,3-dione (Popic, V. V. et al., *Synthesis* 1991 (3), 195) following the procedure described in Preparation 1.
δ(CDCl$_3$): 1.10 (t, 3H), 2.42 (s, 3H), 2.58 (s, 3H), 4.18 (q, 2H), 7.30 (d, 2H), 7.70 (d, 2H).

Preparation 77

3-Methyl-4-p-tolyl-6H-isoxazolo[3,4-d]pyridazin-7-one

Obtained as a solid (38%) from the title compound of Preparation 76 using the experimental procedure described in Preparation 3.
δ(CDCl$_3$): 2.48 (s, 3H), 2.58 (s, 3H), 7.35 (d, 2H), 7.42 (d, 2H).

Preparation 78

6-Ethyl-3-methyl-4-p-tolyl-6H-isoxazolo[3,4-d]pyridazin-7-one

Obtained as a solid (89%) from the title compound of Preparation 77 using the experimental procedure described in Preparation 5.
δ(CDCl$_3$): 1.42 (t, 3H), 2.48 (s, 3H), 2.58 (s, 3H), 4.30 (q, 2H), 7.35 (d, 2H), 7.45 (d, 2H).
LRMS (m/z): 270 (M+1)$^+$.
Retention Time: 9.60 min.

Preparation 79

5-Acetyl-4-amino-2-ethyl-6-p-tolyl-2H-pyridazin-3-one

Obtained as a solid (91%) from the title compound of Preparation 78 using the experimental procedure described in Preparation 14.
δ(CDCl$_3$): 1.42 (t, 3H), 1.80 (s, 3H), 2.42 (s, 3H), 4.28 (q, 2H), 7.30 (d, 2H), 7.38 (d, 2H).
LRMS (m/z): 272 (M+1)$^+$.
Retention Time: 9.27 min.

Preparation 80

5-Methyl-4-(3-methyl-benzoyl)-isoxazole-3-carboxylic acid ethyl ester

The title compound was synthesized (73%) from 1-m-tolyl-butane-1,3-dione (Popic, V. V. et al., *Synthesis* 1991 (3), 195) following the procedure described in Preparation 1.
δ(CDCl$_3$): 1.10 (t, 3H), 2.40 (s, 3H), 2.58 (s, 3H), 4.15 (q, 2H), 7.30-7.50 (m, 3H), 7.58 (m, 1H).

Preparation 81

3-Methyl-4-m-tolyl-6H-isoxazolo[3,4-d]pyridazin-7-one

Obtained as a solid (73%) from the title compound of Preparation 80 using the experimental procedure described in Preparation 3.
δ(CDCl$_3$): 2.45 (s, 3H), 2.58 (s, 3H), 7.30-7.50 (m, 4H), 10.05 (bs, 1H, NH).

Preparation 82

6-Ethyl-3-methyl-4-m-tolyl-6H-isoxazolo[3,4-d]pyridazin-7-one

Obtained as a solid (88%) from the title compound of Preparation 81 using the experimental procedure described in Preparation 5.
δ(CDCl$_3$): 1.42 (t, 3H), 2.45 (s, 3H), 2.58 (s, 3H), 4.30 (q, 2H), 7.30-7.50 (m, 4H).

Preparation 83

5-Acetyl-4-amino-2-ethyl-6-m-tolyl-2H-pyridazin-3-one

Obtained as a solid (80%) from the title compound of Preparation 82 using the experimental procedure described in Preparation 14.

δ(CDCl$_3$): 1.42 (t, 3H), 1.80 (s, 3H), 2.42 (s, 3H), 4.28 (q, 2H), 7.20-7.40 (m, 4H).

LRMS (m/z): 272 (M+1)$^+$.

Retention Time: 9.25 min.

Preparation 84

4-(3-Oxo-butyryl)-benzoic acid methyl ester

A solution of dimethyl terephthalate (10 g, 51.5 mmole) and acetone (4.15 mL, 56.6 mmole) in a mixture of toluene/dimethoxyethane (75 mL/25 mL) was added to a suspension of NaH 60% (2.68 g, 66.9 mmole) in dry toluene (25 mL) under argon. The mixture was heated at 100° C. for 4 hours. The reaction mixture was cooled to rt and 25 mL of water were added. The pH was adjusted to 3-4 with HCl 2N and the mixture was poured into water (300 mL). The aqueous mixture was extracted with ethyl acetate (3×150 mL), dried over sodium sulphate and evaporated to afford a yellow solid which was purified by column cromatography (n-Hex/EtOAc 9:1 to 7:3) to afford the title compound (2.78 g, 25% yield) as a yellow solid.

δ(CDCl$_3$): 2.25 (s, 3H), 3.95 (s, 3H), 6.20 (s, 1H), 7.90 (d, 2H), 8.10 (d, 2H).

LRMS (m/z): 221 (M+1)$^+$.

Retention Time: 9.42 min.

Preparation 85

4-(4-Methoxycarbonyl-benzoyl)-5-methyl-isoxazole-3-carboxylic acid ethyl ester The title compound was synthesized (64%) from the title compound of Preparation 84 following the procedure described in Preparation 1.

δ(CDCl$_3$): 1.10 (t, 3H), 2.58 (s, 3H), 3.98 (s, 3H), 4.18 (q, 2H), 7.80 (d, 2H), 8.15 (d, 2H).

Preparation 86

4-(3-Methyl-7-oxo-6,7-dihydro-isoxazolo[3,4-d]pyridazin-4-yl)-benzoic acid methyl ester Obtained as a solid (91%) from the title compound of Preparation 85 using the experimental procedure described in Preparation 3.

δ(CDCl$_3$): 2.58 (s, 3H), 3.98 (s, 3H), 7.62 (d, 2H), 8.20 (d, 2H), 9.85 (bs, 1H. NH).

Preparation 87

4-(6-Ethyl-3-methy-7-oxo-6,7-dihydro-isoxazolo[3,4-d]pyridazin-4-yl)-benzoic acid methyl ester Obtained as a solid (70%) from the title compound of Preparation 86 using the experimental procedure described in Preparation 5.

δ(CDCl$_3$): 1.42 (t, 3H), 2.58 (s, 3H), 3.98 (s, 3H), 4.30 (q, 2H), 7.62 (d, 2H), 8.20 (d, 2H).

Preparation 88

4-(4-Acetyl-5-amino-1-ethyl-6-oxo-1,6-dihydro-pyridazin-3-yl)-benzoic acid methyl ester Obtained as a solid (97%) from the title compound of Preparation 87 using the experimental procedure described in Preparation 14.

δ(CDCl$_3$): 1.42 (t, 3H), 1.78 (s, 3H), 3.96 (s, 3H), 4.26 (q, 2H), 7.55 (d, 2H), 8.14 (d, 2H).

LRMS (m/z): 316 (M+1)$^+$.

Retention Time: 8.80 min.

Preparation 89

3-(3-Oxo-butyryl)-benzoic acid methyl ester

A solution of dimethyl isophthalate (12 g, 61.85 mmole) and acetone (5 mL, 68 mmole) in a mixture of toluene/dimethoyethane (90 mL/30 mL) was added to a suspension of NaH 60% (2.97 g, 74.23 mmole) in dry toluene (30 mL) under argon. The mixture was heated at 100° C. for 4 hours. The reaction mixture was cooled to rt and 25 mL of water were added. The mixture was poured into water (250 mL) and the pH was adjusted to 3-4 with HCl 2N. The aqueous mixture was extracted with ethyl acetate (2×250 mL), washed with brine, dried over sodium sulphate and evaporated to afford a yellow solid which was purified by column cromatography (n-Hex/EtOAc 9:1 to 8:2) to afford the title compound (1.78 g, 11% yield) as a yellow solid.

δ(CDCl$_3$): 2.23 (s, 3H), 3.96 (s, 3H), 6.25 (s, 1H), 7.57 (d, 1H), 8.20 (m, 2H), 8.51 (s, 1H).

LRMS (m/z): 221 (M+1)$^+$.

Retention Time: 9.32 min.

Preparation 90

4-(3-Methoxycarbonyl-benzoyl)-5-methyl-isoxazole-3-carboxylic acid ethyl ester The title compound was synthesized (62%) from the title compound of Preparation 89 following the procedure described in Preparation 1.

LRMS (m/z): 318 (M+1)$^+$.

Retention Time: 9.07 min.

Preparation 91

3-(3-Methyl-7-oxo-6,7-dihydro-isoxazolo[3,4-d]pyridazin-4-yl)-benzoic acid methyl ester Obtained as a solid (80%) from the title compound of Preparation 90 using the experimental procedure described in Preparation 3.

LRMS (m/z): 286 (M+1)$^+$.

Retention Time: 7.73 min.

Preparation 92

3-(6-Ethyl-3-methyl-7-oxo-6,7-dihydro-isoxazolo[3,4-d]pyridazin-4-yl)-benzoic acid methyl ester Obtained as a solid (99%) from the title compound of Preparation 91 using the experimental procedure described in Preparation 5.

δ(CDCl$_3$): 1.42 (t, 3H), 2.58 (s, 3H), 3.96 (s, 3H), 4.26 (q, 2H), 7.65 (dd, 1H), 7.80 (d, 1H), 8.20 (d, 1H), 8.25 (s, 1H).

LRMS (m/z): 314 (M+1)$^+$.

Retention Time: 9.02 min.

Preparation 93

3-(4-Acetyl-5-amino-1-ethyl-6-oxo-1,6-dihydro-pyridazin-3-yl)-benzoic acid methyl ester Obtained as a solid (98%) from the title compound of Preparation 92 using the experimental procedure described in Preparation 14.

δ(CDCl$_3$): 1.42 (t, 3H), 1.78 (s, 3H), 3.96 (s, 3H), 4.26 (q, 2H), 7.45-7.70 (m, 4H), 8.15 (d, 1H), 8.18 (s, 1H).

LRMS (m/z): 316 (M+1)$^+$.

Retention Time: 8.68 min.

Preparation 94

(3-Methyl-7-oxo-4-phenyl-7H-isoxazolo[3,4-d]pyridazin-6-yl)-acetic acid methyl ester Obtained as a white solid (89%) from 3-methyl-4-phenyl-isoxazolo[3,4-d]pyridazin-7(6H)-one (Renzi, G.; Pinzauti, S., *Il Farmaco Ed. Sci.* 1969, 24, 885-889) and methyl bromoacetate following the experimental procedure described in Preparation 5.

δ(CDCl$_3$): 2.55 (s, 3H), 3.78 (s, 3H), 4.98 (s, 2H), 7.57 (m, 5H).

Preparation 95

(4-Acetyl-5-amino-6-oxo-3-phenyl-6H-pyridazin-1-yl)-acetic acid methyl ester

Obtained as a white solid (99%) from the title compound of Preparation 94 following the experimental procedure described in Preparation 14.

δ(CDCl$_3$): 1.80 (s, 3H), 3.80 (s, 3H), 4.92 (s, 2H), 7.42 (m, 5H).

Preparation 96

6-Cyclopropylmethyl-3-methylphenyl-6H-isoxazolo[3,4d]pyridazin-7-one

Obtained (91%) from 3-methyl-4-phenyl-6H-isoxazolo[3,4-d]pyridazin-7-one (Dal Piaz, V. et al. *J. Med. Chem.* 1997, 40, 1417) and cyclopropylmethyl bromide following the experimental procedure described in Preparation 5.

δ(CDCl$_3$): 0.50 (m, 4H), 1.4 (m, 1H), 2.50 (s, 3H), 4.10 (q, 2H), 7.50 (m, 5H).

Preparation 97

5-Acetyl-2-cyclopropylmethyl-4-nitro-6-phenyl-2H-pyridazin-3-one

Obtained (15.4%) from the title compound of Preparation 96 following the experimental procedure described in Preparation 30. The crude was purified by column chromatography (silica gel, hexane/ethyl acetate 8:1).

δ(CDCl$_3$): 0.50 (m, 2H), 0.70 (m, 2H), 1.4 (m, 1H), 2.20 (s, 3H), 4.20 (q, 2H), 7.50 (m, 5H).

Preparation 98

5-Nitroquinoline-8-carboxylic acid methyl ester

To a stirred solution of 300 mg (1.375 mmol) of 5-nitroquinoline-8-carboxylic acid (Breckenridge, J. G. Et al., *Canadian J. of Research Sect. B;* 1947, 25, 49) in DMF (6 mL), 546 mg (3.850 mmol) of iodomethane and 190 mg (1.375 mmol) of potassium carbonate were added. The resulting mixture was stirred at room temperature for one hour. Water (10 mL) was added and the product collected by filtration. The residue was washed with water and dried to yield the title compound (250 mg, 78.4%).

LRMS: m/Z 233 (M+1)$^{+\delta(CDCl_3)}$: 4.05 (s, 3H), 7.70 (m, 1H), 8.00 (d, 1H), 8.30 (d, 1H), 9.00 (d, 1H), 9.15 (m, 1H).

Preparation 99

5-Aminoquinoline-8-carboxylic acid methyl ester

A mixture of the title compound of Preparation 98 (100 mg, 0.431 mmol) and 10% palladium on charcoal (46 mg) in ethanol (5 mL) was shaken under hydrogen at room temperature and 1 bar for 15 minutes. The catalyst was filtered off and the solvent removed under reduced pressure to yield the title compound (84 mg, 96%)

LRMS: m/Z 203 (M+1)$^+$

EXAMPLES

In the following tables some acronyms have been used with the following meanings:

| Acronym | Meaning |
|---|---|
| 2-Pyr | 2-pyridyl |
| 3-Pyr | 3-pyridyl |
| 4-Pyr | 4-pyridyl |
| Ph | Phenyl |
| (2-F)Ph | 2-fluorophenyl |
| (3-F)Ph | 3-fluorophenyl |
| (4-F)Ph | 4-fluorophenyl |
| (2-Cl)Ph | 2-chlorophenyl |
| (3-Cl)Ph | 3-chlorophenyl |
| (2-Me)Ph | 2-methylphenyl or o-tolyl |
| (3-Me)Ph | 3-methylphenyl or m-tolyl |
| (4-Me)Ph | 4-methylphenyl or p-tolyl |
| (2-MeO)Ph | 2-methoxyphenyl |
| (3-MeO)Ph | 3-methoxyphenyl |
| (4-MeO)Ph | 4-methoxyphenyl |
| (3-CO$_2$Me)Ph | 3-methoxycarbonylphenyl |
| (4-CO$_2$Me)Ph | 4-methoxycarbonylphenyl |
| (4-CO$_2$H)Ph | 4-hydroxycarbonylphenyl |
| (4-CH$_2$OH)Ph | 4-hydroxymethylphenyl |
| (3-CN)Ph | 3-cyanophenyl |
| (4-CN)Ph | 4-cyanophenyl |
| (3-NO$_2$)Ph | 3-nitrophenyl |
| 1-Naph | 1-naphtyl |
| (3,5-diCl)Ph | 3,5-dichlorophenyl |
| C$_3$H$_5$CH$_2$ | cyclopropylmethyl |

In addition in formulas of radicals R3 or R5 depicted in the tables the symbol X does not symbolize any atoms and has only been used to symbolize the point of attachment of the radicals.

TABLE 2

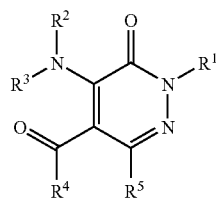

| Example | R1 | R2 | R3 | R4 | R5 |
|---|---|---|---|---|---|
| 1 | Et | H | (3-F)Ph | Me | 3-Pyr |
| 2 | Et | H | (3-Cl)Ph | Me | 3-Pyr |
| 3 | Et | H | (3,5-diCl)Ph | Me | 3-Pyr |
| 4 | Et | H | 1-Naph | Me | 3-Pyr |
| 5 | Et | H | (4-CO$_2$Me)Ph | Me | 3-Pyr |
| 6 | Et | H | (2-F)Ph | Me | 3-Pyr |
| 7 | Et | H | (2-Cl)Ph | Me | 3-Pyr |
| 8 | Et | H | (4-CH$_2$OH)Ph | Me | 3-Pyr |
| 9 | Et | H | (3-CN)Ph | Me | 3-Pyr |
| 10 | C$_3$H$_5$CH$_2$ | H | (3-Cl)Ph | Me | 3-Pyr |
| 11 | C$_3$H$_5$CH$_2$ | H | (3,5-diCl)Ph | Me | 3-Pyr |
| 12 | C$_3$H$_5$CH$_2$ | H | (2-F)Ph | Me | 3-Pyr |
| 13 | C$_3$H$_5$CH$_2$ | H | (2-Cl)Ph | Me | 3-Pyr |
| 14 | C$_3$H$_5$CH$_2$ | H | (3-CN)Ph | Me | 3-Pyr |
| 15 | HOCH$_2$CH$_2$ | H | (4-CO$_2$Me)Ph | Me | 3-Pyr |
| 16 | HOCH$_2$CH$_2$ | H | (2-F)Ph | Me | 3-Pyr |
| 17 | HOCH$_2$CH$_2$ | H | (2-Cl)Ph | Me | 3-Pyr |
| 18 | HOCH$_2$CH$_2$ | H | (3-Cl)Ph | Me | 3-Pyr |
| 19 | Et | H | (3-Cl)Ph | Me | 2-Pyr |
| 20 | Et | H | (3-CN)Ph | Me | 2-Pyr |
| 21 | Et | H | (4-CH$_2$OH)Ph | Me | 2-Pyr |
| 22 | C$_3$H$_5$CH$_2$ | H | (3-CN)Ph | Me | 2-Pyr |
| 23 | C$_3$H$_5$CH$_2$ | H | (3-Cl)Ph | Me | 2-Pyr |
| 24 | C$_3$H$_5$CH$_2$ | H | (4-CH$_2$OH)Ph | Me | 2-Pyr |
| 25 | C$_3$H$_5$CH$_2$ | H | (3,5-diCl)Ph | Me | 2-Pyr |
| 26 | HOCH$_2$CH$_2$ | H | (3-CN)Ph | Me | 2-Pyr |
| 27 | HOCH$_2$CH$_2$ | H | (3-Cl)Ph | Me | 2-Pyr |
| 28 | HOCH$_2$CH$_2$ | H | (3,5-diCl)Ph | Me | 2-Pyr |
| 29 | HOCH$_2$CH$_2$ | H | (4-CH$_2$OH)Ph | Me | 2-Pyr |
| 30 | Et | H | (3-F)Ph | Me | 4-Pyr |
| 31 | Et | H | (3-Cl)Ph | Me | 4-Pyr |
| 32 | Et | H | 1-Naph | Me | 4-Pyr |
| 33 | Et | H | (2-Me)Ph | Me | 4-Pyr |
| 34 | Et | H | (4-CO$_2$Me)Ph | Me | 4-Pyr |
| 35 | Et | H | (2-MeO)Ph | Me | 4-Pyr |
| 36 | Et | H | (3-MeO)Ph | Me | 4-Pyr |
| 37 | Et | H | (2-F)Ph | Me | 4-Pyr |
| 38 | Et | H | (2-Cl)Ph | Me | 4-Pyr |
| 39 | Et | H | (3-CN)Ph | Me | 4-Pyr |
| 40 | Et | H | (4-CH$_2$OH)Ph | Me | 4-Pyr |
| 41 | Et | H | (4-CO$_2$H)Ph | Me | 4-Pyr |
| 42 | C$_3$H$_5$CH$_2$ | H | (2-F)Ph | Me | 4-Pyr |
| 43 | C$_3$H$_5$CH$_2$ | H | (2-Cl)Ph | Me | 4-Pyr |
| 44 | C$_3$H$_5$CH$_2$ | H | (3-CN)Ph | Me | 4-Pyr |
| 45 | C$_3$H$_5$CH$_2$ | H | (4-CH$_2$OH)Ph | Me | 4-Pyr |
| 46 | C$_3$H$_5$CH$_2$ | H | (3-Cl)Ph | Me | 4-Pyr |
| 47 | HOCH$_2$CH$_2$ | H | (2-F)Ph | Me | 4-Pyr |
| 48 | HOCH$_2$CH$_2$ | H | (2-Cl)Ph | Me | 4-Pyr |
| 49 | HOCH$_2$CH$_2$ | H | (3-CN)Ph | Me | 4-Pyr |
| 50 | HOCH$_2$CH$_2$ | H | (4-CH$_2$OH)Ph | Me | 4-Pyr |
| 51 | HOCH$_2$CH$_2$ | H | (3-Cl)Ph | Me | 4-Pyr |
| 52 | Et | H | (3-Cl)Ph | Me | 2-Thienyl |
| 53 | Et | (3-F)Ph | (3-F)Ph | Me | 3-Pyr |
| 54 | Et | (4-CO$_2$Me)Ph | (4-CO$_2$Me)Ph | Me | 3-Pyr |
| 55 | Et | (4-CH$_2$OH)Ph | (4-CH$_2$OH)Ph | Me | 3-Pyr |
| 56 | Et | (3-NO2)Ph | (3-NO2)Ph | Me | 4-Pyr |
| 57 | Et | (3-F)Ph | (3-F)Ph | Me | 4-Pyr |
| 58 | C$_3$H$_5$CH$_2$ | (3-Cl)Ph | (3-Cl)Ph | Me | 3-Pyr |
| 59 | C$_3$H$_5$CH$_2$ | (3,5-diCl)Ph | (3,5-diCl)Ph | Me | 3-Pyr |
| 60 | HOCH$_2$CH$_2$ | (4-CO$_2$Me)Ph | (4-CO$_2$Me)Ph | Me | 3-Pyr |
| 61 | HOCH$_2$CH$_2$ | (3-Cl)Ph | (3-Cl)Ph | Me | 2-Pyr |

TABLE 2-continued
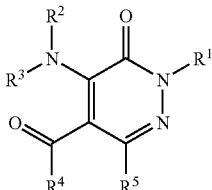
| Example | R1 | R2 | R3 | R4 | R5 |
|---|---|---|---|---|---|
| 62 | C₃H₅CH₂ | (3-Cl)Ph | (3-Cl)Ph | Me | 4-Pyr |
| 63 | Et | H | 3-Pyr | Me | Ph |
| 64 | Et | H | 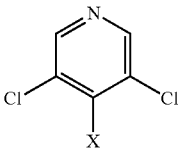 | Me | Ph |
| 65 | Et | H | 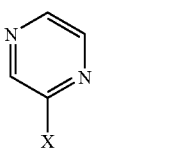 | Me | Ph |
| 66 | Et | H | 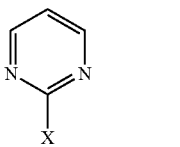 | Me | Ph |
| 67 | Et | H | 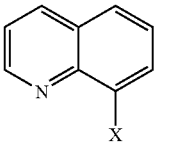 | Me | Ph |
| 68 | Et | H | 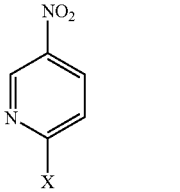 | Me | Ph |
| 69 | Et | H | 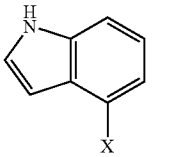 | Me | Ph |
| 70 | Et | H | 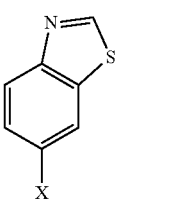 | Me | Ph |

TABLE 2-continued
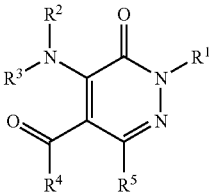
| Example | R1 | R2 | R3 | R4 | R5 |
|---|---|---|---|---|---|
| 71 | Et | H | 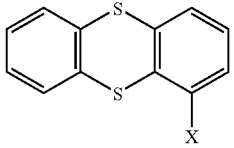 | Me | Ph |
| 72 | Et | H | 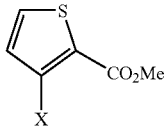 | Me | Ph |
| 73 | Et | H | 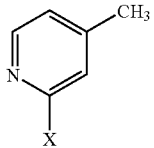 | Me | Ph |
| 74 | Et | H | | Me | Ph |
| 75 | Et | H | 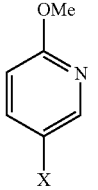 | Me | Ph |
| 76 | Et | H | 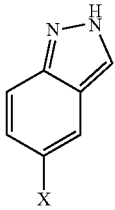 | Me | Ph |
| 77 | Et | H | 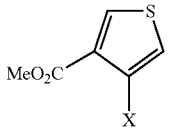 | Me | Ph |
| 78 | Et | H | 2-Pyr | Me | Ph |
| 79 | Et | H | 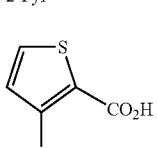 | Me | Ph |

TABLE 2-continued
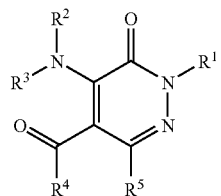
| Example | R1 | R2 | R3 | R4 | R5 |
|---|---|---|---|---|---|
| 80 | Et | H | 3-methylcinnolin-5-yl | Me | Ph |
| 81 | Et | H | 2-methylquinolin-8-yl | Me | Ph |
| 82 | Et | H | quinolin-5-yl | Me | Ph |
| 83 | Et | H | 1H-indol-5-yl | Me | Ph |
| 84 | Et | H | isoquinolin-5-yl | Me | Ph |
| 85 | Et | H | 6-methoxyquinolin-8-yl | Me | Ph |
| 86 | Et | H | 5-bromoquinolin-8-yl | Me | Ph |
| 87 | Et | H | 4-methylpyrimidin-2-yl | Me | Ph |
| 88 | Et | H | 3-Pyr | Me | (3-Cl)Ph |
| 89 | C3H5CH2 | H | 3-Pyr | Me | (3-Cl)Ph |

TABLE 2-continued
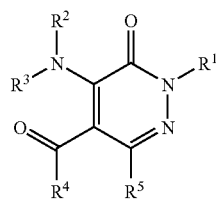
| Example | R1 | R2 | R3 | R4 | R5 |
|---|---|---|---|---|---|
| 90 | Et | H | 3-Pyr | Me | (3-F)Ph |
| 91 | iPr | H | 3-Pyr | Me | (3-F)Ph |
| 92 | C3H5CH2 | H | 3-Pyr | Me | (3-F)Ph |
| 93 | Et | H | 3-Pyr | Me | (4-F)Ph |
| 94 | Et | H | (3-Cl)Ph | Me | 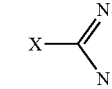 |
| 95 | Et | H | (3-Cl)Ph | Me | 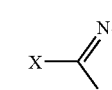 |
| 96 | Et | H | (3-F)Ph | Me | 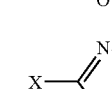 |
| 97 | Et | (3-Cl)Ph | (3-Cl)Ph | Me |  |
| 98 | Et | (3-F)Ph | (3-F)Ph | Me | 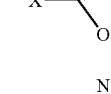 |
| 99 | Et | H | (3-MeO)Ph | Me | 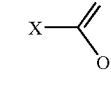 |
| 100 | Et | H | (4-CH2OH)Ph | Me | 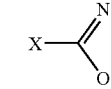 |
| 101 | Et | H | 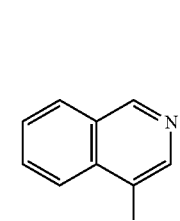 | Me | Ph |
| 102 | Et | H | 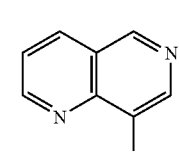 | Me | Ph |
| 103 | Et | H | 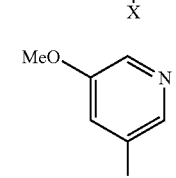 | Me | Ph |

TABLE 2-continued
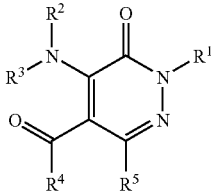
| Example | R1 | R2 | R3 | R4 | R5 |
|---|---|---|---|---|---|
| 104 | Et | H | 3-Pyr | Me | 4-Pyr |
| 105 | Et | H | 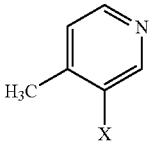 | Me | 4-Pyr |
| 106 | Et | H |  | Me | 4-Pyr |
| 107 | Et | H | 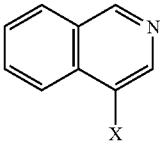 | Me | 4-Pyr |
| 108 | Et | H |  | Me | 3-Pyr |
| 109 | Et | H | 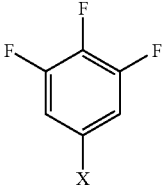 | Me | 3-Pyr |
| 110 | Et | H |  | Me | 3-Pyr |
| 111 | Et | H | 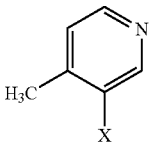 | Me | 2-Thienyl |
| 112 | Et | H | 3-Pyr | Me | 2-Thienyl |
| 113 | Et | H | (4-CN)Ph | Me | 2-Thienyl |

TABLE 2-continued

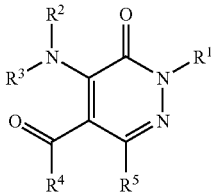

| Example | R1 | R2 | R3 | R4 | R5 |
|---|---|---|---|---|---|
| 114 | Et | H | 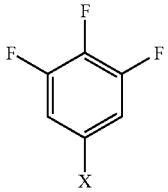 2,3,5-trifluorophenyl (X position) | Me | 2-Thienyl |
| 115 | Et | (4-CN)Ph | (4-CN)Ph | Me | 2-Thienyl |
| 116 | C3H5CH2 | H | 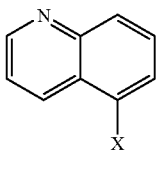 quinolin-5-yl (X position) | Me | 2-Thienyl |
| 117 | C3H5CH2 | H | 3-Pyr | Me | 2-Thienyl |
| 118 | Et | H | 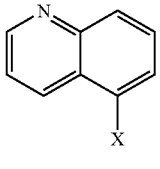 quinolin-5-yl (X position) | Me | 3-Thienyl |
| 119 | Et | H | (3-Cl)Ph | Me | 3-Thienyl |
| 120 | Et | H | 3-Pyr | Me | 3-Thienyl |
| 121 | Et | H | (4-CN)Ph | Me | 3-Thienyl |
| 122 | Et | H | 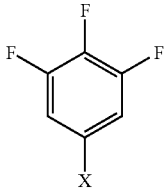 2,3,5-trifluorophenyl (X position) | Me | 3-Thienyl |
| 123 | Et | H | 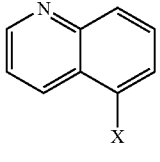 quinolin-5-yl (X position) | Ph(CH2)2 | Ph |
| 124 | Et | H | 3-Pyr | Ph(CH2)2 | Ph |
| 125 | Et | H | 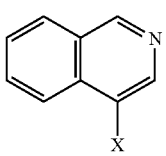 isoquinolin-4-yl (X position) | Ph(CH2)2 | Ph |

TABLE 2-continued
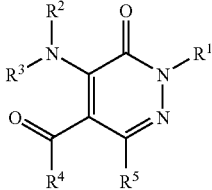
| Example | R1 | R2 | R3 | R4 | R5 |
|---|---|---|---|---|---|
| 126 | Et | H | 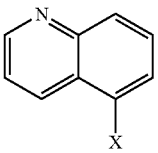 | 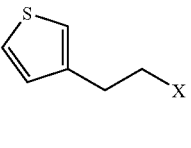 | Ph |
| 127 | Et | H | 3-Pyr | 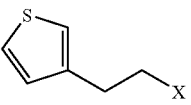 | Ph |
| 128 | Et | H | (3-Cl)Ph | Me | 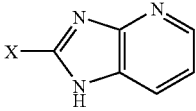 |
| 129 | Et | H | (3-Cl)Ph | Me | 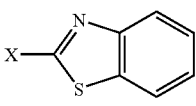 |
| 130 | Et | H | (3-Cl)Ph | Me | 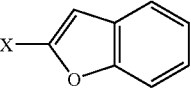 |
| 131 | Et | H | 3-Pyr | Me | 3-Pyr |
| 132 | Et | H | (4-CO2H)Ph | Me | 3-Pyr |
| 133 | Et | H | 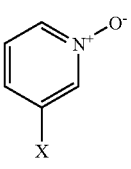 | Me | Ph |
| 134 | Et | H | 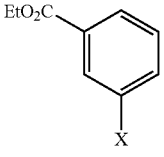 | Me | 4-Pyr |
| 135 | Et | H | 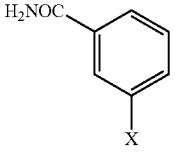 | Me | 4-Pyr |
| 136 | Et | H | 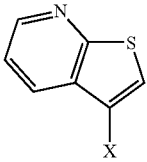 | Me | Ph |

TABLE 2-continued

| Example | R1 | R2 | R3 | R4 | R5 |
|---|---|---|---|---|---|
| 137 | Et | H | 2-fluoropyridin-5-yl | Me | Ph |
| 138 | Et | H | 2-methylpyridin-3-yl | Me | Ph |
| 139 | Et | H | 2-(dimethylamino)pyridin-3-yl | Me | Ph |
| 140 | Et | H | 6-carboxypyridin-3-yl | Me | Ph |
| 141 | Et | H | 2-methoxypyridin-3-yl | Me | Ph |
| 142 | Et | H | 1H-indazol-4-yl | Me | Ph |
| 143 | Et | H | 2-chloropyridin-3-yl | Me | Ph |
| 144 | Et | H | 3-chloropyridin-5-yl | Me | Ph |

TABLE 2-continued
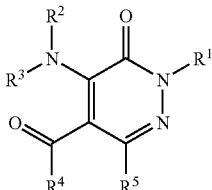
| Example | R1 | R2 | R3 | R4 | R5 |
|---|---|---|---|---|---|
| 145 | Et | H | 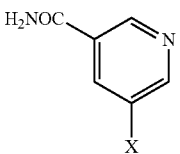 | Me | Ph |
| 146 | Et | H | 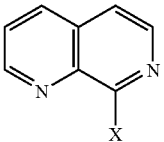 | Me | Ph |
| 147 | Et | H | 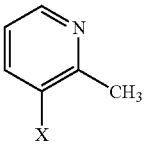 | CH2OH | Ph |
| 148 | Et | H | 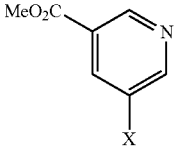 | Me | Ph |
| 149 | Et | H | 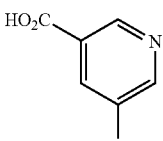 | Me | Ph |
| 150 | Et | H | 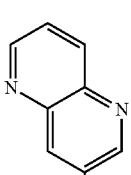 | Me | Ph |
| 151 | Et | H | 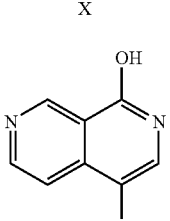 | Me | Ph |
| 152 | Et | H | 2-Thienyl | Me | Ph |

TABLE 2-continued
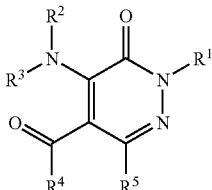
| Example | R1 | R2 | R3 | R4 | R5 |
|---|---|---|---|---|---|
| 153 | Et | H | 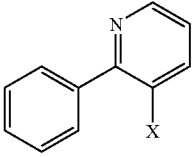 | Me | Ph |
| 154 | Et | H | 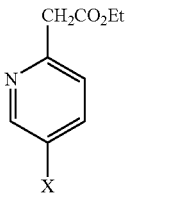 | Me | Ph |
| 155 | Et | H | 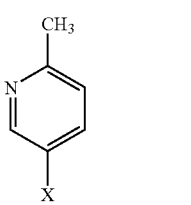 | Me | Ph |
| 156 | Et | H | 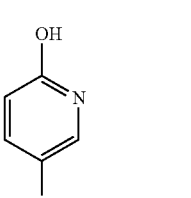 | Me | Ph |
| 157 | Et | H | 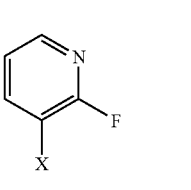 | Me | Ph |
| 158 | Et | H | 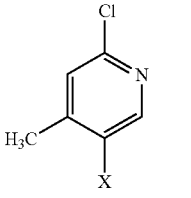 | Me | Ph |
| 159 | Et | H | 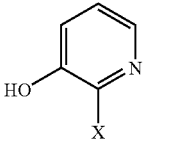 | Me | Ph |

TABLE 2-continued
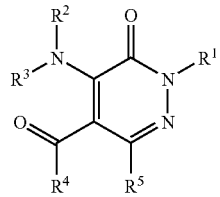
| Example | R1 | R2 | R3 | R4 | R5 |
|---|---|---|---|---|---|
| 160 | Et | H | 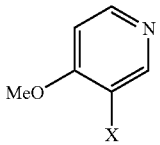 | Me | Ph |
| 161 | Et | H | 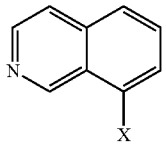 | Me | Ph |
| 162 | Et | H | 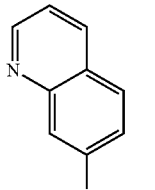 | Me | Ph |
| 163 | Et | H | 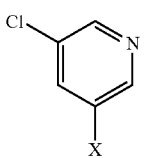 | Me | (3-F)Ph |
| 164 | Et | H | 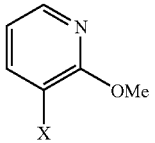 | Me | (4-F)Ph |
| 165 | Et | H | 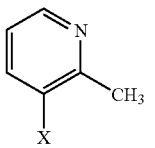 | Me | (4-F)Ph |
| 166 | Et | H | 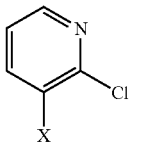 | Me | (4-F)Ph |
| 167 | Et | H | 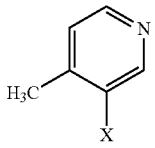 | Me | (4-F)Ph |

TABLE 2-continued
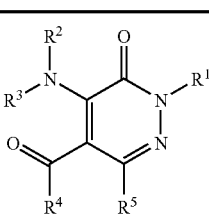
| Example | R1 | R2 | R3 | R4 | R5 |
| --- | --- | --- | --- | --- | --- |
| 168 | Et | H | 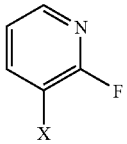 | Me | (4-F)Ph |
| 169 | C3H5CH2 | H | 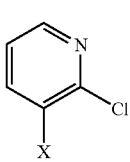 | Me | (4-F)Ph |
| 170 | C3H5CH2 | H | 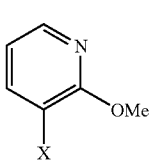 | Me | (4-F)Ph |
| 171 | C3H5CH2 | H | 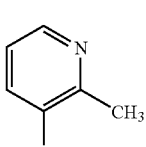 | Me | (4-F)Ph |
| 172 | C3H5CH2 | H | 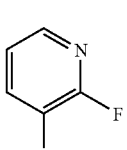 | Me | (4-F)Ph |
| 173 | C3H5CH2 | H | 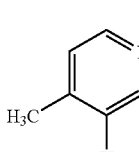 | Me | (4-F)Ph |
| 174 | C3H5CH2 | H | 3-Pyr | Me | (4-F)Ph |
| 175 | Et | H | 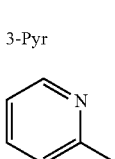 | Me | (3-Cl)Ph |
| 176 | Et | H | 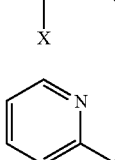 | Me | (3-Cl)Ph |

TABLE 2-continued
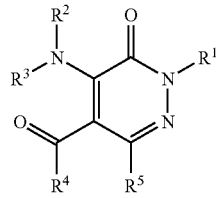
| Example | R1 | R2 | R3 | R4 | R5 |
|---|---|---|---|---|---|
| 177 | Et | H | 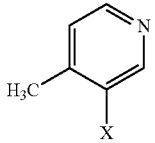 | Me | (3-Cl)Ph |
| 178 | Et | H | 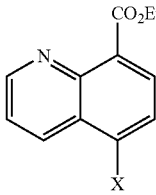 | Me | Ph |
| 179 | Et | H | 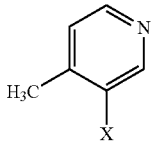 | Me | Ph |
| 180 | Et | H | 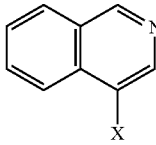 | Me | (4-MeO)Ph |
| 181 | Et | H | 3-Pyr | Me | (4-MeO)Ph |
| 182 | Et | H | 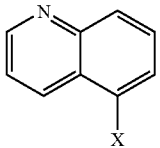 | Me | (4-MeO)Ph |
| 183 | Et | H | 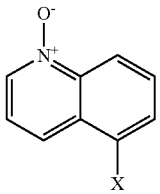 | Me | (4-MeO)Ph |
| 184 | Et | H | 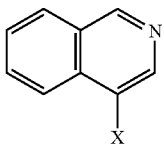 | Me | (3-MeO)Ph |
| 185 | Et | H | 3-Pyr | Me | (3-MeO)Ph |

TABLE 2-continued
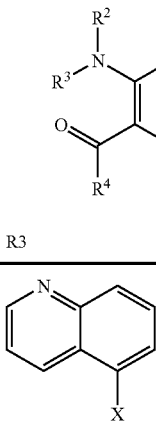
| Example | R1 | R2 | R3 | R4 | R5 |
|---|---|---|---|---|---|
| 186 | Et | H | 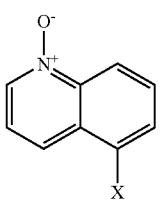 | Me | (3-MeO)Ph |
| 187 | Et | H | 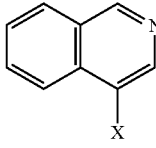 | Me | (3-MeO)Ph |
| 188 | Et | H | 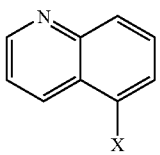 | Me | (4-Me)Ph |
| 189 | Et | H | 3-Pyr | Me | (4-Me)Ph |
| 190 | Et | H | 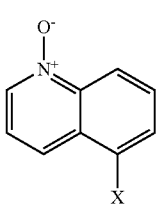 | Me | (4-Me)Ph |
| 191 | Et | H | 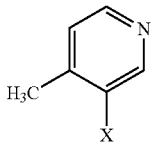 | Me | (4-Me)Ph |
| 192 | Et | H | 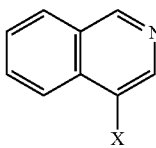 | Me | (4-Me)Ph |
| 193 | Et | H |  | Me | (3-Me)Ph |
| 194 | Et | H | 3-Pyr | Me | (3-Me)PH |

TABLE 2-continued
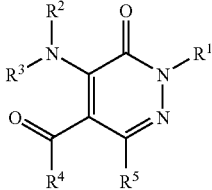
| Example | R1 | R2 | R3 | R4 | R5 |
|---|---|---|---|---|---|
| 195 | Et | H | quinolin-5-yl | Me | (3-Me)PH |
| 196 | Et | H | 4-methylpyridin-3-yl | Me | (3-Me)PH |
| 197 | Et | H | isoquinolin-4-yl | Me | (4-CO2Me)Ph |
| 198 | Et | H | 3-Pyr | Me | (4-CO2Me)Ph |
| 199 | Et | H | 3-Pyr | Me | (4-CO2H)Ph |
| 200 | Et | H | 4-methylpyridin-3-yl | Me | (4-CO2Me)Ph |
| 201 | Et | H | 4-methylpyridin-3-yl | Me | (4-CO2H)Ph |
| 202 | Et | H | 3-Pyr | Me | (3-CO2Me)Ph |
| 203 | Et | H | 3-Pyr | Me | (3-CO2H)Ph |
| 204 | Et | H | 2-chloro-1-fluoro-4-yl (2-Cl,1-F-phenyl) | Me | 4-Pyr |
| 205 | Et | 2-Cl,1-F-phenyl | 2-Cl,1-F-phenyl | Me | 4-Pyr |

TABLE 2-continued
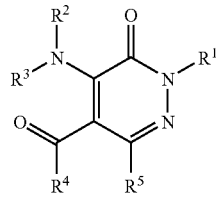
| Example | R1 | R2 | R3 | R4 | R5 |
| --- | --- | --- | --- | --- | --- |
| 206 | Et | H | 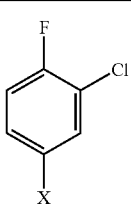 | Me | 3-Pyr |
| 207 | Et | 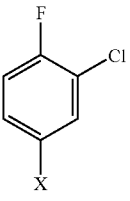 | 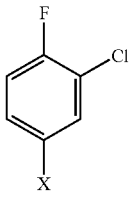 | Me | 3-Pyr |
| 208 | CH2CO2Me | H | 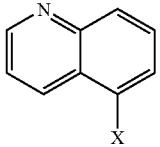 | Me | Ph |
| 209 | CH2CO2H | H | 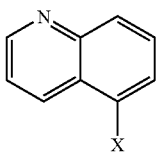 | Me | Ph |
| 210 | Et | H | 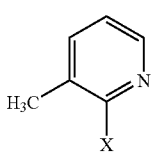 | Me | Ph |
| 211 | Et | H | 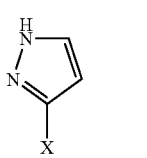 | Me | Ph |
| 212 | Et | H | 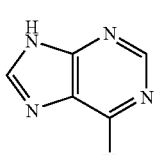 | Me | Ph |

TABLE 2-continued
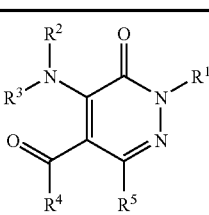
| Example | R1 | R2 | R3 | R4 | R5 |
|---|---|---|---|---|---|
| 213 | Et | H | 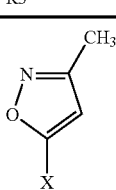 | Me | Ph |
| 214 | Et | H | 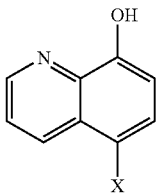 | Me | Ph |
| 215 | Et | H | 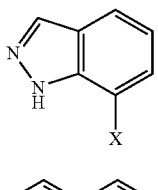 | Me | Ph |
| 216 | Et | H | 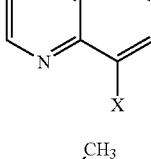 | Me | Ph |
| 217 | Et | H | 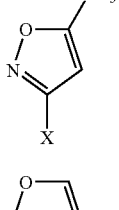 | Me | Ph |
| 218 | Et | H | 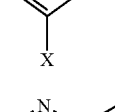 | Me | Ph |
| 219 | C3H5CH2 | H | 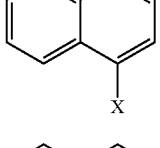 | Me | Ph |
| 220 | C3H5CH2 | H | 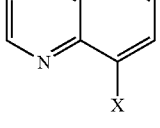 | Me | Ph |

TABLE 2-continued
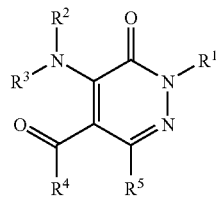
| Example | R1 | R2 | R3 | R4 | R5 |
|---|---|---|---|---|---|
| 221 | Et | H | 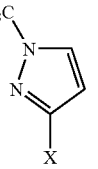 | Me | Ph |
| 222 | Et | H | 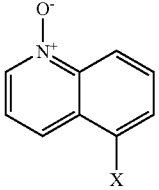 | Me | Ph |
| 223 | Et | H | 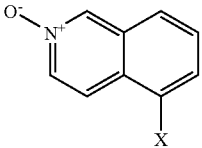 | Me | Ph |
| 224 | Et | H | 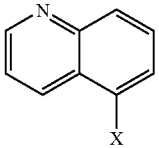 | Me | (3-Cl)Ph |
| 225 | Et | H | 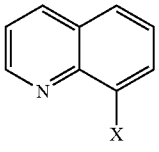 | Me | (3-Cl)Ph |
| 226 | Et | H | 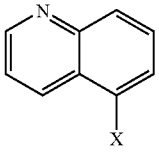 | Me | 4-Pyr |
| 227 | Et | H | 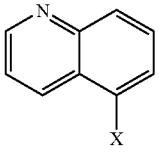 | Me | 3-Pyr |

TABLE 2-continued
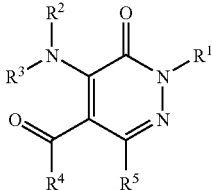
| Example | R1 | R2 | R3 | R4 | R5 |
|---|---|---|---|---|---|
| 228 | Et | H | 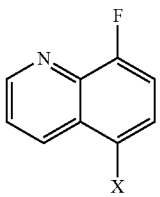 | Me | Ph |
| 229 | C3H5CH2 | H | 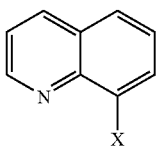 | Me | (4-F)Ph |
| 230 | Et | H | 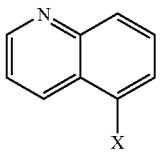 | Me | (4-F)Ph |
| 231 | Et | H | 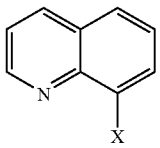 | Me | (4-F)Ph |
| 232 | C3H5CH2 | H | 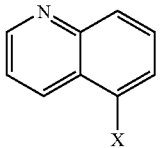 | Me | (4-F)Ph |
| 233 | Et | H | 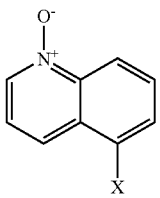 | Me | (3-Cl)Ph |
| 234 | Et | H | 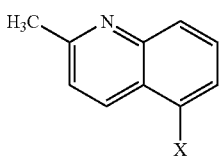 | Me | Ph |
| 235 | Et | H | 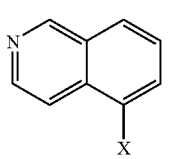 | Me | (3-Cl)Ph |

TABLE 2-continued

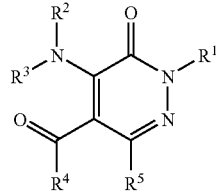

| Example | R1 | R2 | R3 | R4 | R5 |
|---|---|---|---|---|---|
| 236 | Et | H | 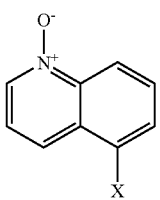 | Me | (4-F)Ph |
| 237 | Et | H | 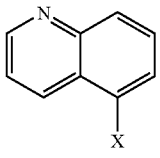 | Me | (3-F)Ph |
| 238 | Et | H | 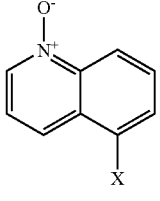 | Me | (3-F)Ph |
| 239 | Et | H | 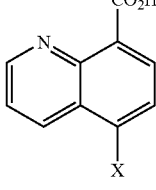 | Me | Ph |

Example 1 (Scheme 1)

5-Acetyl-2-ethyl-4-[(3-fluorophenyl)amino]-6-pyridin-3-ylpyridazin-3(2H)-one

A mixture of the title compound of Preparation 14 (520 mg, 2.0 mmol), 3-fluorophenylboronic acid (560 mg, 4.0 mmol), anhydrous cupric acetate (540 mg, 3.0 mmol), triethylamine (0.56 mL, 4.0 mmol) and activated molecular sieves (1.6 g, 4 Å) in dry dichloromethane (25 mL) was stirred under air exposure at room temperature for 48 h. The reaction was filtered and the solvent removed under reduced pressure. The resulting residue was recrystallized from ethyl acetate (202 mg, 30% yield).

m.p. 196.6-197.7° C.

δ(CDCl$_3$): 1.46 (t, 3H), 1.82 (s, 3H), 4.32 (q, 2H), 6.83 (m, 3H), 7.31 (m, 1H), 7.49 (bs, 1H), 7.87 (d, 1H), 8.15 (s, 1H), 8.68 (bs, 2H).

Example 2 (Scheme 1)

5-Acetyl-4-[(3-chlorophenyl)amino]-2-ethyl-6-pyridin-3-ylpyridazin-3(2H)-one

Obtained as a solid (27%) from the title compound of Preparation 14 and 3-chlorophenylboronic acid following the procedure of Example 1.

m.p. 180.2-180.8° C.

δ(CDCl$_3$): 1.46 (t, 3H), 1.80 (s, 3H), 4.31 (q, 2H), 6.98 (d, 1H), 7.08 (m, 1H), 7.18 (m, 1H), 7.25 (m, 1H), 7.41 (bs, 1H), 7.78 (d, 1H), 8.17 (s, 1H), 8.67 (bs, 2H).

Example 3 (Scheme 1)

5-Acetyl-4-[(3,5-dichlorophenyl)amino]-2-ethyl-pyridin-3-ylpyridazin-3(2H)-one

Obtained as a solid (30%) from the title compound of Preparation 14 and 3,5-dichlorophenylboronic acid following the procedure of Example 1.

m.p. 219.9-220.4° C.

δ(CDCl₃): 1.46 (t, 3H), 1.88 (s, 3H), 4.31 (q, 2H), 6.98 (s, 2H), 7.18 (s, 1H), 7.18 (m, 1H), 7.60 (bs, 1H), 8.03 (m, 1H), 8.17 (s, 1H), 8.72 (bs, 2H).

Examples 4-9 (Scheme 1)

4. 5-Acetyl-2-ethyl-4-(1-naphthylamino)-6-pyridin-3-ylpyridazin-3(2H)-one
5. Methyl 4-[(5-acetyl-2-ethyl-3-oxo-6-pyridin-3-yl-2,3-dihydropyridazin-4-yl)amino]benzoate
6. 5-Acetyl-2-ethyl-4-[(2-fluorophenyl)amino]-6-pyridin-3-ylpyridazin-3(2H)-one
7. 5-Acetyl-4[(2-chlorophenyl)amino]-2-ethyl-6-pyridin-3-ylpyridazin-3(2H)-one
8. 5-Acetyl-2-ethyl-4-{[4-(hydroxymethyl)phenyl]amino}-6-pyridin-3-ylpyridazin-3(2H)-one
9. 3-[(5-Acetyl-2-ethyl-3-oxo-6-pyridin-3-yl-2,3-dihydropyridazin-4-yl)amino]benzonitrile The title compounds were synthesized from the title compound of Preparation 14 and the corresponding boronic acid following the procedure of Example 1. The ESI/MS data and HPLC retention times are summarized in Table 2.

TABLE 2

| EXAMPLE | ESI/MS m/e (M + H)⁺ | Retention Time (min) |
| --- | --- | --- |
| 4 | 385 | 8.1 |
| 5 | 393 | 7.2 |
| 6 | 353 | 7.1 |
| 7 | 369 | 7.7 |
| 8 | 365 | 5.7 |
| 9 | 360 | 6.8 |

Examples 10-14 (Scheme 1)

10. 5-Acetyl-4-[(3-chlorophenyl)amino]-2-(cyclopropylmethyl)-6-pyridin-3-ylpyridazin-3(2H)-one
11. 5-Acetyl-2-(cyclopropylmethyl)-[(3,5-dichlorophenyl)amino]-6-pyridin-3-ylpyridazin-3(2H)-one
12. 5-Acetyl-2-(cyclopropylmethyl)-4-[(2-fluorophenyl)amino]-6-pyridin-3-ylpyridazin-3(2H)-one
13. 5-Acetyl-4-[(2-chlorophenyl)amino]-2-(cyclopropylmethyl)-6-pyridin-3-ylpyridazin-3(2H)-one
14. 3-{[5-Acetyl-2-(cyclopropylmethyl)-3-oxo-6-pyridin-3-yl-2,3-dihydropyridazin-4-yl]amino}benzonitrile The title compounds were synthesized from the title compound of Preparation 17 and the corresponding boronic acid following the procedure of Example 1. The ESI/MS data and HPLC retention times are summarized in Table 3.

TABLE 3

| EXAMPLE | ESI/MS m/e (M + H)⁺ | Retention Time (min) |
| --- | --- | --- |
| 10 | 395 | 8.6 |
| 11 | 430 | 9.4 |
| 12 | 379 | 7.9 |
| 13 | 395 | 8.5 |
| 14 | 386 | 7.6 |

Example 15-18 (Scheme 1)

15. Methyl 4-{[5-acetyl-2-(2-hydroxyethyl)-3-oxo-6-pyridin-3-yl-2,3-dihydropyridazin-4-yl]amino}benzoate
16. 5-Acetyl-4-[(2-fluorophenyl)amino]-2-(2-hydroxyethyl)-6-pyridin-3-ylpyridazin-3(2H)-one
17. 5-Acetyl-4-[(2-chlorophenyl)amino]-2-(2-hydroxyethyl)-6-pyridin-3-ylpyridazin-3(2H)-one
18. 5-Acetyl-4-[(3-chlorophenyl)amino]-2-(2-hydroxyethyl)-6-pyridin-3-ylpyridazin-3(2H)-one The title compounds were synthesized from the title compound of Preparation 20 and 4-methoxycarbonylphenyl boronic acid following the procedure of Example 1. The ESI/MS data and HPLC retention times are summarized in Table 4.

TABLE 4

| EXAMPLE | ESI/MS m/e (M + H)⁺ | Retention Time (min) |
| --- | --- | --- |
| 15 | 408 | 6.1 |
| 16 | 368 | 5.9 |
| 17 | 384 | 6.5 |
| 18 | 384 | 6.9 |

Example 19 (Scheme 1)

5-Acetyl-4-[(3-chlorophenyl)amino]-2-ethyl-6-pyridin-2-ylpyridazin-3(2H)-one

Obtained as a solid (27%) from the title compound of Preparation-15 and 3-chlorophenylboronic acid following the procedure of Example 1.

LRMS: m/z 369 (M+1)⁺.

δ(CDCl₃): 1.42 (t, 3H), 2.01 (s, 3H), 4.38 (q, 2H), 6.90 (m, 1H), 7.20 (m, 4H), 7.82 (m, 3H), 8.42 (d, 1H).

Example 20 (Scheme 1)

3-[(5-Acetyl-2-ethyl-3-oxo-6-pyridin-2-yl-2,3-dihydropyridazin-4-yl)amino]benzonitrile Obtained as a solid (53%) from the title compound of Preparation 15 and 3-cyanophenylboronic acid following the procedure of Example 1.

δ(DMSO-d₃): 1.37 (t, 3H), 2.09 (s, 3H), 4.22 (q, 2H), 7.42 (m, 5H), 7.92 (m, 2H), 8.49 (m, 1H), 8.89 (s, 1H).

Example 21 (Scheme 1)

5-Acetyl-2-ethyl-4-{[4-(hydroxymethyl)phenyl]amino}-6-pyridin-2-ylpyridazin-3(2H)-one Obtained as a solid (13%) from the title compound of Preparation 15 and 4-hydroxymethylphenylboronic acid following the procedure of Example 1.

LRMS: m/Z 364 (M+1)⁺.

Retention Time: 4.9 min.

Example 22 (Scheme 1)

3-{[5-Acetyl-2-(cyclopropylmethyl)-3-oxo-6-pyridin-2-yl-2,3-dihydropyridazin-4-yl]amino}benzonitrile Obtained as a solid (40%) from the title compound of Preparation 18 and 3-cyanophenylboronic acid following the procedure of Example 1.
m.p. 168.1-169.6° C.
δ(CD$_3$OD): 0.49 (m, 2H), 0.59 (m, 2H), 1.36 (m, 1H), 2.11 (s, 3H), 4.13 (d, 2H), 7.38 (m, 5H), 7.92 (m, 32H), 8.44 (m, 1H).

Example 23-25 (Scheme 1)

23. 5-Acetyl-4-[(3-chlorophenyl)amino]-2-(cyclopropylmethyl)-6-pyridin-2-ylpyridazin-3(2H)-one
24. 5-Acetyl-2-(cyclopropylmethyl)-4-{[4-(hydroxymethyl)phenyl]amino}-6-pyridin-2-ylpyridazin-3(2H)-one
25. 5-Acetyl-2-(cyclopropylmethyl)-4-[(3,5-dichlorophenyl)amino]-6-pyridin-2-ylpyridazin-3(2H)-one The title compounds were synthesized from the title compound of Preparation 18 and the corresponding boronic acid following the procedure of Example 1. The ESI/MS data, and HPLC retention times are summarized in Table 5.

TABLE 5

| EXAMPLE | ESI/MS m/e (M + H)$^+$ | Retention Time (min) |
|---|---|---|
| 23 | 394 | 8.5 |
| 24 | 390 | 8.9 |
| 25 | 429 | 9.7 |

Example 26 (Scheme 1)

3-{[5-Acetyl-2-(2-hydroxyethyl)-3-oxo-6-pyridin-2-yl-2,3-dihydropyridazin-4-yl]amino}benzonitrile Obtained as a solid (26%) from the title compound of Preparation 21 and 3-cyanophenylboronic acid following the procedure of Example 1.
m.p. 194.3-195.0° C.
δ(CD$_3$OD): 2.10 (s, 3H), 4.01 (t, 2H), 4.40 (t, 2H), 6.90 (m, 1H), 7.35 (m, 6H), 7.92 (m, 2H), 8.46 (d, 1H).

Example 27 (Scheme 1)

5-Acetyl-4-[(3-chlorophenyl)amino]-2-(2-hydroxyethyl)-6-pyridin-2-ylpyridazin-3(2H)-one Obtained as a solid (22%) from the title compound of Preparation 21 and 3-chlorophenylboronic acid following the procedure of Example 1.
LRMS: m/Z 385 (M+1)$^+$.
Retention Time: 6.0 min.

Examples 28-29 (Scheme 1)

28. 5-Acetyl-4-[(3,5-dichlorophenyl)amino]-2-(2-hydroxyethyl)-6-pyridin-2-ylpyridazin-3(2H)-one
29. 5-Acetyl-2-(2-hydroxyethyl)-4-{[4-(hydroxymethyl)phenyl]amino}-6-pyridin-2-ylpyridazin-3(2H)-one The title compounds were synthesized from the title compound of Preparation 21 and the corresponding boronic acid following the procedure of Example 1. The ESI/MS data and HPLC retention times are summarized in Table 6.

TABLE 6

| EXAMPLE | ESI/MS m/e (M + H)$^+$ | Retention Time (min) |
|---|---|---|
| 28 | 420 | 7.2 |
| 29 | 381 | 4.0 |

Example 30 (Scheme 1)

5-Acetyl-2-ethyl-4-[(3-fluorophenyl)amino]-6-pyridin-4-ylpyridazin-3(2H)-one

Obtained as a solid (15%) from the title compound of Preparation 16 and 3-fluorophenylboronic acid following the procedure of Example 1.
m.p. 195.1-195.9° C.
δ(DMSO-d$_6$): 1.33 (t, 3H), 1.87 (s, 3H), 4.18 (q, 2H), 6.88 (m, 3H), 7.28 (m, 1H), 7.31 (d, 2H), 8.58 (d, 2H), 9.24 (so 1H).

Example 31 (Scheme 1)

5-Acetyl-4-[(3-chlorophenyl)amino]-2-ethyl-6-pyridin-4-ylpyridazin-3(2H)-one

Obtained as a solid (68%) from the title compound of Preparation 16 and 3-chlorophenylboronic acid following the procedure of Example 1.
m.p. 176.4-177.0° C.
δ(DMSO-d$_6$): 1.33 (t, 3H), 1.87 (s, 3H), 4.18 (q, 2H), 7.01 (m, 3H), 7.29 (m, 3H), 8.60 (m, 2H), 9.24 (s, 1H).

Example 32 (Scheme 1)

5-Acetyl-2-ethyl-4-(1-naphthylamino)-6-pyridin-4-ylpyridazin-3(2H)-one

Obtained as a solid (53%) from the title compound of Preparation 16 and naphthalene-1-boronic acid following the procedure of Example 1.
m.p. 177.6-179.3° C.
δ(DMSO-d$_6$, 75° C.): 1.37 (m, 6H), 4.23 (q, 2H), 7.23 (m, 3H), 7.37 (m, 1H), 7.54 (m, 2H), 7.70 (m, 1H), 7.92 (m, 1H), 8.01 (m, 1H), 8.55 (m, 2H), 8.89 (s, 1H).

Example 33 (Scheme 1)

5-Acetyl-2-ethyl-4-[(2-methylphenyl)amino]-6-pyridin-4-ylpyridazin-3(2H)-one

Obtained as a solid (17%) from the title compound of Preparation 16 and 2-methylphenylboronic acid following the procedure of Example 1.
m.p. 187.8-189.4° C.
δ(CD$_3$OD): 1.42 (t, 3H), 1.60 (s, 3H), 2.29 (s, 3H), 4.30 (q, 2H), 7.02 (m, 1H), 7.14 (m, 2H), 7.25 (m, 1H), 7.40 (m, 2H), 8.54 (m, 2H).

Examples 34-40 (Scheme 1)

34. Methyl 4-[(5-acetyl-2-ethyl-3-oxo-6-pyridin-4-yl-2,3-dihydropyridazin-4-yl)amino]benzoate
35. 5-Acetyl-2-ethyl-4-[(2-methoxyphenyl)amino]-6-pyridin-4-ylpyridazin-3(2H)-one
36. 5-Acetyl-2-ethyl-4-[(3-methoxyphenyl)amino]-6-pyridin-4-ylpyridazin-3(2H)-one
37. 5-Acetyl-2-ethyl-4-[(2-fluorophenyl)amino]-6-pyridin-4-ylpyridazin-3(2H)-one
38. 5-Acetyl-4-[(2-chlorophenyl)amino]-2-ethyl-6-pyridin-4-ylpyridazin-3(2H)-one
39. 3-[(5-Acetyl-2-ethyl-3-oxo-6-pyridin-4-yl-2,3-dihydropyridazin-4-yl)amino]benzonitrile
40. 5-Acetyl-2-ethyl-4-{[4-(hydroxymethyl)phenyl]amino}-6-pyridin-4-ylpyridazin-3(2H)-one The title compounds were synthesized from the title compound of Preparation 16 and the corresponding boronic acid following the procedure of Example 1. The ESI/MS data and HPLC retention times are summarized in Table 7.

TABLE 7

| EXAMPLE | ESI/MS m/e (M + H)+ | Retention Time (min) |
|---|---|---|
| 34 | 392 | 7.0 |
| 35 | 364 | 6.9 |
| 36 | 364 | 6.9 |
| 37 | 352 | 6.8 |
| 38 | 368 | 7.5 |
| 39 | 359 | 6.4 |
| 40 | 364 | 5.4 |

Example 41 (Hydrolisis No Scheme)

4-[(5-acetyl-2-ethyl-3-oxo-6-pyridin-4-yl-2,3-dihydropyridazin-4-yl)amino]benzoic acid To a stirred solution of the title product of example 34 (0.38 g, 0.97 mmol) in 40 mL of a 3:2 MeOH/THF mixture a solution of lithium hydroxide (0.25 g, 5.88 mmol) in 4 mL of water was added and the mixture was stirred at room temperature overnight. It was acidified with HCl 2N until pH 6 and it was extracted with dichloromethane and washed with water and brine. It was dried on Na2SO4 and solvent removed to yield a crude product that was purified by column chromatography on SiO2 using CH2Cl2/MeOH as eluent. The title product was obtained in a 16% yield.

m.p. 251.6-252.6° C.

δ(DMSO-$d_6$): 1.34 (m, 3H), 1.93 (s, 3H), 4.20 (q, 2H), 7.08 (d, 2H), 7.33 (d, 2H), 7.79 (d, 2H), 8.60 (d, 2H), 9.38 (s, 1H).

Examples 42-46 (Scheme 1)

42. 5-Acetyl-2-(cyclopropylmethyl)-4-[(2-fluorophenyl)amino]-6-pyridin-4-ylpyridazin-3(2H)-one
43. 5-Acetyl-4-[(2-chlorophenyl)amino]-2-(cyclopropylmethyl)-6-pyridin-4-ylpyridazin-3(2H)-one
44. 3-{[5-Acetyl-2-(cyclopropylmethyl)-3-oxo-6-pyridin-4-yl-2,3-dihydropyridazin-4-yl]amino}benzonitrile
45. 5-Acetyl-2-(cyclopropylmethyl)-4-{[4-(hydroxymethyl)phenyl]amino}-6-pyridin-4-ylpyridazin-3(2H)-one
46. 5-Acetyl-4-[(3-chlorophenyl)amino]-2-(cyclopropylmethyl)-6-pyridin-4-ylpyridazin-3(2H)-one The title compounds were synthesized from the title compound of Preparation 19 and the corresponding boronic acid following the procedure of Example 1. The ESI/MS data and HPLC retention times are summarized in Table 8.

TABLE 8

| | ESI/MS m/e (M + H)+ | Retention Time (min) |
|---|---|---|
| 42 | 378 | 7.8 |
| 43 | 394 | 8.5 |
| 44 | 385 | 7.4 |
| 45 | 390 | 6.4 |
| 46 | 394 | 8.4 |

Examples 47-51 (Scheme 1)

47. 5-Acetyl-4-[(2-fluorophenyl)amino]-2-(2-hydroxyethyl)-6-pyridin-4-ylpyridazin-3(2H)-one
48. 5-Acetyl-4-[(2-chlorophenyl)amino]-2-(2-hydroxyethyl)-6-pyridin-4-ylpyridazin-3(2H)-one
49. 3-{[5-Acetyl-2-(2-hydroxyethyl)-3-oxo-6-pyridin-4-yl-2,3-dihydropyridazin-4-yl]amino}benzonitrile
50. 5-Acetyl-2-(2-hydroxyethyl)-4-{[4-(hydroxymethyl)phenyl]amino}-6-pyridin-4-ylpyridazin-3(2H)-one
51. 5-Acetyl-4-[(3-chlorophenyl)amino]-2-(2-hydroxyethyl)-6-pyridin-4-ylpyridazin-3(2H)-one The title compounds were synthesized from the title compound of Preparation 22 and the corresponding boronic acid following the procedure of Example 1. The ESI/MS data and HPLC retention times are summarized in Table 9.

TABLE 9

| | ESI/MS m/e (M + H)+ | Retention Time (min) |
|---|---|---|
| 47 | 368 | 5.5 |
| 48 | 384 | 6.2 |
| 49 | 375 | 5.2 |
| 50 | 380 | 4.3 |
| 51 | 384 | 6.4 |

Example 52 (Scheme 1)

5-Acetyl-4-[(3-chlorophenyl)amino]-2-ethyl-6-thien-2-ylpyridazin-3(2H)-one

Obtained as a solid (20%) from the title compound of Preparation 26 and 3-chlorophenylboronic acid following the procedure of Example 1.

LRMS: m/Z 374 (M+1)+.

δ(CDCl$_3$): 1.46 (t, 3H), 1.88 (s, 3H), 4.29 (q, 2H), 7.00 (m, 3H), 7.08 (m, 1H), 7.26 (m, 2H), 7.27 (m, 1H), 7.98 (m, 1H).

Examples 53-55 (Scheme 1)

53. 5-Acetyl-4-[bis(3-fluorophenyl)amino]-2-ethyl-6-pyridin-3-ylpyridazin-3(2H)-one
54. 5-Acetyl-4-[bis-4-methoxycarbonylphenyl)-amino]-2-ethyl-6-pyridin-3-ylpyridazin-3(2H)-one
55. 5-Acetyl-4-{bis[4-(hydroxymethyl)phenyl]amino}-2-ethyl-6-pyridin-3-ylpyridazin-3(2H)-one The title compounds were synthesized from the title compound of Preparation 14 and an excess of the corresponding arylboronic acid following the experimental procedure described in example 1. The ESI/MS data and HPLC retention times are summarized in Table 10.

TABLE 10

| EXAMPLE | ESI/MS m/e (M + H)+ | Retention Time (min) |
|---------|---------------------|----------------------|
| 53 | 446 | 8.9 |
| 54 | 526 | 8.7 |
| 55 | 470 | 6.2 |

Examples 56-57 (Scheme 1)

56. 5-Acetyl-4-[bis(3-nitrophenyl)amino]-2-ethyl-6-pyridin-4-ylpyridazin-3(2H)-one
57. 5-acetyl-4-[bis(3-fluorophenyl)amino]-2-ethyl-6-pyridin-4-ylpyridazin-3(2H)-one The title compounds were synthesized from the title compound of Preparation 16 and an excess of the corresponding arylboronic acid following the experimental procedure described in example 1. The ESI/MS data and HPLC retention times are summarized in Table 11.

TABLE 11

| EXAMPLE | ESI/MS m/e (M + H)+ | Retention Time (min) |
|---------|---------------------|----------------------|
| 56 | 501 | 8.5 |
| 57 | 447 | 8.9 |

Examples 58-59 (Scheme 1)

58. 5-Acetyl-4-[bis(3-chlorophenyl)amino]-2-(cyclopropylmethyl)-6-pyridin-3-ylpyridazin-3(2H)-one
59. 5-Acetyl-4-[bis(3,5-dichlorophenyl)amino]-2-(cyclopropylmethyl)-6-pyridin-3-ylpyridazin-3(2H)-one The title compounds were synthesized from the title compound of Preparation 17 and an excess of the corresponding arylboronic acid following the experimental procedure described in example 1. The ESI/MS data and HPLC retention times are summarized in Table 12.

TABLE 12

| EXAMPLE | ESI/MS m/e (M + H)+ | Retention Time (min) |
|---------|---------------------|----------------------|
| 58 | 505 | 10.2 |
| 59 | 574 | 11.0 |

Example 60 (Scheme 1)

5-Acetyl-4-[bis(4-methoxycarbonylphenyl)amino]-2-(2-hydroxyethyl)-6-pyridin-3-ylpyridazin-3(2H)-one The title compound was synthesized from the title compound of Preparation 20 and an excess of 4-methoxycarbonylphenylboronic acid following the experimental procedure described in example 1.

LRMS: m/Z 542 (M+1)+.
Retention Time: 8.0 min.

Example 61 (Scheme 1)

5-Acetyl-4-[bis(3-chlorophenyl)amino]-2-(2-hydroxyethyl)-6-pyridin-2-ylpyridazin-3(2H)-one The title compound was synthesized from the title compound of Preparation 21 and an excess of 3-chlorophenylboronic acid following the experimental procedure described in example 1.

LRMS: m/Z 495 (M+1)+.
Retention Time: 9.6 min.

Example 62 (Scheme 1)

5-Acetyl-4-[bis(3-chlorophenyl)amino]-2-(cyclopropylmethyl)-6-pyridin-4-ylpyridazin-3(2H)-one The title compound was synthesized from the title compound of Preparation 19 and an excess of 3-chlorophenylboronic acid following the experimental procedure described in example 1;

LRMS: m/Z 505 (M+1)+.
Retention Time: 10.2 min.

Example 63 (Scheme 2)

5-Acetyl-2-ethyl-6-phenyl-4-(pyridin-3-ylamino)pyridazin-3(2H)-one

To a stirred solution of 200 mg (0.7 mmol) of 5-acetyl-2-ethyl-4-nitro-6-phenylpyridazin-3(2H)-one (Dal Piaz, V et al, *J. Med. Chem.* 1997, 40, 1417) in ethanol (10 mL), 3-aminopyridine (0.098 mg, 1.04 mmol) was added portionwise. The resulting mixture was stirred at room temperature for five hours. The solvent was evaporated and the residue purified by column chromatography (silica gel, dichloromethane/methanol 97:3) to yield the title compound (60 mg, 26% yield).

m.p. 185.6-186.3° C.

δ(DMSO-$d_6$): 1.34 (m, 3H), 1.72 (s, 3H), 4.18 (q, 2H), 7.29 (m, 3H), 7.41 (m, 4H) 8.26 (d, 1H), 8.33 (d, 1H), 9.10 (s, 1H).

Example 64 (Scheme 2)

5-Acetyl-4-[(3,5-dichloropyridin-4-yl)amino]-2-ethyl-6-phenylpyridazin-3(2H)-one To a stirred suspension of 50 mg (1.25 mmol) of sodium hydride in 5 ml of THF, 100 mg (0.62 mmol) of 4-amino-3,5-dichloropyridine in 5 ml of THF was added. The mixture was allowed stirring 30 minutes at room temperature and then cooled to 0° C. 150 mg (0.52 mmol) of 5-acetyl-2-ethyl-4-nitro-6-phenylpyridazin-3(2H)-one (Dal Piaz, V et al, *J. Med. Chem.* 1997, 40, 1417) in 10 ml of THF was added. The reaction was allowed to warm to room temperature and to continue stirring for 12 hours. The mixture was acidified with 2N HCl to pH 2. Ethyl acetate was added and the organic layer was washed with water, brine, dried over $Na_2SO_4$ anhydride and evaporated. The residue obtained (210 mg) was purified by column chromatography (silica gel, hexane/ethyl acetate 1:1) to yield the title compound (35 mg, 16.7% yield).

m.p. 195.5-197.1° C.

δ($CDCl_3$): 1.40 (m, 3H), 1.85 (s, 3H), 4.10 (q, 2H), 7.45 (bs, 5H), 8.40 (s, 2H), 8.80 (s, 1H).

Example 65 (Scheme 2)

5-Acetyl-2-ethyl-6-phenyl-4-(pyrazin-2-ylamino)pyridazin-3(2H)-one

To a stirred solution of 75 mg (0.261 mmol) of 5-acetyl-2-ethyl-4-nitro-6-phenylpyridazin-3(2H)-one (Dal Piaz, V et al, *J. Med. Chem.* 1997, 40, 1417) in 4 ml of ethanol, 37 mg (0.392 mmol) of aminopyrazine was added. The resulting mixture was stirred at room temperature during 3 days and the final product was collected by filtration and washed with diethylether to yield the title compound (12 mg, 13.6% yield).

m.p. 228.9-229.7° C.

$\delta$(DMSO-$d_6$): 1.34 (m, 3H), 1.84 (s, 3H), 4.21 (q, 2H), 7.34 (m, 2H), 7.48 (m, 3H) 8.12 (m, 2H), 8.67 (s, 1H), 9.93 (s, 1H).

Example 66 (Scheme 2)

5-Acetyl-2-ethyl-6-phenyl-4-(pyrimidin-2-ylamino)pyridazin-3(2H)-one

To a stirred solution of 100 mg (0.348 mmol) of 5-acetyl-2-ethyl-4-nitro-6-phenylpyridazin-3(2H)-one (Dal Piaz, V et al, *J. Med. Chem.* 1997, 40, 1417) in 5 ml of ethanol, 430 mg (4.524 mmol) of 2-aminopyrimidine was added. The resulting mixture was stirred at 50° C. during five days and the final product was collected by filtration and washed with diethylether to yield the title compound (42 mg, 35.6% yield).

m.p. 197.1-198.3° C.

$\delta$(DMSO-$d_6$): 1.33 (m, 3H), 1.96 (s, 3H), 4.19 (q, 2H), 7.02 (m, 1H), 7.37 (m, 2H) 7.49 (m, 3H), 8.52 (m, 2H), 9.02 (s, 1H).

Example 67 (Scheme 2)

5-Acetyl-2-ethyl-6-phenyl(quinolin-8-ylamino)pyridazin-3(2H)-one

To a stirred solution of 100 mg (0.348 mmol) of 5-acetyl-2-ethyl-4-nitro-6-phenylpyridazin-3(2H)-one (pal Piaz, V et al., *J. Med. Chem.* 1997, 40, 1417) in 5 ml of ethanol, 75 mg (0.522 mmol) of 8-aminoquinoline was added. The resulting mixture was stirred at room temperature for two hours and the final product was collected by filtration and washed with diethylether to yield the title compound (100 mg, 74.6% yield).

m.p. 179.2.1-180.3° C.

$\delta$(CDCl$_3$): 1.49 (m, 3H), 1.75 (s, 3H), 4.34 (q, 2H), 7.25 (m, 1H), 7.45 (m, 7H) 7.56 (m, 1H), 8.17 (dd, 1H), 8.92 (d, 1H), 9.55 (s, 1H).

Example 68 (Scheme 2)

5-Acetyl-2-ethyl-4-[(5-nitropyridin-2-yl)amino]-6-phenylpyridazin-3(2H)-one

To a solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in 4 ml of ethanol, 77 mg (0.556 mmol) of 2-amino-5-nitropyridine was added. The resulting mixture was irradiated in microwave oven for seven hours at 120° C. The final product was collected by filtration and washed with diethylether to yield the title compound (36 mg, 34.3% yield).

m.p. 200.3-201.1° C.

$\delta$(DMSO-$d_6$): 1.35 (m, 3H), 1.92 (s, 3H), 4.22 (q, 2H), 7.39 (m, 3H), 7.49 (m, 3H), 8.41-8.45 (dd, 1H), 8.92 (d, 1H), 10.34 (s, 1H).

Example 69 (Scheme 2)

5-Acetyl-2-ethyl-4-(1H-indol-4-ylamino)-6-phenylpyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in 4 ml of ethanol, 55 mg (0.417 mmol) of 4-aminoindole was added. The resulting mixture was stirred at room temperature for one hour and the final product was collected by filtration and washed with diethylether to yield the title compound (83 mg, 79.8% yield).

m.p. 223.2-224.9° C.

$\delta$(CDCl$_3$): 1.27 (s, 3H), 1.36 (m, 3H), 4.19 (q, 2H), 6.33 (s, 1H), 6.66-6.67 (d, 1H), 6.95 (m, 1H), 7.25 (m, 3H), 7.31-7.37 (m, 4H), 8.76 (s, 1H), 11.20 (s, 1H).

Examples 70-78

70. 5-Acetyl-4-(1,3-benzothiazol-6-ylamino)-2-ethyl-6-phenylpyridazin-3(2H)-one
71. 5-Acetyl-2-ethyl-6-phenyl-4-(thianthren-1-ylamino)pyridazin-3(2H)-one
72. Methyl 3-[(5-acetyl-2-ethyl-3-oxo-6-phenyl-2,3-dihydropyridazin-4-yl)amino]thiophene-2-carboxylate
73. 5-Acetyl-2-ethyl-4-[(4-methylpyridin-2-yl)amino]-6-phenylpyridazin-3(2H)-one
74. 5-Acetyl-2-ethyl-6-phenyl-4-(1H-1,2,4-triazol-5-ylamino)pyridazin-3(2H)-one
75. 5-Acetyl-2-ethyl-4-[(6-methoxypyridin-3-yl)amino]-6-phenylpyridazin-3(2H)-one
76. 5-Acetyl-2-ethyl-4-(2H-indazol-5-ylamino)-6-phenylpyridazin-3(2H)-one
77. Methyl 4-[(5-acetyl-2-ethyl-3-oxo-6-phenyl-2,3-dihydropyridazin-4-yl)amino]thiophene-3-carboxylate
78. 5-Acetyl-2-ethyl-6-phenyl-4-(pyridin-2-ylamino)pyridazin-3(2H)-one The title compounds were synthesized from 5-acetyl-2-ethyl-4-nitro-6-phenylpyridazin-3(2H)-one (Dal Piaz, V et al, *J. Med. Chem.* 1997, 40, 1417) and the corresponding aniline or aminopyridine following the procedure of Example 67. The ESI/MS data and HPLC retention times are summarized in Table 13.

TABLE 13

| EXAMPLE | ESI/MS m/e (M + H)$^+$ | Retention Time (min) |
| --- | --- | --- |
| 70 | 390 | 8.2 |
| 71 | 471 | 10.5 |
| 72 | 397 | 9.1 |
| 73 | 348 | 5.0 |
| 74 | 324 | 7.5 |
| 75 | 364 | 8.3 |
| 76 | 373 | 7.7 |
| 77 | 398 | 8.8 |
| 78 | 335 | 4.8 |

Example 79 (Hydrolisis: No Scheme)

3-[(5-acetyl-2-ethyl-3-oxo-6-phenyl-2,3-dihydropyridazin-4-yl)amino]thiophene-2-carboxylic acid The title compound was synthesized from the title compound of example 72 following the experimental procedure described in example 41.

LRMS: m/Z 383 (M+1)$^+$.
Retention Time: 8.5 min.

Example 80 (Scheme 2)

5-Acetyl-2-ethyl-4-[(3-methylcinnolin-5-yl)amino]-6-phenylpyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in 4 ml of ethanol, 66 mg (0.417 mmol) of 3-methylcinnolin-5-amine was added. The resulting mixture was stirred at room temperature for one day. The final product was collected by filtration and purified by column chromatography (silica gel, ethyl acetate/hexane 2:1) to yield the title compound (65 mg, 58.6% yield).

m.p. 235.4-237.7° C.

δ(DMSO-d$_6$): 1.37 (m, 3H), 1.41 (s, 3H), 2.91 (s, 3H), 4.22 (q, 2H), 7.25 (m, 2H) 7.35-7.40 (m, 3H), 7.53 (d, 1H), 7.67-7.72 (t, 1H), 8.10 (s, 1H), 8.24 (d, 1H), 9.19 (s, 1H).

Example 81 (Scheme 2)

5-Acetyl-2-ethyl-4-[(2-methylquinolin-8-yl)amino]-6-phenylpyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in 4 ml of ethanol, 66 mg (0.417 mmol) of 2-methylquinolin-8-amine was added. The resulting mixture was stirred at room temperature for one hour and the final product was collected by filtration and washed with diethylether to yield the title compound (97 mg, 93.3% yield).

m.p. 172.2-172.6° C.

δ(DMSO-d$_6$): 1.22 (m, 3H), 1.52 (s, 3H), 2.54 (s, 3H), 4.07 (q, 2H), 7.02 (d, 1H), 7.21-7.30 (m, 6H), 7.35 (d, 1H), 7.46 (d, 1H), 8.13 (d, 1H), 9.15 (s, 1H).

Example 82 (Scheme 2)

5-Acetyl-2-ethyl-6-phenyl-4-(quinolin-5-ylamino)pyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in 4 ml of ethanol, 60 mg (0.417 mmol) of 5-aminoquinoline was added. The resulting mixture was stirred at room temperature for four hours and the final product was collected by filtration and washed with diethylether to yield the title compound (80 mg, 74.8% yield).

m.p. 219.9-221.1° C.

δ(DMSO-d$_6$): 1.31 (s, 3H), 1.38 (m, 3H), 4.22 (q, 2H), 7.24 (m, 2H), 7.34-7.38 (m, 4H), 7.55-7.63 (m, 2H), 7.86 (d, 1H), 8.42 (d, 1H), 8.92 (d, 1H), 9.19 (s, 1H).

Example 83 (Scheme 2)

5-Acetyl-2-ethyl-4-(1H-indol-5-ylamino)-6-phenylpyridazin-3(2H)-one

To a stirred solution of 80 mg (9.278 mmol) of 5-acetyl-2-ethyl-4-nitro-6-phenylpyridazin-3(2H)-one (Dal Piaz, V et al, *J. Med. Chem.* 1997, 40, 1417) in 4 ml of ethanol, 55 mg (0.417 mmol) of 5-aminoindole was added. The resulting mixture was stirred at room temperature for one hour and the final product was collected by filtration and washed with diethylether to yield the title compound (97 mg, 93.3% yield).

m.p. 242.6-243.1° C.

δ(DMSO-d$_6$): 1.34 (m, 3H), 1.47 (s, 3H), 4.17 (q, 2H), 6.33 (bs, 1H), 6.83 (d, 1H), 7.24-7.37 (m, 8H), 8.77 (s, 1H), 11.09 (s, 1H).

Example 84 (Scheme 2)

5-Acetyl-2-ethyl-4-(isoquinolin-5-ylamino)-6-phenylpyridazin-3(2H)-one

To a stirred solution of 80 mg (0.278 mmol) of 5-acetyl-2-ethyl-4-nitro-phenylpyridazin-3(2H)-one (Dal Piaz, V et al, *J. Med. Chem.* 1997, 40, 1417) in 4 ml of ethanol, 60 mg (0.417 mmol) of 5-isoquinolinamine was added. The resulting mixture was stirred at room temperature for three days. The final product was collected by filtration and purified by column chromatography (silica gel, ethyl acetate/hexane 7:3) to yield the title compound (20 mg, 12.4% yield).

δ(DMSO-d$_6$): 1.31 (s, 3H), 1.38 (m, 3H), 4.22 (q, 2H), 7.24 (m, 2H), 7.38 (m, 3H), 7.53 (m, 2H), 7.85 (d, 1H), 7.97 (d, 1H), 8.53 (d, 1H), 9.18 (s, 1H), 9.32 (s, 1H).

Example 85 (Scheme 2)

5-Acetyl-2-ethyl-4-[(6-methoxyquinolin-8-yl)amino]-6-phenylpyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in 4 ml of ethanol, 73 mg (0.417 mmol) of 8-amino-6-methoxyquinoline was added. The resulting mixture was stirred at room temperature for two hours and the final product was collected by filtration and washed with diethylether to yield the title compound (88 mg, 76.5% yield).

m.p. 183.1-184.0° C.

δ(DMSO-d$_6$): 1.34 (m, 3H), 1.68 (s, 3H), 3.84 (s, 3H), 4.21 (q, 2H), 6.81 (s, 1H), 7.08 (s, 1H), 7.36-7.46 (m, 5H), 7.53-7.57 (m, 1H), 8.27 (d, 1H), 8.73 (d, 1H), 9.31 (s, 1H).

Example 86 (Scheme 2)

5-Acetyl-4-[(5-bromoquinolin-8-yl)amino]-2-ethyl-6-phenylpyridazin-3(2H)-one

To a stirred solution of 40 mg (0.139 mmol) of 5-acetyl-2-ethyl-4-nitro-6-phenylpyridazin-3(2H)-one (Dal Piaz, V et al, *J. Med. Chem.* 1997, 40, 1417) in ethanol (4 mL), 8-amino-5-bromoquinoline (47 mg, 0.209 mmol) was added. The resulting mixture was stirred at room temperature for five days and heated at 50° C. during four days. The solvent was evaporated and the residue purified by column chromatography (silica gel, hexane/ethyl acetate 4:1) to yield the title compound (16 mg, 25% yield).

m.p. 148.1-149.0° C.

δ(DMSO-d$_6$): 1.35 (m, 3H), 1.70 (s, 3H), 4.20 (q, 2H), 7.13 (d, 1H), 7.39-7.46 (m, 5H), 7.76 (m, 1H), 7.84 (d, 1H), 8.50 (d, 1H), 8.99 (d, 1H), 9.41 (s, 1H).

Example 87 (Scheme 2)

5-Acetyl-2-ethyl-4-[(4-methylpyrimidin-2-yl) amino]-6-phenylpyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in ethanol (4 mL), 2-amino-4-methylpyrimidine (46 mg, 0.417 mmol) was added. The resulting mixture was stirred at 50° C. during five days. The solvent was evaporated and the residue purified by column chromatography (silica gel, hexane/ethyl acetate 2:1) to yield the title compound (11 mg, 11.3% yield).
LRMS: m/Z 350 (M+1)$^+$.
Retention Time: 7.4 min.

Example 88 (Scheme 2)

5-Acetyl-6-(3-chlorophenyl)-2-ethyl-4-(pyridin-3-ylamino)-pyridazin-3(2H)-one

Obtained from 5-acetyl-2-ethyl-4-nitro-6-(3-chlorophenyl)pyridazin-3(2H)-one (Dal Piaz, V et al., *J. Med. Chem.* 1997, 40, 1417) and pyridin-3-ylamine following the procedure of Example 67. The product was purified by preparative HPLC/MS.
LRMS: m/Z 369 (M+1)$^+$.
Retention Time: 8.2 min.

Example 89 (Scheme 2)

5-Acetyl-6-(3-chlorophenyl)-2-cyclopropylmethyl-4-(pyridin-3-ylamino)-pyridazin-3(2H)-one Obtained from the title compound of preparation 40 and pyridin-3-ylamine following the procedure of Example 67. The product was purified by preparative HPLC/MS.
LRMS: m/Z 395 (M+1)$^+$.
Retention Time: 9.1 min.

Example 90 (Scheme 2)

5-Acetyl-2-ethyl-6-(3-fluorophenyl)-4-(pyridin-3-ylamino)-pyridazin-3(2H)-one

Obtained from the title compound of preparation 36 and pyridin-3-ylamine following the procedure of Example 67. The product was purified by preparative HPLC/MS.
LRMS: m/Z 353(M+1)$^+$.
Retention Time: 7.4 min.

Example 91 (Scheme 2)

5-Acetyl-6-(3-fluorophenyl)-2-isopropyl-4-pyridin-3-ylamino)-pyridazin-3(2H)-one Obtained from the title compound of preparation 38 and pyridin-3-ylamine following the procedure of Example 67. The product was purified by preparative HPLC/MS.
LRMS: m/Z 367 (M+1)$^+$.
Retention Time: 8.3 min.

Example 92 (Scheme 2)

5-Acetyl-2-cyclopropylmethyl-6-(3-fluorophenyl)-4-(pyridin-3-ylamino)-pyridazin-3(2H)-one Obtained from the title compound of preparation 37 and pyridin-3-ylamine following the procedure of Example 67. The product was purified by preparative HPLC/MS.
LRMS: m/Z 379 (M+1)$^+$.
Retention Time: 8.4 min.

Example 93 (Scheme 2)

5-Acetyl-6-(4-fluorophenyl)-2-ethyl 4-(pyridin-3-ylamino)-pyridazin-3(2H)-one

Obtained from the title compound of preparation 30 and pyridin-3-ylamine following the procedure of Example 67. The product was purified by preparative HPLC/MS.
LRMS: m/Z 353 (M+1)$^+$.
Retention Time: 7.4 min.

Example 94

5-Acetyl-6-(1H-benzoimidazol-2-yl)-4-(3-chlorophenylamino)-2-ethyl-2H-pyridazin-3-one To 10 mL of dry toluene under nitrogen, trimethylaluminium (1.05 mL of a 2M solution in toluene) was added and the solution was cooled down to 0° C. Then 1,2-diaminobenzene (68 mg, 0.63 mmol) was added in portions and the mixture was stirred at 0° C. for 30 min and at 15° C. for 1 hour. Then, the title product of preparation 45 (150 mg, 0.42 mmol) was added in one portion and the final mixture was refluxed for 1.5 hours. Then it was let to warm to room temperature and water and methanol were carefully added. The white precipitate thus formed was filtered and the mother liquor was neutralized with HCl 2N and solvent was removed. Finally the residue was partiotioned between water and dichloromethane and the organic layer was washed with brine. Dried and solvent removed to yield a crude product that was purified by column chromatography.
LRMS: m/Z 408 (M+1)$^+$.
Retention Time: 8.0 min.
$\delta$(CDCl$_3$): 1.41 (t, 3H), 2.01 (s, 3H), 4.38 (q, 2H), 6.85 (m, 2H), 7.10 (m, 5H), 7.38 (s, 1H), 7.78 (s, 1H)

Examples 95-96 (Scheme 1)

95. 5-Acetyl-6-benzooxazol-2-yl-4-(3-chlorophenylamino)-2-ethyl-pyridazin-3(2H)-one
96. 5-Acetyl-6-benzooxazol-2-yl-4-(3-fluorophenylamino)-2-ethyl-pyridazin-3(2H)-one The title compounds were synthesized from the title compound of Preparation 48 and the corresponding boronic acid following the procedure of Example 1. The ESI/MS data and HPLC retention times are summarized in Table 14.

TABLE 14

| EXAMPLE | ESI/MS m/e (M + H)$^+$ | Retention Time (min) |
|---|---|---|
| 95 | 408 | 9.7 |
| 96 | 392 | 9.4 |

Examples 97-98 (Scheme 1)

97. 5-Acetyl-6-benzooxazol-2-yl-4-[bis-(3-chlorophenyl)-amino]-2-ethyl-pyridazin-3(2H)-one
98. 5-Acetyl-6-benzooxazol-2-yl-4-[bis-(3-fluorophenyl)-amino]-2-ethyl-pyridazin-3(2H)-one The title compounds were synthesized from the title compound of Preparation 48 and an excess of the corresponding arylboronic acid following the experimental procedure described in example 1. The ESI/MS data and HPLC retention times are summarized in Table 15.

TABLE 15

| EXAMPLE | ESI/MS m/e (M + H)+ | Retention Time (min) |
|---|---|---|
| 97 | 519 | 10.9 |
| 98 | 486 | 10.4 |

Examples 99-100

99. 5-Acetyl-6-(1,3-benzoxazol-2-yl)-2-ethyl-4-[(3-methoxyphenyl)amino]pyridazin-3(2H)-one
100. 5-Acetyl-6-(1,3-benzoxazol-2-yl)-2-ethyl-4-{[4-(hydroxymethyl)phenyl]amino}pyridazin-3(2H)-one The title compounds were synthesized from the title compound of Preparation 48 and the corresponding boronic acid following the procedure of Example 1. The ESI/MS data and HPLC retention times are summarized in Table 16.

TABLE 16

| EXAMPLE | ESI/MS m/e (M + H)+ | Retention Time (min) |
|---|---|---|
| 99 | 405 | 9.4 |
| 100 | 405 | 8.2 |

Example 101

5-Acetyl-2-ethyl-4-(isoquinolin-4-ylamino)-6-phenylpyridazin-3(2H)-one

A mixture of the title compound of Preparation 49 (2.2 g, 8.56 mmol), 4-bromoisoquinoline (2.14 g, 10.3 mmol), anhydrous cuprous iodide (170 mg, 0.89 mmol) mmol), N,N'-dimethylethylenediamine (0.185 ml, 0.89 mmol) and potassium carbonate (1.73 g, 12.5 mmol) in dry dioxane under argon was stirred in a sealed tube at 130° C. for 24 h. The reaction was filtered and the solvent removed under reduced pressure. The resulting residue was purified by flash column cromathography (SiO$_2$, dichloromethane-ethyl acetate) to yield the title product (450 mg, 14% yield).

m.p. 215.9-216.5° C.

δ(CDCl$_3$): 1.43 (s, 3H), 1.48 (t, 3H), 4.34 (q, 2H), 7.35 (m, 5H), 7.70 (m, 1H), 7.79 (m, 1H), 8.08 (m, 2H), 8.29 (m, 2H), 9.16 (s, 1H).

Examples 102-103

102. 5-Acetyl-2-ethyl-4-(1,6-naphthyridin-8-ylamino)-6-phenylpyridazin-3(2H)-one
103. 5-Acetyl-2-ethyl-4-[(5-methoxypyridin-3-yl)amino]-6-phenylpyridazin-3(2H)-one The title compounds were synthesized from the title compound of Preparation 49 and the corresponding bromide following the procedure of Example 101. The ESI/MS data and HPLC retention times are summarized in Table 17.

TABLE 17

| EXAMPLE | ESI/MS m/e (M + H)+ | Retention Time (min) |
|---|---|---|
| 102 | 386 | 15* |
| 103 | 365 | 7.9 |

*Chromatografic method B.

Example 104

5-Acetyl-2-ethyl-6-pyridin-4-yl-4-(pyridin-3-ylamino)pyridazin-3(2H)-one

Obtained as a yellow solid (69%) from the title compound of Preparation 16 and 3-bromopyridine following the procedure of Example 101.

LRMS: m/Z 336 (M+1)+.

Retention Time: 6 min*.

*Chromatografic method B.

δ(CDCl$_3$): 1.45 (t, 3H), 1.79 (s, 3H), 4.30 (q, 2H), 7.30 (m, 3H), 7.41 (m, 1H), 8.42 (m, 3H), 8.68 (m, 2H).

Example 105

5-Acetyl-2-ethyl-4-[(4-methylpyridin-3-yl)amino]-6-pyridin-4-ylpyridazin-3(2H)-one Obtained as a solid (31%) from the title compound of Preparation 16 and 3-bromo-4-methylpyridine following the procedure of Example 101.

m.p. 207.8-208.9° C.

δ(DMSO-d$_3$): 1.33 (t, 3H), 1.68 (s, 3H), 2.21 (s, 3H), 4.16 (m, 2H), 7.22 (m, 1H), 7.27 (m, 2H), 8.17 (m, 2H), 8.57 (m, 2H), 8.82 (m, 1H).

Examples 106-107

106. 5-Acetyl-2-ethyl-4-(isoquinolin-4-ylamino)-6-pyridin-4-ylpyridazin-3(2H)-one
107. 5-Acetyl-2-ethyl-6-pyridin-4-yl-4-[(3,4,5-trifluorophenyl)amino]pyridazin-3(2H)-one The title compounds were synthesized from the title compound of Preparation 16 and the corresponding bromide following the procedure of Example 101. The ESI/MS data and HPLC retention times are summarized in Table 18.

TABLE 18

| EXAMPLE | ESI/MS m/e (M + H)+ | Retention Time (min) |
|---|---|---|
| 106 | 386 | 6.4 |
| 107 | 388 | 7.9 |

Example 108

5-Acetyl-2-ethyl-4-[(4-methylpyridin-3-yl)amino]-6-pyridin-3-ylpyridazin-3(2H)-one Obtained as a solid (21%) from the title compound of Preparation 14 and 3-bromo-4-methylpyridine following the procedure of Example 101.
m.p. 194.7-195.4° C.
$\delta$(DMSO-$d_3$): 1.35 (t, 3H), 1.52 (s, 3H), 2.22 (s, 3H), 4.20 (q, 2H), 7.24 (d, 1H), 7.40 (m, 1H), 7.68 (m, 1H), 8.25 (m, 2H), 8.48 (s, 1H), 8.58 (m, 1H), 8.87 (s, 1H).

Examples 109-110

109. 5-Acetyl-2-ethyl-4-(isoquinolin-4-ylamino)-6-pyridin-3-ylpyridazin-3(2H)-one
110. 5-Acetyl-2-ethyl-6-pyridin-3-yl-4-[(3,4,5-trifluorophenyl)amino]pyridazin-3(2H)one The title compounds were synthesized from the title-compound of Preparation 14 and the corresponding bromide following the procedure of Example 101. The ESI/MS data and HPLC retention times are summarized in Table 19.

TABLE 19

| EXAMPLE | ESI/MS m/e $(M + H)^+$ | Retention Time (min) |
|---|---|---|
| 109 | 386 | 6.6 |
| 110 | 389 | 15* |

*Chromatografic method B.

Example 111

5-Acetyl-2-ethyl-4-quinolin-5-ylamino)-6-thien-2-ylpyridazin-3(2H)-one

Obtained as a solid (50%) from the title compound of Preparation 26 and quinoline-5-boronic acid following the procedure of Example 1.
m.p. 214.2-215.0° C.
$\delta$(CDCl$_3$): 1.43 (t, 3H), 1.51 (s, 3H), 4.32 (q, 2H), 6.85 (m, 1H), 6.90 (m, 1H), 7.36 (m, 2H), 7.52 (m, 1H), 7.64 (m, 1H), 8.05 (m, 2H), 8.42 (m, 1H), 9.00 (m, 1H).

Examples 112-114

112. 5-Acetyl-2-ethyl-4-(pyridin-3-ylamino)-6-thien-2-ylpyridazin-3(2H)-one
113. 4-[(5-Acetyl-2-ethyl-3-oxo-6-thien-2-yl-2,3-dihydropyridazin-4-yl)amino]benzonitrile
114. 5-Acetyl-2-ethyl-6-thien-2-yl-4-[(3,4,5-trifluorophenyl)amino]pyridazin-3(2H)-one The title compounds were synthesized from the title compound of Preparation 26 and the corresponding boronic acid following the procedure of Example 1. The ESI/MS data and HPLC retention times are summarized in Table 20.

TABLE 20

| EXAMPLE | ESI/MS m/e $(M + H)^+$ | Retention Time (min) |
|---|---|---|
| 112 | 341 | 12* |
| 113 | 365 | 8.9 |
| 114 | 394 | 10.2 |

Example 115

5-Acetyl-4-(bis(4-cyanophenyl)amino)-2-ethyl-6-thien-2-ylpyridazin-3(2H)-one

Obtained as a solid from the title, compound of Preparation 26 and an excess of 4-cyanophenylboronic acid following the experimental procedure described in Example 1.
LRMS: m/Z 466 (M+1)$^+$.
Retention Time: 9.9 min.

Examples 116-117

116. 5-Acetyl-2-(cyclopropylmethyl)-4-(quinolin-5-ylamino)-6-thien-2-ylpyridazin-3(2H)-one
117. 5-Acetyl-2-(cyclopropylmethyl)-4-(pyridin-3-ylamino)-6-thien-2-ylpyridazin-3(2H)-one The title compounds were synthesized from the title compound of Preparation 51 and the corresponding boronic acid following the procedure of Example 1. The ESI/MS data and HPLC retention times are summarized in Table 21.

TABLE 21

| EXAMPLE | ESI/MS m/e $(M + H)^+$ | Retention Time (min) |
|---|---|---|
| 116 | 417 | 15* |
| 117 | 367 | 14* |

*Chromatografic method B.

Example 118

5-Acetyl-2-ethyl-4-(quinolin-5-ylamino)-6-thien-3-ylpyridazin-3(2H)-one

Obtained as a solid (52%) from the title compound of Preparation 55 and quinoline-5-boronic acid following the procedure of Example 1.
m.p. 186.6-187.3° C.
$\delta$(CDCl$_3$): 1.45 (s, 3H), 1.51 (t, 3H), 4.34 (q, 2H), 7.11 (m, 1H), 7.30 (m, 3H), 7.52 (m, 1H), 7.65 (m, 1H), 8.08 (m, 2H), 8.43 (m, 1H), 8.99 (m, 1H).

Examples 119-122

119. 5-Acetyl-4-[(3-chlorophenyl)amino]-2-ethyl-6-thien-3-ylpyridazin-3(2H)-one
120. 5-Acetyl-2-ethyl-4-(pyridin-3-ylamino)-6-thien-3-ylpyridazin-3(2H)-one
121. 4-[(5-Acetyl-2-ethyl-3-oxo-6-thien-3-yl-2,3-dihydropyridazin-4-yl)amino]benzonitrile
122. 5-Acetyl-2-ethyl-6-thien-3-yl-4-[(3,4,5-trifluorophenyl)amino]pyridazin-3(2H)-one The title compounds were synthesized from the title compound of Preparation 55 and the corresponding boronic acid following the procedure of Example 1. The ESI/MS data and HPLC retention times are summarized in Table 22.

TABLE 22

| EXAMPLE | ESI/MS m/e $(M + H)^+$ | Retention Time (min) |
|---|---|---|
| 119 | 374 | 9.4 |
| 120 | 341 | 6.9 |

TABLE 22-continued

| EXAMPLE | ESI/MS m/e (M + H)+ | Retention Time (min) |
|---|---|---|
| 121 | 365 | 9.3 |
| 122 | 394 | 10.1 |

Example 123

2-Ethyl-6-phenyl-5-(3-phenylpropanoyl)-4-quinolin-5-ylamino)pyridazin-3(2H)-one

Obtained as a solid (50%) from the title compound of Preparation 58 and quinoline-5-boronic acid following the procedure of Example 1.
m.p. 164.0-165.8° C.
δ(CDCl$_3$): 1.48 (t, 3H), 1.79 (t, 2H), 2.01 (t, 2H), 4.35 (q, 2H), 6.42 (m, 2H), 7.05 (m, 3H), 7.32 (m, 6H), 7.51 (m, 1H), 7.64 (m, 1H), 8.09 (m, 2H), 8.46 (m, 1H), 9.00 (m, Examples 124-125

124. 2-Ethyl-6-phenyl-5-(3-phenylpropanoyl)-4-(pyridin-3-ylamino)pyridazin-3(2H)-one
125. 2-Ethyl-4-(isoquinolin-4-ylamino)-6-phenyl-5-(3-phenylpropanoyl)pyridazin-3(2H)-one The title compounds were synthesized from the title compound of Preparation 58 and the corresponding bromide following the procedure of Example 101. The ESI/MS data and HPLC retention times are summarized in Table 23.

TABLE 23

| EXAMPLE | ESI/MS m/e (M + H)+ | Retention Time (min) |
|---|---|---|
| 124 | 425 | 17* |
| 125 | 475 | 17* |

Examples 126-127

126. 2-Ethyl-6-phenyl-4-(quinolin-5-ylamino)-5-(3-thien-3-ylpropanoyl)pyridazin-3(2H)-one
127. 2-Ethyl-6-phenyl-4-(pyridin-3-ylamino)-5-(3-thien-3-ylpropanoyl)pyridazin-3(2H)-one The title compounds were synthesized from the title compound of Preparation 59 and the corresponding boronic acid following the procedure of Example 1. The ESI/MS data and HPLC retention times are summarized in Table 24.

TABLE 24

| EXAMPLE | ESI/MS m/e (M + H)+ | Retention Time (min) |
|---|---|---|
| 126 | 481 | 17* |
| 127 | 431 | 16* |

*Chromatografic method B.

Example 128

5-Acetyl-4-[(3-chlorophenyl)amino]-2-ethyl-6-(1H-imidazo[4,5-b]pyridin-2-yl)pyridazin-3(2H)-one Obtained as a solid (7%) from the title compound of Preparation 45 and 2,3-diaminopyridine acid following the experimental procedure described in example 94.
LRMS: m/Z 409 (M+1)+.
Retention Time: 6.3 min.

Example 129

5-Acetyl-6-(1,3-benzothiazol-2-yl)-4-[(3-chlorophenyl)amino]-2-ethylpyridazin-3(2H)-one Obtained as a solid (22%) from the title compound of Preparation 45 and 2-aminobenzenethiol following the experimental procedure described in example 94.
LRMS: m/Z 425 (M+1)+.
Retention Time: 10.5 min.

Example 130

5-Acetyl-6-(1-benzofuran-2-yl)-4-[(3-chlorophenyl)amino]-2-ethylpyridazin-3(2H)-one Obtained as a solid (31%) from the title compound of Preparation 63 and 3-chlorophenyl boronic acid following the procedure of Example 1.
LRMS: m/Z 408 (M+1)+.
Retention Time: 10.2 min.

Example 131

5-Acetyl-2-ethyl-6-pyridin-3-yl-4-pyridin-3-ylamino)pyridazin-3(2H)-one

Obtained as a solid from the title compound of Preparation 14 and 3-pyridineboronic acid following the procedure of Example 1.
LRMS: m/Z 334 (M+1)+.
Retention Time: 4.9 min.

Example 132

4-[(5-Acetyl-2-ethyl-3-oxo-6-pyridin-3-yl-2,3-dihydropyridazin-4-yl)amino]benzoic acid Obtained as a solid from the title compound of Example 5 following the procedure of Example 41.
LRMS: m/Z 379 (M+1)+.
Retention Time: 6.1 min.

Example 133

5-Acetyl-2-ethyl-4-[(1-oxidopyridin-3-yl)amino]-6-phenylpyridazin-3(2H)-one

To a stirred solution of 50-55% m-chloroperbenzoic acid (1.30 mg, 0.38 mmol aprox.) in dichloromethane (2 ml); a solution of the title product of example 63 (126 mg, 0.38 mmol) in dichloromethane (2 ml) was added dropwise and the resulting mixture was stirred at rt overnight. Then it was diluted with dichloromethane and poured onto 10% sodium sulphite solution. The organic layer was further washed with saturated sodium bicarbonate solution and brine. It was then

Example 134

Ethyl 3-(5-acetyl-2-ethyl-3-oxo-6-pyridin-4-yl-2,3-dihydro-pyridazin-4-ylamino)benzoate Obtained as a solid (67%) from the title compound of Preparation 16 and 3-ethoxycarbonylphenylboronic acid following the procedure of Example 1.

LRMS: m/Z 407 (M+1)$^+$. δ(CDCl$_3$): 1.38 (t, 3H), 1.46 (t, 3H), 1.58 (s, 3H), 4.35 (m, 4H), 7.28 (m, 3H), 7.41 (m, 1H), 7.70 (s, 1H), 7.88 (m, 1H), 8.29 (s, 1H), 8.63 (m, 2H).

Example 135

3-[(5-Acetyl-2-ethyl-3-oxo-6-pyridin-4-yl-2,3-dihydropyridazin-4-yl)amino]benzamide To a 0° C. precooled solution of saturated ammonia in THF (2 ml) under argon, trimethylaluminium (0.307 mL, 0.615 mmol) was added and the mixture was stirred for 30 min. Then, a solution of the title compound of Example 134 (50 mg, 0.123 mmol) in dry THF (1 mL) was added dropwise and the final mixture was stirred at rt overnight. Some more trimethylalumminium (0.307 mL, 0.615 mmol) was added and the mixture was refluxed overnight. It was then let to cool down and water was added. The solid thus formed was removed by filtration and the mother liquor was diluted with water, neutralized with 0.1 M HCl and extracted with dichloromethane. The organic layer was washed with water and brine and dried. Finally, solvent was removed to yield a crude product that was purified by preparative HPLC/MS (20% yield).

LRMS: m/Z 78 (M+1)$^+$.
Retention Time: 5.1 min.

Example 136

5-Acetyl-2-ethyl-6-phenyl-4-(thieno[2,3-b]pyridin-3-ylamino)pyridazin-3(2H)-one

Obtained, (27%) from 5-acetyl-2-ethyl-4-nitro-6-phenylpyridazin-3(2H)-one (Dal Piaz, V et al, *J. Med. Chem.* 1997, 40, 1417) and thieno[2,3-b]pyridin-3-ylamine (Klemm, L. H., Zell, R., Barnish, I. T., Klemm, R. A., *J. Het. Chem,* 1970, 373-379) following the procedure of Example 67.

LRMS: m/Z 391 (M+1)$^+$
Retention Time: 14 min*.
*Chromatografic method B.

Example 137

5-Acetyl-2-ethyl-4-[(6-fluoropyridin-3-yl)amino]-6-phenylpyridazin-3(2H)-one

Obtained (65%) from 5-acetyl-2-ethyl-4-nitro-6-phenylpyridazin-3(2H)one (Dal Piaz, V et al., *J. Med. Chem.* 1997, 40, 1417) and 6-fluoropyridin-3-ylamine (Rewcastle, G. W., Denny, W. A, Winters, R. T, *J. Chem Soc, Perkin Trans.* 1, 1996, 18, 2221-2226) following the procedure of Example 67.

m.p. 183.1-184.3° C.

δ(CDCl3): 1.43 (t, 3H), 1.68 (s, 3H), 4.26 (q, 2H), 6.92 (dd, 1H), 7.42 (m, 5H), 7.54 (m, 1H), 8.05 (d, 1H), 8.61 (s, 1H)

Example 138

5-Acetyl-2-ethyl-4-[(2-methylpyridin-3-yl)amino]-6-phenylpyridazin-3(2H)-one

Obtained (17%) from 5-acetyl-2-ethyl-4-nitro-6-phenylpyridazin-3(2H)-one (Dal Piaz, V et al, *J. Med. Chem.* 1997, 40, 1417) and 2-methylpyridin-3-ylamine (Nantka-Namirski, P., Kaczmarczyk, C., Toba, L., *Acta Poloniae Pharmaceutica.* 1967, 24(3), 231-237) following the procedure of Example 63. The product was purified by column cromatography (silica gel, hexane/ethyl acetate 1:1).

m.p. 167.9-168.6° C.

δ(CDCl3): 1.42 (t, 3H), 1.64 (s, 3H), 2.60 (s, 3H), 4.27 (q, 2H), 7.18 (m, 1H), 7.26 (m, 1H), 7.42 (m, 5H), 8.25 (s, 1H), 8.39 (m, 1H)

Example 139

5-Acetyl-4-{[2-(dimethylamino)pyridin-3-yl]amino}-2-ethyl-6-phenylpyridazin-3(2H)-one Obtained (20%) from 5-acetyl-2-ethyl-4-nitro-6-phenylpyridazin-3(2H)-one (Dal Piaz, V et al, *J. Med. Chem.* 1997, 40, 1417) and 3-amino-2-dimethylaminopyridine following the procedure of Example 63. The product was purified by column cromatography (silica gel, hexane/ethyl acetate 5:1).

m.p. 135.1-137.0° C.

δ(CDCl3): 1.42 (t, 3H), 1.64 (s, 3H), 2.93 (s, 6H), 4.31 (q, 2H), 6.88 (m, 1H), 7.16 (m, 1H), 7.42 (m, 5H), 8.05 (m, 1H), 8.19 (m, 1H)

Example 140

5-[(5-Acetyl-2-ethyl-3-oxo-6-phenyl-2,3-dihydropyridazin-4-yl)amino]pyridine-2-carboxylic acid Obtained (43%) from 5-acetyl-2-ethyl-4-nitro-6-phenylpyridazin-3(2H)-one (Dal Piaz, V et al, *J. Med. Chem.* 1997, 40, 1417) and 5-aminopyridine-2-carboxylic add (De Waal, A., Hartog, A. F., De Jong, L., *Biochimica et Biophysica Acta,* 1988, 953(1), 20-25) following the procedure of Example 67.

m.p. 226.1-226.8° C.

δ(DMSO-d6): 1.38 (m, 3H), 1.92 (s, 3H), 4.18 (q, 2H), 7.38 (m, 1H), 7.42 (m, 5H), 7.86 (d, 1H), 8.42 (s, 1H), 9.38 (s, 1H), 12.92 (1H, s).

Example 141

5-Acetyl-2-ethyl-4-[(2-methoxypyridin-3-yl)amino]-6-phenylpyridazin-3(2H)-one

Obtained (43%) from 5-acetyl-2-ethyl-4-nitro-6-phenylpyridazin-3(2H)-one (Dal Piaz, V et al, *J. Med. Chem.* 1997, 40, 1417) and 2-methoxypyridin-3-ylamine (Hwu, J. R., Wong, F. F., Shiao, M. J., *J. Org. Chem,* 1992, 57(19), 5254-5255) following the procedure of Example 67.

m.p. 170.2-170.5° C.

δ(CDCl3): 1.42 (t, 3H), 1.68 (s, 3H), 3.98 (s, 3H), 4.29 (q, 2H), 6.86 (m, 1H), 7.26 (m, 1H), 7.39 (m, 5H), 7.98 (m, 1H), 8.32 (s, 1H)

Example 142

5-Acetyl-2-ethyl-4-(1H-indazol-4-ylamino)-6-phenylpyridazin-3(2H)-one

Obtained (83%) from 5-acetyl-2-ethyl-4-nitro-6-phenylpyridazin-3(2H)-one (Dal Piaz, V et al, *J. Med. Chem.* 1997, 40, 1417) and 1H-indazol-4-ylamine (Gamage, S. A.; Spicer, J. A; Rewcastle, G. W.; Milton, J.; *J. Med. Chem.*, 2002, 45(3), 740-743) following the procedure of Example 67.
m.p. 217.8-219.0° C.
δ(CDCl3): 1.48 (t, 3H), 1.58 (s, 3H), 4.34 (q, 2H), 6.82 (dd, 1H), 7.35 (m, 7H), 8.22 (s, 1H), 8.38 (s, 1H), 10.22 (s, 1H)

Example 143

5-Acetyl-4-[(2-chloropyridin-3-yl)amino]-2-ethyl-6-phenylpyridazin-3(2H)-one

Obtained (30%) from 5-acetyl-2-ethyl-4-nitro-6-phenylpyridazin-3(2H)-one (Dal Piaz, V et al, *J. Med. Chem.* 1997, 40, 1417) and 2-chloropyridin-3-ylamine following the procedure of Example 63. The product was purified by column cromatography (silica gel, hexane/ethyl acetate 2:1).
m.p. 153.0-153.6° C.
δ(CDCl3): 1.43 (t, 3H), 1.81 (s, 3H), 4.30 (q, 2H), 7.22 (m, 1H), 7.39 (m, 6H), 8.45 (m, 1H), 8.2 (s, 1H)

Example 144

5-Acetyl-4-[(5-chloropyridin-3-yl)amino]-2-ethyl-6-phenylpyridazin-3(2H)-one

Obtained from 5-acetyl-2-ethyl-4-nitro-6-phenylpyridazin-3(2H)-one (Dal Piaz, V et al, *J. Med. Chem.* 1997, 40, 1417) and 5-chloropyridin-3-ylamine (Heindl, J., Kessler, H. J., DE2607012) following the procedure of Example 63. The product was purified by preparative HPLC/MS.
LRMS: m/Z 369 (M+1)$^+$
Retention Time: 15.0 min*.
*Chromatografic method B.

Example 145

5-[(5-Acetyl-2-ethyl-3-oxo-6-phenyl-2,3-dihydropyridazin-4-yl)amino]nicotinamide Obtained (54%) from 5-acetyl-2-ethyl-4-nitro-6-phenylpyridazin-3(2H)-one. (Dal Piaz, V et al, *J. Med. Chem.* 1997, 40, 1417) and 5-amino-nicotinamide (Ueno, Y. *Chemica Scripta* 1984, 24(4-5), 185-7) following the procedure of Example 67.
m.p. 235.8-236.8° C.
δ(CDCl3): 1.43 (t, 3H), 1.82 (s, 3H), 4.30 (q, 2H), 5.64 (s, 1H), 6.22 (s, 1H), 7.41 (m, 5H), 7.73 (s, 1H), 8.55 (d, 1H), 8.69 (s, 1H), 8.76 (d, 1H)

Example 146

5-Acetyl-2-ethyl-4-(1,7-naphthyridin-8-ylamino)-6-phenylpyridazin-3(2H)-one

Obtained from 5-acetyl-2-ethyl-4-nitro-6-phenylpyridazin-3(2H)-one (Dal Piaz, V. et al, *J. Med. Chem.* 1997, 40, 1417) and [1,7]naphthyridin-8-ylamine (Van den Haak, H. J. W.; Van der Plas, H. C.; Van Veldhuizen, B. Journal of Heterocyclic Chemistry 1981, 18(7), 1349-52.) following the procedure of Example 63. The product was purified by preparative HPLC/MS.
LRMS: m/Z 386 (M+1)$^+$
Retention Time: 10.0 min*.
*Chromatografic method B.

Example 147

2-Ethyl-5-glycoloyl-4-[(2-methylpyridin-3-yl)amino]-6-phenylpyridazin-3(2H)-one

To a 0° C. stirred solution of potassium hydroxide (510 mg, 9 mmol) in methanol (15 mL) a solution of the title compound of Example 138 (348 mg, 1 mmol) was added dropwise within 10 min. Then, diacetoxyiodobenzene (644 mg, 2 mmol) was added portionwise and the final mixture was stirred at rt overnight. Solvent was removed under reduced pressure and the residue was suspended in ethyl acetate and washed with saturated NH$_4$Cl solution and brine. The organic layer was dried and solvent was removed to yield a crude product that was purified by column chromathography (10% yield).
LRMS: m/Z 365 (M+1)$^+$.
Retention Time: 13 min*.
*Chromatografic method B.

Example 148

Methyl 5-[(5-acetyl-2-ethyl-3-oxo-6-phenyl-2,3-dihydropyridazin-4-yl)amino]nicotinate Obtained (21%) from 5-acetyl-2-ethyl-4-nitro-6-phenylpyridazin-3(2H)-one (Dal Piaz, V et al, *J. Med. Chem.* 1997, 40, 1417) and 5-aminonicotinic acid methyl esther (Jensen, H. H.; Lyngbye, L.; Jensen, A.; Bols, M. *Chemistry—A European Journal* 2002, 8(5), 1218-1226) following the procedure of Example 63. The product was purified by preparative HPLC/MS.
m.p. 144.6-145.8° C.
δ(CDCl3): 1.44 (t, 3H), 1.77 (s, 3H), 3.94 (s, 3H), 4.29 (q, 2H), 7.43 (m, 5H), 7.92 (s, 1H), 8.54 (d, 1H), 8.85 (s, 1H), 9.05 (d, 1H)

Example 149

5-[(5-Acetyl-2-ethyl-3-oxo-6-phenyl-2,3-dihydropyridazin-4-yl)amino]nicotinic acid Obtained from 5-acetyl-2-ethyl-4-nitro-6-phenylpyridazin-3(2H)-one (Dal Piaz, V et al, *J. Med. Chem.* 1997, 40, 1417) and 5-aminonicotinic acid (Delarge, *J. Pharmaceutica Acta Helvetiae* (1969), 44(10), 637-43) following the procedure of Example 63. The product was purified by preparative HPLC/MS.
LRMS: m/Z 379 (M+1)$^+$
Retention Time: 12.0 min*
*Chromatografic method B.

Example 150

5-Acetyl-2-ethyl-4-(1,5-naphthyridin-3-ylamino)-6-phenylpyridazin-3(2H)-one

Obtained from 5-acetyl-2-ethyl-4-nitro-6-phenylpyridazin-3(2H)-one (Dal Piaz, V et al, *J. Med. Chem.* 1997, 40, 1417) and [1,5]naphthyridin-3-ylamine (Czuba W., Akad, M., Wroclaw, P., *Rocniki Chemii,* 1967, 41(2), 289-297) following the procedure of Example 63. The product was purified by preparative HPLC/MS.

LRMS: m/Z 386 (M+1)$^+$
Retention Time: 13.0 min*.
*Chromatografic method B.

Example 151

5-Acetyl-2-ethyl-4-[(8-hydroxy-1,7-naphthyridin-5-yl)amino]-6-phenylpyridazin-3(2H)-one Obtained (43%) from 5-acetyl-2-ethyl-4-nitro-6-phenylpyridazin-3(2H)-one (Dal Piaz, V et al, *J. Med. Chem.* 1997, 40, 1417) and the title compound of Preparation 67 following the procedure of Example 67.

m.p. 269.5-271.3° C.
δ(DMSO-d6): 1.35 (m, 3H), 1.48 (s, 3H), 4.19 (q, 2H), 7.44 (m, 6H), 8.59 (s, 1H), 8.75 (d, 1H), 9.28 (s, 1H), 11.66 (s, 1H)

Example 152

5-Acetyl-2-ethyl-6-phenyl-4-(thien-2-ylamino)pyridazin-3(2H)-one

To a solution of thiophen-2-ylcarbamic acid tert-butyl ester (157 mg, 0.78 mmol) (Binder, D., Habison, G., Noe, C. R., *Synthesis,* 1977, 4, 255-256) in ethyl ether (6.5 ml), 12N chlorhidric acid (2.8 mL) was added. The mixture was stirred for 30 min. and the solvent was removed to yield the deprotected thiophen-2-yl-ammonium chloride. Then a solution of 5-acetyl-2-ethyl-4-nitro-6-phenylpyridazin-3(2H)-one (150 mg, 0.52 mmol) (Dal Piaz, V et al, *J. Med. Chem.* 1997, 40, 1417) in ethanol (9 ml) and triethylamine (0.26 ml, 3.6 mmol) were added. The resulting mixture was stirred at room temperature for 3 h. The final product was collected by filtration and washed with diethylether to yield the title compound as a yellow solid (38%).

m.p. 182.6-183.5
δ(DMSO-d6): 1.33 (m, 3H), 1.62 (s, 3H), 4.16 (q, 2H), 6.73 (m, 1H), 6.82 (m, 1H), 7.27 (m, 3H), 7.40 (m, 3H), 8.89 (s, 1H)

Example 153

5-Acetyl-2-ethyl-6-phenyl-4-[(2-phenylpyridin-3-yl)amino]pyridazin-3(2H)-one

Obtained (46%) from 5-acetyl-2-ethyl-4-nitro-6-phenylpyridazin-3(2H)-one (Dal Piaz, V et al, J. Med. Chem. 1997, 40, 1417) and 2-phenylpyridin-3-ylamine (Miller, J. A, Farrell, R. P., *Tetrahedron Lett.,* 1998, 39(36), 6441-6444) following the procedure of Example 67.

m.p. 181.8-182.4° C.
δ(DMSO-d6): 1.25 (m, 3H), 1.54 (s, 3H), 4.08 (q, 2H), 7.21 (m, 2H), 7.37 (m, 7H), 7.67 (m, 3H), 8.48 (m, 1H), 8.95 (s, 1H)

Example 154

Ethyl {5-[(5-acetyl-2-ethyl-3-oxo-6-phenyl-2,3-dihydropyridazin-4-yl)amino]pyridin-2-yl}acetate Obtained (30%) from 5-acetyl-2-ethyl-4-nitro-6-phenylpyridazin-3(2H)-one (Dal Piaz, V et al, J. Med. Chem. 1997, 40, 1417) and 5-aminopyridine-2-carboxylic acid ethyl ester (Cooper, G. H.; Rickard, R. L, *J. Chem. Soc.,* 1971, 19, 3257-3260.) following the procedure of Example 67.

LRMS: m/Z 421 (M+1)$^+$
Retention Time: 14.0 min*.
*Chromatografic method B.

Example 155

5-Acetyl-2-ethyl-4-[(6-methylpyridin-3-yl)amino]-6-phenylpyridazin-3(2H)-one

To a stirred solution of the title compound of Example 154 (77 mg, 0.18 mmol) in 2 ml of ethanol, 1M NaOH solution (0.5 ml) was added and the mixture was stirred at rt for 1 hour and at 60° C. for 1 h. Then it was let to cool down, acidified to pH 6 and refluxed for 3 days. It was the basified to pH 8 and extracted with dichloromethane. The organic layer was finally washed with water and brine, dried and solvent was removed to yield the title product (20%).

LRMS: m/Z 349 (M+1)$^+$.
Retention Time: 12 min*.
*Chromatografic method B.

Example 156-162

156. 5-Acetyl-2-ethyl-4-[(6-hydroxypyridin-3-yl)amino]-6-phenylpyridazin-3(2H)-one
157. 5-Acetyl-2-ethyl-4-[(2-fluoropyridin-3-yl)amino]-6-phenylpyridazin-3(2H)-one
158. 5-Acetyl-4-[(6-chloro-4-methylpyridin-3-yl)amino]-2-ethyl-6-phenylpyridazin-3(2H)-one
159. 5-Acetyl-2-ethyl-4-[(3-hydroxypyridin-2-yl)amino]-6-phenylpyridazin-3(2H)-one
160. 5-Acetyl-2-ethyl-4-[(4-methoxypyridin-3-yl)amino]-6-phenylpyridazin-3(2H)-one
161. 5-Acetyl-2-ethyl-4-(isoquinolin-8-ylamino)-6-phenylpyridazin-3(2H)-one
162. 5-Acetyl-2-ethyl-6-phenyl-4-(quinolin-7-ylamino)pyridazin-3(2H)-one The title compounds were sinthesized from 5-acetyl-2-ethyl-4-nitro-6-phenylpyridazin-3(2H)-one (Dal Piaz, V et al, *J. Med. Chem.* 1997, 40, 1417) and the corresponding amines following the proedure of example 67. The ESI/MS data and HPLC retention times are summarized in Table 25.

TABLE 25

| EXAMPLE | ESI/MS m/e (M + H)$^+$ | Retention Time (min) |
|---|---|---|
| 156 | 351 | 6.9 |
| 157 | 353 | 8.3 |
| 158 | 383 | 9.0 |
| 159 | 351 | 8.5 |
| 160 | 365 | 6.5 |
| 161 | 385 | 6.5 |
| 162 | 385 | 9.6 |

Example 163

5-Acetyl-4-[(5-chloropyridin-3-yl)amino]-2-ethyl-6-(3-fluorophenyl)pyridazin-3(2H)-one Obtained as a solid (54%) from the title compound of Preparation 36 and 5-chloro pyridin-3-ylamine (Heindl, J.; Kessler, H. J. DE 2607012) following the procedure of Example 67.

m.p. 146.3-147.3° C.

δ(DMSO-d₃): 1.33 (t, 3H), 1.90 (s, 3H), 4.17 (q, 2H), 7.18 (m, 2H), 7.29 (m, 1H), 7.46 (m, 1H), 7.56 (m, 1H), 8.27 (m, 2H), 9.25 (m, 1H).

Example 164

5-Acetyl-2-ethyl-6-(4-fluorophenyl)-4-[(2-methoxypyridin-3-yl)amino]pyridazin-3(2H)-one Obtained as a solid (90%) from the title compound of Preparation 30 and 2-methoxypyridin-3-ylamine (Hwu, J. R; Wong, F. F.; Shiao, M. J., *J. Org. Chem.*, 1992, 57, 5254-5 following the procedure of Example 67.

m.p. 168.8-169.7° C.

δ(CDCl₃): 1.44 (t, 3H), 1.71 (s, 3H), 3.97 (s, 3H), 4.29 (q, 2H), 6.87 (m, 1H), 7.10 (m, 2H), 7.27 (m, 1H), 7.39 (m, 2H), 8.00 (m, 1H), 8.22 (s, 1H).

Examples 165-168

165. 5-Acetyl-2-ethyl-6-(4-fluorophenyl)-4-[(2-methylpyridin-3-yl)amino]pyridazin-3(2H)-one
166. 5-Acetyl-4-[(2-chloropyridin-3-yl)amino]-2-ethyl-6-(4-fluorophenyl)pyridazin-3(2H)-one
167. 5-Acetyl-2-ethyl-6-(4-fluorophenyl)-4-[(4-methylpyridin-3-yl)amino]pyridazin-3(2H)-one
168. 5-Acetyl-2-ethyl-6-(4-fluorophenyl)-4-[(2-fluoropyridin-3-yl)amino]pyridazin-3(2H)-one The title compounds were synthesized from the title compound of Preparation 30 and the corresponding pyridinylamines following the procedure of Example 93. The ESI/MS data and HPLC retention times are summarized in Table 26.

TABLE 26

| EXAMPLE | ESI/MS m/e (M + H)⁺ | Retention Time (min) |
|---|---|---|
| 165 | 367 | 7.4 |
| 166 | 387 | 8.7 |
| 167 | 367 | 8.4 |
| 168 | 371 | 8.9 |

Example 169

5-Acetyl-4-[2-chloropyridin-3-yl)amino]-2-(cyclopropylmethyl)-6-(4-fluorophenyl)pyridazin-3(2H)-one Obtained as a solid (20%) from the title compound of Preparation 65 and 2-chloropyridin-3-amine following the procedure of Example 67.

LRMS: m/Z 413 (M+1)⁺.

Retention Time: 16 min*.

*Chromatografic method B. δ(CDCl₃): 0.47 (m, 2H), 0.57 (m, 2H), 1.42 (m, 1H), 1.84 (s, 3H), 4.09 (d, 2H), 7.09 (m, 2H), 7.22 (m, 1H), 7.41 (m, 3H), 8.21 (m, 1H), 8.63 (s, 1H).

Example 170

5-Acetyl-2-(cyclopropylmethyl)-6-(4-fluorophenyl)-4-[(2-methoxypyridin-3-yl)amino]pyridazin-3(2H)-one Obtained as a solid (66%) from the title compound of Preparation 65 and 2-methoxypyridin-3-ylamine (Hwu, J. R; Wong, F. F.; Shiao, M. J., *J. Org. Chem.*, 1992, 57, 5254-5) following the procedure of Example 67.

m.p. 148.1-148.8° C.

δ(CDCl₃): 0.46 (m, 2H), 0.57 (m, 2H), 1.43 (m, 1H), 1.73 (s, 3H), 3.96 (s, 3H), 4.10 (d, 2H), 6.85 (m, 1H), 7.09 (m, 2H), 7.27 (m, 1H), 7.38 (m, 2H), 7.99 (m, 1H), 8.22 (s, 1H).

Example 171

5-Acetyl-2-(cyclopropylmethyl)-6-(4-fluorophenyl)-4-[(2-methylpyridin-3-yl)amino]pyridazin-3(2H)-one Obtained as a solid (23%) from the title compound of Preparation 65 and 2-methylpyridin-3-ylamine (Nantka-Namirski, P.; Kaczmarczyk, C.; Toba, L., *Acta Poloniae Pharmaceutica* 1967, 24, 231-7) following the procedure of Example 67.

LRMS: m/Z 393 (M+1)⁺.

Retention Time: 14 min*.

*Chromatografic method B.

δ(CDCl₃): 0.50 (m, 2H), 0.58 (m, 2H), 1.43 (m, 1H), 1.65 (s, 3H), 2.57 (s, 3H), 4.10 (d, 2H), 7.09 (m, 3H), 7.35 (m, 3H), 8.12 (s, 1H), 8.38 (m, 1H).

Examples 172-174

172. 5-Acetyl-2-cyclopropylmethyl-6-(4-fluorophenyl)-4-[(2-fluoropyridin-3-yl)amino]pyridazin-3(2H)-one
173. 5-Acetyl-2-(cyclopropylmethyl)-6-(4-fluorophenyl)-4-[(4-methylpyridin-3-yl)amino]pyridazin-3(2H)-one
174. 5-Acetyl-2-(cyclopropylmethyl)-6-(4-fluorophenyl)-4-[(pyridin-3-yl) amino]pyridazin-3(2H)-one The title compounds were synthesized from the title compound of Preparation 65 and the corresponding pyridinylamines following the procedure of Example 93. The ESI/MS data and HPLC retention times are summarized in Table 27.

TABLE 27

| EXAMPLE | ESI/MS m/e (M + H)⁺ | Retention Time (min) |
|---|---|---|
| 172 | 397 | 9.2 |
| 173 | 393 | 9.2 |
| 174 | 379 | 8.3 |

Examples 175-177

175. 5-Acetyl-6-(3-chlorophenyl)-2-ethyl-4-[(2-methylpyridin-3-yl)amino]pyridazin-3(2H)-one
176. 5-Acetyl-6-(3-chlorophenyl)-4-[(2-chloropyridin-3-yl)amino]-2-ethylpyridazin-3(2H)-one
177. 5-Acetyl-6-(3-chlorophenyl)-2-ethyl-4-[(4-methylpyridin-3-yl)amino]pyridazin-3(2H)-one The title compounds were synthesized from 5-acetyl-2-ethyl-4-nitro-6-(3-chlorophenyl)pyridazin-3(2H)-one (Dal Piaz, V et al, *J. Med. Chem.* 1997, 40, 1417) and the corresponding pyridinylamines following the procedure of Example 93. The ESI/MS data and HPLC retention times are summarized in Table 28.

TABLE 28

| EXAMPLE | ESI/MS m/e (M + H)⁺ | Retention Time (min) |
|---|---|---|
| 175 | 383 | 8.3 |
| 176 | 404 | 9.3 |
| 177 | 383 | 9.1 |

Example 178

Methyl 5-[(5-acetyl-2-ethyl-3-oxo-6-phenyl-2,3-dihydropyridazin-4-yl)amino]quinoline-8-carboxylate A mixture of (160 mg, 0.556 mmol) of 5-acetyl-2-ethyl-4-nitro-6-phenylpyridazin-3(2H)-one (Dal Piaz, V et al, *J. Med. Chem.* 1997, 40, 1417), 5-aminoquinoline-8-carboxilic acid methyl ester (226 mg, 1.114 mmol) (Preparation 99) and ethanol (8 mL) was introduced in the microwave oven. The mixture was stirred at 126.0° C. during 45 minutes. The solvent was evaporated and the residue purified by column chromatography (silica gel, dichloromethane/methanol 100:1) and preparative HPLC/MS to yield the title compound (7 mg, 3% yield).

LRMS: m/Z 443 (M+1)$^+$. Retention time: 13 min*.

*Chromatografic method B

Example 179

5-Acetyl-2-ethyl-4-[(4-methylpyridin-3-yl)amino]-6-phenylpyridazin-3(2H)-one

A mixture of the title compound of Preparation 49 (2.0 g, 7.77 mmol), 3-bromo-4-methylpyridine (1.8 ml, 15.5 mmol), anhydrous cuprous iodide (10.0 mg; 0.52 mmol) and potassium carbonate (1.60 g, 11.6 mmol) stirred at 145° C. for 12 h. It was let lo cool down and was partiotioned between ethyl acetate and water. The organic layer was wshed with water and brine, dried and solvent was removed in vacuo. The solid thus obtained was thoroughly washed with warm ethyl ether and recrystallized from methanol to yield the final product as a cream solid (0.97 g, 34% yield).

m.p. 215.9-216.3° C.

δ(DMSO-d$_3$): 1.18 (t, 3H), 1.28 (s, 3H), 2.05 (s, 3H), 4.04 (q, 2H), 7.15 (m, 3H), 7.28 (m, 3H), 8.12 (m, 2H), 8.62 (s, 1H).

Example 180

5-Acetyl-2-ethyl-4-(isoquinolin-4-ylamino)-6-(4-methoxyphenyl)pyridazin-3(2H)-one Obtained as a solid (13%) from the title compound of preparation 71 and 4-bromoisoquinoline following the procedure of Example 101.

m.p. 210.8-212.7° C.

δ(DMSO-d$_6$): 1.28 (s, 3H), 1.37 (t, 3H), 3.7 (s, 3H), 4.2 (q, 2H), 6.9 (d, 2H), 7.15 (d, 2H), 7.7 (t, 1H), 7.8 (t, 1H), 7.97 (d, 1H), 8.15 (d, 1H), 8.29 (s, 1H), 9.17 (s, 1H).

Example 181

5-Acetyl-2-ethyl-6-(4-methoxyphenyl)-4-(pyridin-3-ylamino)pyridazin-3(2H)-one

Obtained as a solid (33%) from the title compound of Preparation 71 and 3-bromopyridine following the procedure of Example 101.

m.p. 175.0-175.7° C.

δ(DMSO-d$_6$): 1.3 (t, 3H), 1.7 (s, 3H), 3.8 (s, 3H), 4.16 (q, 2H), 6.97 (d, 2H), 7.23 (d, 2H), 7.27 (m, 1H), 7.43 (d, 1H), 8.27 (bs, 1H), 8.32 (s, 1H), 9.04 (s, 1H, NH).

Example 182

5-Acetyl-2-ethyl-6-(4-methoxyphenyl)-4-(quinolin-5-ylamino)pyridazin-3(2H)-one

Obtained as a solid (15%) from the title compound of Preparation 71 and 5-quinolylboronic acid following the procedure of Example 1.

m.p. 233.2-233.9° C.

δ(DMSO-d$_6$): 1.33 (s, 3H), 1.37 (t, 3H), 3.74 (s, 3H), 4.21 (q, 2H), 6.91 (d, 2H), 7.16 (d, 2H), 7.35 (d, 1H), 7.55 (m, 1H), 7.60 (m, 1H), 7.86 (d, 1H), 8.41 (d, 1H), 8.92 (m, 1H), 9.13 (s, 1H, NH).

Example 183

5-Acetyl-2-ethyl-6-(4-methoxy-phenyl)-4-(1-oxy-quinolin-5-ylamino)- -pyridazin-3(2H)-one A solution of m-chloroperbenzoic acid (36.4 mg, 0.16 mmol) in dry dichloromethane (1 mL) was added to a solution of the title compound of Example 182 (70 mg, 0.16 mmol) in 2 mL of dichloromethane and the mixture was stirred at RT under argon overnight. The solvent was removed under reduced pressure and the residue was purified by column chromatography (C-18 reverse phase Biotage® cartridge (water (0.1M ammonium acetate)/acetonitrile 99:1 to 1:99) to yield the title compound as a solid (43 mg, 62% yield).

m.p. 259.7-261.3° C.

δ(DMSO-d$_6$): 1.37 (t, 3H), 1.43 (s, 3H), 3.75 (s, 3H), 4.20 (q, 2H), 6.94 (d, 2H), 7.18 (d, 2H), 7.48 (m, 2H), 7.66 (t, 1H), 7.95 (d, 1H), 8.37 (d, 1H), 8.61 (d, 1H), 9.19 (s, 1H, NH).

Example 184

5-Acetyl-2-ethyl-4-(isoquinolin-4-ylamino)-6-(3-methoxyphenyl)pyridazin-3(2H)-one Obtained as a solid (24%) from the title compound of Preparation 75 and 4-bromoisoquinoline following the procedure of Example 101.

m.p. 190.0-190.5° C.

δ(DMSO-d$_6$): 1.28 (s, 3H), 1.38 (t, 3H), 3.70 (s, 3H), 4.22 (q, 2H), 6.77 (s, 1H), 6.79 (d, 1H), 6.95 (d, 1H), 7.28 (t, 1H), 7.71 (t, 1H), 7.82 (t, 1H), 7.97 (d, 1H), 8.15 (d, 1H), 8.30 (s, 1H), 9.17 (s, 1H, NH), 9.18 (s, 1H).

Example 185

5-Acetyl-2-ethyl-6-(3-methoxyphenyl)-4-(pyridin-3-ylamino)pyridazin-3(2H)-one

Obtained as a solid (33%) from the title compound of Preparation 75 and 3-bromopyridine following the procedure of Example 101.

m.p. 152.7-153.8° C.

δ(DMSO-d$_6$): 1.33 (t, 3H), 1.73 (s, 3H), 3.75 (s, 3H), 4.16 (q, 2H), 6.85 (m, 2H), 6.98 (d, 1H), 7.27-731 (m, 2H), 7.42 (d, 1H), 8.27 (m, 1H), 8.32 (s, 1H), 9.08 (s, 1H, NH).

Example 186

5-Acetyl-2-ethyl-6-(3-methoxyphenyl)-(quinolin-5-ylamino)pyridazin-3(2H)-one

Obtained as a solid (28%) from the title compound of Preparation 75 and 5-quinolylboronic acid following the procedure of Example 1.
m.p. 194.3-195.8° C.
δ(DMSO-d$_6$): 1.32 (s, 3H), 1.37 (t, 3H), 3.70 (s, 3H), 4.21 (q, 2H), 6.77 (s, 1H), 6.78 (d, 1H), 6.95 (d, 1H), 7.30 (t, 1H), 7.34 (d, 1H), 7.54-7.63 (m, 2H), 7.86 (d, 1H), 8.42 (d, 1H), 8.92 (m, 1H), 9.18 (s, 1H, NH).

Example 187

5-Acetyl-2-ethyl-6-(3-methoxyphenyl)-4-[(1-oxidoquinolin-5-yl)amino]pyridazin-3(2H)-one Obtained as a yellow solid (58%) from the title compound of Example 186 following the procedure of Example 183.
m.p. 215.5-216.1° C.
δ(DMSO-d$_6$): 1.37 (t, 3H), 1.43 (s, 3H), 3.71 (s, 3H), 4.21 (q, 2H), 6.80 (s, 1H), 6.81 (d, 1H), 6.96 (d, 1H), 7.30 (t, 1H), 7.48 (m, 2H), 7.66 (t, 1H), 7.95 (d, 1H), 8.37 (d, 1H), 8.61 (d, 1H), 9.24 (s, 1H, NH).

Example 188

5-Acetyl-2-ethyl-4-(isoquinolin-4-ylamino)-6-(4-methylphenyl)pyridazin-3(2H)-one Obtained as a solid (18%) from the title compound of Preparation 79 and 4-bromoisoquinoline following the procedure of Example 101.
m.p. 201.7-202.1° C.
δ(DMSO-d$_6$): 1.27 (s, 3H), 1.37 (t, 3H), 2.29 (s, 3H), 4.21 (q, 2H), 7.12 (d, 2H), 7.17 (d, 2H), 7.72 (t, 1H), 7.82 (t, 1H), 7.97 (d, 1H), 8.15 (d, 1H), 8.30 (s, 1H), 9.15 (s, 1H, NH), 9.17 (s, 1H).

Example 189

5-Acetyl-2-ethyl-6-(4-methylphenyl)-4-(pyridin-3-ylamino)pyridazin-3(2H)-one

Obtained as a solid (18%) from the title compound of Preparation 79 and 3-bromopyridine following the procedure of Example 101.
m.p. 187.8-189.1° C.
δ(DMSO-d$_6$): 1.33 (t, 3H), 1.72 (s, 3H), 2.32 (s, 3H), 4.17 (q, 2H), 7.20 (q, 4H), 7.27 (m, 1H), 7.43 (d, 1H), 8.26 (d, 1H), 8.32 (s, 1H), 9.05 (s, 1H, NH).

Example 190

5-Acetyl-2-ethyl-6-(4-methylphenyl)-4-(quinolin-5-ylamino)pyridazin-(2H)-one

Obtained as a solid (40%) from the title compound of Preparation 79 and 5-quinolylboronic acid following the procedure of Example 1.
LRMS (m/z): 399 (M+1)$^+$.
Retention Time: 15 min*.
*Chromatografic method B
m.p. 269.8-271.6° C.

Example 191

5-Acetyl-2-ethyl-6-(4-methylphenyl)-4-[(1-oxidoquinolin-5-yl)amino]pyridazin-3(2H)-one Obtained as a solid (48%) from the title compound of Example 190 following the procedure of Example 183.
m.p. 231.7-232.5° C.
δ(MeOH-d$_4$): 1.44 (t, 3H), 1.47 (s, 3H), 2.35 (s, 3H), 4.29 (q, 2H), 7.20 (s, 4H), 7.52 (d, 1H), 7.6 (dd, 1H), 7.80 (t, 1H), 8.35 (d, 1H), 8.53 (d, 1H), 8.72 (d, 1H).

Example 192

5-Acetyl-2-ethyl-6-(4-methylphenyl)-4-[(4-methylpyridin-3-yl)amino]pyridazin-3(2H)-one Obtained as a solid (9%) from the title compound of Preparation 79 and 4-methyl-3-bromopyridine following the procedure of Example 101.
m.p. 196.1-197.3° C.
δ(DMSO-d$_6$): 1.34 (t, 3H), 1.43 (s, 3H), 2.22 (s, 3H), 2.31 (s, 3H), 4.17 (q, 2H), 7.15 (d, 2H), 7.19 (d, 2H), 7.24 (d, 1H), 8.21 (s, 1H), 8.26 (d, 1H), 8.72 (s, 1H, NH).

Example 193

5-Acetyl-2-ethyl-4-(isoquinolin-4-ylamino)-6-(3-methylphenyl)pyridazin-3(2H)-one Obtained as a solid (27%) from the title compound of Preparation 83 and 4-bromoisoquinoline following the procedure of Example 101.
Retention Time: 15 min*.
*Chromatografic method B
δ(DMSO-d$_6$): 1.26 (s, 3H), 1.37 (t, 3H), 2.27 (s, 3H), 4.22 (q, 2H), 6.99 (d, 1H), 7.07 (s, 1H), 7.18-7.26 (m, 2H), 7.72 (t, 1H), 7.82 (t, 1H), 7.97 (d, 1H), 8.15 (d, 1H), 8.29 (s, 1H), 9.17 (s, 2H).

Example 194

5-Acetyl-2-ethyl-6-(3-methylphenyl)-4-(pyridin-3-ylamino)pyridazin-3(2H)-one

Obtained as a solid (21%) from the title compound of Preparation 83 and 3-bromopyridine following the procedure of Example 101.
m.p. 134:9-136.1° C.
δ(DMSO-d$_6$): 1.33 (t, 3H), 1.72 (s, 3H), 2.32 (s, 3H), 4.17 (q, 2H), 7.06 (d, 1H), 7.15 (s, 1H), 7.22-7.31 (m, 3H), 7.43 (dd, 1H), 8.26 (dd, 1H), 8.32 (s, 1H), 9.08 (s, 1H, NH).

Example 195

5-Acetyl-2-ethyl-6-(3-methylphenyl)-4-(quinolin-5-ylamino)pyridazin-3(2H)-one

Obtained as a solid (25%) from the title compound of Preparation 83 and 5-quinolylboronic acid following the procedure of Example 1.
LRMS (m/z): 399 (M+1)$^+$.
Retention Time: 14 min*.
*Chromatografic method B
m.p. 245.0-246.1° C.

Example 196

5-acetyl-2-ethyl-6-(3-methylphenyl)-4-[(4-methylpyridin-3-yl)amino]pyridazin-3(2H)-one Obtained as a solid (24%) from the title compound of Preparation 83 and 4-methyl-3-bromopyridine following the procedure of Example 1.

m.p. 171.1-172.0° C.

δ(DMSO-d$_6$): 1.34 (t, 3H), 1.43 (s, 3H), 2.22 (s, 3H), 2.30 (s, 3H), 4.18 (q, 2H), 7.02 (d, 1H), 7.10 (s, 1H), 7.20-7.28 (m, 3H), 8.21 (s, 1H), 8.25 (d, 1H), 8.75 (s, 1H, NH).

Example 197

Methyl 4-[4-acetyl-1-ethyl-5-(isoquinolin-4-ylamino)-6-oxo-1,6-dihydropyridazin-3-yl]benzoate Obtained as a solid (16%) from the title compound of Preparation 88 and 4-bromoisoquinoline following the procedure of Example 101.

m.p. 182.9-183.6° C.

δ(DMSO-d$_6$): 1.28 (s, 3H), 1.36 (t, 3H), 3.82 (s, 3H), 4.20 (q, 2H), 7.37 (d, 2H), 7.72 (t, 1H), 7.80 (t, 1H), 7.91 (d, 2H), 7.97 (d, 1H), 8.12 (d, 1H), 8.27 (s, 1H), 9.14 (s, 1H), 9.22 (s, 1H, NH).

Example 198

Methyl 4-[4-acetyl-1-ethyl-6-oxo-5-(pyridin-3-ylamino)-1,6-dihydropyridazin-3-yl]benzoate Obtained as a solid (15%) from the title compound of Preparation 88 and 3-bromopyridine following the procedure of Example 101.

δ(DMSO-d$_6$): 1.3 (t, 3H), 1.7 (s, 3H), 3.82 (s, 3H), 4.20 (q, 2H), 7.27 (m, 1H), 7.44 (d, 3H), 7.97 (d, 2H), 8.27 (d, 1H), 8.32 (s, 1H), 9.18 (s, 1H, NH).

LRMS (m/z): 393 (M+1)$^+$.

Retention Time: 13 min*.

*Chromatografic method B

Example 199

4-[4-Acetyl-1-ethyl-6-oxo-5-(pyridin-3-ylamino)-1,6-dihydropyridazin-3-yl]benzoic acid Obtained as a solid (46%) from the title compound of Example 198 following the procedure of Example 41.

m.p. 237.5-238.8° C.

δ(DMSO-d$_6$): 1.34 (t, 3H), 1.77 (s, 3H), 4.19 (q, 2H), 7.27 (m, 1H), 7.44 (d, 3H), 7.95 (d, 2H), 8.27 (d, 1H), 8.32 (s, 1H), 9.16 (s, 1H, NH), 13.09 (s, 1H; COOH).

Example 200

Methyl 4-{4-acetyl-1-ethyl-5-[(4-methylpyridin-3-yl)amino]-6-oxo-1,6-dihydropyridazin-3-yl}benzoate Obtained as a solid (32%) from the title compound of Preparation 88 and 4-methyl-3-bromopyridine following the procedure of Example 101.

m.p. 195.5-197.0° C.

δ(DMSO-d$_6$): 1.35 (t, 3H), 1.48 (s, 3H), 2.22 (s, 3H), 3.86 (s, 3H), 4.19 (q, 2H), 7.24 (d, 1H), 7.43 (d, 2H), 7.96 (d, 2H), 8.22 (s, 1H), 8.25 (d, 1H), 8.80 (s, 1H, NH).

Example 201

4-{4-Acetyl-1-ethyl-5-[(4-methylpyridin-3-yl)amino]-6-oxo-1,6-dihydropyridazin-3-yl}benzoic acid Obtained as a solid (13%) from the title compound of Example 200 following the procedure of Example 41.

m.p. 242.7-243.3° C.

δ(DMSO-d$_6$): 1.35 (t, 3H), 1.48 (s, 3H), 2.22 (s, 3H), 4.19 (q, 2H), 7.24 (d, 1H), 7.40 (d, 2H), 7.96 (d, 2H), 8.22 (s, 1H), 8.25 (d, 1H), 8.80 (s, 1H, NH).

Example 202

Methyl 3-[4-acetyl-1-ethyl-6-oxo-5-(pyridin-3-ylamino)-1,6-dihydropyridazin-3-yl]benzoate Obtained as a solid (20%) from the title compound of Preparation 93 and 3-bromopyridine following the procedure of Example 101.

m.p. 148.8-150.2° C.

δ(MeOH-d$_4$): 1.33 (t, 3H), 1.68 (s, 3H), 3.82 (s, 3H), 4.19 (q, 2H), 7.27 (m, 1H), 7.44-7.52 (m, 3H), 7.93 (s, 1H), 7.97 (d, 1H), 8.20 (dd, 1H), 8.25 (s, 1H).

Example 203

3-[4-Acetyl-1-ethyl-6-oxo-5-(pyridin-3-ylamino)-1,6-dihydropyridazin-3-yl]benzoic acid Obtained as a solid (42%) from the title compound of Example 202 following the procedure of Example 41.

m.p. 269.1-270.3° C.

δ(DMSO-d$_6$): 1.34 (t, 3H), 1.75 (s, 3H), 4.19 (q, 2H), 7.27 (m, 1H), 7.44-7.51 (m, 2H), 7.54 (s, 1H), 7.89 (s, 1H), 7.97 (d, 1H), 8.27 (s, 1H), 8.35 (s, 1H), 9.13 (s, 1H, NH), 13.13 (s, 1H, COOH).

Example 204

5-Acetyl-4-[(3-chloro-4-fluorophenyl)amino]-2-ethyl-6-ethyl-6-pyridin-4-ylpyridazin-3(2H)-one Obtained as a solid (12%) from the title compound of Preparation 16 and 3-chloro fluoro-boronic acid following the procedure of Example 1.

m.p. 168.6-169.6° C.

δ(DMSO-d$_6$): 1.33 (t, 3H), 1.85 (s, 3H), 4.18 (q, 2H), 7.08 (m, 1H), 7.29-7.35 (m, 4H), 8.60 (d, 2H), 9.19 (s, 1H, NH).

Example 205

5-Acetyl-4-[bis(3-chloro-4-fluorophenyl)amino]-2-ethyl-6-pyridin-4-ylpyridazin-3(2H)-one Obtained as a solid (4%) from the title compound of Preparation 16 and an exces of 3-chloro-4-fluoro-boronic acid following the procedure of Example 1.

m.p. 155.7-156.2° C.

δ(DMSO-d₆): 1.33 (t, 3H), 2.18 (s, 3H), 4.16 (q, 2H), 7.06 (m, 2H), 7.31-7.41 (m, 6H), 8.65 (bs, 2H).

Example 206

5-Acetyl-4-[(3-chloro-4-fluorophenyl)amino]-2-ethyl-6-pyridin-3-ylpyridazin-3(2H)-one Obtained as a solid (10%) from the title compound of Preparation 14 and 3-chloro-4-fluoro-boronic acid following the procedure of Example 1.
m.p. 159.8-160.3° C.
δ(DMSO-d₆): 1.34 (t, 3H), 1.82 (s, 3H), 4.18 (q, 2H), 7.08 (m, 1H), 7.29-7.35 (m, 3H), 7.43 (bs, 1H), 7.73 (d, 1H), 8.61 (bs, 1H), 9.18 (s, 1H, NH).

Example 207

5-Acetyl-4-[bis(3-chloro-4-fluorophenyl)amino]-2-ethyl-6-pyridin-3-ylpyridazin-3(2H)-one Obtained as a solid (11%) from the title compound of Preparation 14 and 3-chloro-4-fluoro-boronic acid following the procedure of Example 1.
δ(DMSO-d₆): 1.33 (t, 3H), 2.14 (s, 3H), 4.16 (q, 2H), 7.06 (m, 2H), 7.32-7.38 (m, 4H), 7.48 (bs, 1H), 7.80 (d, 1H), 8.61 (bs, 2H).
LRMS (m/z): 515 (M+1)⁺.
Retention Time: 18 min*.
*Chromaotgrafic method B.

Example 208

Methyl [4-acetyl-6-oxo-3-phenyl-5-(quinolin-5-ylamino)pyridazin-1(6H)-yl]acetate Obtained as a solid (44%) from the title compound of Preparation 95 and quinoline-5-boronic acid following the procedure of Example 1.
m.p. 193.6-194.3° C.
δ(CDCl₃): 1.40 (s, 3H), 3.80 (s, 3H), 4.98 (S, 2H), 7.32 (m, 6H), 7.48 (m, 1H), 7.62 (m, 1H), 8.06 (m, 1H), 8.41 (m, 2H), 8.98 (m, 1H).

Example 209

[4-Acetyl-6-oxo-3-phenyl-5-(quinolin-5-ylamino)pyridazin-1(6H)-yl]acetic acid

Obtained from the title compound of Example 208 following the procedure of Example 41.
LRMS: m/Z 415 (M+1)⁺.
Retention Time: 7.7 min Example 210

5-Acetyl-2-ethyl-4-[(3-methylpyridin-2-yl)amino]-6-phenylpyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in ethanol (4 mL), 2-amino-3-methylpyridine (45 mg, 0.417 mmol) was added portionwise. The resulting mixture was stirred at room temperature for five days. The solvent was evaporated and the residue purified by column chromatography (silica gel, hexane/ethyl acetate 2:1) to yield the title compound (26 mg, 27% yield).

δ(DMSO-d₆): 1.35 (t, 3H), 1.80 (s, 3H), 2.32 (s, 3H), 4.22 (q, 2H), 6.95 (m, 1H), 7.35 (m, 2H), 7.47 (m, 3H), 7.60 (d, 1H), 7.95 (d, 1H), 8.50 (s, 1H).

Example 211

5-Acetyl-2-ethyl-6-phenyl-4-(1H-pyrazol-3-ylamino)pyridazin-3(2H)-one

To a stirred solution of 80 mg (0.278 mmol) of 5-acetyl-2-ethyl-4-nitro-6-phenylpyridazin-3(2)-one (Dal Piaz, V et al, *J. Med. Chem.* 1997, 40, 1417) in ethanol (4 mL) under nitrogen atmosphere, 3-aminopyrazol (35 mg, 0.417 mmol) was added. The resulting mixture was stirred at room temperature during 30 minutes and the final product was collected by filtration and washed with diethylether to yield the title compound (50 mg, 55.7% yield).
δ(DMSO-d₆): 1.29 (t, 3H), 1.55 (s, 3H), 4.15 (q, 2H), 5.73 (s, 1H), 7.14 (s, 1H), 7.38-7.52 (m, 6H), 10.80 (s, 1H).

Example 212

5-Acetyl-2-ethyl-6-phenyl-4-(9H-purin-6-ylamino)pyridazin-3(2H)-one

To a stirred solution of 250 mg (0.870 mmol) of 5-acetyl-2-ethyl-4-nitro-6-phenylpyridazin-3(2H)-one (Dal Piaz, V et al, *J. Med. Chem.* 1997, 40, 1417) in ethanol (12 mL), adenine (235 mg, 1.740 mmol) was added. The resulting mixture was stirred and refluxed during two days. The solvent was evaporated and the residue purified by column chromatography (silica gel, dichloromethane/methanol 95:5) and preparative HPLC/MS to yield the title compound (4.4 mg, 1.4% yield).
LRMS: m/Z 376 (M+1)⁺.
Retention time: 7.5 min.

Example 213

5-Acetyl-2-ethyl-4-[(3-methylisoxazol-5-yl)amino]-6-phenylpyridazin-3(2H)-one

To a stirred solution of 200 mg (0.696 mmol) of 5-acetyl-2-ethyl-4-nitro-6-phenylpyridazin-3(2H)-one (Dal Piaz, V et al, *J. Med. Chem.* 1997, 40, 1417) in ethanol (10 mL), 5-amino-3-methylisoxazole (204 mg, 2.088 mmol) was added. The resulting mixture was stirred at 50° C. for four days. The solvent was evaporated and the residue purified by column chromatography (silica gel, hexane/ethyl acetate 2:1) to yield the title compound (35 mg, 14.9% yield).
m.p. 177.6-178.7° C. δ(DMSO-d₆): 1.33 (t, 3H), 1.82 (s, 3H), 2.13 (s, 3H), 4.19 (q, 2H), 5.71 (s, 1H), 7.34 (m, 2H), 7.47 (m, 3H), 10.02 (s, 1H).

Example 214

5-Acetyl-2-ethyl-4-[(8-hydroxyquinolin-5-yl)amino]-6-phenylpyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in ethanol (4 mL), 5-amino-8-quinolinol (67 mg, 0.417 mmol) was added. The resulting mixture was stirred at room temperature during 40 hours and the final product was collected by filtration and washed with diethylether to yield the title compound (100 mg, 90% yield).
m.p. 261.9-262.6° C.

δ(DMSO-d$_6$): 1.25 (s, 3H), 1.37 (t, 3H), 4.20 (q, 2H), 6.90 (d, 1H), 7.22-7.36 (m, 6H), 7.60 (m, 1H), 8.30 (d, 1H), 8.80 (m, 2H), 9.97 (s, 1H).

Example 215

5-Acetyl-2-ethyl-4-(1H-indazol-7-ylamino)-6-phenylpyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in ethanol (4 mL), 1H-indazol-7-amine (56 mg, 0.417 mmol) was added. The resulting mixture was stirred at room temperature during one hour and the final product was collected by filtration and washed with diethylether to yield the title compound (90 mg, 86.5% yield).
m.p. 262.6-263.8° C.
δ(DMSO-d$_6$): 1.12 (s, 3H), 1.37 (t, 3H), 4.20 (q, 2H), 7.03 (m, 2H), 7.25 (m, 2H), 7.38 (m, 3H), 7.57 (m, 1H), 8.06 (s, 1H), 9.04 (s, 1H), 13.08(s, 1H).

Example 216

5-Acetyl-4-[(6-bromoquinolin-8-yl)amino]-2-ethyl-6-phenylpyridazin-3(2H)-one

To a stirred solution of 80 mg (0.279 mmol) of 5-acetyl-2-ethyl-4-nitro-6-phenylpyridazin-3(2H)-one (Dal Piaz, V et al, *J. Med. Chem.* 1997, 40, 1417) in ethanol (4 mL), 8-amino-6-bromoquinoline (93 mg, 0.417 mmol) was added. The resulting mixture was stirred at room temperature or one day. The solvent was evaporated and the residue purified by column chromatography (silica gel, hexane/ethyl acetate 3:1) to yield the title compound (110 mg, 85.3% yield).
m.p. 146.8-147.5° C.
δ(DMSO-d$_6$): 1.35 (t, 3H), 1.76 (s, 3H), 4.21 (q, 2H), 7.27 (s, 1H), 7.40-7.48 (m, 5H), 7.65 (m, 1H), 7.91 (s, 1H), 8.36 (d, 1H), 8.93 (m, 1H), 9.36 (s, 1H).

Example 217

5-Acetyl-2-ethyl-4-[(5-methylisoxazol-3-yl)amino]-6-phenylpyridazin-3(2H)-one

To a stirred solution of 80 mg (0.278 mmol) of 5-acetyl-2-ethyl nitro-6-phenylpyridazin-3(2H)-one (Dal Piaz, V et al., *J. Med. Chem.* 1997, 40, 1417) in ethanol (4 mL), 3-amino-5-methylisoxazol (96 mg, 0.978 mmol) was added. The resulting mixture was stirred, at room temperature for four days and the final product was collected by filtration and washed with diethylether to yield the title compound (35 mg, 37.2% yield).
m.p. 170.1-170.8° C.
δ(DMSO-d$_6$): 1.33 (t, 3H), 1.82 (s, 3H), 2.32 (s, 3H), 4.19 (q, 2H), 6.12 (s, 1H), 7.32 (m, 2H), 7.45 (m, 3H), 9.36 (s, 1H).

Example 218

5-Acetyl-2-ethyl-4-(isoxazol-3-ylamino)-6-phenylpyridazin-3(2H)-one

To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in ethanol (4 mL), 3-aminoisoxazol (70 mg, 0.834 mmol) was added. The resulting mixture was stirred at room temperature for four days and the final product was collected by filtration and washed with diethylether to yield the title compound (58 mg, 63.7% yield).
m.p. 176.4-177.1° C.
δ(DMSO-d$_6$): 1.34 (t, 3H), 1.84 (s, 3H), 4.20 (q, 2H), 6.43 (s, 1H), 7.32 (m, 2H), 7.46 (m, 3H), 8.67 (s, 1H), 9.45 (s, 1H).

Example 219

5-Acetyl-2-(cyclopropylmethyl)-6-phenyl-4-(quinolin-5-ylamino)pyridazin-3(2H)-one To a stirred solution of 100 mg (0.319 mmol) of Preparation 97 in ethanol (4 mL), 5-aminoquinoline (69 mg, 0.479 mmol) was added. The resulting mixture was stirred at room temperature during one day and the final product was collected by filtration and washed with diethylether to yield the title compound (53 mg, 40.4% yield).
m.p. 203.9-205.1° C.
δ(DMSO-d$_6$): 0.46 (m, 2H), 0.55 (m, 2H), 1.33 (m, 4H), 4.06 (q, 2H), 7.24 (m, 2H), 7.35 (m, 4H), 7.58 (m, 2H), 7.86 (d, 1H), 8.44 (d, 1H), 8.93 (m, 1H), 9.21 (s, 1H).

Example 220

5-Acetyl-2-(cyclopropylmethyl)-6-phenyl-4-(quinolin-8-ylamino)pyridazin-3(2H)-one To a stirred solution of 100 mg (0.319 mmol) of the title compound of Preparation 97 in ethanol (4 mL), 8-aminoquinoline (69 mg, 0.479 mmol) was added. The resulting mixture was stirred at room temperature during 22 hours. The solvent was evaporated and the residue purified by column chromatography (silica gel, hexane/ethyl acetate 3:1) to yield the title compound (110 mg, 84.6% yield).
m.p. 123.1-124.7° C.
δ(DMSO-d$_6$): 0.45 (m, 2H), 0.53 (m, 2H), 1.30 (m, 1H), 1.61 (s, 3H), 4.05 (q, 2H), 7.24 (d, 1H), 7.37-7.49 (m, 6H), 7.61 (m, 1H), 7.71 (d, 1H), 8.40 (d, 1H), 8.93 (m, 1H), 9.35 (s, 1H).

Example 221

5-Acetyl-2-ethyl-4-[(1-methyl-1H-pyrazol-3-yl)amino]-6-phenylpyridazin-3(2H)-one To a stirred solution of 80 mg (0.278 mmol) of 5-acetyl-2-ethyl-4-nitro-6-phenylpyridazin-3(2H)-one (Dal Piaz, V et al, *J. Med. Chem.* 1997, 40, 1417) in ethanol (4 mL), 3-amino-1-methylpyrazol (40 mg, 0.417 mmol) was added. The resulting mixture was stirred at room temperature during three hours and the final product was collected by filtration and washed with diethylether to yield the title compound (56 mg, 59.6% yield).
m.p. 202.8-203.9° C.
δ(DMSO-d$_6$): 1.32 (t, 3H), 1.72 (s, 3H), 3.62 (s, 3H), 4.16 (q, 2H), 5.94 (m, 1H), 7.29 (m, 2H), 7.43 (m, 3H), 7.52 (s, 1H), 8.84 (s, 1H).

Example 222

5-Acetyl-2-ethyl-4-[(1-oxidoquinolin-5-yl)amino]-6-phenylpyridazin-3(2H)-one

A solution of the compound synthesized in Example 82 (210 mg, 0.546 mmol) in dichloromethane (3 mL) was added dropwise to a cold solution of 3-chloroperoxybenzoic acid (111 mg, 0.546 mmol) in dichloromethane (7 mL). The mixture was stirred at room temperature for 27 hours and added to a solution of KHSO$_4$ in water (20 mL, 25%). The organic layer was washed with water, dried over sodium sulfate anhydride and evaporated.

The crude obtained was purified by column chromatography (silica gel, dichloromethane/methanol 110:5) to yield 160 mg (0.399 mmol) of the title compound (73%).

m.p. 264.0-264.8° C.

δ(DMSO-d$_6$): 1.37 (t, 3H), 1.41 (s, 3H), 4.21 (q, 2H), 7.26 (bs, 2H), 7.39 (bs, 3H), 7.48 (m, 2H), 7.65 (m, 1H), 7.96 (d, 1H), 8.35 (d, 1H), 8.61 (m, 1H), 9.24 (s, 1H).

Example 223

5-Acetyl-2-ethyl-4-[(2-oxidoisoquinolin-5-yl) amino]-6-phenylpyridazin-3(2H)-one The title compound was synthesized from the title compound of Example 84 following the procedure of Example 222. The crude obtained was purified by preparative HPLC/MS to yield the title compound (24% yield).

LRMS: m/Z 1401 (M+1)$^+$. Retention time: 7.3 min.

Example 224

5-Acetyl-6-(3-chlorophenyl)-2-ethyl-4-(quinolin-5-ylamino)pyridazin-3(2H)-one

To a stirred solution of 100 mg (0.311 mmol) of 5-acetyl-2-ethyl-4-nitro-6-(3-chlorophenyl)pyridazin-3(2M-one- (Dal Piaz, V et al, *J. Med. Chem.* 1997, 40, 1417) in ethanol (5 mL); 5-aminoquinoline (67 mg, 0.467 mmol) was added. The resulting mixture was stirred at room temperature during two hours and the final product was collected by filtration and washed with diethylether to yield the title compound (67 mg, 51.5% yield).

m.p. 186.2-186.9° C.

δ(DMSO-d$_6$): 1.37 (m, 6H), 4.22 (q, 2H), 7.17 (d, 1H), 7.33-7.45 (m, 4H), 7.60 (m, 2H), 7.87 (d, 1H), 8.44 (d, 1H), 8.93 (m, 1H), 9.28 (s, 1H).

Example 225

5-Acetyl-6-(3-chlorophenyl)-2-ethyl 4-(quinolin-8-ylamino)pyridazin-3(2H)-one

To a stirred solution of 100 mg (0.311 mmol) of 5-acetyl-2-ethyl-4-nitro-6-(3-chlorophenyl)pyridazin-3(2H)-one (Dal Piaz, V et al, J. Med. Chem. 1997, 40, 1417) in ethanol (4 mL), 8-aminoquinoline (67 mg, 0.467 mmol) was added. The resulting mixture was stirred at room temperature for two hours. The solvent was evaporated and the residue purified by column chromatography (silica gel, hexane/ethyl acetate 2:1) to yield the title compound (65 mg, 50% yield).

m.p. 127.0-127.7° C.

δ(DMSO-d$_6$): 1.36 (t, 3H), 1.65 (s, 3H), 4.22 (q, 2H), 7.27 (m, 2H), 7.41-7.51 (m, 4H), 7.62 (m, 1H), 7.72 (d, 1H), 8.42 (d, 1H), 8.93 (m, 1H), 9.36 (s, 1H).

Example 226

5-Acetyl-2-ethyl-6-pyridin-4-yl-4-(quinolin-5-ylamino)pyridazin-3(2H)-one

The title compound was synthesized from the title compound of Preparation 16 and the corresponding boronic acid following the procedure of Example 1. The resulting residue was purified by column chromatography (silica gel, dichloromethane/methanol 96:4) to yield the title compound (62.6% yield).

m.p. 214.0-215.5° C.

δ(DMSO-d$_6$): 1.38 (m, 6H), 4.23 (q, 2H), 7.26 (m, 2H), 7.34 (d, 1H), 7.58 (m, 2H), 7.86 (d, 1H), 8.50 (d, 1H), 8.56 (m, 2H), 8.92 (m, 1H), 9.35 (s, 1H).

Example 227

5-Acetyl-2-ethyl-6-pyridin-3-yl-4-(quinolin-5-ylamino)pyridazin-3(2H)-one

The title compound was synthesized from the title compound of Preparation 14 and the corresponding boronic acid following the procedure of Example 1. The resulting residue was purified by column chromatography (silica gel, dichloromethane/methanol 97:3) to yield the title compound (32% yield).

m.p. 180.7-181.6° C.

δ(DMSO-d$_6$): 1.38 (m, 6H), 4.23 (q, 2H), 7.33-7.41 (m, 2H), 7.56-7.67 (m, 3H), 7.87 (d, 1H), 8.46 (m, 2H), 8.56 (m, 1H), 8.93 (m, 1H), 9.32 (s, 1H).

Example 228

5-Acetyl-2-ethyl-4-[(8-fluoroquinolin-5-yl)amino]-6-phenylpyridazin-3(2H)-one

To a stirred solution of 150 mg (0.522 mmol) of 5-acetyl-2-ethyl-4-nitro-phenylpyridazin-3(2H)-one (Dal Piaz, V et al, *J. Med. Chem.* 1997, 40, 1417) in ethanol (8 mL), 5-amino-8-fluoroquinoline (127 mg, 0.783 mmol) (Lee, Jae Keun et al., *Bull. Korean Chem. Soc.,* 1996, 17(1), 90) was added. The resulting mixture was stirred at room temperature for five hours. The solvent was evaporated and the residue purified by column chromatography (silica gel, hexane/ethyl acetate 3:1) to yield the title compound (140 mg, 66.7% yield).

m.p. 245.7-246-6° C.

δ(DMSO-d$_6$): 1.36 (m, 6H), 4.22 (q, 2H), 7.23 (m, 2H), 7.37-7.47 (m, 5H), 7.70 (m, 1H), 8.43 (d, 1H), 8.99 (m, 1H), 9.16 (s, 1H).

Example 229

5-Acetyl-2-(cyclopropylmethyl)-6-(4-fluorophenyl)-4-(quinolin-8-ylamino) pyridazin-3(2H)-one To a stirred solution of 150 mg (0.453 mmol) of the title compound of Preparation 65 in ethanol (8 mL), 8-aminoquinoline (98 mg, 0.680 mmol) was added. The resulting mixture was stirred at room temperature during four hours and the final product was collected by filtration and washed with diethylether to yield the title compound (115 mg, 59.3% yield).

m.p. 149.7-150.6° C.

δ(DMSO-d$_6$): 0.44 (m, 2H), 0.53 (m, 2H), 1.35 (m, 1H), 1.63 (s, 3H), 4.05 (q, 2H), 7.27 (m, 3H), 7.38 (m, 2H), 7.45 (m, 1H), 7.61 (m, 1H), 7.70 (d, 1H), 8.40 (d, 1H), 8.93 (m, 1H), 9.35 (s, 1H).

Example 230

5-Acetyl-2-ethyl-6-(4-fluorophenyl)-4-quinolin-5-ylamino)pyridazin-3(2H)-one

To a stirred solution of 150 mg (0.491 mmol) of the title compound of Preparation 30 in ethanol (8 mL), 5-aminoquinoline (106 mg, 0.737 mmol) was added. The resulting mixture was stirred at room temperature during two hours and the final product was collected by filtration and washed with diethylether to yield the title compound (140 mg, 70.7% yield).

m.p. 217.5-218.3° C.

$\delta$(DMSO-$d_6$): 1.37 (m, 6H), 4.21 (q, 2H), 7.17-7.36 (m, 5H), 7.58 (m, 2H), 7.87 (d, 1H), 8.43 (d, 1H), 8.92 (m, 1H), 9.23 (s, 1H).

Example 231

5-Acetyl-2-ethyl-6-(4-fluorophenyl)-4-(quinolin-8-ylamino)pyridazin-3(2H)-one

To a stirred solution of 150 mg (0.491 mmol) of the title compound of Preparation 30 in ethanol (8 mL), 8-aminoquinoline (106 mg, 0.737 mmol) was added. The resulting mixture was stirred at room temperature during one hour and the final product was collected by filtration and washed with diethylether to yield the title compound (130 mg, 65.6% yield).

m.p. 153.5-154.3° C.

$\delta$(DMSO-$d_6$): 1.36 (t, 3H), 1.62 (s, 3H), 4.21 (q, 2H), 7.26 (m, 3H), 7.38-7.51 (m, 3H), 7.61 (m, 1H), 7.70 (d, 1H), 8.40 (d, 1H), 8.92 (m, 1H), 9.35 (s, 1H).

Example 232

5-Acetyl-2-(cyclopropylmethyl)-6-(4-fluorophenyl)-4-(quinolin-5-ylamino) pyridazin-3(2H)-one To a stirred solution of 150 mg (0.453 mmol) of the title compound of Preparation 30 in ethanol (8 mL), 5-aminoquinoline (98 mg, 0.680 mmol) was added. The solvent was evaporated and the residue purified by column chromatography (silica gel, hexane/ethyl acetate 1:1) to yield the title compound (174 mg, 89.7% yield).

m.p. 169.2-170.0° C.

$\delta$(DMSO-$d_6$): 0.45 (m, 2H), 0.55 (m, 2H), 1.36 (m, 4H), 4.05 (q, 2H), 7.18-7.37 (m, 5H), 7.55-7.64 (m, 2H), 7.87 (d, 1H), 8.43 (d, 1H), 0.92 (m, 1H), 9.23 (s, 1H).

Example 233

5-Acetyl-6-(3-chlorophenyl)-2-ethyl-4-[(1-oxidoquinolin-5-yl)amino]pyridazin-3(2H)-one The title compound was synthesized from the title compound of Example 224 (390 mg, 0.931 mmol) following the procedure of Example 222. The crude obtained was purified by column chromatography (silica gel, dichloromethane/methanol 160:5) to yield the title compound (300 mg, 74.1% yield).

m.p. 244.0-244.9° C.

$\delta$(DMSO-$d_6$): 1.37 (t, 3H), 1.48 (s, 3H), 4.21 (q, 2H), 7.19 (d, 1H), 7.35-7.52 (m, 5H), 7.66 (t, 1H), 7.96 (d, 1H), 8.36 (d, 1H), 8.61 (d, 1H), 9.32 (s, 1H).

Example 234

5-Acetyl-2-ethyl-4-[(2-methylquinolin-5-yl)amino]-6-phenylpyridazin-3(2H)-one

To a stirred solution of 100 mg (0.348 mmol) of 5-acetyl-2-ethyl-4-nitro-6-phenylpyridazin-3(2H)-one (Dal Piaz, V et al, *J. Med. Chem.* 1997, 40, 1417) in ethanol (5 mL), 5-amino-2-methylquinoline (83 mg, 0.522 mmol) was added. The resulting mixture was stirred at room temperature during three hours and the final product was collected by filtration and washed with diethylether to yield the title compound (80 mg, 57.6% yield).

m.p. 204.5-205.1° C.

$\delta$(DMSO-$d_6$): 1.30 (s, 3H), 1.37 (t, 3H), 2.66 (s, 3H), 4.21 (q, 2H), 7.25 (m, 3H) 7.36 (m, 3H), 7.45 (d, 1H), 7.54 (t, 1H), 7.76 (d, 1H), 8.30 (d, 1H), 9.16 (s, 1H).

Example 235

5-Acetyl-6-(3-chlorophenyl)-2-ethyl-4-(isoquinolin-5-ylamino)pyridazin-3(2H)-one To a stirred solution of 100 mg (0.311 mmol) of 5-acetyl-2-ethyl-4-nitro-6-(3-chlorophenyl)pyridazin-3(2H)-one (Dal Piaz, V et al, *J. Med. Chem.* 1997, 40, 1417) in ethanol (4 mL), 5-amino-isoquinoline (67 mg, 0.467 mmol) was added. The resulting mixture was stirred at room temperature for two hours. The solvent was evaporated and the residue purified by column chromatography (silica gel, hexane/ethyl acetate 1:2) to yield the title compound (28 mg, 21.5% yield).

m.p. 189.2-190.6° C.

$\delta$(DMSO-$d_6$): 1.37 (m, 6H), 4.22 (q, 2H), 7.18 (d, 1H), 7.34-7.58 (m, 5H), 7.86 (d, 1H), 7.99 (d, 1H), 8.54 (d, 1H), 9.25 (s, 1H), 9.33 (s, 1H).

Example 236

5-Acetyl-2-ethyl-6-(4-fluorophenyl)-4-[(1-oxidoquinolin-5-yl)amino]pyridazin-3(2H)-one The title compound was synthesized from the title compound of Example 230 (430 mg, 1.069 mmol) following the procedure of Example 222. The crude obtained was purified by column chromatography (silica gel, dichloromethane/methanol 110:5) to yield the title compound (360 mg, 80.5% yield).

m.p. 245.1-246.0° C.

$\delta$(DMSO-$d_6$): 1.37 (t, 3H), 1.44 (s, 3H), 4.21 (q, 2H), 7.20-7.31 (m, 4H), 7.46-7.50 (m, 2H), 7.64 (m, 1H), 7.98 (d, 1H), 8.36 (d, 1H), 8.62 (d, 1H), 9.28 (s, 1H).

Example 237

5-Acetyl-2-ethyl-6-(3-fluorophenyl)-4-(quinolin-5-ylamino)pyridazin-3(2H)-one

To a stirred solution of 400 mg (1.31 mmol) of the title compound of Preparation 36 in ethanol (20 mL), 5-aminoquinoline (283 mg, 1.965 mmol) was added. The resulting mixture was stirred at room temperature during two hours and the final product was collected by filtration and washed with diethylether to yield the title compound (320 mg 60.7% yield).

m.p. 205.3-206.7° C.

δ(DMSO-d$_6$): 1.38 (m, 6H), 4.20 (q, 2H), 7.10 (m, 2H), 7.22 (m, 1H), 7.35 (m, 2H), 7.60 (m, 2H), 7.85 (d, 1H), 8.42 (d, 1H), 8.95 (m, 1H), 9.25 (s, 1H).

Example 238

5-Acetyl-2-ethyl-6-(3-fluorophenyl)-4-[(1-oxi-doquinolin-5-yl)amino]pyridazin-3(2H)-one The title compound was synthesized from the title compound of Example 237 (200 mg, 0.497 mmol) following the procedure of Example 222. The crude obtained was purified by column chromatography (silica gel, dichloromethane/methanol 200:5) to yield the title compound (150 mg, 72.1% yield).
m.p. 249.4-250.6° C.
δ(DMSO-d$_6$): 1.23 (t, 3H), 1.33 (s, 3H), 4.07 (q, 2H), 6.92-7.00 (m, 2H), 7.11 (m, 1H), 7.25-7.38 (m, 3H), 7.51 (m, 1H), 7.82 (d, 1H), 8.22 (d, 1H), 8.48 (d, 1H), 9.17 (s, 1H).

Example 239

5-[(5-Actyl-2-ethyl-3-oxo-6-phenyl-2,3-dihydropyridazin-4-yl)amino]quinoline-carboxylic acid A mixture of (160 mg, 0.556 mmol) of 5-acetyl-2-ethyl-4-nitro-6-phenylpyridazin-3(2H)-one (Dal Piaz, V et al, *J. Med. Chem.* 1997, 40, 1417), 5-aminoquinoline-8-carboxilic acid (210 mg, 1.114 mmol) (Breckenridge, J. G. et al. *Canadian J. of Research Sect. B*, 1947, 25, 49) and ethanol (8 mL) was introduced in the microwave. The mixture was stirred at 120° C. during 45 minutes. The solvent was evaporated and the residue purified by column chromatography (silica gel, dichloromethane/methanol 300:1) to yield the title compound (50 mg, 41.7% yield).
LRMS: m/Z 429 (M+1)$^+$. Retention time: 14 min*.
*Chromatografic method B The following examples illustrate pharmaceutical compositions according to the present invention.

COMPOSITION EXAMPLES

Composition Example 1

Preparation of Tablets

Formulation:

| | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention are mixed with 340.8 g of lactose and 85.2 g of microcrystalline cellulose. The mixture is subjected to compression moulding using a roller compactor to give a flake-like compressed material. The flake-like compressed material is pulverised using a hammer mill, and the pulverised material is screened through a 20 mesh screen. A 4.5 g portion of light silicic anhydride and 4.5 g of magnesium stearate are added to the screened material and mixed. The mixed product is subjected to a tablet making machine equipped with a die/punch system of 7.5 mm in diameter, thereby obtaining 3,000 tablets each having 150 mg in weight.

Composition Example 2

Preparation of Coated Tablets

Formulation:

| | |
|---|---|
| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidised bed granulating machine, 15 g of the compound of the present invention are mixed with 285.6 g of lactose and 122.4 g of corn starch. Separately, 22.5 g of polyvinylpyrrolidone is dissolved in 127.5 g of water to prepare a binding solution. Using a fluidised bed granulating machine, the binding solution is sprayed on the above mixture to give granulates. A 4.5 g portion of magnesium stearate is added to the obtained granulates and mixed. The obtained mixture is subjected to a tablet making machine equipped with a die/punch biconcave system of 6.5 mm in diameter, thereby obtaining 3,000 tablets, each having 150 mg in weight.

Separately, a coating solution is prepared by suspending 6.9 g of hydroxypropylmethyl-cellulose 2910, 1.2 g of polyethylene glycol 6000, 3.3 g of titanium dioxide and 2.1 g of purified talc in 72.6 g of water. Using a High Coated, the 3,000 tablets prepared above are coated with the coating solution to give film-coated tablets, each having 154.5 mg in weight.

Composition Example 3

Preparation of Capsules

Formulation:

| | |
|---|---|
| Compound of the present invention | 5.0 mg |
| Lactose monohydrate | 200 mg |
| Colloidal silicon dioxide | 2 mg |
| Corn starch | 20 mg |
| Magnesium stearate | 4 mg |

25 g of active compound, 1 Kg of lactose monohydrate, 10 g of colloidal silicon dioxide, 100 g of corn starch and 20 g of magnesium stearate are mixed. The mixture is sieved through a 60 mesh sieve, and then filled into 5,000 gelatine capsules.

Composition Example 4

Preparation of a Cream

Formulation:

| | |
|---|---|
| Compound of the present invention | 1% |
| Cetyl alcohol | 3% |
| Stearyl alcohol | 4% |
| Gliceryl monostearate | 4% |

| | |
|---|---|
| Sorbitan monostearate | 0.8% |
| Sorbitan monostearate POE | 0.8% |
| Liquid vaseline | 5% |
| Methylparaben | 0.18% |
| Propylparaben | 0.02% |
| Glycerine | 15% |
| Purified water csp. | 100% |

An oil-in-water emulsion cream is prepared with the ingredients listed above, using conventional methods.

The invention claimed is:

1. A pyridazin-3(2H)-one derivative compound of formula (I):

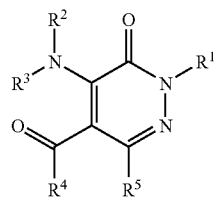

wherein
R$^1$ and R$^2$ represent independently from each other:
a hydrogen atom;
a group chosen from acyl, hydroxycarbonyl, alkoxycarbonyl, carbamoyl, monoalkylcarbamoyl and dialkylcarbamoyl;
an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, carbamoyl and mono- and di-alkylcarbamoyl groups;
an aryl or heteroaryl group, wherein said aryl or heteroaryl group is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;
a saturated or unsaturated heterocyclic group, which is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, oxo, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;
a group of formula

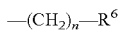

wherein n is an integer from 0 to 4 and R$^6$ represents:
a cycloalkyl or cycloalkenyl group;
an aryl group, which is optionally substituted by one or more substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups;
or a 3- to 7-membered ring having from 1 to 4 heteroatoms chosen from nitrogen, oxygen and sulphur, which ring is optionally substituted by one or more substituents chosen from halogen atoms, alkyl, hydroxy, alkoxy, alkylenedioxy, amino, mono- and di-alkylamino, nitro, cyano and trifluoromethyl groups;
R$^3$ represents a monocyclic or polycyclic aryl or heteroaryl group, which is optionally substituted by one or more substituents chosen from:
halogen atoms;
alkyl and alkylene groups, which are optionally substituted by one or more substituents chosen from halogen atoms; phenyl, hydroxy, hydroxyalkyl, alkoxy, aryloxy, alkylthio, oxo, amino, mono- and di-alkylamino, acylamino, hydroxycarbonyl, alkoxycarbonyl, carbamoyl, and mono- and di-alkylcarbamoyl groups;
phenyl, hydroxy, hydroxyalkyl, alkoxy, cycloalkoxy, nitro, aryloxy, alkylthio, alkylsulphinyl, alkylsulphonyl, alkylsulfamoyl, acyl, amino, mono- and di-alkylamino, acylamino, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
R$^5$ represents a group —COOR$^7$ or a monocyclic or polycyclic aryl or heteroaryl group, wherein said —COOR$^7$ or monocyclic or polycyclic aryl or heteroaryl group is optionally substituted by one or more substituents chosen from:
halogen atoms;
alkyl and alkenyl groups, which are optionally substituted by one or more substituents chosen from halogen atoms, phenyl, hydroxy, hydroxyalkyl, alkoxy, aryloxy, alkylthio, oxo, amino, mono- and di-alkylamino, acylamino, hydroxycarbonyl, alkoxycarbonyl, carbamoyl, and mono- and di-alkylcarbamoyl groups; and
phenyl, hydroxy, alkylenedioxy, alkoxy, cycloalkyloxy, alkylthio, alkylsuiphinyl, alkylsulphonyl, alkylsulfamoyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsuiphamido, aminosuphonyl, mono- and di-alkylaminosulphonyl, cyano, difluoromethoxy and trifluoromethoxy groups;
wherein R$^7$ represents an alkyl, which is optionally substituted by one or more substituents chosen from halogen atoms, hydroxy, alkoxy, aryloxy, alkylthio, oxo, amino, mono- and di-alkylamino, acylamino, hydroxycarbonyl, alkoxycarbonyl, carbamoyl, mono- and di-alkylcarbamoyl groups, and a group of formula

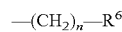

wherein n and R$^6$ are as defined above; and
R$^4$ represents:
a hydrogen atom;
a hydroxy, alkoxy, amino, mono- or di-alkylamino group;
an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups;
or a group of formula

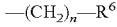

wherein n and $R^6$ are as defined above
or a N-oxide obtainable from heteroaryl radicals present in the structure when said heteroradical comprise at least one N atom or a pharmaceutically acceptable salt thereof;
with the proviso that when $R^5$ is neither an optionally substituted heteroaryl group nor a group $COOR^7$, $R^3$ is an optionally substituted heteroaryl group.

2. A compound according to claim 1 wherein $R^2$ represents a hydrogen atom or an aryl group, which is optionally substituted by one or more substituents chosen from halogen atoms, nitro, $C_1$-$C_4$ alkoxy, $C_1$-$C_4$ hydroxyalkyl and $CO_2$—($C_1$-$C_4$ alkyl) groups.

3. A compound according to claim 2, wherein $R^2$ is a hydrogen atom or a phenyl group, which is unsubstitued or substituted with 1 or 2 unsubstituted substituents chosen from fluorine atoms, chlorine atoms, and nitro, $C_1$-$C_4$ hydroxyalkyl and —$CO_2$—($C_1$-$C_4$alkyl) groups.

4. A compound according to claim 1, wherein $R^1$ represents a group chosen from:
a ($C_1$-$C_4$) alkyl group, which is optionally substituted by one or more hydroxy groups; and
groups of formula

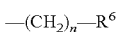

wherein n is an integer from 1 to 3 and $R^6$ represents a ($C_3$-$C_6$) cycloalkyl group.

5. A compound according to claim 4, wherein $R^1$ is an unsubstituted $C_1$-$C_4$ alkyl, an unsubstituted $C_1$-$C_4$ hydroxyalkyl or an unsubstituted cyclopropyl-($C_1$-$C_4$ alkyl)— group.

6. A compound according to claim 1, wherein $R^3$ represents a monocyclic or polycyclic aryl or heteroaryl group, wherein said monocyclic or polycyclic aryl or heteroaryl group is optionally substituted by one or more substituents chosen from:
halogen atoms;
alkyl and alkylene groups, wherein said alkyl and alkylene groups are optionally substituted by one or more substituents chosen from halogen atoms;
phenyl, hydroxy, hydroxycarbonyl, hydroxyalkyl, alkoxycarbonyl, alkoxy, cycloalkoxy, nitro, aryloxy, alkylthio, alkylsuiphinyl, alkylsuiphonyl, alkylsulfamoyl, acyl, amino, mono- or di-alkylamino, acylamino, hydroxycarbonyl, alkoxycarbonyl, carbamoyl, mono- and di-alkylcarbamoyl, ureido, N'-alkylureido, N',N'-dialkylureido, alkylsuiphamido, aminosuphonyl, mono- and di-alkylaminosuiphonyl, cyano, difluoromethoxy and trifluoromethoxy groups.

7. A compound according to claim 6, wherein $R^3$ represents a group chosen from monocyclic or polycyclic aryl or heteroaryl groups, wherein said monocyclic or polycyclic aryl or heteroaryl groups are optionally substituted by one or more substituents chosen from:
halogen atoms;
($C_1$-$C_4$) alkyl groups, which are optionally substituted by one or more hydroxy groups;
and ($C_1$-$C_4$) alkoxy, nitro, hydroxy, hydroxycarbonyl, carbamoyl, ($C_1$-$C_4$ alkoxy)-carbonyl and cyano groups.

8. A compound according to claim 7, wherein $R^3$ represents a phenyl group, a naphtyl group or a 5- to 14-membered monocylic or polycyclic heteroaryl group containing 1, 2 or 3 heteroatoms chosen from N, O and S, the phenyl, naphthyl and heteroaryl groups being unsubstituted or substituted with 1 or 2 unsubstituted substituents chosen from:
halogen atoms;
$C_1$-$C_4$ alkyl and $C_1$-$C_4$ hydroxyalkyl groups; and
$C_1$-$C_4$ alkoxy, nitro, hydroxy, hydroxycarbonyl, carbamoyl, ($C_1$-$C_4$ alkoxy)-carbonyl and cyano groups.

9. A compound according to claim 8 wherein $R^3$ represents a phenyl group, a naphtyl group or a substituted or unsubtituted heteroaryl group chosen from substituted or unsubstituted oxadiazolyl, oxazolyl, pyridyl, pyrrolyl, imidazolyl, thiazolyl, thiadiazolyl, thienyl, furanyl, quinolinyl, isoquinolinyl, indolyl, benzoxazolyl, naphthyridinyl, benzofuranyl, pyrazinyl, pyrimidinyl and pyrrolopyridyl radicals.

10. A compound according to claim 1, wherein $R^4$ represents:
an unsubstituted mono-($C_1$-$C_4$ alkyl)amino or unsubstituted di-($C_1$-$C_4$ alkyl)amino group;
a $C_1$-$C_4$ alkyl group which is unsubstituted or substituted by one or more substituents chosen from hydroxy, $C_1$-$C_4$ alkoxy, amino, mono-($C_1$-$C_4$ alkyl)amino and di-($C_1$-$C_4$ alkyl)amino groups;
an unsubstituted phenyl-($C_1$-$C_4$ alkyl)— group; or a group of formula

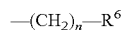

wherein n is 2 and $R^6$ represents a radical chosen from phenyl, pyridyl and thienyl, optionally substituted by one or more substituents chosen from halogen atoms, alkyl, hydroxy, alkoxy, alkylenedioxy, amino, mono- and di-alkylamino, nitro, ciano and trifluoromethyl groups.

11. A compound according to claim 10 wherein $R^4$ represents an alkyl group having from 1 to 6 carbon atoms and which is optionally substituted by one or more substituents chosen from halogen atoms and hydroxy groups.

12. A compound according to claim 1, wherein $R^5$ represents a group $COOR^7$ or a monocyclic or polycyclic aryl or heteroaryl group, wherein said —$COOR^7$ or monocyclic or polycyclic aryl or heteroaryl group is optionally substituted by one or more substituents chosen from halogen atoms, $C_1$-$C_4$ alkyl groups, $C_1$-$C_4$ alkoxycarbonyl groups, hydroxycarbonyl groups and $C_1$-$C_4$ alkoxy groups.

13. A compound according to claim 12, wherein $R^5$ represents a group $COOR^7$ or a monocyclic or polycyclic aryl or heteroaryl group, wherein said $COOR^7$ or a monocyclic or polycyclic aryl or heteroaryl group is optionally substituted by one or more substituents chosen from halogen atoms and $C_1$-$C_4$ alkoxy groups.

14. A compound according to claim 12, wherein $R^5$ represents —$CO_2R^7$, wherein $R^7$ represents an unsubstituted $C_1$-$C_4$ alkyl group, or $R^5$ represents a phenyl group or a 5- to 10- membered monocyclic or polycyclic heteroaryl group containing 1 or 2 heteroatoms chosen from N, O and S, the phenyl and heteroaryl groups being unsubstituted or substituted by 1 or 2 substituents chosen from $C_1$-$C_4$ alkoxy groups and halogen atoms.

15. A compound according to claim 14, wherein $R^5$ represents a phenyl group, or a substituted or unsubstituted heteroaryl group chosen from substituted or unsubstituted oxadiazolyl, oxazolyl, pyridyl, pyrrolyl, imidazolyl, thiazolyl, thiadiazolyl, thienyl, furanyl, quinolinyl, isoquinolinyl, indolyl, benzoxazolyl, naphthyridinyl, benzofuranyl, pyrazinyl, pyrimidinyl and pyrrolopyridyl radicals.

16. A pyridazin-3(2H)-one derivative compound of formula (I):

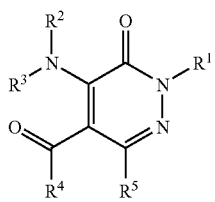

wherein
R¹ and R² represent independently from each other:
a hydrogen atom;
a group chosen from acyl, hydroxycarbonyl, alkoxycarbonyl, carbamoyl, monoalkylcarbamoyl and dialkylcarbamoyl;
an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, carbamoyl and mono- and di-alkylcarbamoyl groups;
an aryl or heteroaryl group, wherein said aryl or heteroaryl group is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;
a saturated or unsaturated heterocyclic group, which is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, oxo, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;
a group of formula

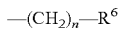

wherein n is an integer from 0 to 4 and $R^6$ represents:
a cycloalkyl or cycloalkenyl group;
an aryl group, which is optionally substituted by one or more substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups;
or a 3- to 7-membered ring having from 1 to 4 heteroatoms chosen from nitrogen, oxygen and sulphur, which ring is optionally substituted by one or more substituents chosen from halogen atoms, alkyl, hydroxy, alkoxy, alkylenedioxy, amino, mono- and di-alkylamino, nitro, cyano and trifluoromethyl groups;
R³ represents a monocyclic or polycyclic aryl or heteroaryl group, which is optionally substituted by one or more substituents chosen from:
halogen atoms;
alkyl and alkylene groups, which are optionally substituted by one or more substituents chosen from halogen atoms; phenyl, hydroxy, hydroxyalkyl, alkoxy, aryloxy, alkylthio, oxo, amino, mono- and di-alkylamino, acylamino, hydroxycarbonyl, alkoxycarbonyl, carbamoyl, and mono- and di-alkylcarbamoyl groups;
phenyl, hydroxy, hydroxyalkyl, alkoxy, cycloalkoxy, nitro, aryloxy, alkylthio, alkylsulphinyl, alkylsulphonyl, alkylsulfamoyl, acyl, amino, mono- and di- alkylamino, acylamino, hydroxycarbonyl, alkoxycarbonyl, carbamoyl, mono- and di-alkylcarbamoyl, ureido, N'-alkylureido, N', N'-dialkylureido, alkylsulphamido, aminosuphonyl, mono- and di-alkylaminosulphonyl, cyano, difluoromethoxy and trifluoromethoxy groups;
$R^5$ represents a group —$COOR^7$ or a monocyclic or polycyclic aryl or heteroaryl group, wherein said —$COOR^7$ or monocyclic or polycyclic aryl or heteroaryl group is optionally substituted by one or more substituents chosen from:
halogen atoms;
alkyl and alkenyl groups, which are optionally substituted by one or more substituents chosen from halogen atoms, phenyl, hydroxy, hydroxyalkyl, alkoxy, aryloxy, alkylthio, oxo, amino, mono- and di-alkylamino, acylamino, hydroxycarbonyl, alkoxycarbonyl, carbamoyl, and mono- and di-alkylcarbamoyl groups; and
phenyl, hydroxy, alkylenedioxy, alkoxy, cycloalkyloxy, alkylthio, alkylsuiphinyl, alkylsulphonyl, alkylsulfamoyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
$R^7$ represents an alkyl, which is optionally substituted by one or more substituents chosen from halogen atoms, hydroxy, alkoxy, aryloxy, alkylthio, oxo, amino, mono- and di-alkylamino, acylamino, hydroxycarbonyl, alkoxycarbonyl, carbamoyl, mono- and di-alkylcarbamoyl groups, and a group of formula

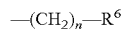

wherein n and $R^6$ are as defined above; and
$R^4$ represents:
a hydrogen atom;
a hydroxy, alkoxy, amino, mono- or di-alkylamino group;
an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups;
or a group of formula

wherein n and $R^6$ are as defined above
or a N-oxide obtainable from heteroaryl radicals present in the structure when said heteroradical comprise at least one N atom or a pharmaceutically acceptable salt thereof
with the proviso that when $R^5$ is neither an optionally substituted heteroaryl group nor a group $COOR^7$, $R^3$ is an optionally substituted heteroaryl group;

wherein when R⁵ represents a polycyclic heteroaryl group, R⁵ represents a group of formula (XXIII):

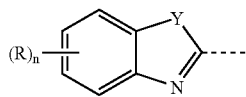

wherein Y represents an O atom, a S atom or an —NH— group, n is 0, 1 or 2 and each R is the same or different and is a $C_1$-$C_4$ alkoxy group or a halogen atom.

17. A compound as claimed in claim 1, chosen from:

5-acetyl-2-ethyl-4-[(3-fluorophenyl)amino]-6-pyridin-3-ylpyridazin-3(2H)-one;
5-acetyl-4-[(3-chlorophenyl)amino]-2-ethyl-6-pyridin-3-ylpyridazin-3(2H)-one;
5-acetyl-4-[(3,5-dichlorophenyl)amino]-2-ethyl-6-pyridin-3-ylpyridazin-3(2H)-one;
5-acetyl-2-ethyl-4-(1-naphthylamino)-6-pyridin-3-ylpyridazin-3(2H)-one;
methyl 4-[(5-acetyl-2-ethyl-3-oxo-6-pyridin-3-yl-2,3-dihydropyridazin-4-yl)amin]benzoate;
5-acetyl-2-ethyl-4-[(2-fluorophenyl)amino]-6-pyridin-3-ylpyridazin-3(2H)-one;
5-acetyl-4-[(2-chlorophenyl)amino]-2-ethyl-6-pyridin-3-ylpyridazin-3(2H)-one;
5-acetyl-2-ethyl-4-{[4-(hydroxymethyl)phenyl]amino}-6-pyridin-3-ylpyridazin-3(2H)-one;
3-[(5-acetyl-2-ethyl-3-oxo-6-pyridin-3-yl-2,3-dihydropyridazin-4-yl)amino]benzonitrile;
5-acetyl-4-[(3-chlorophenyl)amino]-2-(cyclopropylmethyl)-6-pyridin-3-ylpyridazin-3(2H)-one;
5-acetyl-2-(cyclopropylmethyl)-4-[(3,5-dichlorophenyl)amino]-6-pyridin-3-ylpyridazin-3(2H)-one;
5-acetyl-2-(cyclopropylmethyl)-4-[(2-fluorophenyl)amino]-6-pyridin-3-ylpyridazin-3(2H)-one;
5-acetyl-4-[(2-chlorophenyl)amino]-2-(cyclopropylmethyl)-6-pyridin-3-ylpyridazin-3(2H)-one;
3-{[5-acetyl-2-(cyclopropylmethyl)-3-oxo-6-pyridin-3-yl-2,3-dihydropyridazin-4-yl]amino}benzonitrile;
methyl 4-{[5-acetyl-2-(2-hydroxyethyl)-3-oxo-6-pyridin-3-yl-2,3-dihydropyridazin-4-yl]amino}benzoate;
5-acetyl-4-[(2-fluorophenyl)amino]-2-(2-hydroxyethyl)-6-pyridin-3-ylpyridazin-3(2H)-one;
5-acetyl-4-[(2-chlorophenyl)amino]-2-(2-hydroxyethyl)-6-pyridin-3-ylpyridazin-3(2H)-one;
5-acetyl-4-[(3-chlorophenyl)amino]-2-(2-hydroxyethyl)-6-pyridin-3-ylpyridazin-3(2H)-one;
5-acetyl-4-[(3-chlorophenyl)amino]-2-ethyl-6-pyridin-2-ylpyridazin-3(2H)-one;
3-[(5-acetyl-2-ethyl-3-oxo-6-pyridin-2-yl-2,3-dihydropyridazin-4-yl)amino]benzonitrile;
5-acetyl-2-ethyl-4-{[4-(hydroxymethyl)phenyl]amino}-6-pyridin-2-ylpyridazin-3(2H)-one;
3-{[5-acetyl-2-(cyclopropylmethyl)-3-oxo-6-pyridin-2-yl-2,3-dihydropyridazin-4-yl]amino}benzonitrile;
5-acetyl-4-[(3-chlorophenyl)amino]-2-(cyclopropylmethyl)-6-pyridin-2-ylpyridazin-3(2H)-one;
5-acetyl-2-(cyclopropylmethyl)-4-{[4-(hydroxymethyl)phenyl]amino}-6-pyridin-2-ylpyridazin-3(2H)-one;
5-acetyl-2-(cyclopropylmethyl)-4-[(3,5-dichlorophenyl)amino]-6-pyridin-2-ylpyridazin-3(2H)-one;
3-{[5-acetyl-2-(2-hydroxyethyl)-3-oxo-6-pyridin-2-yl-2,3-dihydropyridazin-4-yl]amino}benzonitrile;
5-acetyl-4-[(3-chlorophenyl)amino]-2-(2-hydroxyethyl)-6-pyridin-2-ylpyridazin-3(2H)-one;
5-acetyl-4-[(3,5-dichlorophenyl)amino]-2-(2-hydroxyethyl)-6-pyridin-2-ylpyridazin-3(2H)-one;
5-acetyl-2-(2-hydroxyethyl)-4-{[4-(hydroxymethyl)phenyl]amino}-6-pyridin-2-ylpyridazin-3(2H)-one;
5-acetyl-2-ethyl-4-[(3-fluorophenyl)amino]-6-pyridin-4-ylpyridazin-3(2H)-one;
5-acetyl-4-[(3-chlorophenyl)amino]-2-ethyl-6-pyridin-4-ylpyridazin-3(2H)-one;
5-acetyl-2-ethyl-4-(1-naphthylamino)-6-pyridin-4-ylpyridazin-3(2H)-one;
5-acetyl-2-ethyl-4-[(2-methylphenyl)amino]-6-pyridin-4-ylpyridazin-3(2H)-one;
methyl 4-[(5-acetyl-2-ethyl-3-oxo-6-pyridin-4-yl-2,3-dihydropyridazin-4-yl)amino]benzoate;
5-acetyl-2-ethyl-4-[(2-methoxyphenyl)amino]-6-pyridin-4-ylpyridazin-3(2H)-one;
5-acetyl-2-ethyl-4-[(3-methoxyphenyl)amino]-6-pyridin-4-ylpyridazin-3(2H)-one;
5-acetyl-2-ethyl-4-[(2-fluorophenyl)amino]-6-pyridin-4-ylpyridazin-3(2H)-one;
5-acetyl-4-[(2-chlorophenyl)amino]-2-ethyl-6-pyridin-4-ylpyridazin-3(2H)-one;
3-[(5-acetyl-2-ethyl-3-oxo-6-pyridin-4-yl-2,3-dihydropyridazin-4-yl)amino]benzonitrile;
5-acetyl-2-ethyl-4-{[4-(hydroxymethyl)phenyl]amino}-6-pyridin-4-ylpyridazin-3(2H)-one;
4-[(5-acetyl-2-ethyl-3-oxo-6-pyridin-4-yl-2,3-dihydropyridazin-4-yl)amino]benzoic acid;
5-acetyl-2-(cyclopropylmethyl)-4-[(2-fluorophenyl)amino]-6-pyridin-4-ylpyridazin-3(2H)-one;
5-acetyl-4-[(2-chlorophenyl)amino]-2-(cyclopropylmethyl)-6-pyridin-4-ylpyridazin-3(2H)-one;
3-{[5-acetyl-2-(cyclopropylmethyl)-3-oxo-6-pyridin-4-yl-2,3-dihydropyridazin-4-yl]amino}benzonitrile;
5-acetyl-2-(cyclopropylmethyl)-4-{[4-(hydroxymethyl)phenyl]amino}-6-pyridin-4-ylpyridazin-3(2H)-one;
5-acetyl-4-[(3-chlorophenyl)amino]-2-(cyclopropylmethyl)-6-pyridin-4-ylpyridazin-3(2H)-one;
5-acetyl-4-[(2-fluorophenyl)amino]-2-(2-hydroxyethyl)-6-pyridin-4-ylpyridazin-3(2H)-one;
5-acetyl-4-[(2-chlorophenyl)amino]-2-(2-hydroxyethyl)-6-pyridin-4-ylpyridazin-3(2H)-one;
3-{[5-acetyl-2-(2-hydroxyethyl)-3-oxo-6-pyridin-4-yl-2,3-dihydropyridazin-4-yl]amino}benzonitrile;
5-acetyl-2-(2-hydroxyethyl)-4-{[4-(hydroxymethyl)phenyl]amino}-6-pyridin-4-ylpyridazin-3(2H)-one;
5-acetyl-4-[(3-chlorophenyl)amino]-2-(2-hydroxyethyl)-6-pyridin-4-ylpyridazin-3(2H)-one;
5-acetyl-4-[(3-chlorophenyl)amino]-2-ethyl-6-thien-2-ylpyridazin-3(2H)-one;
5-acetyl-4-[bis(3-fluorophenyl)amino]-2-ethyl-6-pyridin-3-ylpyridazin-3(2H)-one;
5-acetyl-4-[bis-(4-methoxycarbonylphenyl)-amino]-2-ethyl-6-pyridin-3-ylpyridazin-3(2H)-one;
5-acetyl-4-{bis[4-(hydroxymethyl)phenyl]amino}-2-ethyl-6-pyridin-3-ylpyridazin-3(2H)-one;
5-acetyl-4-[bis(3-nitrophenyl)amino]-2-ethyl-6-pyridin-4-ylpyridazin-3(2H)-one;
5-acetyl-4-[bis(3-fluorophenyl)amino]-2-ethyl-6-pyridin-4-ylpyridazin-3(2H)-one;
5-acetyl-4-[bis(3-chlorophenyl)amino]-2-(cyclopropylmethyl)-6-pyridin-3-ylpyridazin-3(2H)-one;
5-acetyl-4-[bis(3,5-dichlorophenyl)amino]-2-(cyclopropylmethyl)-6-pyridin-3-ylpyridazin-3(2H)-one;

5-acetyl-4-[bis(4-methoxycarbonylphenyl)amino]-2-(2-hydroxyethyl)-6-pyridin-3-ylpyridazin-3(2H)-one;
5-acetyl-4-[bis(3-chlorophenyl)amino]-2-(2-hydroxyethyl)-6-pyridin-2-ylpyridazin-3(2H)-one;
5-acetyl-4-[bis(3-chlorophenyl)amino]-2-(cyclopropylmethyl)-6-pyridin-4-ylpyridazin-3(2H)-one;
5-acetyl-2-ethyl-6-phenyl-4-(pyridin-3-ylamino)pyridazin-3(2H)-one
5-acetyl-4-[(3,5-dichloropyridin-4-yl)amino]-2-ethyl-6-phenylpyridazin-3(2H)-one;
5-acetyl-2-ethyl-6-phenyl-4-(pyrazin-2-ylamino)pyridazin-3(2H)-one;
5-acetyl-2-ethyl-6-phenyl-4-(pyrimidin-2-ylamino)pyridazin-3(2H)-one;
5-acetyl-2-ethyl-6-phenyl-4-(quinolin-8-ylamino)pyridazin-3(2H)-one;
5-acetyl-2-ethyl-4-[(5-nitropyridin-2-yl)amino]-6-phenylpyridazin-3(2H)-one;
5-acetyl-2-ethyl-4-(1 h-indol-4-ylamino)-6-phenylpyridazin-3(2H)-one;
5-acetyl-4-(1,3-benzothiazol-6-ylamino)-2-ethyl-6-phenylpyridazin-3(2H)-one;
5-acetyl-2-ethyl-6-phenyl-4-(thianthren-1-ylamino)pyridazin-3(2H)-one;
methyl 3-[(5-acetyl-2-ethyl-3-oxo-6-phenyl-2,3-dihydropyridazin-4-yl)amino]thiophene-2-carboxylate;
5-acetyl-2-ethyl-4-[(4-methylpyridin-2-yl)amino]-6-phenylpyridazin-3(2H)-one;
5-acetyl-2-ethyl-6-phenyl-4-(1h-1,2,4-triazol-5-ylamino)pyridazin-3(2H)-one;
5-acetyl-2-ethyl-4-[(6-methoxypyridin-3-yl)amino]-6-phenylpyridazin-3(2H)-one;
5-acetyl-2-ethyl-4-(2H-indazol-5-ylamino)-6-phenylpyridazin-3(2H)-one;
methyl 4-[(5-acetyl-2-ethyl-3-oxo-6-phenyl-2,3-dihydropyridazin-4-yl)amino]thiophene-3-carboxylate;
5-acetyl-2-ethyl-6-phenyl-4-(pyridin-2-ylamino)pyridazin-3(2H)-one;
3-[(5-acetyl-2-ethyl-3-oxo-6-phenyl-2,3-dihydropyridazin-4-yl)amino]thiophene-2-carboxylic acid;
5-acetyl-2-ethyl-4-[(3-methylcinnolin-5-yl)amino]-6-phenylpyridazin-3(2H)-one;
5-acetyl-2-ethyl-4-[(2-methylquinolin-8-yl)amino]-6-phenylpyridazin-3(2H)-one;
5-acetyl-2-ethyl-6-phenyl-4-(quinolin-5-ylamino)pyridazin-3(2H)-one;
5-acetyl-2-ethyl-4-(1h-indol-5-ylamino)-6-phenylpyridazin-3(2H)-one;
5-acetyl-2-ethyl-4-(isoquinolin-5-ylamino)-6-phenylpyridazin-3(2H)-one;
5-acetyl-2-ethyl-4-[(6-methoxyquinolin-8-yl)amino]-6-phenylpyridazin-3(2H)-one;
5-acetyl-4-[(5-bromoquinolin-8-yl)amino]-2-ethyl-6-phenylpyridazin-3(2H)-one;
5-acetyl-2-ethyl-4-[(4-methylpyrimidin-2-yl)amino]-6-phenylpyridazin-3(2H)-one;
5-acetyl-6-(3-chlorophenyl)-2-ethyl-4-(pyridin-3-ylamino)pyridazin-3(2H)-one;
5-acetyl-6-(3-chlorophenyl)-2-(cyclopropylmethyl)-4-(pyridin-3-ylamino)pyridazin-3(2H)-one;
5-acetyl-2-ethyl-6-(3-fluorophenyl)-4-(pyridin-3-ylamino)pyridazin-3(2H)-one;
5-acetyl-6-(3-fluorophenyl)-2-isopropyl-4-(pyridin-3-ylamino)pyridazin-3(2H)-one;
5-acetyl-2-(cyclopropylmethyl)-6-(3-fluorophenyl)-4-(pyridin-3-ylamino)pyridazin-3(2H)-one;
5-acetyl-2-ethyl-6-(4-fluorophenyl)-4-(pyridin-3-ylamino)pyridazin-3(2H)-one;
5-acetyl-6-(1 h-benzimidazol-2-yl)-4-[(3-chlorophenyl)amino]-2-ethylpyridazin-3(2H)-one;
5-acetyl-6-(1,3-benzoxazol-2-yl)-4-[(3-chlorophenyl)amino]-2-ethylpyridazin-3(2H)-one;
5-acetyl-6-(1,3-benzoxazol-2-yl)-2-ethyl-4-[(3-fluorophenyl)amino]pyridazin-3(2H)-one;
5-acetyl-6-benzooxazol-2-yl-4-[bis-(3-chlorophenyl)-amino]-2-ethyl-pyridazin-3(2H)-one;
5-acetyl-6-benzooxazol-2-yl-4-[bis-(3-fluorophenyl)-amino]-2-ethyl-pyridazin-3(2H)-one;
3-[(5-acetyl-2-ethyl-3-oxo-6-pyridin-3-yl-2,3-dihydropyridazin-4-yl)amino]benzamide;
5-acetyl-2-ethyl-4-(isoquinolin-1-ylamino)-6-phenylpyridazin-3(2H)-one;
5-acetyl-4-[(2-butylquinazolin-4-yl)amino]-2-ethyl-6-phenylpyridazin-3(2H)-one;
5-acetyl-4-(1,2-benzisothiazol-3-ylamino)-2-ethyl-6-phenylpyridazin-3(2H)-one;
5-acetyl-2-ethyl-6-phenyl-4-(pyridin-4-ylamino)pyridazin-3(2H)-one;
5-acetyl-2-ethyl-4-[(2-hydroxy-7h-purin-6-yl)amino]-6-phenylpyridazin-3(2H)-one;
5-acetyl-2-ethyl-6-phenyl-4-(quinazolin-4-ylamino)pyridazin-3(2H)-one;
5-acetyl-4-[(4-chloro-1H-indazol-3-yl)amino]-2-ethyl-6-phenylpyridazin-3(2H)-one;
5-acetyl-4-[(7-chloroquinolin-4-yl)amino]-2-ethyl-6-phenylpyridazin-3(2H)-one;
5-acetyl-4-[(4,6-dichloropyrimidin-2-yl)amino]-2-ethyl-6-phenylpyridazin-3(2H)-one;
5-acetyl-2-ethyl-4-[(6-hydroxy-2H-pyrazolo[3,4-d]pyrimidin-4-yl)amino]-6-phenylpyridazin-3(2H)-one;
5-acetyl-2-ethyl-4-[(2-methylquinolin-4-yl)amino]-6-phenylpyridazin-3(2H)-one;
5-acetyl-2-ethyl-4-(1H-imidazol-2-ylamino)-6-phenylpyridazin-3(2H)-one;
5-acetyl-2-ethyl-6-phenyl-4-(quinolin-4-ylamino)pyridazin-3(2H)-one;
5-acetyl-4-(cinnolin-4-ylamino)-2-ethyl-6-phenylpyridazin-3(2H)-one;
5-acetyl-2-ethyl-6-phenyl-4-(1H-pyrazolo[3,4-d]pyrimidin-4-ylamino)pyridazin-3(2H)-one;
5-acetyl-2-ethyl-6-phenyl-4-(thieno[2,3-d]pyrimidin-4-ylamino)pyridazin-3(2H)-one;
5-acetyl-4-(1H-indazol-6-ylamino)-6-phenylpyridazin-3(2H)-one;
5-acetyl-4-[(3-chlorophenyl)amino]-2-ethyl-6-(2-methoxypyridin-4-yl)pyridazin-3(2H)-one;
5-acetyl-2-ethyl-4-{[4-(hydroxymethyl)phenyl]amino}-6-(6-methoxypyridin-3-yl)pyridazin-3(2H)-one;
5-acetyl-2-ethyl-4-[(3-methoxyphenyl)amino]-6-thien-3-ylpyridazin-3(2H)-one;
5-acetyl-6-(1-benzofuran-5-yl)-2-ethyl-4-[(3-fluorophenyl)amino]pyridazin-3(2H)-one;
1-ethyl-5-[(3-methoxyphenyl)amino]-n,n-dimethyl-6-oxo-3-pyridin-3-yl-1,6-dihydropyridazine-4-carboxamide;
5-[(3-chlorophenyl)amino]-1-ethyl-n-methyl-6-oxo-3-pyridin-4-yl-1,6-dihydropyridazine-4-carboxamide;
2-ethyl-4-[(3-fluorophenyl)amino]-5-glycoloyl-6-pyridin-4-ylpyridazin-3(2H)-one;
2-ethyl-4-[(3-fluorophenyl)amino]-5-(methoxyacetyl)-6-pyridin-3-ylpyridazin-3(2H)-one;
5-[(dimethylamino)acetyl]-2-ethyl-4-[(3-methoxyphenyl)amino]-6-pyridin-3-ylpyridazin-3(2H)-one;

2-ethyl-4-[(3-fluorophenyl)amino]-5-[(methylamino)acetyl]-6-pyridin-4-ylpyridazin-3(2H)-one;
3-{[2-ethyl-3-oxo-5-(3-phenylpropanoyl)-6-pyridin-4-yl-2,3-dihydropyridazin-4-yl]amino}benzamide;
ethyl 4-acetyl-5-[(3-chlorophenyl)amino]-1-ethyl-6-oxo-1,6-dihydropyridazine-3-carboxylate;
ethyl 4-acetyl-5-amino-1-ethyl-6-oxo-1,6-dihydropyridazine-3-carboxylate;
5-acetyl-6-(1,3-benzoxazol-2-yl)-2-ethyl-4-[(3-methoxyphenyl)amino]pyridazin-3(2H)-one;
5-acetyl-6-(1,3-benzoxazol-2-yl)-2-ethyl-4-{[4-(hydroxymethyl)phenyl]amino}pyridazin-3(2H)-one;
5-acetyl-2-ethyl-4-(isoquinolin-4-ylamino)-6-phenylpyridazin-3(2H)-one;
5-acetyl-2-ethyl-4-(1,6-naphthyridin-8-ylamino)-6-phenylpyridazin-3(2H)-one;
5-acetyl-2-ethyl-4-[(5-methoxypyridin-3-yl)amino]-6-phenylpyridazin-3(2H)-one;
5-acetyl-2-ethyl-6-pyridin-4-yl-4-(pyridin-3-ylamino)pyridazin-3(2H)-one;
5-acetyl-2-ethyl-4-[(4-methylpyridin-3-yl)amino]-6-pyridin-4-ylpyridazin-3(2H)-one;
5-acetyl-2-ethyl-4-(isoquinolin-4-ylamino)-6-pyridin-4-ylpyridazin-3(2H)-one;
5-acetyl-2-ethyl-6-pyridin-4-yl-4-[(3,4,5-trifluorophenyl)amino]pyridazin-3(2H)-one;
5-acetyl-2-ethyl-4-[(4-methylpyridin-3-yl)amino]-6-pyridin-3-ylpyridazin-3(2H)-one;
5-acetyl-2-ethyl-4-(isoquinolin-4-ylamino)-6-pyridin-3-ylpyridazin-3(2H)-one;
5-acetyl-2-ethyl-6-pyridin-3-yl-4-[(3,4,5-trifluorophenyl)amino]pyridazin-3(2H)-one;
5-acetyl-2-ethyl-4-(quinolin-5-ylamino)-6-thien-2-ylpyridazin-3(2H)-one;
5-acetyl-2-ethyl-4-(pyridin-3-ylamino)-6-thien-2-ylpyridazin-3(2H)-one;
4-[(5-acetyl-2-ethyl-3-oxo-6-thien-2-yl-2,3-dihydropyridazin-4-yl)amino]benzonitrile;
5-acetyl-2-ethyl-6-thien-2-yl-4-[(3,4,5-trifluorophenyl)amino]pyridazin-3(2H)-one;
5-Acetyl-4-(bis(4-cyanophenyl)amino)-2-ethyl-6-thien-2-ylpyridazin-3(2H)-one;
5-acetyl-2-(cyclopropylmethyl)-4-(quinolin-5-ylamino)-6-thien-2-ylpyridazin-3(2H)-one;
5-acetyl-2-(cyclopropylmethyl)-4-(pyridin-3-ylamino)-6-thien-2-ylpyridazin-3(2H)-one;
5-acetyl-2-ethyl-4-(quinolin-5-ylamino)-6-thien-3-ylpyridazin-3(2H)-one;
5-acetyl-4-[(3-chlorophenyl)amino]-2-ethyl-6-thien-3-ylpyridazin-3(2H)-one;
5-acetyl-2-ethyl-4-(pyridin-3-ylamino)-6-thien-3-ylpyridazin-3(2H)-one;
4-[(5-acetyl-2-ethyl-3-oxo-6-thien-3-yl-2,3-dihydropyridazin-4-yl)amino]benzonitrile;
5-acetyl-2-ethyl-6-thien-3-yl-4-[(3,4,5-trifluorophenyl)amino]pyridazin-3(2H)-one;
2-ethyl-6-phenyl-5-(3-phenylpropanoyl)-4-(quinolin-5-ylamino)pyridazin-3(2H)-one;
2-ethyl-6-phenyl-5-(3-phenylpropanoyl)-4-(pyridin-3-ylamino)pyridazin-3(2H)-one;
2-ethyl-4-(isoquinolin-4-ylamino)-6-phenyl-5-(3-phenylpropanoyl)pyridazin-3(2H)-one;
2-ethyl-6-phenyl-4-(quinolin-5-ylamino)-5-(3-thien-3-ylpropanoyl)pyridazin-3(2H)-one;
2-ethyl-6-phenyl-4-(pyridin-3-ylamino)-5-(3-thien-3-ylpropanoyl)pyridazin-3(2H)-one;
5-acetyl-4-[(3-chlorophenyl)amino]-2-ethyl-6-(1H-imidazo[4,5-b]pyridin-2-yl)pyridazin-3(2H)-one;
5-acetyl-6-(1,3-benzothiazol-2-yl)-4-[(3-chlorophenyl)amino]-2-ethylpyridazin-3(2H)-one;
5-acetyl-6-(1-benzofuran-2-yl)-4-[(3-chlorophenyl)amino]-2-ethylpyridazin-3(2H)-one;
5-acetyl-2-ethyl-6-pyridin-3-yl-4-(pyridin-3-ylamino)pyridazin-3(2H)-one;
4-[(5-acetyl-2-ethyl-3-oxo-6-pyridin-3-yl-2,3-dihydropyridazin-4-yl)amino]benzoic acid;
5-acetyl-2-ethyl-4-[(1-oxidopyridin-3-yl)amino]-6-phenylpyridazin-3(2H)-one;
ethyl 3-(5-acetyl-2-ethyl-3-oxo-6-pyridin-4-yl-2,3-dihydro-pyridazin-4-ylamino)benzoate;
3-[(5-acetyl-2-ethyl-3-oxo-6-pyridin-4-yl-2,3-dihydropyridazin-4-yl)amino]benzamide;
5-acetyl-2-ethyl-6-phenyl-4-(thieno[2,3-b]pyridin-3-ylamino)pyridazin-3(2H)-one;
5-acetyl-2-ethyl-4-[(6-fluoropyridin-3-yl)amino]-6-phenylpyridazin-3(2H)-one;
5-acetyl-2-ethyl-4-[(2-methylpyridin-3-yl)amino]-6-phenylpyridazin-3(2H)-one;
5-acetyl-4-{[2-(dimethylamino)pyridin-3-yl]amino}-2-ethyl-6-phenylpyridazin-3(2H)-one;
5-[(5-acetyl-2-ethyl-3-oxo-6-phenyl-2,3-dihydropyridazin-4-yl)amino]pyridine-2-carboxylic acid;
5-acetyl-2-ethyl-4-[(2-methoxypyridin-3-yl)amino]-6-phenylpyridazin-3(2H)-one;
5-acetyl-2-ethyl-4-(1H-indazol-4-ylamino)-6-phenylpyridazin-3(2H)-one;
5-acetyl-4-[(2-chloropyridin-3-yl)amino]-2-ethyl-6-phenylpyridazin-3(2H)-one;
5-acetyl-4-[(5-chloropyridin-3-yl)amino]-2-ethyl-6-phenylpyridazin-3(2H)-one;
5-[(5-acetyl-2-ethyl-3-oxo-6-phenyl-2,3-dihydropyridazin-4-yl)amino]nicotinamide;
5-acetyl-2-ethyl-4-(1,7-naphthyridin-8-ylamino)-6-phenylpyridazin-3(2H)-one;
2-ethyl-5-glycoloyl-4-[(2-methylpyridin-3-yl)amino]-6-phenylpyridazin-3(2H)-one;
methyl 5-[(5-acetyl-2-ethyl-3-oxo-6-phenyl-2,3-dihydropyridazin-4-yl)amino]nicotinate;
5-[(5-acetyl-2-ethyl-3-oxo-6-phenyl-2,3-dihydropyridazin-4-yl)amino]nicotinic acid;
5-acetyl-2-ethyl-4-(1,5-naphthyridin-3-ylamino)-6-phenylpyridazin-3(2H)-one;
5-acetyl-2-ethyl-4-[(8-hydroxy-1,7-naphthyridin-5-yl)amino]-6-phenylpyridazin-3(2H)-one;
5-acetyl-2-ethyl-6-phenyl-4-(thien-2-ylamino)pyridazin-3(2H)-one;
5-acetyl-2-ethyl-6-phenyl-4-[(2-phenylpyridin-3-yl)amino]pyridazin-3(2H)-one;
ethyl {5-[(5-acetyl-2-ethyl-3-oxo-6-phenyl-2,3-dihydropyridazin-4-yl)amino]pyridin-2-yl}acetate;
5-acetyl-2-ethyl-4-[(6-methylpyridin-3-yl)amino]-6-phenylpyridazin-3(2H)-one;
5-acetyl-2-ethyl-4-[(6-hydroxypyridin-3-yl)amino]-6-phenylpyridazin-3(2H)-one;
5-acetyl-2-ethyl-4-[(2-fluoropyridin-3-yl)amino]-6-phenylpyridazin-3(2H)-one;
5-acetyl-4-[(6-chloro-4-methylpyridin-3-yl)amino]-2-ethyl-6-phenylpyridazin-3(2H)-one;
5-acetyl-2-ethyl-4-[(3-hydroxypyridin-2-yl)amino]-6-phenylpyridazin-3(2H)-one;
5-acetyl-2-ethyl-4-[(4-methoxypyridin-3-yl)amino]-6-phenylpyridazin-3(2H)-one;

5-acetyl-2-ethyl-4-(isoquinolin-8-ylamino)-6-phenylpyridazin-3(2H)-one;
5-acetyl-2-ethyl-6-phenyl-4-(quinolin-7-ylamino)pyridazin-3(2H)-one;
5-acetyl-4-[(5-chloropyridin-3-yl)amino]-2-ethyl-6-(3-fluorophenyl)pyridazin-3(2H)-one;
5-acetyl-2-ethyl-6-(4-fluorophenyl)-4-[(2-methoxypyridin-3-yl)amino]pyridazin-3(2H)-one;
5-acetyl-2-ethyl-6-(4-fluorophenyl)-4-[(2-methylpyridin-3-yl)amino]pyridazin-3(2H)-one;
5-acetyl-4-[(2-chloropyridin-3-yl)amino]-2-ethyl-6-(4-fluorophenyl)pyridazin-3(2H)-one;
5-acetyl-2-ethyl-6-(4-fluorophenyl)-4-[(4-methylpyridin-3-yl)amino]pyridazin-3(2H)-one;
5-acetyl-2-ethyl-6-(4-fluorophenyl)-4-[(2-fluoropyridin-3-yl)amino]pyridazin-3(2H)-one;
5-acetyl-4-[(2-chloropyridin-3-yl)amino]-2-(cyclopropylmethyl)-6-(4-fluorophenyl)pyridazin-3(2H)-one;
5-acetyl-2-(cyclopropylmethyl)-6-(4-fluorophenyl)-4-[(2-methoxypyridin-3-yl)amino]pyridazin-3(2H)-one;
5-acetyl-2-(cyclopropylmethyl)-6-(4-fluorophenyl)-4-[(2-methylpyridin-3-yl)amino]pyridazin-3(2H)-one;
5-acetyl-2-(cyclopropylmethyl)-6-(4-fluorophenyl)-4-[(2-fluoropyridin-3-yl)amino]pyridazin-3(2H)-one;
5-acetyl-2-(cyclopropylmethyl)-6-(4-fluorophenyl)-4-[(4-methylpyridin-3-yl)amino]pyridazin-3(2H)-one;
5-acetyl-2-(cyclopropylmethyl)-6-(4-fluorophenyl)-4-[(pyridin-3-yl)amino]pyridazin-3(2H)-one;
5-acetyl-6-(3-chlorophenyl)-2-ethyl-4-[(2-methylpyridin-3-yl)amino]pyridazin-3(2H)-one;
5-acetyl-6-(3-chlorophenyl)-4-[(2-chloropyridin-3-yl)amino]-2-ethylpyridazin-3(2H)-one;
5-acetyl-6-(3-chlorophenyl)-2-ethyl-4-[(4-methylpyridin-3-yl)amino]pyridazin-3(2H)-one;
methyl 5-[(5-acetyl-2-ethyl-3-oxo-6-phenyl-2,3-dihydropyridazin-4-yl)amino]quinoline-8-carboxylate;
5-acetyl-2-ethyl-4-[(4-methylpyridin-3-yl)amino]-6-phenylpyridazin-3(2H)-one;
5-acetyl-2-ethyl-4-(isoquinolin-4-ylamino)-6-(4-methoxyphenyl)pyridazin-3(2H)-one;
5-acetyl-2-ethyl-6-(4-methoxyphenyl)-4-(pyridin-3-ylamino)pyridazin-3(2H)-one;
5-acetyl-2-ethyl-6-(4-methoxyphenyl)-4-(quinolin-5-ylamino)pyridazin-3(2H)-one;
5-acetyl-2-ethyl-6-(4-methoxy-phenyl)-4-(1-oxy-quinolin-5-ylamino)-2H-pyridazin-3-one;
5-acetyl-2-ethyl-4-(isoquinolin-4-ylamino)-6-(3-methoxyphenyl)pyridazin-3(2H)-one;
5-acetyl-2-ethyl-6-(3-methoxyphenyl)-4-(pyridin-3-ylamino)pyridazin-3(2H)-one;
5-acetyl-2-ethyl-6-(3-methoxyphenyl)-4-(quinolin-5-ylamino)pyridazin-3(2H)-one;
5-acetyl-2-ethyl-6-(3-methoxyphenyl)-4-[(1-oxidoquinolin-5-yl)amino]pyridazin-3(2H)-one;
5-acetyl-2-ethyl-4-(isoquinolin-4-ylamino)-6-(4-methylphenyl)pyridazin-3(2H)-one;
5-acetyl-2-ethyl-6-(4-methylphenyl)-4-(pyridin-3-ylamino)pyridazin-3(2H)-one;
5-acetyl-2-ethyl-6-(4-methylphenyl)-4-(quinolin-5-ylamino)pyridazin-3(2H)-one;
5-acetyl-2-ethyl-6-(4-methylphenyl)-4-[(1-oxidoquinolin-5-yl)amino]pyridazin-3(2H)-one;
5-acetyl-2-ethyl-6-(4-methylphenyl)-4-[(4-methylpyridin-3-yl)amino]pyridazin-3(2H)-one;
5-acetyl-2-ethyl-4-(isoquinolin-4-ylamino)-6-(3-methylphenyl)pyridazin-3(2H)-one;
5-acetyl-2-ethyl-6-(3-methylphenyl)-4-(pyridin-3-ylamino)pyridazin-3(2H)-one;
5-acetyl-2-ethyl-6-(3-methylphenyl)-4-(quinolin-5-ylamino)pyridazin-3(2H)-one;
5-acetyl-2-ethyl-6-(3-methylphenyl)-4-[(4-methylpyridin-3-yl)amino]pyridazin-3(2H)-one;
methyl 4-[4-acetyl-1-ethyl-5-(isoquinolin-4-ylamino)-6-oxo-1,6-dihydropyridazin-3-yl]benzoate;
methyl 4-[4-acetyl-1-ethyl-6-oxo-5-(pyridin-3-ylamino)-1,6-dihydropyridazin-3-yl]benzoate;
4-[4-acetyl-1-ethyl-6-oxo-5-(pyridin-3-ylamino)-1,6-dihydropyridazin-3-yl]benzoic acid;
methyl 4-{4-acetyl-1-ethyl-5-[(4-methylpyridin-3-yl)amino]-6-oxo-1,6-dihydropyridazin-3-yl}benzoate;
4-{4-acetyl-1-ethyl-5-[(4-methylpyridin-3-yl)amino]-6-oxo-1,6-dihydropyridazin-3-yl}benzoic acid;
methyl 3-[4-acetyl-1-ethyl-6-oxo-5-(pyridin-3-ylamino)-1,6-dihydropyridazin-3-yl]benzoate;
3-[4-acetyl-1-ethyl-6-oxo-5-(pyridin-3-ylamino)-1,6-dihydropyridazin-3-yl]benzoic acid;
5-acetyl-4-[(3-chloro-4-fluorophenyl)amino]-2-ethyl-6-pyridin-4-ylpyridazin-3(2H)-one;
5-acetyl-4-[bis(3-chloro-4-fluorophenyl)amino]-2-ethyl-6-pyridin-4-ylpyridazin-3(2H)-one;
5-acetyl-4-[(3-chloro-4-fluorophenyl)amino]-2-ethyl-6-pyridin-3-ylpyridazin-3(2H)-one;
5-acetyl-4-[bis(3-chloro-4-fluorophenyl)amino]-2-ethyl-6-pyridin-3-ylpyridazin-3(2H)-one;
methyl [4-acetyl-6-oxo-3-phenyl-5-(quinolin-5-ylamino)pyridazin-1(6H)-yl]acetate;
[4-acetyl-6-oxo-3-phenyl-5-(quinolin-5-ylamino)pyridazin-1(6H)-yl]acetic acid;
5-acetyl-2-ethyl-4-[(3-methylpyridin-2-yl)amino]-6-phenylpyridazin-3(2H)-one;
5-acetyl-2-ethyl-6-phenyl-4-(1H-pyrazol-3-ylamino)pyridazin-3(2H)-one;
5-acetyl-2-ethyl-6-phenyl-4-(9H-purin-6-ylamino)pyridazin-3(2H)-one;
5-acetyl-2-ethyl-4-[(3-methylisoxazol-5-yl)amino]-6-phenylpyridazin-3(2H)-one;
5-acetyl-2-ethyl-4-[(8-hydroxyquinolin-5-yl)amino]-6-phenylpyridazin-3(2H)-one;
5-acetyl-2-ethyl-4-(1H-indazol-7-ylamino)-6-phenylpyridazin-3(2H)-one;
5-acetyl-4-[(6-bromoquinolin-8-yl)amino]-2-ethyl-6-phenylpyridazin-3(2H)-one;
5-acetyl-2-ethyl-4-[(5-methylisoxazol-3-yl)amino]-6-phenylpyridazin-3(2H)-one;
5-acetyl-2-ethyl-4-(isoxazol-3-ylamino)-6-phenylpyridazin-3(2H)-one;
5-acetyl-2-(cyclopropylmethyl)-6-phenyl-4-(quinolin-5-ylamino)pyridazin-3(2H)-one;
5-acetyl-2-(cyclopropylmethyl)-6-phenyl-4-(quinolin-8-ylamino)pyridazin-3(2H)-one;
5-acetyl-2-ethyl-4-[(1-methyl-1H-pyrazol-3-yl)amino]-6-phenylpyridazin-3(2H)-one;
5-acetyl-2-ethyl-4-[(1-oxidoquinolin-5-yl)amino]-6-phenylpyridazin-3(2H)-one;
5-acetyl-2-ethyl-4-[(2-oxidoisoquinolin-5-yl)amino]-6-phenylpyridazin-3(2H)-one;
5-acetyl-6-(3-chlorophenyl)-2-ethyl-4-(quinolin-5-ylamino)pyridazin-3(2H)-one;
5-acetyl-6-(3-chlorophenyl)-2-ethyl-4-(quinolin-8-ylamino)pyridazin-3(2H)-one;
5-acetyl-2-ethyl-6-pyridin-4-yl-4-(quinolin-5-ylamino)pyridazin-3(2H)-one;

5-acetyl-2-ethyl-6-pyridin-3-yl-4-(quinolin-5-ylamino) pyridazin-3(2H)-one;
5-acetyl-2-ethyl-4-[(8-fluoroquinolin-5-yl)amino]-6-phenylpyridazin-3(2H)-one;
5-acetyl-2-(cyclopropylmethyl)-6-(4-fluorophenyl)-4-(quinolin-8-ylamino)pyridazin-3(2H)-one;
5-acetyl-2-ethyl-6-(4-fluorophenyl)-4-(quinolin-5-ylamino)pyridazin-3(2H)-one;
5-acetyl-2-ethyl-6-(4-fluorophenyl)-4-(quinolin-8-ylamino)pyridazin-3(2H)-one;
5-acetyl-2-(cyclopropylmethyl)-6-(4-fluorophenyl)-4-(quinolin-5-ylamino)pyridazin-3(2H)-one;
5-acetyl-6-(3-chlorophenyl)-2-ethyl-4-[(1-oxidoquinolin-5-yl)amino]pyridazin-3(2H)-one;
5-acetyl-2-ethyl-4-[(2-methylquinolin-5-yl)amino]-6-phenylpyridazin-3(2H)-one;
5-acetyl-6-(3-chlorophenyl)-2-ethyl-4-(isoquinolin-5-ylamino)pyridazin-3(2H)-one;
5-acetyl-2-ethyl-6-(4-fluorophenyl)-4-[(1-oxidoquinolin-5-yl)amino]pyridazin-3(2H)-one;
5-acetyl-2-ethyl-6-(3-fluorophenyl)-4-(quinolin-5-ylamino)pyridazin-3(2H)-one;
5-acetyl-2-ethyl-6-(3-fluorophenyl)-4-[(1-oxidoquinolin-5-yl)amino]pyridazin-3(2H)-one; and
5-[(5-acetyl-2-ethyl-3-oxo-6-phenyl-2,3-dihydropyridazin-4-yl)amino]quinoline-8-carboxylic acid;
and pharmaceutically acceptable salts thereof.

18. A compound as claimed in claim 17, chosen from:
5-Acetyl-2-ethyl-4-[(3-fluorophenyl)amino]-6-pyridin-3-ylpyridazin-3(2H)-one;
5-Acetyl-2-ethyl-4-(1-naphthylamino)-6-pyridin-3-ylpyridazin-3(2H)-one;
5-Acetyl-4-[(3-chlorophenyl)amino]-2-ethyl-6-pyridin-4-ylpyridazin-3(2H)-one;
5-Acetyl-2-ethyl-4-(1-naphthylamino)-6-pyridin-4-ylpyridazin-3(2H)-one;
5-Acetyl-2-ethyl-4-[(2-methylphenyl)amino]-6-pyridin-4-ylpyridazin-3(2H)-one;
5-Acetyl-2-ethyl-4-[(3-methoxyphenyl)amino]-6-pyridin-4-ylpyridazin-3(2H)-one;
4-[(5-Acetyl-2-ethyl-3-oxo-6-pyridin-4-yl-2,3-dihydropyridazin-4-yl)amino]benzoic acid;
5-Acetyl-4-[(3-chlorophenyl)amino]-2-(2-hydroxyethyl)-6-pyridin-4-ylpyridazin-3(2H)-one;
5-Acetyl-4-[(3-chlorophenyl)amino]-2-ethyl-6-thien-2-ylpyridazin-3(2H)-one;
5-Acetyl-2-ethyl-6-phenyl-4-(pyridin-3-ylamino)pyridazin-3(2H)-one;
5-Acetyl-2-ethyl-6-phenyl-4-(quinolin-8-ylamino)pyridazin-3(2H)-one;
5-Acetyl-2-ethyl-4-(1H-indol-4-ylamino)-6-phenylpyridazin-3(2H)-one;
5-Acetyl-2-ethyl-6-phenyl-4-(quinolin-5-ylamino)pyridazin-3(2H)-one;
5-Acetyl-6-(3-fluorophenyl)-2-isopropyl-4-(pyridin-3-ylamino)pyridazin-3(2H)-one;
5-Acetyl-2-(cyclopropylmethyl)-6-(3-fluorophenyl)-4-(pyridin-3-ylamino)pyridazin-3(2H)-one;
5-Acetyl-2-ethyl-6-(4-fluorophenyl)-4-(pyridin-3-ylamino)pyridazin-3(2H)-one;
5-Acetyl-2-ethyl-4-(isoquinolin-5-ylamino)-6-phenylpyridazin-3(2H)-one;
5-Acetyl-6-(1,3-benzoxazol-2-yl)-2-ethyl-4-[(3-fluorophenyl)amino]pyridazin-3(2H)-one;
5-Acetyl-2-ethyl-4-[(1-oxidoquinolin-5-yl)amino]-6-phenylpyridazin-3(2H)-one;
5-Acetyl-2-ethyl-4-(isoquinolin-4-ylamino)-6-phenylpyridazin-3(2H)-one;
2-Ethyl-6-phenyl-5-(3-phenylpropanoyl)-4-(pyridin-3-ylamino)pyridazin-3(2H)-one;
5-Acetyl-2-ethyl-4-(isoquinolin-4-ylamino)-6-(3-methylphenyl)pyridazin-3(2H)-one;
5-Acetyl-2-ethyl-4-(isoquinolin-4-ylamino)-6-pyridin-4-ylpyridazin-3(2H)-one;
5-Acetyl-2-ethyl-4-(isoquinolin-4-ylamino)-6-(4-methylphenyl)pyridazin-3(2H)-one;
5-Acetyl-2-ethyl-6-(4-fluorophenyl)-4-[(4-methylpyridin-3-yl)amino]pyridazin-3(2H)-one;
5-[(5-Acetyl-2-ethyl-3-oxo-6-phenyl-2,3-dihydropyridazin-4-yl)amino]quinoline-8-carboxylic acid;
5-Acetyl-2-ethyl-4-[(4-methylpyridin-3-yl)amino]-6-phenylpyridazin-3(2H)-one;
Methyl 3-[4-acetyl-1-ethyl-6-oxo-5-(pyridin-3-ylamino)-1,6-dihydropyridazin-3-yl]benzoate;
5-acetyl-2-ethyl-6-(3-methylphenyl)-4-[(4-methylpyridin-3-yl)amino]pyridazin-3(2H)-one;
5-Acetyl-2-ethyl-4-(pyridin-3-ylamino)-6-thien-3-ylpyridazin-3(2H)-one;
5-Acetyl-2-ethyl-4-[(2-methylpyridin-3-yl)amino]-6-phenylpyridazin-3(2H)-one;
3-(4-Acetyl-5-amino-1-ethyl-6-oxo-1,6-dihydro-pyridazin-3-yl)-benzoic acid methyl ester;
5-Acetyl-2-ethyl-6-(3-methylphenyl)-4-(pyridin-3-ylamino)pyridazin-3(2H)-one;
5-Acetyl-2-ethyl-6-(3-fluorophenyl)-4-(pyridin-3-ylamino)-pyridazin-3(2H)-one;
5-Acetyl-2-ethyl-4-[(4-methylpyridin-3-yl)amino]-6-pyridin-4-ylpyridazin-3(2H)-one;
5-Acetyl-2-ethyl-4-[(4-methylpyridin-3-yl)amino]-6-pyridin-3-ylpyridazin-3(2H)-one;
5-Acetyl-4-[(2-chloropyridin-3-yl)amino]-2-ethyl-6-phenylpyridazin-3(2H)-one;
5-Acetyl-2-ethyl-6-pyridin-3-yl-4-(pyridin-3-ylamino) pyridazin-3(2H)-one;
5-Acetyl-2-ethyl-6-(4-methylphenyl)-4-[(4-methylpyridin-3-yl)amino]pyridazin-3(2H)-one; and
5-Acetyl-2-ethyl-6-phenyl-4-(thieno[2,3-b]pyridin-3-ylamino)pyridazin-3(2H)-one.

19. A process for the preparation of a compound of formula (XXIV):

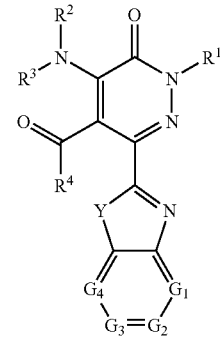

(XXIV)

wherein
$R^1$ and $R^2$ represent independently from each other:
a hydrogen atom;
a group chosen from acyl, hydroxycarbonyl, alkoxycarbonyl, carbamoyl, monoalkylcarbamoyl and dialkylcarbamoyl;

an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, carbamoyl and mono- and di-alkylcarbamoyl groups;

an aryl or heteroaryl group, wherein said aryl or heteroaryl group is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;

a saturated or unsaturated heterocyclic group, which is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, oxo, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;

a group of formula

—(CH$_2$)$_n$—R$^6$ wherein n is an integer from 0 to 4 and R$^6$ represents:
  a cycloalkyl or cycloalkenyl group;
  an aryl group, which is optionally substituted by one or more substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups;
  or a 3- to 7-membered ring having from 1 to 4 heteroatoms chosen from nitrogen, oxygen and sulphur, which ring is optionally substituted by one or more substituents chosen from halogen atoms, alkyl, hydroxy, alkoxy, alkylenedioxy, amino, mono- and di-alkylamino, nitro, cyano and trifluoromethyl groups;

R$^3$ represents a monocyclic or polycyclic aryl or heteroaryl group, which is optionally substituted by one or more substituents chosen from:
  halogen atoms;
  alkyl and alkylene groups, which are optionally substituted by one or more substituents chosen from halogen atoms; phenyl, hydroxy, hydroxyalkyl, alkoxy, aryloxy, alkylthio, oxo, amino, mono- and di-alkylamino, acylamino, hydroxycarbonyl, alkoxycarbonyl, carbamoyl, and mono- and di-alkylcarbamoyl groups;
  phenyl, hydroxy, hydroxyalkyl, alkoxy, cycloalkoxy, nitro, aryloxy, alkylthio, alkylsulphinyl, alkylsulphonyl, alkylsulfamoyl, acyl, amino, mono- and di- alkylamino, acylamino, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups; and R$^4$ represents:
  a hydrogen atom;
  a hydroxy, alkoxy, amino, mono- or di-alkylamino group;

an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups;

or a group of formula

—(CH$_2$)$_n$—R$^6$ wherein n and R$^6$ are as defined above
wherein each G$_1$, G$_2$, G$_3$ and G$_4$ independently represents a nitrogen or carbon atom, Y represents an O atom, a S atom or an —NH— group and the benzene ring may optionally be substituted by one or more substituents, which process comprises reacting a carboxylic acid ester of formula (VII)

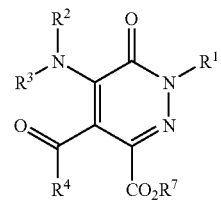

(VII)

wherein R$^1$, R$^2$, R$^3$ and R$^4$ are as defined above, with an ortho-subtituted aniline of formula (VIII) in the presence of a dehydrating agent,

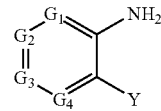

(VIII)

wherein each G$_1$, G$_2$, G$_3$ and G$_4$ independently represent a nitrogen or carbon atom and Y represents an amino, mercapto or hydroxy group.

20. A compound of formula (XXV)

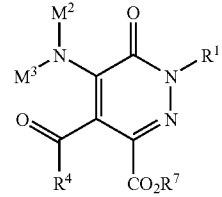

(XXV)

wherein M$^2$ is either a hydrogen atom or a group R$^2$ and M$^3$ is either a
hydrogen atom or
a group R$^3$, and wherein
R$^1$ and R$^2$ represent independently from each other:
a hydrogen atom;
a group chosen from acyl, hydroxycarbonyl, alkoxycarbonyl, carbamoyl, monoalkylcarbamoyl and dialkylcarbamoyl;
an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, carbamoyl and mono- and di-alkylcarbamoyt groups;

an aryl or heteroaryl group, wherein said aryl or heteroaryl group is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;

a saturated or unsaturated heterocyclic group, which is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, oxo, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;

a group of formula $$-(CH_2)_n-R^6$$

wherein n is an integer from 0 to 4 and $R^6$ represents:

a cycloalkyl or cycloalkenyl group;

an aryl group, which is optionally substituted by one or more substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups;

or a 3- to 7-membered ring having from 1 to 4 heteroatoms chosen from nitrogen, oxygen and sulphur, which ring is optionally substituted by one or more substituents chosen from halogen atoms, alkyl, hydroxy, alkoxy, alkylenedioxy, amino, mono- and di-alkylamino, nitro, cyano and trifluoromethyl groups;

$R^3$ represents a monocyclic or polycyclic aryl or heteroaryl group, which is optionally substituted by one or more substituents chosen from:

halogen atoms;

alkyl and alkylene groups, which are optionally substituted by one or more substituents chosen from halogen atoms; phenyl, hydroxy, hydroxyalkyl, alkoxy, aryloxy, alkylthio, oxo, amino, mono- and di-alkylamino, acylamino, hydroxycarbonyl, alkoxycarbonyl, carbamoyl, and mono- and di-alkylcarbamoyl groups;

phenyl, hydroxy, hydroxyalkyl, alkoxy, cycloalkoxy, nitro, aryloxy, alkylthio, alkylsulphinyl, alkylsulphonyl, alkylsulfamoyl, acyl, amino, mono- and di-alkylamino, acylamino, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;

$R^5$ represents a group $—COOR^7$ or a monocyclic or polycyclic aryl or heteroaryl group, wherein said $—COOR^7$ or monocyclic or polycyclic aryl or heteroaryl group is optionally substituted by one or more substituents chosen from:

halogen atoms;

alkyl and alkenyl groups, which are optionally substituted by one or more substituents chosen from halogen atoms, phenyl, hydroxy, hydroxyalkyl, alkoxy, aryloxy, alkylthio, oxo, amino, mono- and di-alkylamino, acylamino, hydroxycarbonyl, alkoxycarbonyl, carbamoyl, and mono- and di-alkylcarbamoyl groups; and phenyl, hydroxy, alkylenedioxy, alkoxy, cycloalkyloxy, alkylthio, alkylsuiphinyl, alkylsuiphonyl, alkylsulfamoyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsuiphamido, aminosuphonyl, mono- and di-alkylaminosuiphonyl, cyano, difluoromethoxy and trifluoromethoxy groups;

wherein $R^7$ represents an alkyl, which is optionally substituted by one or more substituents chosen from halogen atoms, hydroxy, alkoxy, aryloxy, alkylthio, oxo, amino, mono- and di-alkylamino, acylamino, hydroxycarbonyl, alkoxycarbonyl, carbamoyl, mono- and di-alkylcarbamoyl groups, and a group of formula $$-(CH_2)_n-R^6$$

and $R^4$ represents:

a hydrogen atom;

a hydroxy, alkoxy, amino, mono- or di-alkylamino group;

an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups;

or a group of formula $$-(CH_2)_n-R^6$$

where n and $R^6$ are as defined above.

21. A compound according to claim 20, which is ethyl 4-acetyl-5-amino-1-ethyl-6-oxo-1,6-dehydropyridazine-3-carboxylate.

22. A pharmaceutical composition comprising a compound as claimed in claim 1, mixe with a pharmaceutically acceptable diluent or carrier.

23. A method for treating a subject afflicted with a pathological condition or disease susceptible to amelioration by inhibition of phosphodiesterase 4, which method comprises administering to the said subject an effective amount of a compound as claimed in claim 1, wherein the pathological condition or disease is chosen from asthma and atopic dermatitis.

24. A composition comprising:
(i) a pyridazin-3(2H)-one derivative compound of formula (I):

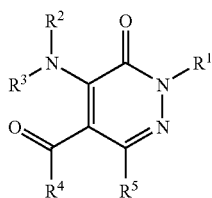 (I)

wherein
R$^1$ and R$^2$ represent independently from each other:
a hydrogen atom;
a group chosen from acyl, hydroxycarbonyl, alkoxycarbonyl, carbamoyl, monoalkylcarbamoyl and dialkylcarbamoyl;
an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, carbamoyl and mono- and di-alkylcarbamoyl groups;
an aryl or heteroaryl group, wherein said aryl or heteroaryl group is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;
a saturated or unsaturated heterocyclic group, which is optionally substituted by one or more substituents chosen from halogen atoms, hydroxy, hydroxyalkyl, hydroxycarbonyl, alkoxy, alkylenedioxy, alkoxyacyl, aryloxy, acyl, acyloxy, alkylthio, oxo, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups;
a group of formula —(CH$_2$)$_n$—R$^6$ wherein n is an integer from 0 to 4 and R$^6$ represents:
a cycloalkyl or cycloalkenyl group;
an aryl group, which is optionally substituted by one or more substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups;
or a 3- to 7-membered ring having from 1 to 4 heteroatoms chosen from nitrogen, oxygen and sulphur, which ring is optionally substituted by one or more substituents chosen from halogen atoms, alkyl, hydroxy, alkoxy, alkylenedioxy, amino, mono- and di-alkylamino, nitro, cyano and trifluoromethyl groups;
R$^3$ represents a monocyclic or polycyclic aryl or heteroaryl group, which is optionally substituted by one or more substituents chosen from:
halogen atoms;
alkyl and alkylene groups, which are optionally substituted by one or more substituents chosen from halogen atoms; phenyl, hydroxy, hydroxyalkyl, alkoxy, aryloxy, alkylthio, oxo, amino, mono- and di-alkylamino, acylamino, hydroxycarbonyl, alkoxycarbonyl, carbamoyl, and mono- and di-alkylcarbamoyl groups;
phenyl, hydroxy, hydroxyalkyl, alkoxy, cycloalkoxy, nitro, aryloxy, alkylthio, alkylsuiphinyl, alkylsulphonyl, alkylsulfamoyl, acyl, amino, mono- and di-alkylamino, acylamino, hydroxycarbonyl, alkoxycarbonyl, carbamoyl, mono- and di-alkylcarbamoyl, ureido, N'-alkylureido, N',N'-dialkylureido, alkylsuiphamido, aminosuphonyl, mono- and di-alkylaminosulphonyl, cyano, difluoromethoxy and trifluoromethoxy groups;
R$^5$ represents a group —COOR$^7$ or a monocyclic or polycyclic aryl or heteroaryl group, wherein said —COOR$^7$ or monocyclic or polycyclic aryl or heteroaryl group is optionally substituted by one or more substituents chosen from:
halogen atoms;
alkyl and alkenyl groups, which are optionally substituted by one or more substituents chosen from halogen atoms, phenyl, hydroxy, hydroxyalkyl, alkoxy, aryloxy, alkylthio, oxo, amino, mono- and di-alkylamino, acylamino, hydroxycarbonyl, alkoxycarbonyl, carbamoyl, and mono- and di-alkylcarbamoyl groups; and
phenyl, hydroxy, alkylenedioxy, alkoxy, cycloalkyloxy, alkylthio, alkylsulphinyl, alkylsuiphonyl, alkylsulfamoyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N', N'-dialkylureido, alkylsuiphamido, aminosuphonyl, mono- and di-alkylaminosu Iphonyl, cyano, difluoromethoxy and trifluoromethoxy groups;
wherein R$^7$ represents an alkyl, which is optionally substituted by one or more substituents chosen from halogen atoms, hydroxy, alkoxy, aryloxy, alkylthio, oxo, amino, mono- and di-alkylamino, acylamino, hydroxycarbonyl, alkoxycarbonyl, carbamoyl, mono- and di-alkylcarbamoyl groups, and a group of formula —(CH$_2$)$_n$—R$^6$ wherein n and R$^6$ are as defined above; and
R$^4$ represents:
a hydrogen atom;
a hydroxy, alkoxy, amino, mono- or di-alkylamino group;
an alkyl, alkenyl or alkynyl group, wherein said alkyl, alkenyl or alkynyl group is optionally substituted by one or more substituents chosen from halogen atoms, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups;
or a group of formula —(CH$_2$)$_n$—R$^6$ wherein n and R$^6$ are as defined above
or a N-oxide obtainable from heteroaryl radicals present in the structure when said heteroradical comprise at least one N atom or a pharmaceutically acceptable salt thereof; with the proviso that when R$^5$ is neither an optionally substituted heteroaryl group nor a group COOR$^7$, R$^3$ is an optionally substituted heteroaryl group;

and
(ii) another compound chosen from (a) steroids, (b) immunosuppressive agents, (c) T-cell receptor blockers and (d) antiinflammatory drugs.

25. A compound according to claim 14, wherein the phenyl and heteroaryl groups are unsubstituted or substituted by 1 or 2 substituents selected from $C_1$-$C_4$ alkoxy groups, chlorine atoms and fluorine atoms.

26. A method for treating a subject afflicted with a pathological condition or disease susceptible to amelioration by inhibition of phosphodiesterase 4, which method comprises administering to the said subject an effective amount of a compound as claimed in claim 1, wherein the pathological condition or disease is psoriasis.

* * * * *

UNITED STATES PATENT AND TRADEMARK OFFICE
CERTIFICATE OF CORRECTION

PATENT NO.       : 7,491,722 B2
APPLICATION NO.  : 10/539821
DATED            : February 17, 2009
INVENTOR(S)      : Vittorio Dal Piaz et al.

It is certified that error appears in the above-identified patent and that said Letters Patent is hereby corrected as shown below:

Claim 1, col. 144, line 44, "alkylsuiphinyl, alkylsuiphonyl" should read --alkylsulphinyl, alkylsulphonyl--;

Claim 1, col. 144, lines 48-49, "alkylsuiphamido" should read --alkylsulphamido--;

Claim 1, col. 144, line 49, "aminosuphonyl" should read --aminosulphonyl--;

Claim 6, col. 145, line 49, "alkylsuiphinyl, alkylsuiphonyl" should read --alkylsulphinyl, alkylsulphonyl--;

Claim 6, col. 145, line 53, "alkylsuiphamido" should read --alkylsulphamido--;

Claim 6, col. 145, line 53, "aminosuphonyl" should read --aminosulphony--;

Claim 6, col. 145, line 54, "di-alkylaminosuiphonyl" should read --di-alkylaminosulphonyl--;

Claim 16, col. 148, line 12, "aminosuphonyl" should read --aminosulphonyl--;

Claim 16, col. 148, line 34, "aminosuphonyl" should read --aminosulphonyl--;

Claim 16, col. 148, line 29, "alkylsuiphinyl" should read --alkylsulphinyl--;

Claim 19, col. 159, line 37, "7-membe red" should read --7-membered--;

Claim 19, col. 159, line 61, "aminosuphonyl" should read --aminosulphonyl--;

Claim 19, col. 160, line 13, "0 atom" should read --O atom--;

Claim 20, col. 161, line 60, "aminosuphonyl" should read --aminosulphonyl--;

Claim 20, col. 162, line 11, "alkylsuiphinyl, alkylsuiphonyl" should read --alkylsulphinyl, alkylsuphonyl--;

Claim 24, col. 164, line 7, "alkylsuiphinyl" should read --alkylsulphinyl--;

Claim 24, col. 164, lines 11-12, "alkylsuiphamido" should read --alkylsulphamido--;

UNITED STATES PATENT AND TRADEMARK OFFICE
CERTIFICATE OF CORRECTION

PATENT NO. : 7,491,722 B2
APPLICATION NO. : 10/539821
DATED : February 17, 2009
INVENTOR(S) : Vittorio Dal Piaz et al.

It is certified that error appears in the above-identified patent and that said Letters Patent is hereby corrected as shown below:

Claim 24, col. 164, line 12, "aminosuphonyl" should read --aminosulphonyl--;

Claim 24, col. 164, line 29, "alkylsuiphonyl" should read --alkylsulphonyl--;

Claim 24, col. 164, lines 33-34, "alkylsuiphamido" should read --alkylsulphamido--;

Claim 24, col. 164, line 34, "aminosuphonyl" should read --aminosulphonyl--; and Claim 24, col. 164, lines 34-35, "di-alkylaminosulphonyl" should read --di-alkylaminosulphonyl--.

Signed and Sealed this

Twelfth Day of May, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,491,722 B2 | Page 1 of 1 |
| APPLICATION NO. | : 10/539821 | |
| DATED | : February 17, 2009 | |
| INVENTOR(S) | : Del Piaz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 452 days.

Signed and Sealed this
Twenty-eighth Day of December, 2010

David J. Kappos
*Director of the United States Patent and Trademark Office*